US011584752B2

(12) United States Patent
Robb et al.

(10) Patent No.: US 11,584,752 B2
(45) Date of Patent: Feb. 21, 2023

(54) METHOD FOR CONTROLLED RELEASE USING MECHANICAL FORCE

(71) Applicant: California Institute of Technology, Pasadena, CA (US)

(72) Inventors: Maxwell J. Robb, Altadena, CA (US); Xiaoran Hu, Pasadena, CA (US); Tian Zeng, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/469,728

(22) Filed: Sep. 8, 2021

(65) Prior Publication Data

US 2022/0073534 A1 Mar. 10, 2022

Related U.S. Application Data

(60) Provisional application No. 63/171,889, filed on Apr. 7, 2021, provisional application No. 63/075,666, filed on Sep. 8, 2020.

(51) Int. Cl.
| | | |
|---|---|---|
| *C07D 491/18* | (2006.01) | |
| *C07D 307/42* | (2006.01) | |
| *C07D 407/12* | (2006.01) | |
| *C07D 311/16* | (2006.01) | |
| *C08F 120/18* | (2006.01) | |
| *C08K 5/3417* | (2006.01) | |

(52) U.S. Cl.
CPC ......... *C07D 491/18* (2013.01); *C07D 307/42* (2013.01); *C07D 311/16* (2013.01); *C07D 407/12* (2013.01); *C08F 120/18* (2013.01); *C08K 5/3417* (2013.01)

(58) Field of Classification Search
None
See application file for complete search history.

(56) References Cited

U.S. PATENT DOCUMENTS

2021/0070741 A1 3/2021 Robb et al.

OTHER PUBLICATIONS

Larsen et al., "Successive mechanochemical activation and small molecule release in an elastomeric material", Journal of the American Chemical Society, vol. 136, No. 4, Jan. 29, 2014, published online Jan. 16, 2014, pp. 1276-1279, doi: 10.1021/ja411891x.
Lee et al., "Controlled Drug Delivery from Polymers by Mechanical Signals", Advanced Materials, vol. 13, Issue 11, Jun. 2001, first published May 31, 2011, pp. 837-839, https://doi.org/10.1002/1521-4095(200106)13:11<837::AID-ADMA837>3.0.CO;2-D.
Lemieux et al., "Reactivity-Gated Photochromism of 1,2-Dithienylethenes for Potential Use in Dosimetry Applications", Organic Letters, Jun. 14, 2005, vol. 7, No. 14, pp. 2969-2972, https://doi.org/10.1021/ol050971p.
Lemieux et al., "Selective and Sequential Photorelease Using Molecular Switches", Angew. Chem. International Edition, Oct. 17, 2006, vol. 45, Issue 41, pp. 6820-6824, https://doi.org/10.1002/anie.200601584.
Li et al., "Mechanophore Activation at Heterointerfaces", Journal of the American Chemical Society, Oct. 31, 2014, vol. 136, No. 45, pp. 15925-15928, https://doi.org/10.1021/ja509949d.
Li et al., "Polymer Mechanochemistry: From Destructive to Productive", Acc. Chem. Res. Jul. 15, 2015, vol. 48, No. 8, pp. 2181-2190, https://doi.org/10.1021/acs.accounts.5b00184.
Lin et al., "A Latent Mechanoacid for Time-Stamped Mechanochromism and Chemical Signaling in Polymeric Materials", Journal of the American Chemical Society, vol. 142, No. 1, Jan. 8, 2020, published online December to, 2019, pp. 99-103, doi: 10.1021/jacs.9b12861.
May et al., "Is Molecular Weight or Degree of Polymerization a Better Descriptor of Ultrasound-Induced Mechanochemical Transduction?", ACS Macro Lett. 2016, vol. 5, pp. 177-180, DOI: 10.1021/acsmacrolett.5b00855.
McFadden et al., "Force-Dependent Multicolor Mechanochromism from a Single Mechanophore", Journal of the American Chemical Society, vol. 141, No. 29, Jul. 24, 2019, published online Jul. 15, 2019, pp. 11388-11392, doi: 10.1021/jacs.9b05280.
Mosey et al., "Versatile approach to α-alkoxy carbamate synthesis and stimulus-responsive alcohol release", Organic & Molecular Chemistry, Aug. 2012, vol. 10, No. 39, pp. 7980-7985, DOI:10.1039/c2ob26571k.
Nguyen et al., "Surface-Dependent Kinetics of Cu(0)-Wire-Catalyzed Single-Electron Transfer Living Radical Polymerization of Methyl Acrylate in DMSO at 25° C.", Macromolecules, vol. 42, No. 7, Mar. 17, 2009, pp. 2379-2386, https://doi.org/10.1021/ma8028562.
Nichol et al., "Multi-stimuli responsive trigger for temporally controlled depolymerization of self-immolative polymers", Organic Chemistry, vol. 10, No. 36, Aug. 12, 2019, pp. 4914-4919, https://doi.org/10.1039/C9PY00301K.
Ohsumi et al., "Chemical control of the photochromic reactivity of diarylethene derivatives", Chemical Communications, Jul. 9, 2005, pp. 3921-3923, DOI: 10.1039/n506801k.
Patrick et al., "Polymers with autonomous life-cycle control", Nature, vol. 540, Dec. 15, 2016, pp. 363-370, doi: 10.1038/nature21002.
Peterson et al., "1,2-oxazine linker as a thermal trigger for self-immolative polymers", Polymer, Nov. 5, 2014, vol. 55, Issue 23, pp. 5980-5985, https://doi.org/10.1016/j.polymer.2014.09.048.

(Continued)

*Primary Examiner* — Samantha L Shterengarts
(74) *Attorney, Agent, or Firm* — KPPB LLP

(57) ABSTRACT

A general and modular mechanophore platform that efficiently releases a cargo molecule via a mechanically triggered cascade reaction is described, along with methods of synthesis and use thereof. The mechanophore platform comprises a stable Diels-Alder adduct mechanophore comprising a 2-furylcarbinol derivative as its diene component, wherein the 2-furylcarbinol derivative is, in turn, pre-loaded with a covalently attached cargo molecule, and wherein the Diels-Alder adduct mechanophore is embedded into a polymer chain or polymer network, such that the mechanophore platform undergoes the retro [4+2] cycloaddition reaction under mechanical force to reveal the unstable 2-furylcarbinol derivative, which, in turn, easily decomposes under mild conditions to release its molecule cargo.

23 Claims, 34 Drawing Sheets

(56) References Cited

OTHER PUBLICATIONS

Peterson et al., "3D-Printed Mechanochromic Materials", ACS Applied Materials and Interfaces, Dec. 5, 2014, vol. 7, pp. 577-583, dx.doi.org/10.1021/am506745m.

Peterson et al., "Kinetic Analysis of Mechanochemical Chain Scission of Linear Poly(phthalaldehyde)", Macromolecular Rapid Communications, vol. 35, Issue 18, Sep. 2014, first published Aug. 11, 2014, pp. 1611-1614, https://doi.org/10.1002/marc.201400271.

Piermattei et al., "Activating catalysts with mechanical force", Nature Chemistry, May 2009, vol. 1, Issue 2, pp. 133-137, published online Apr. 6, 2009, doi: 10.1038/nchem.167.

Ramirez et al., "Mechanochemical strengthening of a synthetic polymer in response to typically destructive shear forces", Nature Chemistry, 2013, vol. 5, pp. 757-761, published online Aug. 4, 2013. DOI: 10.1038/NCHEM.1720.

Robb et al., "A Retro-Staudinger Cycloaddition: Mechanochemical Cycloelimination of a β-Lactam Mechanophore", Journal of the American Chemical Society, Sep. 2, 2015, vol. 137, Issue 34, pp. 10946-10949, doi: 10.1021/jacs.5b07345.

Robb et al., "Regioisomer-Specific Mechanochromism of Naphthopyran in Polymeric Materials", Journal of the American Chemical Society, Sep. 12, 2016, vol. 138, No. 38, pp. 12328-12331, https://doi.org/10.1021/jacs.6b07610.

Ronn et al., "An Expedient Route to 3-Methoxy-2-furaldehyde", Synlett, vol. 1, 2012, Advanced online publication Sep. 12, 2011, pp. 134-136, DOI: 10.1055/s-0031-1290103.

Roth et al., "Dendritic, Oligomeric, and Polymeric Self-Immolative Molecular Amplification", Chemical Reviews, vol. 116, No. 3, Feb. 10, 2016, published online Sep. 10, 2015, pp. 1309-1352, doi: 10.1021/acs.chemrev.5b00372.

Schmid et al., "A self-immolative spacer that enables tunable controlled release of phenols under neutral conditions", The Journal of Organic Chemistry, vol. 77, No. 9, Apr. 2012, pp. 4363-4374, DOI:10.1021/jo300400q.

Sha et al., "Quantitative and Mechanistic Mechanochemistry in Ferrocene Dissociation", ACS Macro Letters, Oct. 16, 2018, vol. 7, No. 10. pp. 1174-1179, published online Sep. 14, 2018, doi: 10.1021/acsmacrolett.8b00625.

Shi et al., "Mechanochemical activation of disulfide-based multifunctional polymers for theranostic drug release", Chemical Science, vol. 12, 2020, pp. 1668-1674, DOI:10.1039/d0sc06054b.

Shi et al., "The Mechanochemical Release of Naphthalimide Fluorophores from β-Carbonate and β-Carbamate Disulfide-Centered Polymers", CCS Chemistry, Nov. 2021, vol. 3, Issue 11, pp. 2333-2344, first published Aug. 13, 2021, https://doi.org/10.31635/ccschem.021.202101147.

Shi et al., "Toward Drug Release Using Polymer Mechanochemical Disulfide Scission", The Journal of the American Chemical Society, Aug. 17, 2020, vol. 142, No. 34, pp. 14725-14732, DOI: 10.1021/jacs.0c07077.

Stevenson et al., "Controlling Reactivity by Geometry in Retro-Diels-Alder Reactions under Tension", Journal of the American Chemical Society, Oct. 31, 2017, vol. 139, No. 46, pp. 16768-16771, https://doi.org/10.1021/jacs.7b08895.

Sulkanen et al., "Spatially Selective and Density-Controlled Activation of Interfacial Mechanophores", Journal of the American Chemical Society, Mar. 6, 2019, vol. 141, No. 9, pp. 4080-4085, published online Feb. 26, 2019. doi: 10.1021/jacs.8b10257.

Sung et al., "Interfacial Mechanophore Activation Using Laser-Induced Stress Waves", Journal of the American Chemical Society, Mar. 29, 2018, vol. 140, No. 15, pp. 5000-5003, https://doi.org/10.1021/jacs.8b01427.

Swager, "Sensor Technologies Empowered by Materials and Molecular Innovations", Agnewandte Chemie International Edition, vol. 57, Issue 16, Apr. 9, 2018, first published Feb. 22, 2018, pp. 4248-4257, https://doi.org/10.1002/anie.201711611.

Toohey et al., "Self-healing materials with microvascular networks", Nature Materials, Aug. 2007, vol. 6, published online Jun. 10, 2007, pp. 581-585, doi:10.1038/nmat1934.

Wang et al., "A Novel Mechanochromic and Photochromic Polymer Film: When Rhodamine Joins Polyurethane", Advanced Materials, vol. 27, Issue 41, Nov. 4, 2015, first published Sep. 24, 2015, pp. 6469-6474, first published Sep. 24, 2015, https://doi.org/10.1002/adma.201503424.

Wang et al., "Mechanical gating of a mechanochemical reaction cascade", Nature Communications, Nov. 16, 2016, vol. 7, 13433, 8 pgs., DOI: 10.1038/ncomms13433.

Wang et al., "Mechanochemical Strengthening of a Multi-mechanophore Benzocyclobutene Polymer", ACS Macro Lett., Jul. 20, 2015, vol. 4, No. 8, pp. 834-837, https://doi.org/10.1021/acsmacrolett.5b00440.

Wang et al., "Single-Molecule Observation of a Mechanically Activated Cis-to-Trans Cyclopropane Isomerization", Journal of the American Chemical Society, Aug. 8, 2016, vol. 138, No. 33, pp. 10410-10412, https://doi.org/10.1021/jacs.6b0645.

Warford et al., "From Slow to Fast—the User Controls the Rate of the Release of Molecules From Masked Forms Using a Photoswitch and Different Types of Light", Chemical Communications, Mar. 2015, vol. 51, No. 32, pp. 7039-7042.

White et al., "Autonomic healing of polymer composites", Nature, vol. 409, No. 6822, Feb. 15, 2001, pp. 794-797, doi: 10.1038/35057232.

Wollenhaupt et al., "Should the Woodward-Hoffmann Rules be Applied to Mechanochemical Reactions?", ChemPhysChem, May 27, 2015, vol. 16, Issue 8, pp. 1593-1597, https://doi.org/10.1002/cphc.201500362.

Wu et al., "Molecular stress relief through a force-induced irreversible extension in polymer contour length", Journal of the American Chemical Society, vol. 132, No. 45, Oct. 26, 2010, pp. 15936-15938, https://doi.org/10.1021/ja108429h.

Yang et al., "Benzoladderene Mechanophores: Synthesis, Polymerization, and Mechanochemical Transformation", Journal of the American Chemical Society, vol. 141, No. 16, Apr. 24, 2019, published online Apr. 16, 2019, pp. 6479-6483, doi: 10.1021/jacs.9b01736.

Yokoyama et al., "Photochromism of a protonated 5-dimethylaminoindolylfulgide: a model of a non-destructive readout for a photon mode optical memory", Journal of Chemical Society Chemical Communications, 1991, pp. 1722-1724, https://doi.org/10.1039/C39910001722.

Zanetti et al., "α-Furfuryl Bromide (2-Bromomethylfuran)", Journal of the American Chemical Society, vol. 61, No. 8, Aug. 1, 1939, pp. 2249-2251, https://doi.org/10.1021/ja01877a506.

Zhang et al., "Mechanical Force-Triggered Drug Delivery", Chemical Reviews, Sep. 29, 2016, vol. 116, pp. 12536-12563, doi: 10.1021/acs.chemrev.6b00369.

Zhang et al., "Mechanical Susceptibility of a Rotaxane", Journal of the American Chemical Society, Sep. 6, 2019, vol. 141, No. 40, pp. 15879-15883, https://doi.org/10.1021/jacs.9b06960.

Zhang et al., "Mechanochromism and Mechanical-Force-Triggered Cross-Linking from a Single Reactive Moiety Incorporated into Polymer Chains", Angew. Chem. International Edition, Jan. 25, 2016, vol. 55, Issue 9, pp. 3040-3044, https://doi.org/10.1002/anie.201510171.

Akbulatov et al., "Critical review of experimental polymer mechanochemistry and its interpretational frameworks", ChemPhysChen, 2017, vol. 18, pp. 1422-1450.

Alouane et al., "Self-Immolative Spacers: Kinetic Aspects, Structure-Property Relationships, and Applications", Angewandte Chemie International Edition, vol. 54, Issue 26, Jun. 22, 2015, first published Jun. 5, 2015, pp. 7492-7509, https://doi.org/10.1002/anie.201500088.

Berkowski et al., "Ultrasound-Induced Site-Specific Cleavage of Azo-Functionalized Poly(ethylene glycol)", Macromolecules, Sep. 27, 2005, vol. 38, No. 22, pp. 8975-8978, https://doi.org/10.1021/ma051394n.

Beyer, "The mechanical strength of a covalent bond calculated by density functional theory", Journal of Chemical Physics, 2002, vol. 112, pp. 7307-7312https://doi.org/10.1063/1.481330.

Beyer et al., "Mechanochemistry: The Mechanical Activation of Covalent Bonds", Chem. Rev., Jul. 19, 2005, vol. 105, No. 8, pp. 2921-2948, https://doi.org/10.1021/cr030697h.

(56) References Cited

OTHER PUBLICATIONS

Binder et al., "A Mechanochemically Triggered "Click" Catalyst", Angewandte Chemie International Edition, vol. 54, Issue 47, Nov. 16, 2015, published online Sep. 30, 2015, pp. 13918-13922, https://doi.org/10.1002/anie.201505678.

Boutelle et al., "Substituent Effects on the Reversibility of Furan-Maleimide Cycloadditions", The Journal of Organic Chemistry, vol. 76, No. 19, Aug. 2011, pp. 7994-8002, DOI:10.1021/jo201606z.

Caruso et al., "Mechanically-Induced Chemical Changes in Polymeric Materials", Chem. Rev., Oct. 14, 2009, vol. 109, No. 11, pp. 5755-5798 https://doi.org/10.1021/cr9001353.

Chen et al., "Mechanically induced chemiluminescene from polymers incorporating a 1,2 dioxetane unit in the main chain", Nature Chemistry, 2012, vol. 4, pp. 559-562, published online Jun. 3, 2012, DOI:10.1038/NCHEM.1358.

Chen et al., "Mechanochemical unzipping of insulating polyladderene to semiconducting polyacetylene", Science, Aug. 4, 2017, vol. 357, Issue 6350, pp. 475-479, DOI: 10.1126/science.aan2797.

Cohen et al., "Excited State Proton-Transfer Reactions of Coumarin 4 in Protic Solvents", The Journal of Physical Chemistry A, vol. 105, No. 30, Jul. 7, 2001, pp. 7157-7164, https://doi.org/10.1021/jp010576q.

Davis et al., "Force-induced activation of covalent bonds in mechanoresponsive polymeric materials", Nature, May 7, 2009, vol. 459, Issue 7243, pp. 68-72, doi: 10.1038/nature07970.

Deng et al., "A Novel Way To Synthesize Star Polymers in One Pot by ATRP of N-[2-(2-Bromoisobutyryloxy)ethyl]maleimide and Styrene", Macromolecules, vol. 37, No. 1, pp. 18-26, 2004, first published Dec. 13, 2003, https://doi.org/10.1021/ma034542n.

Di Giannantonio et al., "Triggered Metal Ion Release and Oxidation: Ferrocene as a Mechanophore in Polymers", Angewandte Chemie International Edition English, Aug. 27, 2018, vol. 57, No. 35, pp. 11445-11450, published online Jul. 26, 2018, doi: 10.1002/anie.201803524.

Diesendruck et al., "Mechanically triggered heterolytic unzipping of a low-ceiling-temperature polymer", Nature Chemistry, Jul. 2014, vol. 6, pp. 623-628, published online Apr. 28, 2014, DOI: https://doi.org/10.1038/nchem.1938.

Diesendruck et al., "Proton-Coupled Mechanochemical Transduction: A Mechanogenerated Acid", Journal of the American Chemical Society, Jul. 9, 2012, vol. 134, No. 30, pp. 12446-12449, https://doi.org/10.1021/ja305645x.

Duan et al., "An Investigation of the Selective Chain Scission at Centered Diels—Alder Mechanophore under Ultrasonication", Macromolecules Feb. 9, 2017, vol. 50, No. 4, pp. 1353-1361, https://doi.org/10.1021/acs.macromol.6b0237.

Esser-Kahn et al., "Triggered Release from Polymer Capsules", Macromolecules, Jul. 6, 2011, vol. 44, pp. 5539-5553, dx.doi.org/10.1021/ma201014n.

Fan et al., "Thermo-responsive self-immolative nanoassemblies: direct and indirect triggering", Chemical Communications, Oct. 6, 2017, vol. 53, No. 89, 43 pgs., 12068-12071, DOI:10.1039/C7CC06410A.

Foster et al., "Irreversibleendo-SelectiveDiels—AlderReactionsofSubstitutedAlkoxyfurans:AGeneralSynthesisofendo-Cantharimides", Chemistry, a European Journal, 2015, vol. 21, pp. 6107-6114, DOI:10.1002/chem.201406286.

Gossweiler et al., "Mechanochemical Activation of Covalent Bonds in Polymers with Full and Repeatable Macroscopic Shape Recovery", ACS Macro Letters, 2014, vol. 3, pp. 216-219, dx.doi.org/10.1021/mz500031q.

Gostl et al., "Controlling covalent connection and disconnection with light", Angew. Chem. International Edition, Aug. 11, 2014, vol. 53, Issue 33, pp. 8784-8787, https://doi.org/10.1002/anie.201310626.

Gostl et al., "π-extended anthracenes as sensitive probes for mechanical stress", Chemical Science, 2016, vol. 7, pp. 370-375, first published Oct. 7, 2015, DOI: 10.1039/c5sc0329/k.

Grady et al., "Shockwave Loading of Mechanochemically Active Polymer Coatings", ACS Applied Materials & Interfaces, vol. 6, No. 8, Mar. 26, 2014, pp. 5350-5355, https://doi.org/10.1021/am406028q.

Groote et al., "Mechanocatalysis: forcing latent catalysts into action", Polymer Chemistry, 2013, vol. 4, pp. 4846-4859, doi: 10.1039/C3PY00071K.

Hay et al., "Substituent effects on the kinetics of reductively-initiated fragmentation of nitrobenzyl carbamates designed as triggers for bioreductive prodrugs", Journal of the Chemical Society Perkin Transactions, Jan. 1999, vol. 119, No. 19, pp. 2759-2770, DOI:10.1039/a904067f.

Heo et al., "Self-Healing Polyurethanes with Shape Recovery", Advanced Function Materials, May 30, 2014, vol. 24, Issue 33, pp. 5261-5268, https://doi.org/10.1002/adfm.201400299.

Hickenboth et al., "Biasing reaction pathways with mechanical force", Nature, Mar. 33, 2007, vol. 446, Issue 7134, pp. 423-427, doi:10.1038/nature05681.

Hu et al., "Mechanically Triggered Release of Functionally Diverse Molecular Payloads from Masked 2-Furylcarbinol Derivatives", ACS Central Science, Jul. 14, 2021, vol. 7, pp. 1216-1224, doi: 10.1021/acscentsci.1c00460.

Hu et al., "Mechanically Triggered Small Molecule Release from a Masked Furfuryl Carbonate", Journal of the American Chemical Society, vol. 141, No. 38, Sep. 25, 2019, published online Sep. 16, 2019, pp. 15018-15023, doi: 10.1021/jacs.9b08663.

Hu et al., "Mechanochemical Regulation of a Photochemical Reaction", Journal of the American Chemical Society, vol. 140, No. 43, Oct. 31, 2018, published online Oct. 19, 2018, pp. 14073-14077, doi: 10.1021/jacs.8b09628.

Huo et al., "Mechanochemical bond scission for the activation of drugs", Nature Chemistry, Feb. 2021, vol. 13, pp. 131-139, first published Jan. 29, 2021, https://doi.org/10.1038/s41557-020-00624-8.

Imato et al., "Mechanophores with a Reversible Radical System and Freezing-Induced Mechanochemistry in Polymer Solutions and Gels", Angew Chem Int Ed Engl., May 18, 2015; vol. 54, Issue 21, pp. 6168-6172, published online Mar. 30, 2015, doi: 10.1002/anie.201412413.

Irie et al., "Blocked photochromism of diarylethenes", Journal of the American Chemical Society, Oct. 1, 1992, vol. 114, No. 22, pp. 8715-8716, https://doi.org/10.1021/ja00048a063.

Irie et al., "Photochromism of Diarylethene Molecules and Crystals: Memories, Switches, and Actuators", Chemical Reviews, Dec. 16, 2014, vol. 114, No. 24, pp. 12174-12277, https://doi.org/10.1021/cr500249p.

Jayathilaka et al., "Force-mediated molecule release from double network hydrogels", Chemical Communications, Sep. 4, 2021, vol. 57, No. 68, pp. 8484-8487, published online Aug. 5, 2021, doi: 10.1039/d1cc02726c.

Kawai et al., "Photochemical pKa-Modulation and Gated Photochromic Properties of a Novel Diarylethene Switch", European Journal of Organic Chemistry, Sep. 1999, vol. 999, Issue 9, pp. 2359-2366, published online Aug. 12, 1999, https://doi.org/10.1002/(SICI)1099-0690(199909) 1999:9<2359::AID-EJOC2359>3.0.CO;2-%23.

Kean et al., "A coumarin dimer probe of mechanochemical scission efficiency in the sonochemical activation of chain-centered mechanophore polymers", Chemical Communications, Apr. 29, 2015, vol. 51, Issue 44, pp. 9157-9160, DOI https://doi.org/10.1039/C5CC01836F.

Kida et al., "The photoregulation of a mechanochemical polymer scission", Nature Communications, 2018, vol. 9, No. 3504, 6 pgs., DOI: 10.1038/s41467-018-05996-7.

Kim et al., "High-intensity focused ultrasound-induced mechanochemical transduction in synthetic elastomers", PNAS, May 21, 2019, vol. 116, No. 21, pp. 10214-10222, published online May 10, 2019, doi: 10.1073/pnas.1901047116.

Klein et al., "Validation of the CoGEF Method as a Predictive Tool for Polymer Mechanochemistry", Journal of the American Chemical Society, vol. 142, No. 38, Sep. 23, 2020, published online Sep. 9, 2020, pp. 16364-16381, doi: 10.1021/jacs.0c06868.

(56) References Cited

OTHER PUBLICATIONS

Kobatake et al., "Acid-induced photochromic system switching of diarylethene derivatives between P- and T-types", Chemical Communications, Feb. 2007, pp. 1698-1700, DOI: 10.1039/b700177k.

Konda et al., "Molecular Catch Bonds and the Anti-Hammond Effect in Polymer Mechanochemistry", Journal of the American Chemical Society, Aug. 2, 2013, vol. 135, No. 34, pp. 12722-12729, https://doi.org/10.1021/ja4051108.

Kryger et al., "Structure-Mechanochemical Activity Relationships for Cyclobutane Mechanophores", Journal of the American Chemical Society, Oct. 27, 2011, vol. 133, No. 46, pp. 18992-18998, https://doi.org/10.1021/ja2086728.

Kuhni et al., "Gated Photochromism of 1,2-Diarylethenes", Organic Letters, Apr. 21, 2007, vol. 9, No. 10, pp. 1919-1922, https://doi.org/10.1021/ol070339r.

Larsen et al., ""Flex-activated" mechanophores: using polymer mechanochemistry to direct bond bending activation", Journal of the American Chemical Society, 3 Jun. 5, 2013, vol. 135, No. 22, pp. 8189-8192, published online May 23, 2013, doi: 10.1021/ja403757p.

X = O, N, or S both in toluene-$d_8$ @ 70 °C both in toluene-$d_8$ @ r.t.

Ð = 1.03–1.06 for all polymers

FIG. 17C

| Polymer | $M_n$ (kg/mol) | $M_p$ (kg/mol) | Đ | Half-Life | Ultimate payload release [b] |
|---|---|---|---|---|---|
| PMA-1(O) | 99.8 | 95.4 | 1.04 | < 5 min | 34% |
| PMA-2(O) | 102 | 103 | 1.05 | < 5 min | 36% |
| PMA-3(O) | 102 | 95.7 | 1.03 | 46 min | 38% |
| PMA-1(NH) | 99.0 | 93.7 | 1.04 | 41 min | 35% |
| PMA-2(NH) | 99.6 | 104 | 1.06 | 6.5 days | 39% |
| PMA-3(NH) | 94.7 | 89.1 | 1.05 | 240 days | 8%[c] |

[a]Polymer solutions (2 mg/mL in 3:1 MeCN/MeOH) were sonicated for 60 min then warmed to room temperature.

[b]Yield of payload (i.e., cargo molecule) release relative to mechanophore concentration estimated from photoluminescence measurements, reported as the average of two trials.

[c]Calculated yield after 30 days post-sonication assuming a mechanophore activation of 36%.

FIG. 20B

| Cargo | $M_n$ (kg/mol) | $M_p$ (kg/mol) | Đ | Half-Life | Ultimate payload release[c] |
|---|---|---|---|---|---|
| (hydroxycoumarin) | 99.8 | 95.4 | 1.04 | < 5 min[b] | 36% |
| (aminocoumarin) | 99.0 | 93.7 | 1.04 | 41 min[b] | 34% |
| (pyrene ester, n=4) | 99.2 | 96.1 | 1.11 | < 30 min | 33% |
| (pyrene amide) | 106 | 96.1 | 1.14 | 4.2 h | 8% |
| (pyrene ester, n=3) | 114 | 110 | 1.10 | 28 h | 41% |
| (naphthalenesulfonate) | 108 | 108 | 1.02 | < 30 min | 41% |

Polymer solutions (2 mg/mL in 3:1 MeCN/MeOH) were sonicated for 60 min then warmed to room temperature and immediately monitored by photoluminescence spectroscopy or HPLC.

[b]Half-lives for the release of hydroxycoumarin and aminocoumarin from photoluminescence measurements, with all others calculated using HPLC.

[c]Yield of payload (cargo) release relative to mechanophore concentration calculated from HPLC measurements, wherein half-lives and payload release are reported as the average of two trials.

METHOD FOR CONTROLLED RELEASE USING MECHANICAL FORCE

CROSS-REFERENCE TO RELATED APPLICATIONS

The present application claims priority under 35 U.S.C. 119(e) to U.S. Provisional Application No. 63/075,666 filed Sep. 8, 2020, and U.S. Provisional Application No. 63/171,889 filed Apr. 7, 2021, the disclosures of which are incorporated herein by reference in their entireties.

FIELD OF THE INVENTION

The current disclosure is directed to a general and modular mechanophore platform for a cargo molecule release via a mechanically triggered cascade reaction, and methods for the synthesis and use thereof.

BACKGROUND OF THE INVENTION

Mechanical to chemical transduction is a powerful strategy for achieving materials with stimuli-responsive properties. The emerging field of polymer mechanochemistry aims to harness mechanical forces in polymers to promote productive chemical transformations in stress-responsive molecules known as mechanophores (see, for example: Beyer, M. K.; et al. Mechanochemistry: The Mechanical Activation of Covalent Bonds. Chem. Rev. 2005, 105, 2921-2948; Caruso, M. M.; et al. Mechanically-Induced Chemical Changes in Polymeric Materials. Chem. Rev. 2009, 109, 5755-5798; and Li, J.; et al. Polymer Mechanochemistry: From Destructive to Productive. Acc. Chem. Res. 2015, 48, 2181-2190; the disclosures of which are incorporated herein by reference). In such molecular systems, mechanical force is delivered to the mechanophores through covalently attached polymer chains using a variety of techniques, including solution-phase ultrasonication (see, for example: Berkowski, K. L.; et al. Ultrasound-Induced Site-Specific Cleavage of Azo-Functionalized Poly(ethylene glycol). Macromolecules 2005, 38, 8975-8978, the disclosure of which is incorporated herein by reference), tension or compression in solid materials (for example: Gossweiler, G. R.; et al. Mechanochemical Activation of Cova-lent Bonds in Polymers with Full and Repeatable Macroscopic Shape Recovery. ACS Macro Lett. 2014, 3, 216-219, the disclosure of which is incorporated herein by reference), atomic force microscopy (for example: Wu, D.; et al. Molecular Stress Relief through a Force-Induced Irreversible Extension in Polymer Contour Length. J. Am. Chem. Soc. 2010, 132, 15936-15938; and Sulkanen, A. R.; et al. Spatially Selective and Density-Controlled Activation of Interfacial Mechanophores. J. Am. Chem. Soc. 2019, 141, 4080-4085, the disclosures of which are incorporated herein by reference), laser-induced stress waves (for example: Grady, M. E.; et al. Shockwave Loading of Mechanochemically Active Polymer Coatings. ACS Appl. Mater. Interfaces 2014, 6, 5350-5355; and Sung, J.; et al. Interfacial Mechanophore Activation Using Laser-Induced Stress Waves. J. Am. Chem. Soc. 2018, 140, 5000-5003, the disclosures of which are incorporated herein by reference), and high intensity focused ultrasound (for example: Kim, G.; et al. High-intensity focused ultrasound-induced mechanochemical transduction in synthetic elastomers. Proc. Natl. Acad. Sci. 2019, 116, 10214, the disclosure of which is incorporated herein by reference). Mechanically coupled chemical activation has been demonstrated for a variety of covalent bond transformations to engender a wide range of functional responses, including changes in color or fluorescence (see, for example: Davis, D. A.; et al. Force-induced activation of covalent bonds in mechanoresponsive polymeric materials. Nature 2009, 459, 68-72; Imato, K.; et al. Mechanophores with a Reversible Radical System and Freezing-Induced Mechanochemistry in Polymer Solutions and Gels. Angew. Chem. Int. Ed. 2015, 54, 6168-6172; Wang, Z.; et al. A Novel Mechanochromic and Photochromic Polymer Film: When Rhodamine Joins Polyurethane. Adv. Mater. 2015, 27, 6469-6474; Göstl, R.; Sijbesma, R. P. π-extended anthracenes as sensitive probes for mechanical stress. Chem Sci 2016, 7, 370-375; Robb, M. J.; et al. Regioisomer-Specific Mechanochromism of Naphthopyran in Polymeric Materials. J. Am. Chem. Soc. 2016, 138, 12328-12331; and McFadden, M. E.; Robb, M. J. Force-Dependent Multicolor Mechanochromism from a Single Mechanophore. J. Am. Chem. Soc. 2019, 141, 11388-11392, the disclosures of which are incorporated herein by reference), chemiluminescence (for example: Chen, Y.; et al. Mechanically induced chemiluminescence from polymers incorporating a 1,2-dioxetane unit in the main chain. Nat. Chem. 2012, 4, 559, the disclosure of which is incorporated herein by reference), switching of electrical conductivity (for example: Chen, Z.; et al. Mechano-chemical unzipping of insulating polyladderene to semiconducting polyacetylene. Science 2017, 357, 475; and Yang, J.; et al. Benzoladderene Mechanophores: Synthesis, Polymerization, and Mechanochemical Transformation. J. Am. Chem. Soc. 2019, 141, 6479-6483, the disclosures of which are incorporated herein by reference), activation of catalysts (for example: Piermattei, A.; et al. Activating catalysts with mechanical force. Nat. Chem. 2009, 1, 133; and Michael, P.; Binder, W. H. A Mechanochemically Triggered "Click" Catalyst. Angew. Chem. Int. Ed. 2015, 13918-13922, the disclosures of which are incorporated herein by reference), and generation of reactive functional groups (for example: Hickenboth, C. R.; et al. Biasing reaction pathways with mechanical force. Nature 2007, 446, 423-427; Ramirez, A. L. B.; et al. Mechanochemical strengthening of a synthetic polymer in response to typically destructive shear forces. Nat. Chem. 2013, 5, 757-761; Robb, M. J.; Moore, J. S. A Retro-Staudinger Cycloaddition: Mechanochemical Cycloelimination of a β-Lactam Mechanophore. J. Am. Chem. Soc. 2015, 137, 10946-10949; Wang, J.; et al. Mechanochemical Strengthening of a Multimechanophore Benzocyclobutene Polymer. ACS Macro Lett. 2015, 4, 834-837; and Zhang, H.; et al. Mechanochromism and Mechanical-Force-Triggered Cross-Linking from a Single Reactive Moiety Incorporated into Polymer Chains. Angew. Chem. Int. Ed. 2016, 55, 3040-3044, the disclosures of which are incorporated herein by reference). Accordingly, continued advancement of this field is highly desirable, as new mechanophore discoveries and development will further expand the repertoire of mechanochemical function and will enable novel applications in organic materials.

SUMMARY OF THE INVENTION

Various embodiments are directed to a mechanophore platform including:
a mechanophore including
a Diels-Alder adduct of a furan and a dienophile, wherein
the furan is a 2-furylcarbinol derivative including a 2-furylcarbinol scaffold according to:

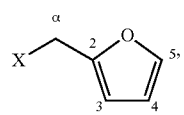

wherein X=O, N, or S;
such that the furan is characterized by an ability to decompose via cleavage of the α-C—X bond, and
a cargo molecule covalently attached to the furan, such that the cargo molecule detaches from the furan upon the furan's decomposition; wherein
the mechanophore is characterized by an ability to undergo a retro-[4+2] cycloaddition reaction upon application of a mechanical force to re-produce the furan and the dienophile; and wherein
the mechanophore is embedded into a polymer, such that at least one chain of the polymer is covalently attached to the furan, and at least one additional chain of the polymer is covalently attached to the dienophile.

In various such embodiments, the furan includes at least one substituent at a position of the 2-furylcarbinol scaffold selected from a group consisting of: α-position, 3-position, 4-position, 5-position, and any combination thereof.

In still various such embodiments, the at least one substituent is an electron-donating functional group.

In yet various such embodiments, the at least one substituent is at at least one position selected from a group consisting of: 3-position, 4-position, 5-position, α-position, and any combination thereof; and wherein the at least one substituent is, each, independently selected from a group consisting of: alkyl, alkenyl, aryl, heteroaryl, any other aromatic or heteroaromatic functional group, alkoxy, aryloxy, amine, sulfide, any other heteroatom-containing group, including silane, a polymer chain of any composition, and any combination thereof.

In still yet various such embodiments, the at least one substituent comprises one of the combinations selected from a group consisting of: α-alkyl and the polymer at 5-position; 3-aryloxy and the polymer at 5-position; 5-aryloxy; α-alkyl, 3-aryloxy, and the polymer at 5-position; α-alkyl and 5-aryloxy; α-alkyl, 3-aryloxy, and 5-aryloxy; 3-aryloxy and 5-aryloxy; α-aryl and the polymer at the 5-position.

In various such embodiments, the dienophile is maleimide.

In still various such embodiments, upon release from the mechanophore platform, the cargo molecule displays a functionality selected from a group consisting of alkyl alcohol, aryl alcohol, alkyl amine, aryl amine, carboxylic acid, and sulfonic acid.

In yet various such embodiments, the polymer includes a polymeric network of chains.

In various such embodiments, the polymer includes a surface instead of the at least one chain of the polymer covalently attached to the furan, or instead of the at least one additional chain of the polymer covalently attached to the dienophile, such that either the furan or the dienophile is immobilized on the surface.

In still various such embodiments, the polymer is selected from a group consisting of: polyacrylate, including poly(methyl acrylate); polymethacrylate, including poly(methyl methacrylate); polysiloxane, including polydimethylsiloxane; polyether, including poly(ethylene glycol); polyurethane; polyacrylamide; polyamide; polyester; and any combination thereof.

Various other embodiments are directed to a method for mechanochemically-gating release of molecular cargo including:
a mechanophore platform including:
a mechanophore including
a Diels-Alder adduct of a furan and a dienophile, wherein
the furan is a 2-furylcarbinol derivative comprising a 2-furylcarbinol scaffold according to:

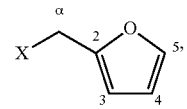

wherein X=O, N, or S;
such that the furan is characterized by an ability to decompose via cleavage of the α-C—X bond, and
a cargo molecule covalently attached to the furan, such that the cargo molecule detaches from the furan upon the furan's decomposition; wherein
the mechanophore is characterized by an ability to undergo a retro-[4+2] cycloaddition reaction upon application of a mechanical force to re-produce the furan and the dienophile; and wherein
the mechanophore is embedded into a polymer, such that at least one chain of the polymer is covalently attached to the furan, and at least one additional chain of the polymer is covalently attached to the dienophile; and
applying a mechanical force to the mechanophore platform for a period of time, such that the polymer transduces the mechanical force to the mechanophore platform and activates the mechanophore platform to reveal the furan, such that the furan further decomposes to release the cargo molecule.

In various such embodiments, the furan includes at least one substituent at a position of the 2-furylcarbinol scaffold selected from a group consisting of: α-position, 3-position, 4-position, 5-position, and any combination thereof.

In still various such embodiments, the at least one substituent is an electron-donating functional group.

In yet various such embodiments, the at least one substituent is at at least one position selected from a group consisting of: 3-position, 4-position, 5-position, α-position, and any combination thereof; and wherein the at least one substituent is, each, independently selected from a group consisting of: alkyl, alkenyl, aryl, heteroaryl, any other aromatic or heteroaromatic functional group, alkoxy, aryloxy, amine, sulfide, any other heteroatom-containing group, including silane, a polymer chain of any composition, and any combination thereof.

In yet still various such embodiments, the at least one substituent comprises one of the combinations selected from a group consisting of: α-alkyl and the polymer at 5-position; 3-aryloxy and the polymer at 5-position; 5-aryloxy; α-alkyl, 3-aryloxy, and the polymer at 5-position; α-alkyl and 5-aryloxy; α-alkyl, 3-aryloxy, and 5-aryloxy; 3-aryloxy and 5-aryloxy; α-aryl and the polymer at the 5-position.

In still various such embodiments, the dienophile is maleimide.

In yet still various such embodiments, upon release from the mechanophore platform, the cargo molecule displays a functionality selected from a group consisting of: alkyl alcohol, aryl alcohol, alkyl amine, aryl amine, carboxylic acid, and sulfonic acid.

In yet various such embodiments, the polymer includes a polymeric network of chains.

In still various such embodiments, the polymer includes a surface instead of the at least one chain of the polymer covalently attached to the furan, or instead of the at least one additional chain of the polymer covalently attached to the dienophile, such that either the furan or the dienophile is immobilized on the surface.

In various such embodiments, the polymer is selected from a group consisting of: polyacrylate, including poly(methyl acrylate); polymethacrylate, including poly(methyl methacrylate); polysiloxane, including polydimethylsiloxane; polyether, including poly(ethylene glycol); polyurethane; polyacrylamide; polyamide; polyester; and any combination thereof.

In still various such embodiments, applying the mechanical force includes deforming the polymer.

In yet still various such embodiments, deforming the polymer is a method selected from a group consisting of: application of tension, compression, shearing, stretching, grinding, and any combination thereof.

In yet various such embodiments, applying the mechanical force is using ultrasound.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein:

FIGS. 2B and 2C illustrate density functional theory (DFT) calculations for various processes affecting decomposition of the mechanophore platform, wherein FIG. 2B illustrates calculations of activation energies for the carbonate fragmentation from a series of variously substituted furfuryl carbonates at the M06-2X/6-311+G** level of theory; and FIG. 2C illustrates calculations for the process of mechanical elongation of a furan-maleimide Diels-Alder adduct using the constrained geometries simulate external force (CoGEF) method at the B3LYP/6-31G* level of theory; and FIG. 2D provides additional examples of variously substituted furfuryl carbonates and their half-lives for decomposition at room temperature, in accordance with embodiments of the invention.

FIG. 3B provides $^1$H NMR spectra (3:1 MeCN-$d_3$:MeOH) demonstrating the clean conversion of 1 to products ([1]$_0$=12 mM) over time; FIG. 3C provides photoluminescence spectra ([1]$_0$=6.1 μM in 3:1 MeCN:MeOH, $\lambda_{ex}$=330 nm) monitoring the generation of 2 over time; FIG. 3D provides quantification of data presented in FIGS. 3B and 3C, illustrating the time-dependent conversion of 1 and the generation of 2 as measured by NMR and fluorescence spectroscopy, respectively; and FIG. 3E provides $^1$H NMR spectra collected for a 27 μM solution of 1 in acetonitrile-$d_3$ upon addition of water (25% by volume) at room temperature over time, thus illustrating enhancing effect of water on decomposition of 1, wherein addition of water results in clean conversion of 1 to furfuryl alcohol 11 and 2 with the estimated half-life of the reaction of approximately 8 min, in accordance with embodiments of the invention.

FIG. 8B provides partial $^1$H NMR spectra (400

MHz, CDCl$_3$) demonstrating the clean conversion of 21 to products ([21]$_0$=19 μM); FIG. 8C shows time course experiments following the conversion of 21 and 22 by NMR spectroscopy (in 3:1 MeCN-d$_3$/MeOH; [21]$_0$=14 mM; [22]$_0$=14 mM), and generation of 23 by photoluminescence spectroscopy (3:1 MeCN/MeOH; $\lambda_{ex}$=365 nm; $\lambda_{em}$=424 nm; [21]$_0$, [22]$_0$=7.6 μM); FIG. 8D schematically illustrates the chemistry of the expected decomposition of 22; FIG. 8E provides partial $^1$H NMR spectra (400 MHz) collected for a 19.6 mM solution of 22 in MeCN-d$_3$:MeOH (3:1) at room temperature over time, which show approximately 40% conversion observed after 134 days; and FIG. 8F provides fluorescence emission spectra for a solution of 22 in 3:1 MeCN:MeOH (7.6 mM) at room temperature, wherein the expected PL intensity from a 7.6 mM solution of 23 is approximately 4.09×10$^4$ based on the calibration curve ($\lambda_{ex}$=365 nm), in accordance with embodiments of the invention.

FIGS. 10A through 10C illustrate thermal stability studies of Diels-Alder adduct (±)-33, comprising the furan moiety comprising 5-aryloxy substituent, conducted in toluene-d$_8$ (7.7 mM), wherein FIG. 10A shows the studied chemical reaction; FIG. 10B provides partial $^1$H NMR spectra (500 MHz) taken at various indicated time periods for (±)-33 at 70° C., which show that (±)-33 undergoes retro-Diels-Alder reaction upon heating at 70° C. with a conversion of approximately 10% after 5 h and 35% after 21 h; and wherein the $^1$H NMR spectrum of the maleimide fragment in toluene-d$_8$ is also provided for reference; while FIG. 10C provides partial $^1$H NMR spectra of (±)-33 after being kept at room temperature for the indicated amount of time, which show that the retro-Diels-Alder conversion of (±)-33 is negligible at this temperature, in accordance with embodiments of the invention.

FIG. 11A through 11C provides data and schemes obtained from the experiments following the room temperature decomposition of furfuryl carbamate 35, comprising 5-OAr (i.e., 5-position aryloxy) substituent, in acetonitrile/methanol (3:1 v/v), wherein FIG. 11A illustrates time course experiments following: 1) (left) the conversion of model compound 35 by $^1$H NMR spectroscopy (3:1 acetonitrile-d$_3$/methanol; [35]$_0$=21 mM); and 2) (right) the generation of aminocoumarin by photoluminescence spectroscopy (3:1 acetonitrile/methanol; $\lambda_{ex}$=365 nm; $\lambda_{em}$=424 nm; [35]$_0$=7.0 μM); wherein the concentration of aminocoumarin from PL spectroscopy was calculated based on a standard calibration curve; and wherein fitting the curves to a first-order rate expression (dashed grey lines) gives half-lives for consumption of 35 (NMR) and generation of aminocoumarin (PL) of $t_{1/2}$=9.3 and 10.8 h, respectively; FIG. 11B provides a scheme illustrating a possible mechanism for the generation of the observed decomposition products; and FIG. 11C provides data from the product analysis of the decomposition of 35 in 3:1 acetonitrile-d$_3$/methanol ([35]$_0$=7.0 μM), wherein the top portion of the figure shows the preparatory-HPLC trace of the reaction mixture after 3 days, as monitored at 285 nm with HPLC conditions: 80% acetonitrile in water, 8 mL/min., while the bottom portion of the figure shows $^1$H NMR spectra (500 MHz, CDCl$_3$) collected for the fractions isolated after HPLC separation, wherein: fraction (i) corresponds to the HPLC chromatogram retention times of 1.0-1.5 min, and appears to comprise aminocoumarin as the major product, as further supported by LCMS measurements, wherein the mass of the analyte (m/z=176.1 amu) matches the calculated m/z for 7-amino-4-methylcoumarin, $[C_{10}H_{10}NO_2]^+$ (M+H)+(176.1); fraction (ii) corresponds to the HPLC peak at 1.7 min, identified as a tyrosol alkyl ester derivative, as further supported by LCMS measurements, wherein the mass of the analyte (m/z=309.0 amu) matches the calculated m/z for 4-hydroxyphenethyl 2-bromo-2-methylpropanoate, $[C_{12}H_{15}BrO_3Na]^+$ (M+Na)$^+$ (309.0); and fraction (iii) corresponds to the HPLC peak at 3.0 min, representing a mixture of products that was not identified, in accordance with embodiments of the invention.

FIG. 16B provides fluorescence spectra for PMA-1 and PMA-control before and after ultrasonication for 150 min, wherein the inset shows photographs of sonicated solutions excited with 365 nm UV light after 6× dilution and addition of 5% water, and wherein photoluminescence data were acquired after ~20 h at rt to allow for complete decomposition of the mechanochemically generated furfuryl carbonate; FIG. 16C provides gel permeation chromatography (GPC) traces as a function of ultrasonication time for PMA-1 monitored with a refractive index (RI) detector, and shows that ultrasound-induced mechanochemical activation causes chain scission near the polymer's midpoint, resulting in attenuation of the initial polymer peak (Mp=101 kg/mol) and an increase in a new peak (Mp=55 kg/mol) at approximately one-half the original molecular weight; and FIG. 16D. provides (on the left) fluorescence spectra for a 2.0 mg/mL solution of PMA-1 in 3:1 acetonitrile/methanol (v/v) before ultrasonication (dotted line), immediately after 150 min ultrasonication at 0° C. (dashed line), and after 150 min ultrasonication followed by incubation at room temperature for 20 h (solid line), and (on the right) concentrations of 2 released from PMA-1 measured by fluorescence spectroscopy as a function of ultrasonication time, wherein aliquots were removed from the sonicated solution and immediately measured, and then subsequently remeasured after being kept at room temperature for 20 h to allow complete decomposition of the mechanically generated furfuryl carbonate—all in accordance with embodiments of the invention.

FIGS. 17A through 17C compare mechanically triggered cargo molecule release from the mechanophore platforms comprising differently substituted furan moiety, wherein FIG. 17A provides data for hydroxycoumarin release and FIG. 17B provides data for aminocoumarin release from the corresponding mechanophore platforms, and wherein each solutions comprising a mechanophore platform (2 mg/mL in 3:1 MeCN/MeOH) was sonicated for 60 min, warmed to room temperature, and the release of coumarin cargo from the mechanically liberated 2-furylcarbinol derivatives was monitored by photoluminescence spectroscopy, wherein PL parameters were: $\lambda_{ex}$=330 nm, $\lambda_{em}$=378 nm (hydroxycoumarin); $\lambda_{ex}$=365 nm, $\lambda_{em}$=424 nm (aminocoumarin); and wherein the initial PL intensity was subtracted from each measurement and the data were normalized to the plateau value; with, the data for PMA-3(N) being normalized assuming 36% mechanophore activation, wherein the dashed line represents a first-order reaction with a half-life of 240 days; while FIG. 17C provides a table summarizing the characterization data from FIGS. 17A and 17B, in accordance with embodiments of the invention.

FIGS. 20A through 20C illustrate the scope of the cargo molecules that can be released from the mechanophore platform comprising the α-methyl and 3-phenoxy substituted furan moiety; wherein FIGS. 20A and 20B provide characterizations of the ultrasound-induced release kinetics for such cargo molecules; while FIG. 20C provides the same data for the mechanochemically inert analogs prepared as controls, in accordance with embodiments of the invention.

DETAILED DISCLOSURE

Figure 1A:
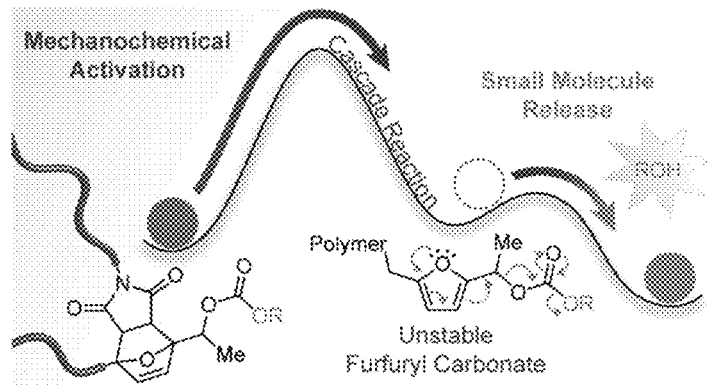
FIGS. 1A through 1C schematically illustrate various aspects of the mechanically triggered reaction cascade resulting in release of a covalently pre-installed cargo molecule from the designer mechanophore platform, in accordance with embodiments of the invention.

The embodiments of the invention described herein are not intended to be exhaustive or to limit the invention to precise forms disclosed. Rather, the embodiments selected for description have been chosen to enable one skilled in the art to practice the invention.

Turning to the drawings, schemes, and data, embodiments of a modular molecular mechanophore platform for small molecule cargo release via a mechanically triggered cascade reaction are provided. In many embodiments, the mechanophore platform comprises a furan-dienophile Diels-Alder adduct and a cargo molecule covalently attached to the furan moiety of the Diels-Alder adduct, wherein the Diels-Alder adduct is flanked by polymeric chains or otherwise embedded into a polymeric network. In many embodiments, the furan moiety is a 2-furylcarbinol derivative, wherein the 2-furylcarbinol derivative is prone to decomposition via, presumably, although not to be bound by any theory, the corresponding transient furfuryl cation intermediate. Accordingly, in many such embodiments, mechanochemical activation of the mechanophore platform reveals the latent and unstable furan moiety via the retro Diels-Alder reaction, wherein the furan moiety, subsequently, decomposes, such as to release the cargo molecule. More specifically, in many embodiments, application of mechanical force to the mechanophore platform mechanochemically generates (i.e., unmasks) the furan moiety of the platform's Diels-Alder adduct and, thus, enables the decomposition of the platform with release of its cargo molecule. In many embodiments, various judicious substitutions of the furan moiety's 2-furylcarbinol scaffold and the cargo molecule attachment to the furan moiety allow to control the cargo molecule's release kinetics. In many such embodiments, the cargo molecule release from the mechanophore platform proceeds quickly under mild conditions, such as, for example, room temperature. In many embodiments, mechanical force alone is responsible for the "unlocking" of the unstable furan moiety of the mechanophore platform, wherein the mechanophore platform is otherwise chemically stable under similar chemical and physical conditions in absence of any mechanical stress. In many embodiments, the mechanical activation of the mechanophore platform is induced using ultrasound. In many embodiments, the functional scope of the cargo molecules that can be released from the mechanophore platform is highly general and broad. In many embodiments, the functionality of the released cargo molecules includes (but is not limited to): alkyl and aryl alcohols, alkyl and aryl amines, carboxylic and sulfonic acids. In some embodiments, the cargo molecule is a fluorogenic molecule, such as, for example, a coumarin derivative, wherein its release from the mechanophore platform allows for the facile tracking and quantification. In many embodiments, the mechanophore platform of the instant disclosure is useful in facilitating applications including, but not limited to: the mechanically triggered release of functional molecules in drug delivery, stress sensing, depolymerization, catalysis, self-healing materials, and other applications.

Polymers that release functional molecules in response to a specific stimulus, are desirable for a variety of applications including catalysis, sensing, self-healing materials, and drug delivery (see, for example: Swager, T. M. Sensor Technologies Empowered by Materials and Molecular Innovations. Angew. Chem. Int. Ed. 2018, 57, 4248-4257; Roth, M. E.; et al. Dendritic, Oligomeric, and Polymeric Self-Immolative Molecular Amplification. Chem. Rev. 2016, 116, 1309-1352; White, S. R.; et al. Autonomic healing of polymer composites. Nature 2001, 409, 794-797; and Patrick, J. F.; et al. Polymers with autonomous life-cycle control. Nature 2016, 540, 363-370, the disclosures of which are incorporated herein by reference). In this context, mechanically triggered release is particularly appealing, and, as such, several different approaches have been demonstrated, including physically entrapping payloads within a polymeric matrix (for example, Lee, K. Y.; et al. Controlled Drug Delivery from Polymers by Mechanical Signals. Adv. Mater. 2001, 13, 837-839, the disclosure of which is incorporated herein by reference), and the use of fluid-filled microcapsules or vascular networks (see Toohey, K. S.; et al. Self-healing materials with microvascular networks. Nat. Mater. 2007, 6, 581-585, the disclosure of which is incorporated herein by reference) embedded within a material that release their payload after being ruptured. Furthermore, the use of mechanical force as an external stimulus to drive covalent chemical transformations leading to a payload release has also emerged as an attractive strategy. In these recent developments, force is typically transduced via polymer chains attached to mechanically sensitive molecules (i.e., mechanophores) that respond in a chemoselective fashion, resulting in a productive chemical reaction. Such platforms could be useful, for example, in drug delivery applications, wherein, in the context of such applications, the activating force can be applied via ultrasound, which, in turn, is capable of penetrating deep within biological tissues to stimulate mechanochemical transformations noninvasively and with spatial and temporal precision (as described, for example in Kim, G.; et al. High-intensity focused ultrasound-induced mechanochemical transduction in synthetic elastomers. Proc. Natl. Acad. Sci. USA 2019, 116, 10214-10222, the disclosure of which is incorporated herein by reference). In light of these advantages, the field of polymer mechanochemistry has attracted significant interest for the design of autonomous materials that respond innately and specifically to mechanically dynamic environments, as well as abundant opportunities to advance fundamental understanding of mechanochemical reactivity, which is underdeveloped compared to other areas of organic chemistry (see, for example, Akbulatov, S.; Boulatov, R. Critical review of experimental polymer mechanochemistry and its interpretational frameworks. ChemPhysChem 2017, 18, 1422-1450, the disclosure of which is incorporated herein by reference).

Accordingly, several mechanophores have been designed to achieve mechanically triggered release of functional organic molecules. For example, molecular release from mechanophores has been achieved via mechanically triggered cycloreversion (for additional examples, see P. B. Jayathilaka, et al., Chem. Commun., 2021, DOI: 10.1039/D1CC02726C, the disclosure of which is incorporated herein by reference), rearrangement (for examples, see: Diesendruck, C. E.; et al. Proton-Coupled Mechanochemical Transduction: A Mechanogenerated Acid. J. Am. Chem. Soc. 2012, 134, 12446-12449; and Lin, Y.; et al. A Latent Mechanoacid for Time-Stamped Mechanochromism and Chemical Signaling in Polymeric Materials. J. Am. Chem. Soc. 2020, 142, 99-103, the disclosures of which are incorporated herein by reference), and various other cascade reactions (for examples, see: Z. Shi, et al., J. Am. Chem. Soc., 2020, 142, 14725-14732; Z. Shi, et al., Chem. Sci., 2021, 12, 1668-1674; S. Huo, et al., Nat. Chem., 2021, 13, 131-139; and Z. Shi, et al., CCS Chem., 2021, 2333-2344, the disclosures of which are incorporated herein by reference). However, the scope of molecules (payload) that can be released from the mechanophores reported to date is still relatively limited. For example, Moore and Craig have designed mechanophores based on gem-dichlorocyclopropane motifs that undergo mechanochemical rearrangement reactions with subsequent release of HCl. In addition, Boydston developed an oxanorbornadiene mechanophore that releases a benzyl furfuryl ether molecule via a mechanically induced cycloelimination reaction (Larsen, M. B.; Boydston, A. J. "Flex-Activated" Mechanophores: Using Polymer Mechanochemistry To Direct Bond Bending Activation. J. Am. Chem. Soc. 2013, 135, 8189-8192; and Larsen, M. B.; Boydston, A. J. Successive Mechanochemical Activation and Small Molecule Release in an Elastomeric Material. J. Am. Chem. Soc. 2014, 136, 1276-1279, the disclosures of which are incorporated herein by reference). Moreover, metal ion release from the mechanical dissociation of ferrocene was also recently demonstrated (see Di Giannantonio, M.; et al. Triggered Metal Ion Release and Oxidation: Ferrocene as a Mechanophore in Polymers. Angew. Chem. Int. Ed. 2018, 57, 11445-11450; and Sha, Y.; et al. Quantitative and Mechanistic Mechanochemistry in Ferrocene Dissociation. ACS Macro Lett. 2018, 7, 1174-1179, the disclosures of which are incorporated herein by reference). Nevertheless, each of these approaches uses a judiciously designed mechanophore to release a very specific compound upon mechanical activation, which, consequently, limits the scope of molecules that can be released. As another example, small molecule release has also been achieved through the mechanically triggered heterolytic scission and subsequent depolymerization of a unique metastable cyclic poly(ortho-phthalaldehyde) polymer to regenerate its constituent monomers (Diesendruck, C. E.; et al. Mechanically triggered heterolytic unzipping of a low-ceiling-temperature polymer. Nat. Chem. 2014, 6, 623-628; and Peterson, G. I.; Boydston, A. J. Kinetic Analysis of Mechanochemical Chain Scission of Linear Poly(phthalaldehyde). Macromol. Rapid Commun. 2014, 35, 1611-1614, the disclosures of which are incorporated herein by reference). In addition, most recently, Herrmann and Göstl have introduced a mechanophore design that relies on mechanochemical scission of a chain-centered disulfide unit and ensuing 5-exo-trig cyclization to release an alcohol attached via a β-carbonate linker. However, while the release of several different alcohols has been demonstrated using this disulfide mechanophore platform, it is susceptible to nonspecific activation via chemical reduction or thiol exchange and cargo scope is relatively limited (as explained by Shi, Z., et al. in The Mechanochemical Release of Naphthalimide Fluorophores from β-Carbonate and β-Carbamate Disulfide-Centered Polymers, *CCS Chemistry* 2021, https://doi.org/10.31635/ccschem.021.202101147, the disclosure of which is incorporated herein by reference). Therefore, more modular and generalized mechanophore designs for the triggered release of functional organic molecules are needed to enable new opportunities for polymer mechanochemistry.

The concept of mechanically gated reactivity (see, for example, Wang, J.; et al. Mechanical gating of a mechanochemical reaction cascade. Nat. Commun. 2016, 7, 13433, the disclosure of which is incorporated herein by reference), wherein, for example, a cascade reaction is initiated by an external stimulus, such as, for example, mechanical stress, offer a unique and particularly useful approach for controlling molecular release, because, in such strategies, the mechanochemical reaction is generally decoupled from the ultimate functional response For example, externally triggered cascade reactions include retro-Diels-Alder reactions that serve as thermal triggers for, for example, the depolymerization of self-immolative polymers. In other examples, Boydston and coworkers reported a 1,2-oxazine linker (Peterson, G. I.; et al. 1,2-oxazine linker as a thermal trigger for self-immolative polymers. Polymer 2014, 55, 5980-5985, the disclosure of which is incorporated herein by reference), while Gillies and coworkers reported a furan-maleimide adduct—both capable of initiating a depolymerization cascade reaction at elevated temperatures (Fan, B.; et al. Thermo-responsive self-immolative nanoassemblies: direct and indirect triggering. Chem. Commun. 2017, 53, 12068-12071, the disclosure of which is incorporated herein by reference). The latter example invoked the thermal instability of a furfuryl carbonate, similar to the decomposition of furfuryl bromide that was first described by Zanetti and Bashour (Zanetti, J. E.; Bashour, J. T. α-Furfuryl Bromide (2-Bromomethylfuran). J. Am. Chem. Soc. 1939, 61, 2249-2251, the disclosure of which is incorporated herein by reference). As a more specific example of an external stimulus-gated reactivity, Branda and coworkers designed a photo-gated system, wherein a diarylethene photoswitch allowed for electronic conjugation between a remote electron donating group and a labile carbonate group to be modulated with light, resulting in fragmentation of the carbonate upon photochemical electrocyclization (Warford, C. C.; et al. From slow to fast—the user controls the rate of the release of molecules from masked forms using a photoswitch and different types of light. Chem. Commun. 2015, 51, 7039-7042, the disclosure of which is incorporated herein by reference). Moreover, the concept of mechanochemical gating to regulate a photochemical transformation, in which a mechanically facilitated retro-Diels-Alder reaction unmasked a diarylethene photoswitch, was also recently extended (see, for example: Hu, X.; et al. Mechano-chemical Regulation of a Photochemical Reaction. J. Am. Chem. Soc. 2018, 140, 14073-14077, and U.S. patent application Ser. No. 17/019,107, the disclosures of which are incorporated herein by reference). Overall, the mechanochemical gating paradigm offers a powerful approach for the design of highly modular platforms for release of functionally diverse molecular cargo, as the mechanochemical behavior of the mechanophore and the functional properties of the masked intermediate can be controlled independently.

Figure 1B:
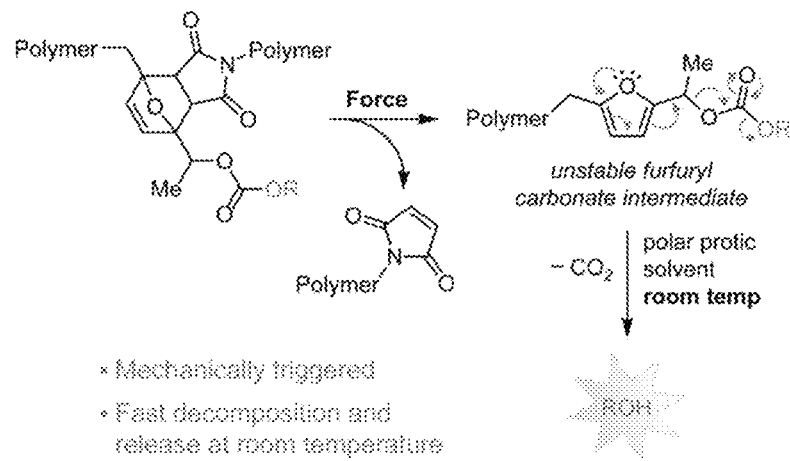
Figure 1C:
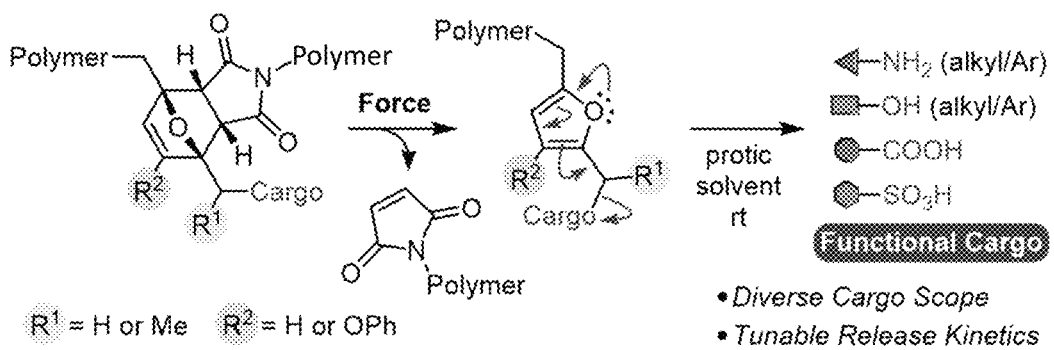

This application is directed to embodiments of a modular mechanophore platform for release of a cargo molecule, and methods of synthesis and use thereof. In particular, the application is directed to embodiments of the macromolecular mechanophore platform comprising a furan-dienophile Diels-Alder adduct, wherein the furan moiety is a 2-furylcarbinol derivative covalently pre-loaded with a cargo molecule of choice, and wherein the Diels-Alder adduct is embedded into a polymeric chain or another polymeric network, such that it undergoes the retro [4+2]cycloaddition reaction under mechanical force to reveal the unstable, cargo molecule-carrying furan moiety. In many such embodiments, the furan moiety is a 2-furylcarbinol derivative prone to decomposition via the corresponding furfuryl cation resulting in scission of the α-C-heteroatom bond. In many such embodiments the furan moiety's 2-furylcarbinol scaffold is judiciously designed to spontaneously and quickly (or slowly, if desired) decompose, such as to release the cargo molecule. More specifically, in many embodiments, the 2-furylcarbinol scaffold of the furan moiety is substituted according to the guidelines provided in the instant disclosure to control (e.g., promote or impede) the furan moiety's decomposition and cargo molecule release kinetics. In many such embodiments, judiciously chosen substituents installed at positions: α-, 3-, and 5- of the 2-furylcarbinol scaffold, or any combination thereof, or substituents installed at other positions of the 2-furylcarbinol scaffold, promote the decomposition of the mechanophore platform and the release of the cargo molecule under mild conditions, such as for example, at room temperature, upon the mechanically triggered reaction cascade. Accordingly, in many embodiments, some of which are illustrated in FIGS. 1A-1C, mechanochemical activation of the otherwise stable mechanophore platform of the instant disclosure results in the retro-Diels-Alder reaction, revealing a metastable designer furan, wherein the furan quickly decomposes to release the mechanophore platform's cargo molecule. In many embodiments, depending on the substitution design chosen for the furan moiety and the functionality of the cargo molecule, the complete decomposition of the mechanophore platforms and the release of the cargo molecule proceeds spontaneously and quickly under mild conditions, upon the prerequisite mechanochemical cycloelimination reaction. However, in some embodiments, wherein a slower cargo molecules release profile is preferred, the furan moiety's functionalization and substitution is adjusted accordingly. In many embodiments, the functionality scope of the cargo molecules that can be released from the mechanophore platform at least comprises the functionalities selected from a group consisting of: alkyl and aryl alcohols, alkyl and aryl amines, carboxylic and sulfonic acids. In some embodiments, the cargo molecule is covalently conjugated to the furan moiety of the Diels-Alder adduct via a carbonate or carbamate spacer. In such embodiments, the cargo molecule release is accompanied by the release of $CO_2$. However, in some embodiments, the cargo molecule is covalently conjugated to the furan moiety directly, for example, via a carboxylate or sulfonate linkage that the cargo molecule comprises natively.

In many embodiments, the dienophile moiety of the Diels-Alder adduct of the mechanophore platform of the instant disclosure is any substituted alkene. In many such embodiments, the substituents on the substituted alkene are each independently selected from a group consisting of (but not limited to): H, halogen, alkyl, alkenyl, aryl, heteroaryl, alkoxy, alkylamine, carbonyl, a polymer chain of any composition. In some embodiments, the dienophile is an alkene selected from a group consisting of, but not limited to: acrylate, methacrylate, maleate, fumarate, and any other similarly substituted alkene. In some embodiments, the dienophile is a maleimide of any substitution.

Figure 2A:
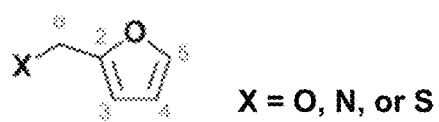
FIGS. 2A through 2D illustrate various aspects of this invention, wherein FIG. 2A schematically illustrates the 2-furylcarbinol scaffold.
Figure 2B:
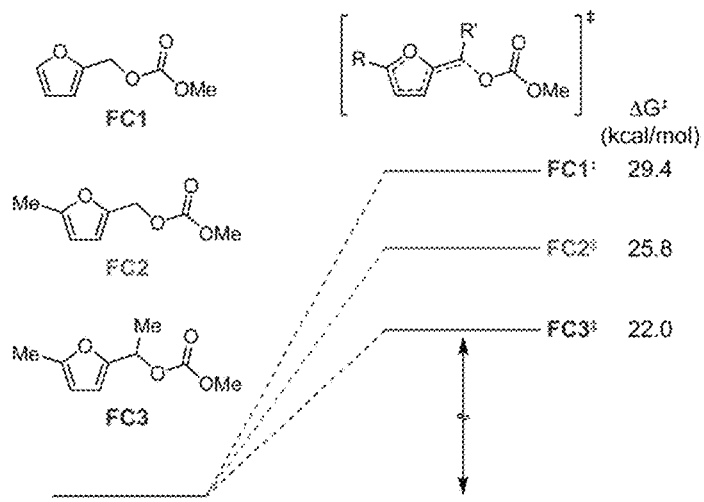
Figure 2C:
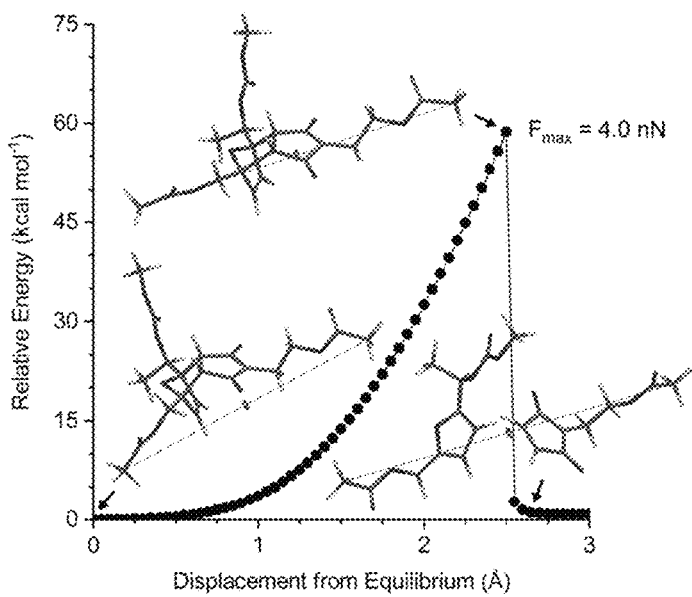
Figure 2D:
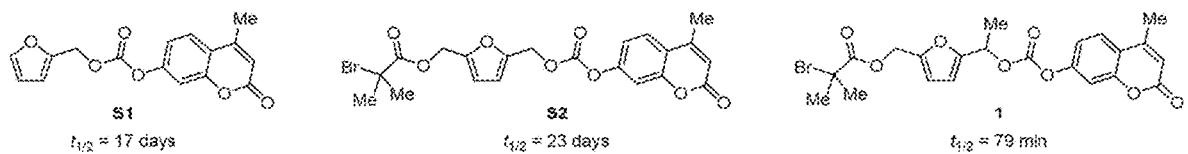

In many embodiments, the furan moiety of the Diels-Alder adduct of the mechanophore platform of the instant disclosure is a 2-furylcarbinol derivative comprising a 2-furylcarbinol scaffold schematically depicted in FIG. 2A. In many such embodiments, the 2-furylcarbinol scaffold of the furan moiety comprises any number of judiciously chosen substituents installed at any of the positions: 3-, 4-, 5-, and α- (shown in FIG. 2A), and any combination thereof, such as to promote (or, in some other embodiments, to hinder) facile decomposition of the furan moiety by stabilizing, to various extent, the formation of the corresponding furfuryl cation decomposition intermediate. For example, FIGS. 2B and 2C illustrate density functional theory (DFT) calculations performed to probe the effect of various substitution patterns applied to a furfuryl carbonate on the rate of its decomposition. More specifically, here, activation energies for the reaction of a series of three model furfuryl carbonates (FC1, FC2, and FC3 depicted in FIG. 2B) were calculated at the M06-2X/6-311+G** level of density functional theory (DFT) to gauge the substitution effects. To this end, the activation energy for the fragmentation of FC1, which is analogous to Gillies' design, was calculated to be 29.4 kcal/mol, suggesting slow decomposition reaction at room temperature. Furthermore, according to these calculations, addition of methyl group to the 5-position of the furan (FC2) reduces the decomposition reaction barrier to 25.8 kcal/mol. However, model compounds S1 and S2 (FIG. 2D) with structures analogous to FC1 and FC2, which were synthesized to conduct experiments for estimation of half-lives for decomposition, still proved to be slow to decompose, with estimated half-lives for decomposition at room temperature on the order of several weeks.

Nevertheless, the same DFT calculations indicated that substitution with an α-methyl group (FC3 in FIG. 2B), resulted in a pronounced decrease in activation energy for FC3 ($\Delta G_+^{\ddagger}=22.0$ kcal/mol). Not to be bound by any theory, such beneficial substituent effect might be expected from stabilization of the putative furfuryl cation intermediate suggested by the mechanism shown in FIGS. 1A-1C. Additional DFT calculations using the simple constrained geometries simulate external force (CoGEF) technique (as explained, for example in: Beyer, M. K. The mechanical strength of a covalent bond calculated by density functional theory. J. Chem. Phys. 2000, 112, 7307-7312; and Kryger, M. J.; et al. Structure-Mechanochemical Activity Relationships for Cyclobutane Mechanophores. J. Am. Chem. Soc. 2011, 133, 18992-18998, the disclosures of which are incorporated herein by reference) indicated that mechanical elongation of an appropriately substituted furan-maleimide adduct generates the expected furfuryl carbonate (FIG. 2C). Furthermore, according to these calculations, the retro-Diels-Alder reaction occurs with an estimated rupture force of 4.0 nN, which is comparable to rupture forces calculated with the CoGEF method for other active furan-maleimide mechanophores (see, for example, Stevenson, R.; De Bo, G. Controlling Reactivity by Geometry in Retro-Diels-Alder Reactions under Tension. J. Am. Chem. Soc. 2017, 139, 16768-16771, the disclosure of which is incorporated herein by reference). Accordingly, in many embodiments, the furan moiety of the mechanophore platform is a furfuryl carbonate or furfuryl carbamate (i.e., a 2-furylcarbinol derivative), wherein the furfuryl carbonate or furfuryl carbamate is substituted at α-position. In many such embodiments, the α-position substituent is a functional group selected from a group consisting of: alkyl, alkenyl, aryl, heteroaryl, or any other aromatic or heteroaromatic functional group, alkoxy, aryloxy, amine, sulfide, another heteroatom-containing group, such as silane, a polymer chain of any composition, and any combination thereof. In many embodiments, the α-position substituent is methyl. In many embodiments, the furan moiety also comprises a 5-position substituent. In many such embodiments, 5-position of the furan moiety is used for the attachment of the polymer component of the mechanophore platform. In some such embodiments, attaching the polymer at 5-position increases mechanochemical activity of the mechanophore platform.

Figure 3A:
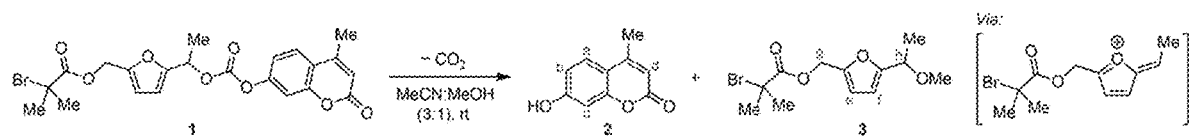
FIGS. 3A through 3E, provide characterization of the decomposition reaction of furfuryl carbonate 1 at room temperature, wherein FIG. 3A schematically illustrates the decomposition reaction of 1 in 3:1 MeCN:MeOH to generate fluorescent hydroxycoumarin 2 and furfuryl methyl ether 3 via a putative furfuryl cation intermediate.
Figure 3B:
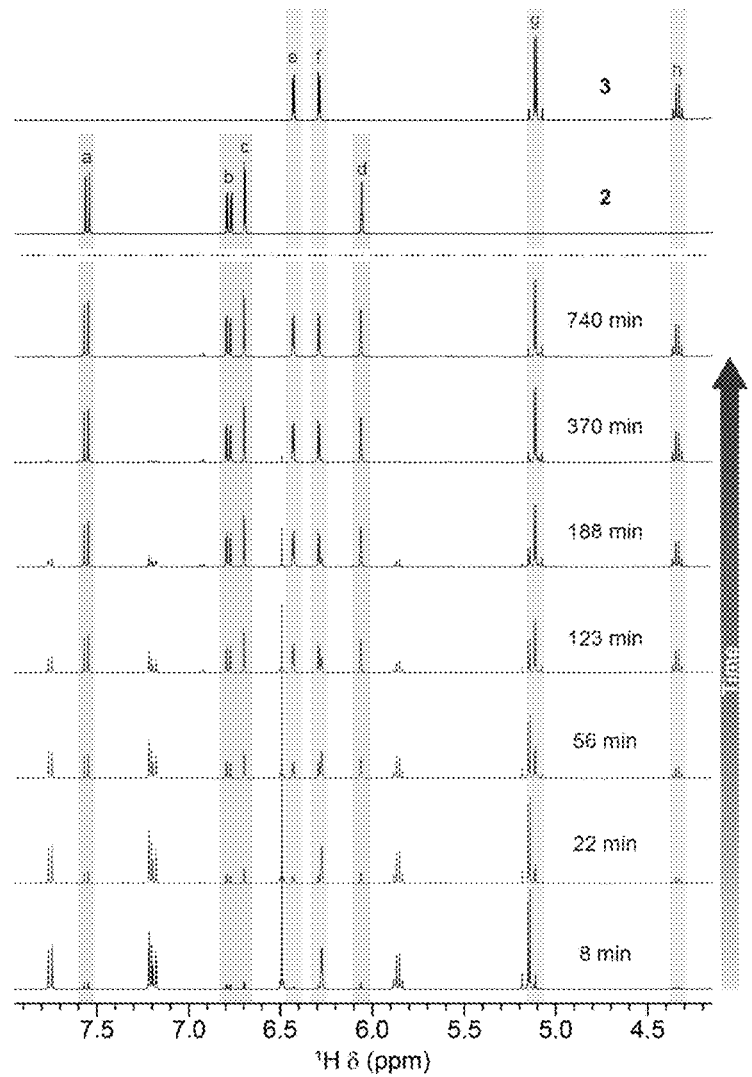
Figure 3C:
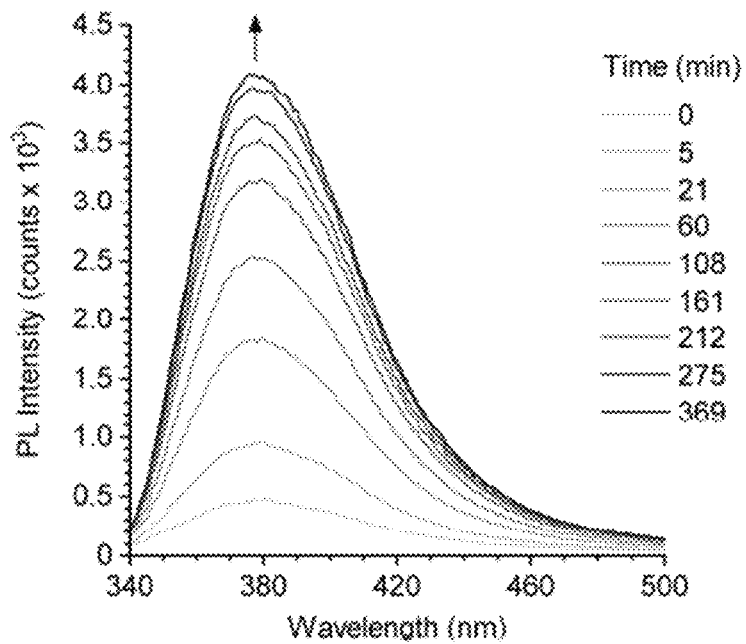
Figure 3D:
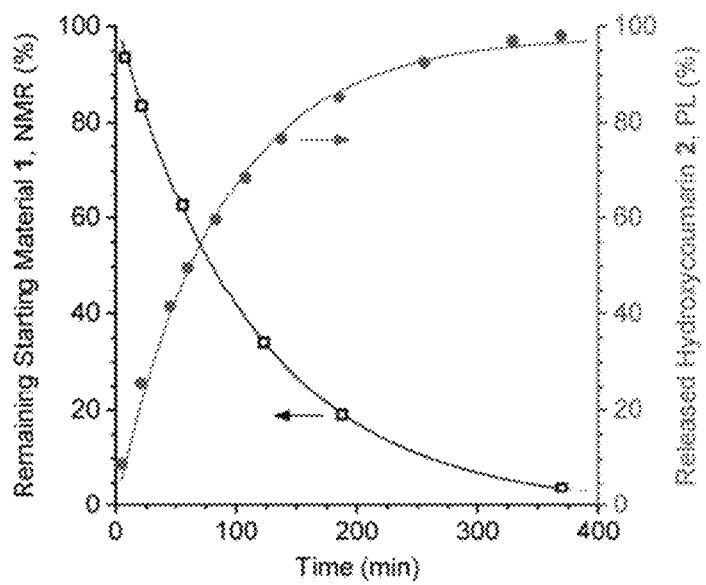
Figure 3E:
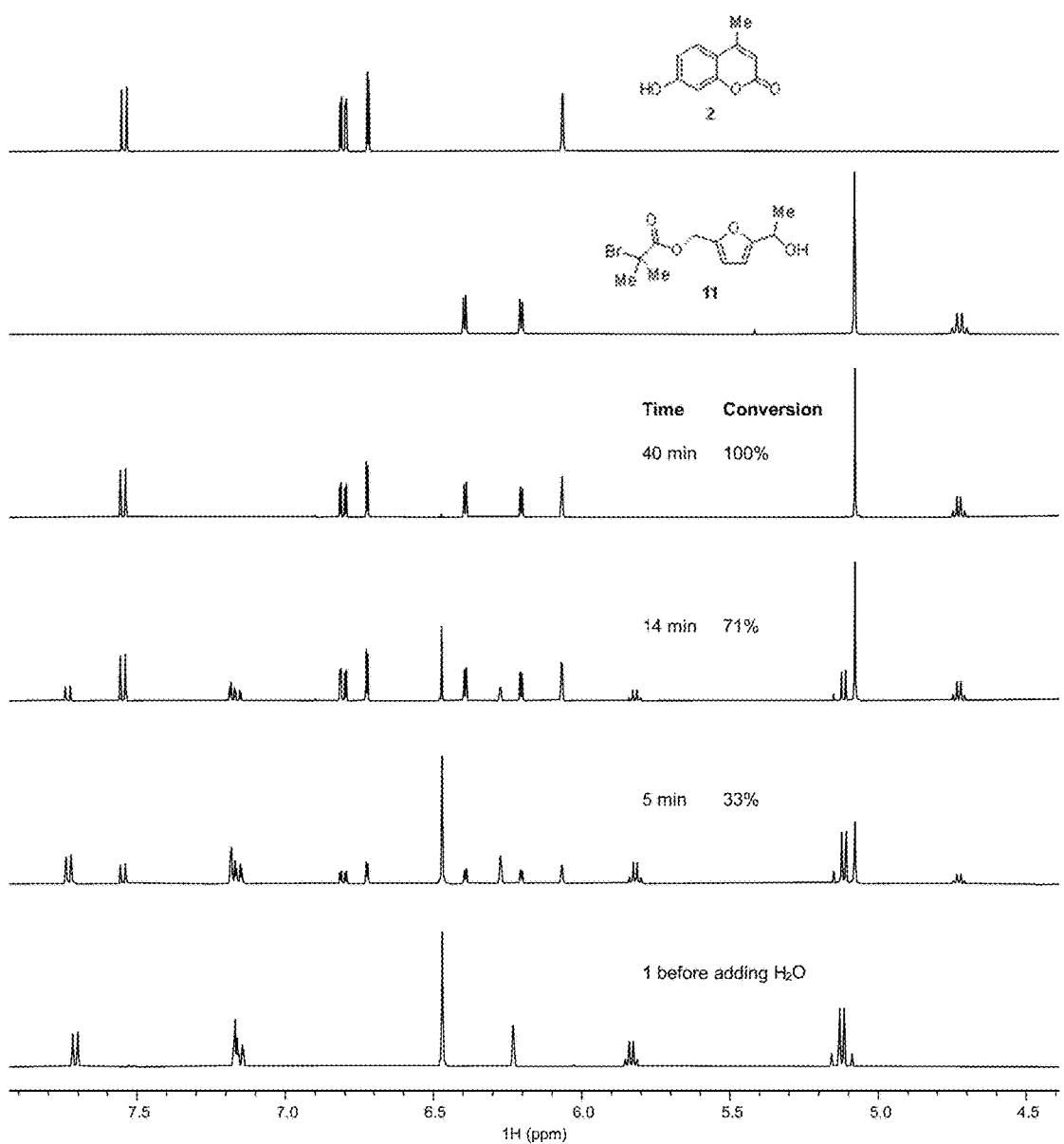

As one particular example of the suitable furan moieties of many embodiments, FIGS. 3A through 3E show a fluorogenic furfuryl carbonate model compound 1 (also shown in FIG. 2D), with a structure analogous to computational model FC3 (FIG. 2B), and also illustrate experiments investigating 1's propensity towards decomposition to release its cargo molecule. In these experiments, furfuryl carbonate 1 carries a covalently attached coumarin payload (i.e., the cargo molecule), which exhibits enhanced photoluminescence (PL) upon release from 1, allowing reaction (i.e., decomposition) progress to be tracked using fluorescence spectroscopy in addition to NMR spectroscopy. As such, furfuryl carbonate 1 appears to be relatively stable in chloroform and acetonitrile. However, the addition of methanol (i.e., a protic solvent) to the acetonitrile solution of 1 leads to fast decomposition at room temperature and clean formation of hydroxycoumarin 2 (via decarboxylation) and furfuryl ether 3 (FIG. 3A). Not to be bound by any theory, this generation of furfuryl ether 3 is consistent with a mechanism involving initial fragmentation of the α-C—O bond to form a furfuryl cation, which is subsequently attacked by methanol followed by proton transfer. Accordingly, FIG. 3B shows the decomposition of furfuryl carbonate 1 in a 3:1 (v/v) mixture of acetonitrile-$d_3$ and methanol monitored by $^1$H NMR spectroscopy over time. Signals corresponding to 1 fully disappear in a few hours with the concomitant formation of two new sets of resonances that match the spectra of the isolated hydroxycoumarin and furfuryl methyl ether products. The generation of hydroxycoumarin 2 in the room temperature solution of furfuryl carbonate 1 in MeCN:MeOH (3:1) was also monitored over time using fluorescence spectroscopy (FIG. 3C). Excitation at 330 nm revealed an emission peak around 380 nm that increased in intensity over time and matched the emission spectrum for hydroxycoumarin 2. Here, approximately 98% of the theoretical yield of hydroxycoumarin 2 was released over about 6 h (FIG. 3D). The conversion of furfuryl carbonate 1 and the generation of hydroxycoumarin 2 followed exponential decay models under these conditions with the reaction half-life estimated from NMR measurements to be $t_{1/2}$=79 min. Notably, the decomposition of furfuryl carbonate 1 occurred even faster in a water/acetonitrile mixture ($t_{1/2}$<10 min) (FIG. 3E), indicating the potential of this system for molecular release in aqueous environments.

Figure 4:
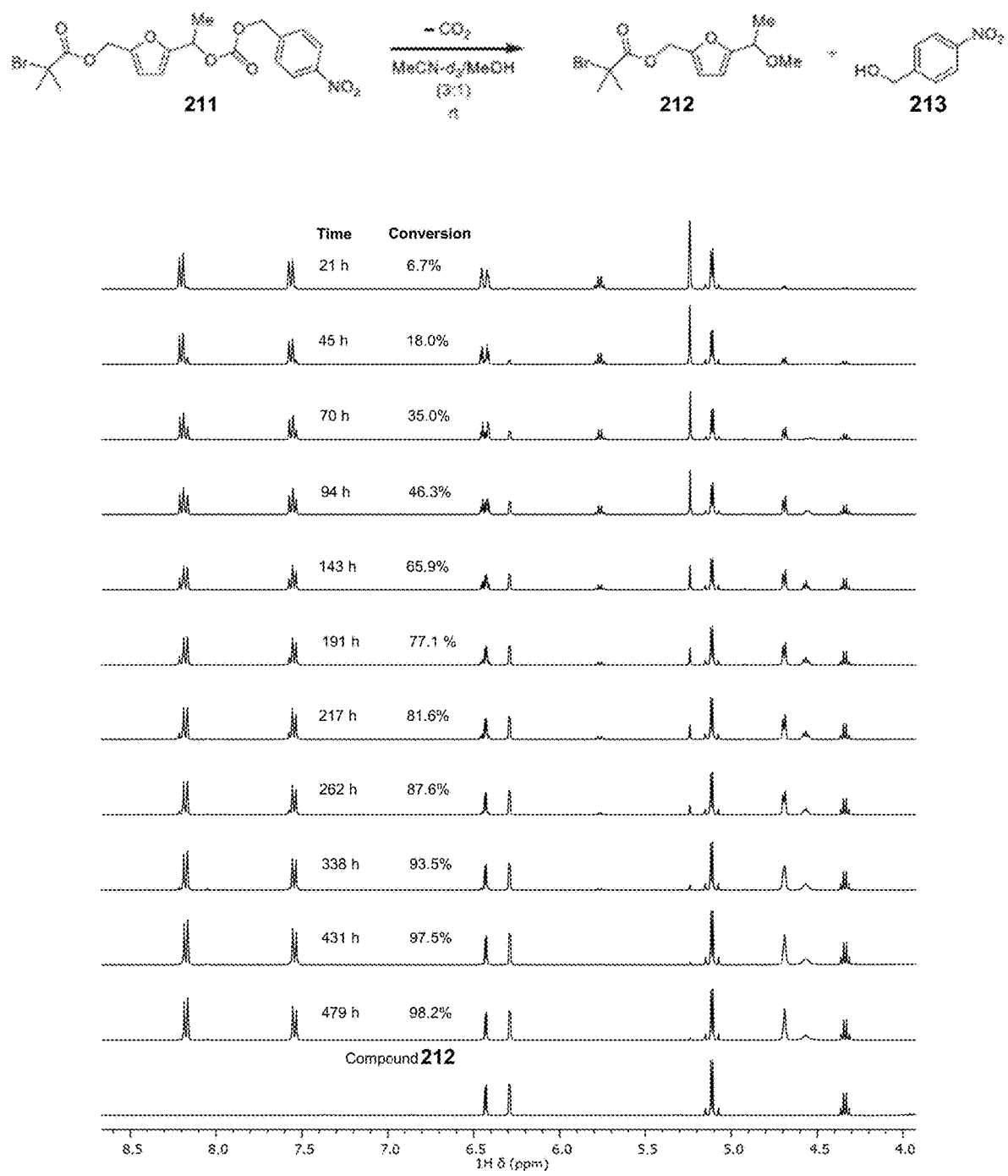
FIG. 4 provides partial $^1$H NMR spectra (400 MHz) collected for a 42 mM solution of furfuryl carbonate 211 in MeCN-$d_3$/MeOH (3:1) at room temperature over time, illustrating the decomposition reaction of 211, wherein it cleanly converted to primary alcohol 212 over a period of approximately 500 h, with the reaction half-life of approximately 4.1 days, in accordance with embodiments of the invention.

Nevertheless, while the furan moiety's substitution pattern of some embodiments, wherein the α- and 5-positions feature substituents, is sufficient to enable the release of a phenolic cargo molecule with a half-life of approximately 1 h, the rate of fragmentation is still prohibitively slow for some applications for, for example, alcohol-derived furfuryl carbonates and amine-derived furfuryl carbamates. For example, FIG. 4 illustrates kinetic studies performed on a small molecule model compound 211, which revealed that the release of primary alcohol 212 from the furfuryl carbonate substituted according to some embodiments at only α- and 5-positions occurs with a half-life of approximately 4 days, or nearly 100× slower than the release of hydroxycoumarin from an equivalently substituted substrate.

Accordingly, in many embodiments, especially wherein the mechanophore platform of the instant disclosure needs to release a non-phenolic cargo, i.e., wherein the furan moiety is, for example, an alcohol-derived furfuryl carbonate or an amine-derived furfuryl carbamate, or another 2-furylcarbinol derivative, alternative and or additional substitution or substitutions of the 2-furylcarbinol scaffold is employed to further promote rapid and facile decomposition of the mechanophore platform and the cargo molecule release. More specifically, in many embodiments, an electron-donating substituent (see, for example, Schmid, K. M.; et al. A Self-Immolative Spacer That Enables Tunable Controlled Release of Phenols under Neutral Conditions. J. Org. Chem. 2012, 77, 4363-4374, the disclosure of which is incorporated herein by reference), such as, for example, phenoxy, or any other aryloxy, at the 3-position of the furan moiety is installed. Not to be bound by any theory, it is believed that such substituent further suppresses the activation barrier for fragmentation of the 2-furylcarbinol scaffold, since this substituent is in resonance with the furfuryl cation, and enables the efficient release of more challenging payloads, including amines (as explained, for example, in Nichol, M. F.; et al. Multi-stimuli responsive trigger for temporally controlled depolymerization of self-immolative polymers. Polym. Chem. 2019, 10, 4914-4919, the disclosure of which is incorporated herein by reference), under mild conditions. In other words, the incorporation of an electron donating substituent at 3-position of the furan heterocycle is believed to reduce the activation barrier for fragmentation of the α-C—X bond (FIG. 2A), presumably through resonance stabilization of the developing positive charge in the transition state leading to the furfuryl cation intermediate.

Figure 5:
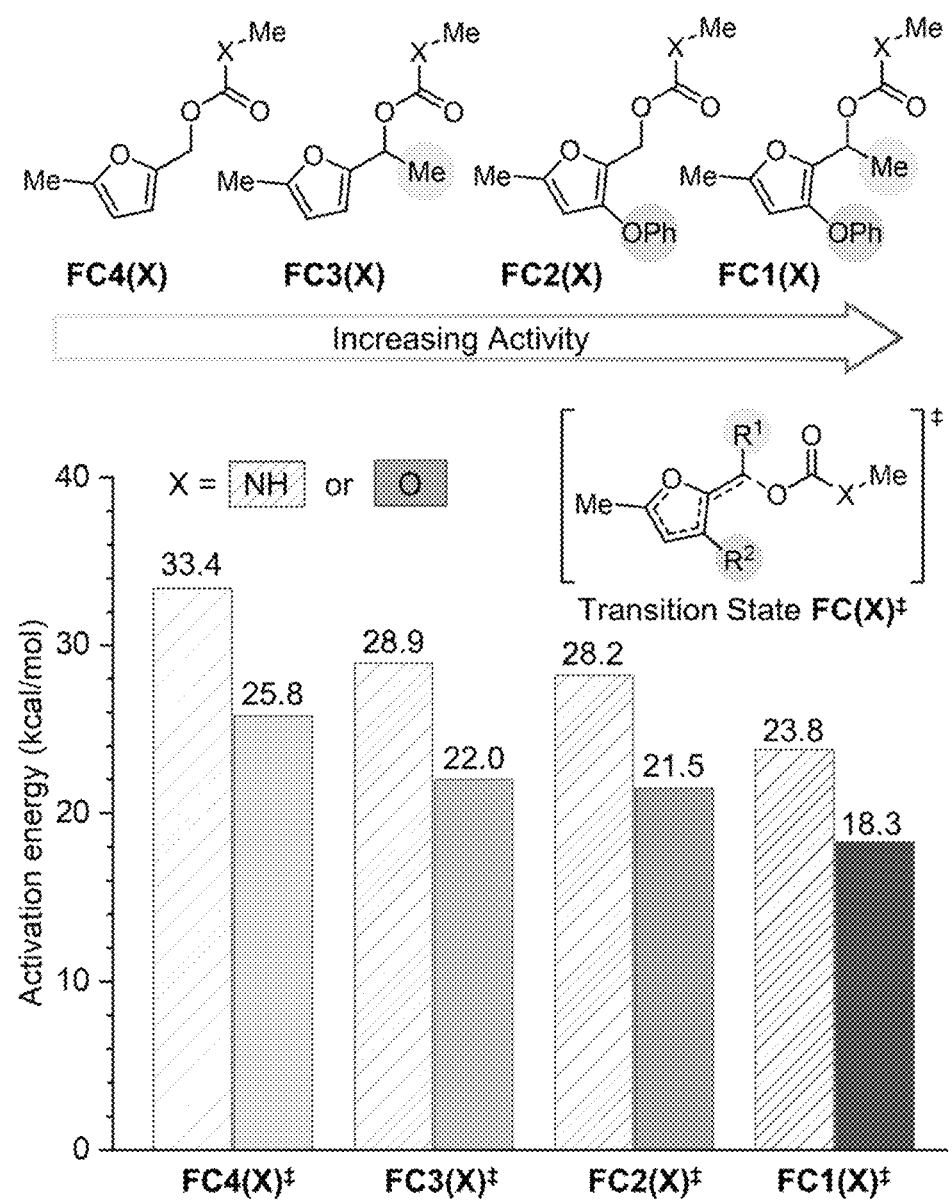
FIG. 5 illustrates substituent effects on the reactivity of 2-furylcarbinol derivatives, including model furfuryl carbonates (X=O) and furfuryl carbamates (X=NH) with varying substitution patterns, by providing corresponding activation energies for fragmentation of the α-C—X bond calculated at the M06-2X/6-311+G** level of density functional theory for each derivative, in accordance with embodiments of the invention.

For example, FIG. 5 illustrates the effect of an electron-donating substituent, such as, for example, phenoxy, installed at the 3-position of the furan moiety, on the release of the cargo molecule from such furan moiety according to many embodiments. More specifically, FIG. 5 provides computations of the activation energies for the fragmentation of a series of model primary and secondary furfuryl carbonate (FC1(O)-FC4(O)) and furfuryl carbamate ((FC1(N)-FC4(N)) substrates with different substitution schemes for the α- and 3-positions of the furan moiety. Here, activation energies were calculated using DFT at the M06-2X/6-311+G** level of theory using a polarizable continuum model to simulate a polar solvent environment. For the furfuryl carbonate series, α-methyl substitution reduces the activation energy for fragmentation by 3.2-3.8 kcal/mol relative to the primary furfuryl carbonate substrates. Similarly, the addition of the electron-donating phenoxy substituent at the 3-position lowers the computed activation energies by 3.7-4.3 kcal/mol. Remarkably, the combination of α-methyl and 3-phenoxy substituents installed on FC1(O) results in a computed activation energy of 18.3 kcal/mol, suggesting nearly instantaneous decomposition reaction at room temperature. These values indicate that the half-life for reaction of FC1(O) is nearly five orders of magnitude shorter than for minimally substituted FC4(O), and approximately 500× shorter than for FC3(O) without 3-phenoxy substitution.

A similar trend in reactivity is observed for the furfuryl carbamate model series (FC(N)); however, calculated activation energies are 5.5-7.6 kcal/mol larger for the furfuryl carbamates compared to the analogous furfuryl carbonate substrates in all cases (FIG. 5). Notably, the higher activation energies calculated for the furfuryl carbamate series are consistent with experimentally determined reaction kinetics for different self-immolative spacers (as provided by, for example, Alouane, A.; et al. Self-Immolative Spacers: Kinetic Aspects, Structure-Property Relationships, and Applications. Angewandte Chemie International Edition 2015, 54, 7492-7509, the disclosure of which is incorporated herein by reference), which suggests, although not to be bound by any theory, that the more electron-withdrawing carbonate leaving group is able to better stabilize the partial negative charge on the oxygen atom of the fragmenting α-C—O bond in the transition state relative to a carbamate leaving group. Consequently, the activation energies calculated for furfuryl carbamates FC2(N)-FC4(N) suggest that decomposition of similarly substituted substrates occurs on timescales that may be impractical for some triggered release application. However, the combination of α-methyl and 3-phenoxy substitution according to many embodiments significantly reduces the activation barrier for furfuryl carbamate FC1(N) to 23.8 kcal/mol, which approaches the activation energy calculated for furfuryl carbonate with α- and 5-position substitutions, and suggests that release of challenging amine-based cargo molecules may be accessible on shorter timescales.

Figure 6:
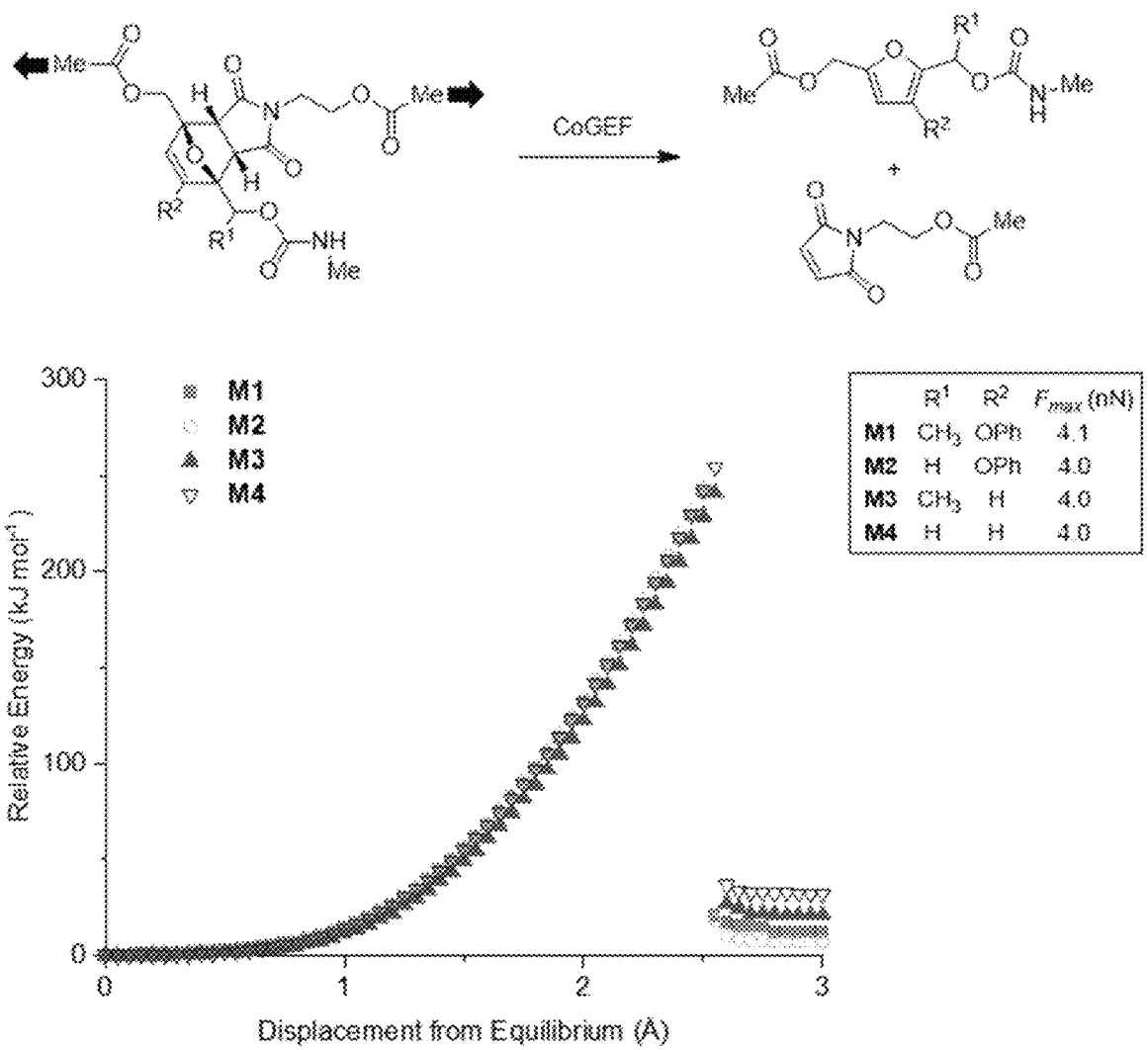
FIG. 6 shows DFT calculations performed on furan-maleimide Diels-Alder adducts M1-M4 using the constrained geometries simulate external force (CoGEF) method at the B3LYP/6-31G* level of theory, wherein the energy-displacement profiles of all four adducts match closely with each other with Fmax values calculated to be 4.0-4.1 nN; and wherein CoGEF calculations predict that all four furan-maleimide adducts generate the expected furan and maleimide products upon mechanical elongation, in accordance with embodiments of the invention.

Furthermore, in many embodiments, the 3-phenoxy, or similar aryloxy, substituent on the furan moiety does not affect the mechanochemical properties of the mechanophore platforms of the instant disclosure. To demonstrate the mechanochemical stability of the mechanophore platforms comprising differently substituted furan moieties, DFT calculations were performed on model compounds M1 through M4 depicted in FIG. 6 using the constrained geometries simulate external force (CoGEF) method, which is a simple and reliable computational technique for predicting mechanochemical reactivity (as explained, for example, in Klein, I. M.; et al. Validation of the CoGEF Method as a Predictive Tool for Polymer Mechanochemistry. J. Am. Chem. Soc. 2020, 142, 16364-16381, the disclosure of which is incorporated herein by reference). These calculations confirmed that mechanical elongation of each furan-maleimide adduct resulted in a predicted retro-[4+2] cycloaddition reaction to produce the expected furfuryl carbamate and maleimide fragments with nearly identical energy-displacement profiles (FIG. 6). Furthermore, the calculated rupture force ($F_{max}$) was essentially the same regardless of the substitution, which occurs at 4.0-4.1 nN, and suggests similar mechanochemical activity of each mechanophore that is primarily dictated by pulling geometry (for additional examples, see Konda, S. S. M.; et al. Molecular Catch Bonds and the Anti-Hammond Effect in Polymer Mechanochemistry. J. Am. Chem. Soc. 2013, 135, 12722-12729, the disclosure of which is incorporated herein by reference).

Figure 7A:
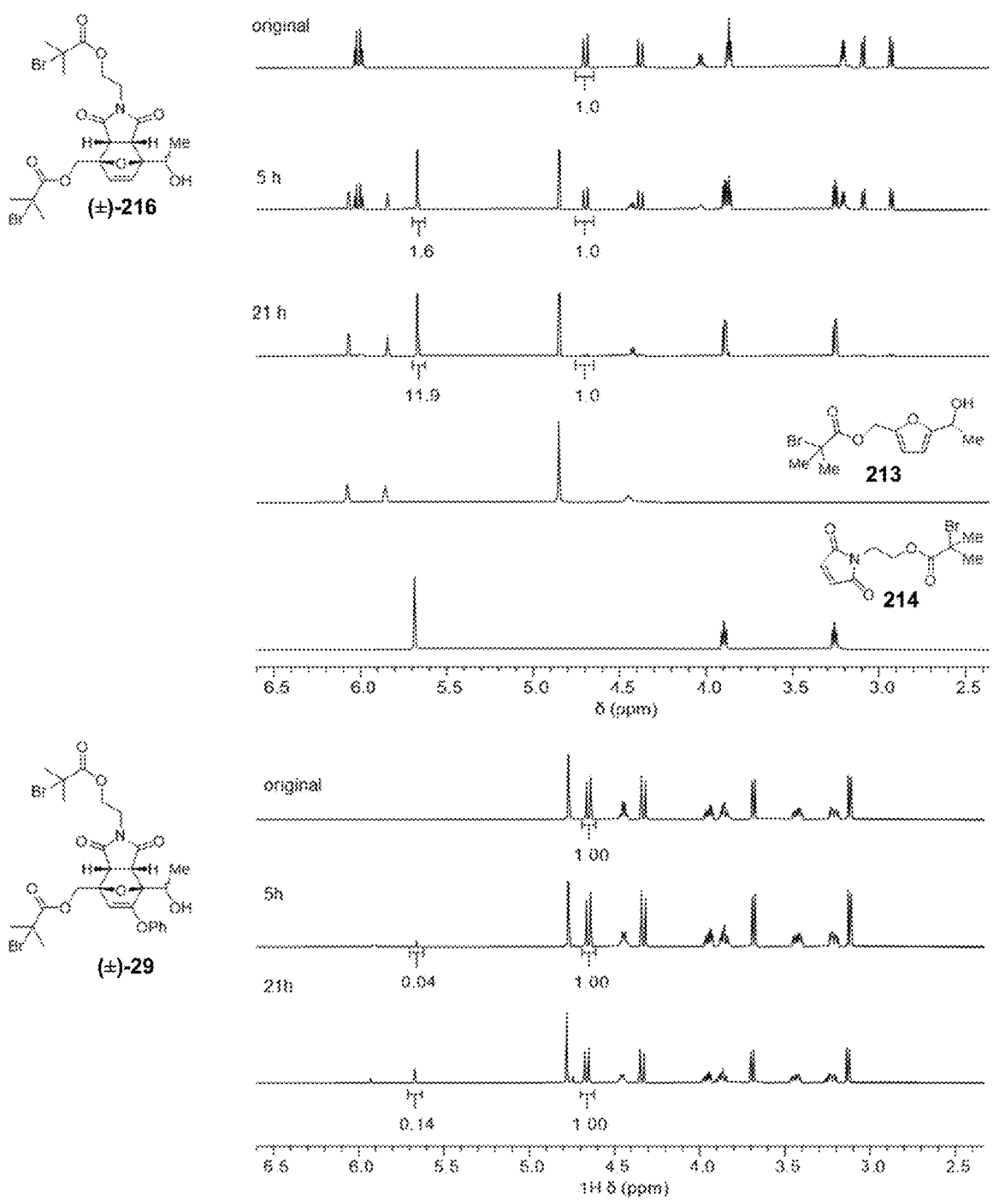
FIGS. 7A and 7B provide partial $^1$H NMR spectra (400 MHz) collected for Diels-Alder adducts (±)-216 (top in each figure) and (±)-29 (bottom in each figure) in toluene-$d_8$ (8.6 mM) over time to compare these compounds' thermal stability, wherein FIG. 7A spectra, obtained after heating at 70° C., show that (±)-216 undergoes retro-Diels-Alder reaction with a conversion of approximately 46% after 5 h, reaching nearly quantitative conversion after 21 h; and that, in contrast, <2% retro-Diels-Alder reaction is observed for (±)-29 after 5 h, and <7% after 21 h; and wherein FIG. 7B spectra, obtained at room temperature, show that after 132 days at room temperature, approximately 23% of (±)-216 is converted via retro-Diels-Alder reaction, while no reaction is observed for compound (±)-29, in accordance with embodiments of the invention.
Figure 7B:
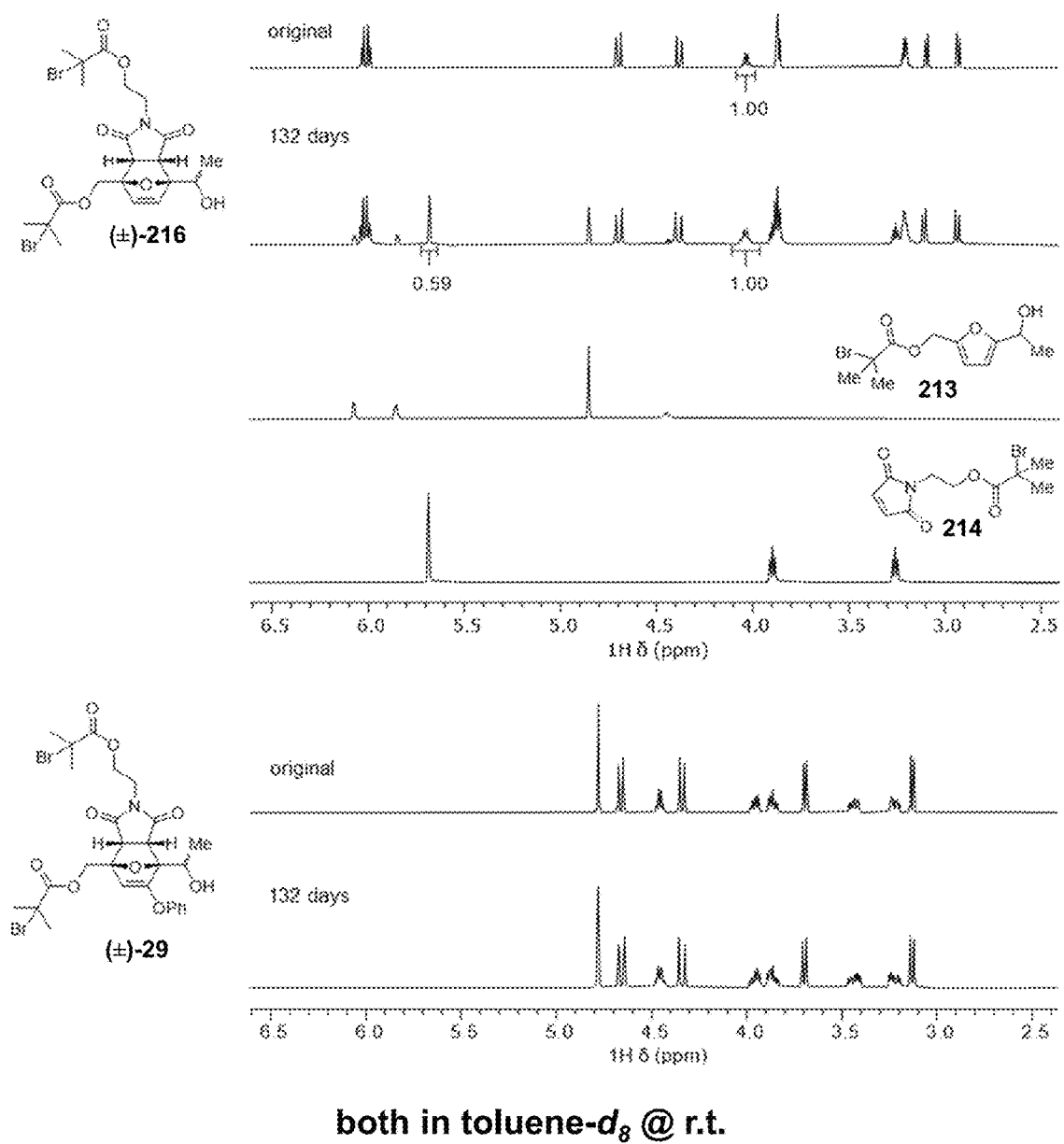

However, notably, in many embodiments, the 3-phenoxy (or similar aryloxy at 3-position) substituent on the furan moiety does affect the thermal properties of the mechanophore platforms of the instant disclosure. For example, FIGS. 7A and 7B illustrate that addition of the 3-phenoxy group to the furan moiety leads to a pronounced increase in the thermal stability of the Diels-Alder adduct of many embodiments. Not to be bound by any theory, this effect has been observed previously for cycloadducts derived from 3-alkoxy-furans, and it has been ascribed to a reduction in the energetic penalty for loss of furan aromaticity (as explained, for example in: Boutelle, R. C.; Northrop, B. H. Substituent Effects on the Reversibility of Furan-Maleimide Cycloadditions. J. Org. Chem. 2011, 76, 7994-8002; and Foster, R. W.; et al. Irreversible endo-Selective Diels-Alder Reactions of Substituted Alkoxyfurans: A General Synthesis of endo-Cantharimides. Chemistry 2015, 21, 6107-6114, the disclosures of which are incorporated herein by reference). Accordingly, FIG. 7A illustrates that, heating a solution of 3-phenoxy substituted (±)-29 in toluene-d$_8$ at 70° C. results in <2% cycloelimination after 5 h, while the same conditions lead to approximately 46% reversion of the analogous Diels-Alder adduct (±)-216 without the 3-phenoxy substituent. Furthermore, as shown in FIG. 7B, at room temperature, 3-phenoxy-substituted (±)-29 is stable indefinitely in toluene-d$_8$, which is in contrast to the slow, but detectable, reversion of (±)-216 without the 3-phenoxy substituent. Accordingly, in many embodiments, 3-phenoxy, or any similar aryloxy substituent at 3-position of the furan moiety enhances the thermal stability of such mechanophore platforms without any detriment to their mechanochemical activity.

Accordingly, in many embodiments, the furan moiety of the mechanophore platform comprises an electron-donating functional group at the 3-position. In some such embodiments, the electron-donating functionality at 3-position of the furan moiety is employed by itself, or in any combination of appropriate (as described herein) substituents at α-position and 5-position, to facilitate the release of the cargo molecule with the desired kinetics. In many embodiments, the substituent at the 3-position is a functional group selected from a group consisting of: alkyl, alkenyl, aryl, heteroaryl, any other aromatic or heteroaromatic functional group, alkoxy, aryloxy, amine, sulfide, any other heteroatom-containing group, such as silane, a polymer chain of any composition, and any combination thereof. In many embodiments, the 3-position substituent is phenoxy. In many embodiments, the 3-position substituent also serves as a linker/point for the attachment of the polymer component of the mechanophore platform.

Figure 8A:
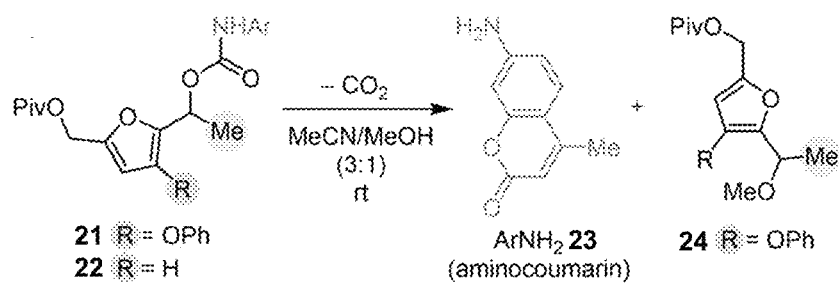
FIGS. 8A through 8F illustrate the effect that the 3-aryloxy substitution of the furan moiety has on the decomposition kinetics of 2-furylcarbinol derivatives, and, more specifically, provide characterization of the decomposition reactions of model furfuryl carbamates 21 and 22, wherein FIG. 8A schematically illustrates the corresponding decomposition chemistry in MeCN/MeOH (3:1) at room temperature, which generates fluorescent 23 and furfuryl methyl ether 24.
Figure 8B:
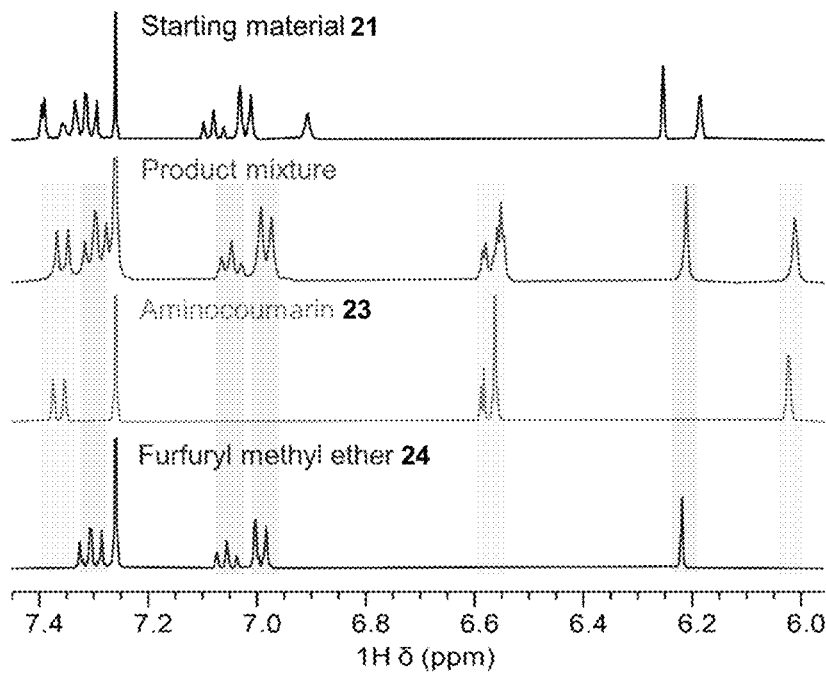
Figure 8C:
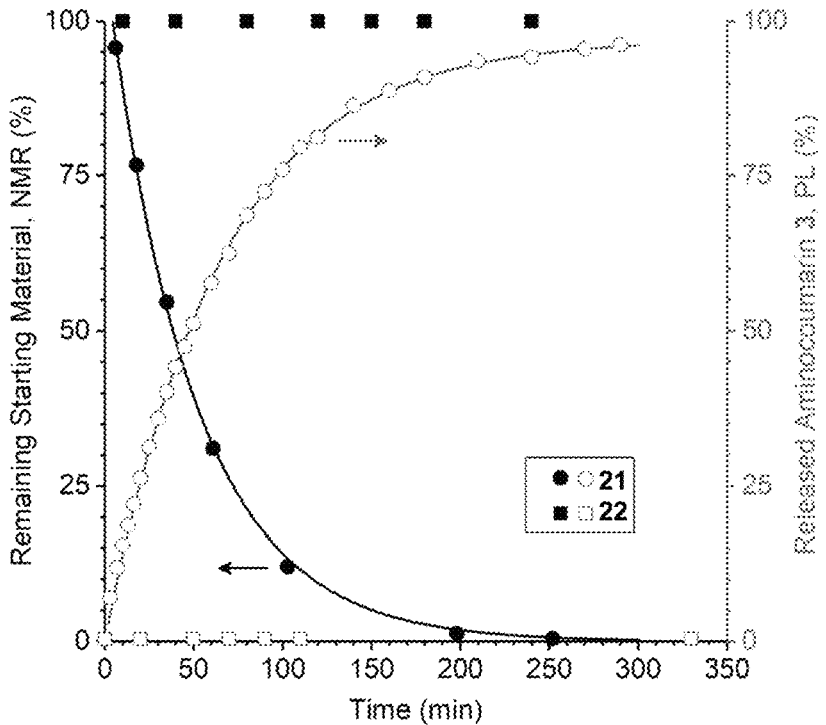
Figure 8D:
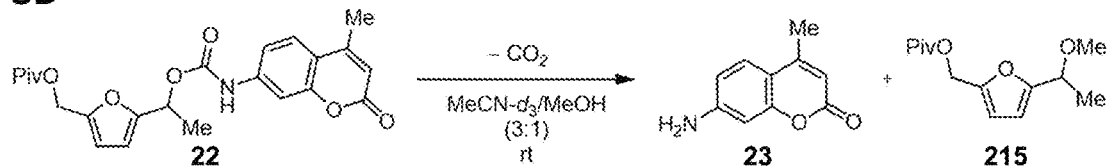
Figure 8E:
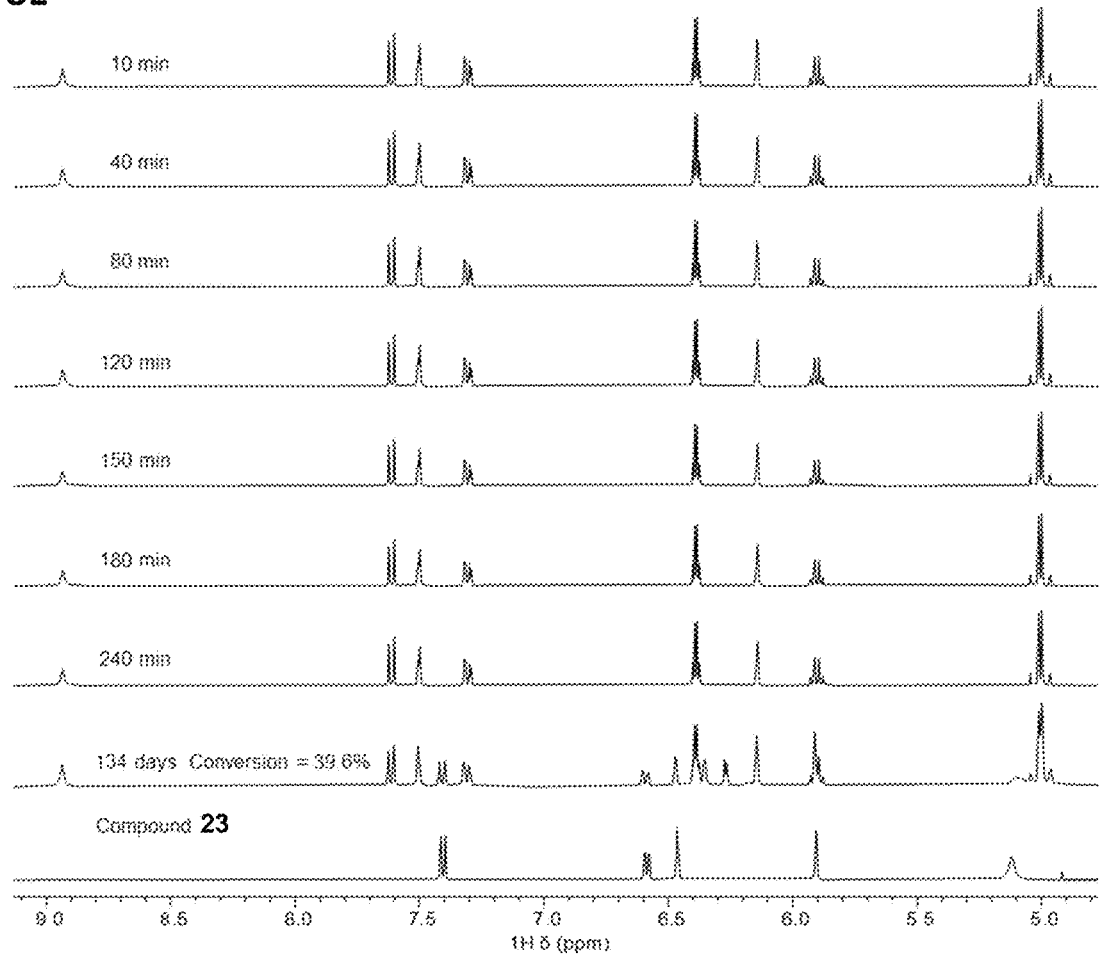
Figure 8F:
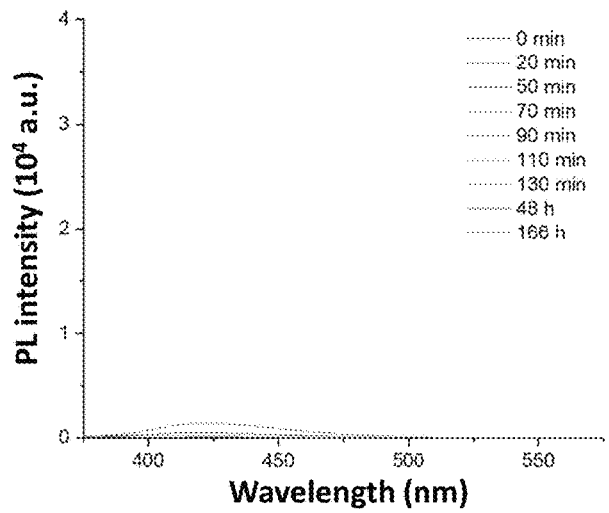

As one example of the suitable furan moiety comprising the advantageous, electron-donating, 3-aryloxy substituent of many embodiments, FIGS. 8A through 8C show fluorogenic furfuryl carbamate compound 21, which comprises all of α-methyl, 3-phenoxy, and 5-position substituents, and provide experimental data illustrating its decomposition reactivity; while FIGS. 8D through 8F provide the same data for compound 22, which is identical to 21, except for the 3-phenoxy substituent, for comparison. In these experiments, the cargo molecule released upon decomposition of 21, is coumarin derivative 23, which exhibits a fluorescence turn-on after the release, allowing the reaction to be conveniently monitored using photoluminescence (PL), in addition to NMR spectroscopy. To this end, as evidenced by NMR spectroscopy analysis provided in FIG. 8B, the addition of methanol (i.e., a protic solvent) to a room temperature solution of 21 in acetonitrile-d$_3$ (19 µM, 3:1 MeCN/MeOH) triggers decomposition of 21, and results in clean conversion of 21 to aminocoumarin 23 and furfuryl methyl ether 24. Here, the formation of furfuryl methyl ether 24 is consistent with the transient formation of a furfuryl cation intermediate that is intercepted by methanol.

It should be noted here, that when the same decomposition of 21 was performed at significantly higher concentrations, another set of peaks was observed in the $^1$H NMR spectra of the reaction, corresponding to the formation of a side product, that was identified to be the furfuryl amine 24N, derived from nucleophilic attack of the furfuryl cation intermediate by liberated aminocoumarin 3:

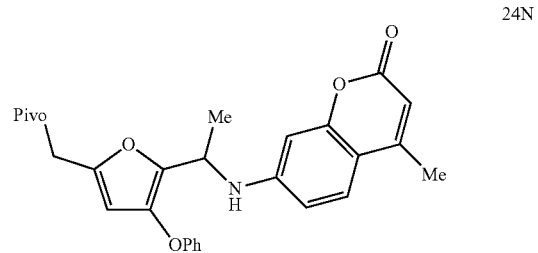

A similar product/reaction was not observed for the furfuryl carbonates, highlighting the increased nucleophilicity of the amine cargo molecules. Importantly, however, this furfuryl amine side product is formed in <2% yield in reactions with a substrate concentration of 19 µM, which is similar to the concentration of mechanophores in typical ultrasonication experiments (vide infra). Therefore, the reaction depicted in FIG. 8A for the decomposition of the furan moieties exemplified by 21 is sufficiently descriptive for relatively low substrate concentrations.

Furthermore, FIG. 8C illustrates the kinetics of the decomposition of furfuryl carbamates comprising α-methyl, 3-phenoxy, and 5-position substituents according to many embodiments, such as exemplified by 21, and compares them to the furfuryl carbamates without the 3-phenoxy substitution, such as exemplified by furfuryl carbamate 22. More specifically, FIG. 8C provides data from experimental studies, wherein the decompositions of 21 and 22 to generate aminocoumarin 23 were monitored as a function of time using NMR and PL spectroscopy. According to the collected data, 21 fully converts to products in approximately 5 h, with concomitant increase in fluorescence corresponding to the generation of 3. The data from both time course experiments were fitted to first-order rate expressions, providing half-lives for decomposition of 21 to be $t_{1/2}$=34 and 45 min from NMR and PL measurements, respectively. In direct contrast, secondary furfuryl carbamate model compound 22, which does not have the 3-phenoxy substituent, is completely unreactive under the same conditions, as further shown with corresponding data in FIGS. 8D through 8F. The striking difference in decomposition behavior between 21 and 22 highlights the impact of an electron-donating substituent, such as phenoxy functional group, installed at 3-position of the 2-furylcarbinol scaffold according to many embodiments, on the decomposition fate of the furan moiety, wherein 3-phenoxy substituent enables the release of previously inaccessible cargo molecules.

Figure 9:
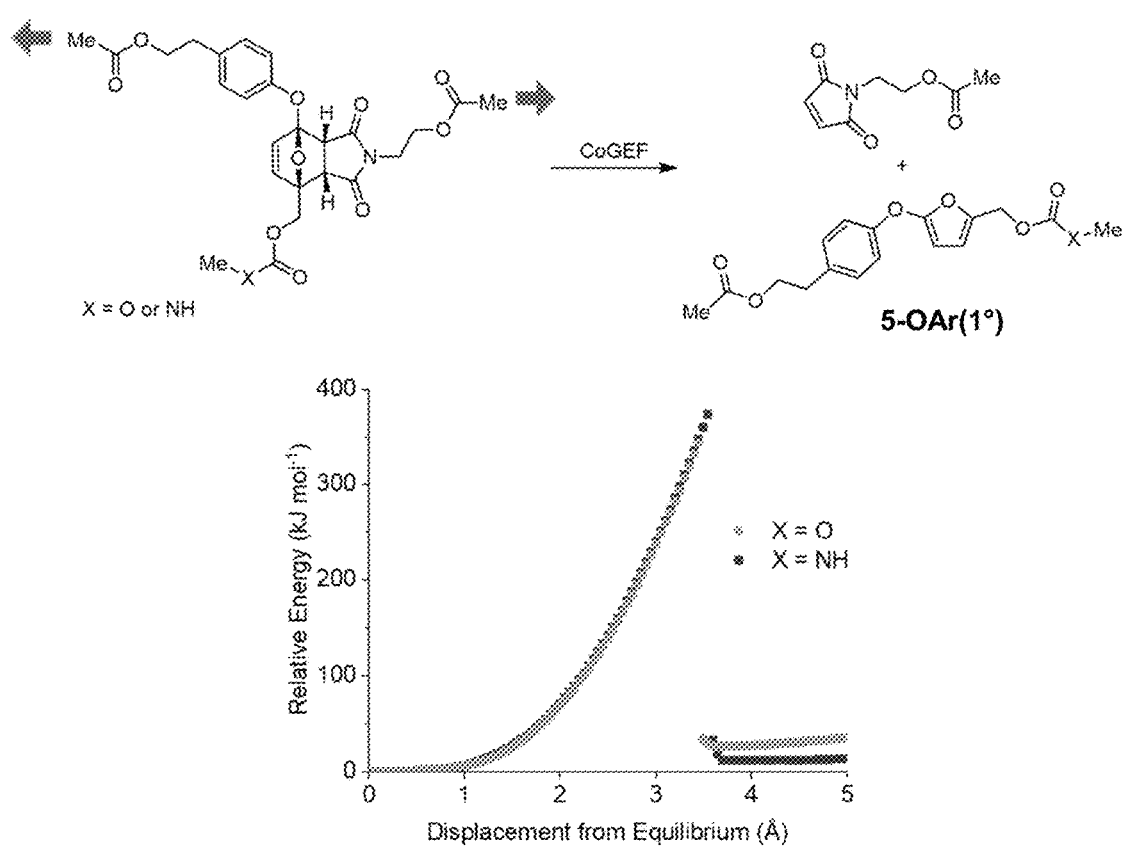
FIG. 9 illustrates DFT calculations performed on a furan-maleimide Diels-Alder adducts comprising 5-aryloxy substituted furan moiety, using the constrained geometries simulate external force (CoGEF) method at the B3LYP/6-31G* level of theory, wherein the Fmax value calculated for the carbonate model (X=O) is 4.2 nN, and that for the carbamate model (X=NH) is 4.4 nN; and wherein CoGEF calculations predict the retro-Diels-Alder reaction to generate the expected furan and maleimide products upon mechanical elongation, in accordance with embodiments of the invention.

Nevertheless, while, in some embodiments, an electron-donating substituent, such as, for example, phenoxy, at 3-position of the furan moiety enables release of challenging payloads, such as amines, on reasonable time scales, installation of such a group at the 3-position may be synthetically onerous and inefficient. Therefore, in some embodiments, other, more synthetically accessible substitution schemes and structural features are applied to the furan moiety, such that the developing positive charge at the α-position in the transition state of the decomposition process is stabilized, and, thus, the rate of the molecular cargo release from 2-furylcarbinol derivative is increased. In other words, in many embodiments, another substituent or substituents that increases the electron density of the furan moiety is employed to enable the rapid release of challenging cargo molecules (e.g., amines), instead of, or in addition to, any combination of, for example, α-methyl substituent (which reduces the activation barrier for fragmentation of its furan host by 3-4 kcal/mol, as compared to the primary 2-furfyl-carbinol derivatives), and an electron-donating 3-phenoxy group (which reduces the activation barrier for fragmentation of its furan host by 4-5 kcal/mol, as compared to the 2-furylcarbinol derivatives without a 3-phenoxy group). In many such embodiments, the furan moiety comprises an electron-donating substituent, such as, for example, aryloxy substituent, at 5-position of the furan moiety, as illustrated, for example by 5-OAr(1°) in FIG. 9.

Notably, in many embodiments, the introduction of the phenoxy substituent at the 5-position of the furan moiety preserves proximal pulling geometry on the Diels-Alder adduct mechanophore, which has been shown to result in greater mechanochemical activity compared to other regioisomers. Furthermore, DFT calculations using the constrained geometries simulate external force (CoGEF) method, illustrated by FIG. 9, predict the desired retro-[4+2]cycloaddition reaction upon molecular elongation of model mechanophore 5-OAr(1°). More specifically, this mechanochemical reaction of many embodiments is predicted to occur with a maximum force ($F_{max}$) of 4.2 nN for the carbonate version (i.e., X=O) of 5-OAr(1°) and 4.4 nN for the carbamate version (X=N) of 5-OAr(1°), which are similar to the $F_{max}$ values of 4.0-4.1 nN computed for other 2-furylcarbinol derivative-based mechanophores of many embodiments described herein.

Figure 10A:
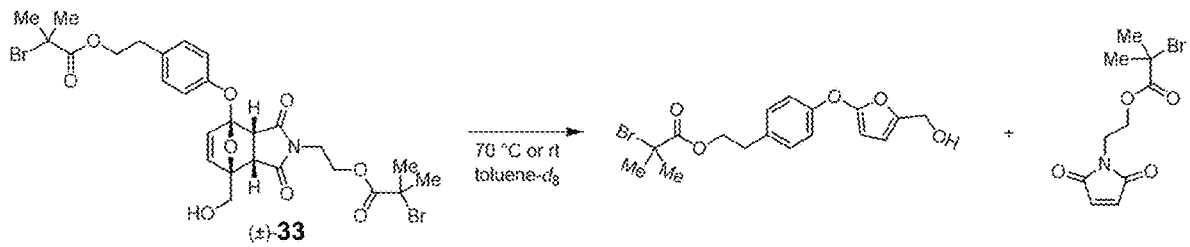
Figure 10B:
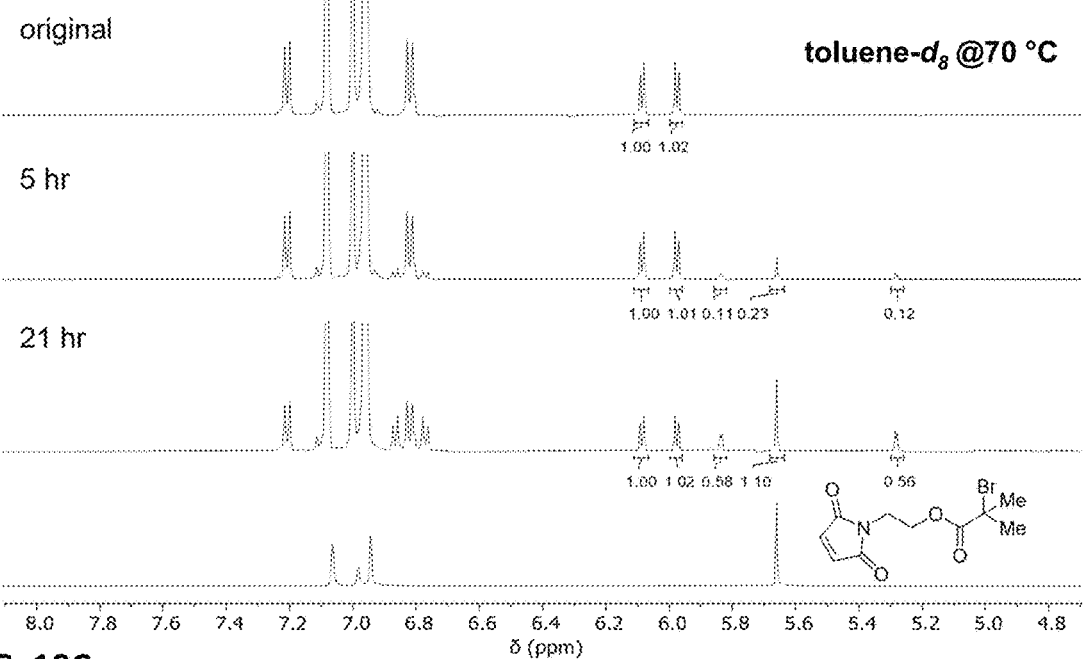
Figure 10C:
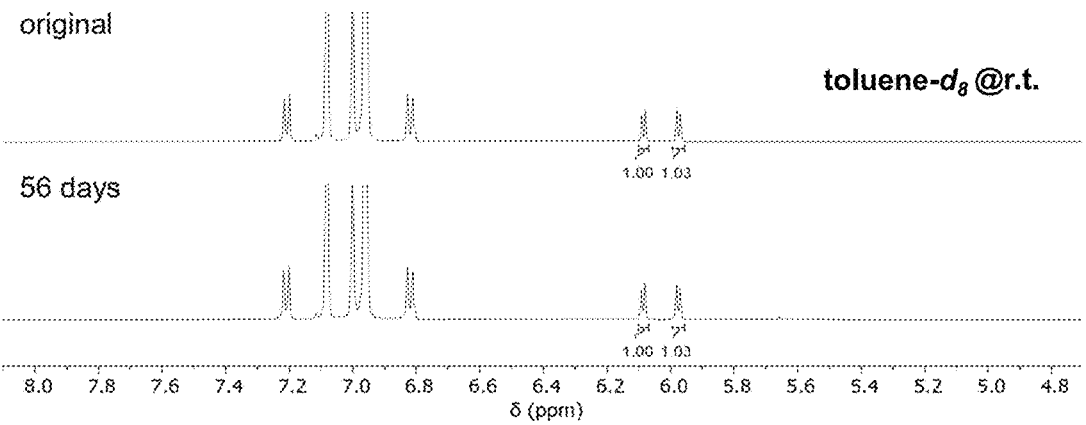

In addition, FIGS. 10A through 10C show that 5-OAr (i.e., 5-position aryloxy) substitution of the furan moiety affords excellent thermal stability for the Diels-Alder mechanophore adducts of many embodiments incorporating such furan moieties. More specifically, these figures show that heating Diels-Alder adduct (±)-33 in toluene-$d_8$ at 70° C. for 5 h results in only ~10% retro-Diels-Alder reaction (FIG. 10B), while keeping (±)-33 at room temperature affords no detectable products of retro-Diels-Alder reaction even after nearly two months (FIG. 10C). In comparison, as described herein, heating the Diels-Alder adduct comprising a 3-OPh substituted furan moiety at 70° C. under the same conditions results in <2% retro-Diels-Alder conversion, while for the Diels-Alder adduct comprising neither substituent the conversion ~46% under the same heating conditions. Therefore, the thermal stability of the Diels-Alder mechanophore adducts comprising the furan moiety with the 5-OAr (1°) substitution scheme is comparable to the thermal stability of the Diels-Alder adducts comprising the furan moiety with the 3-OPh substitution, and is significantly greater than that of the Diels-Alder adducts comprising the furan moiety with neither substituent.

Accordingly, in many embodiments, the furan moiety of the mechanophore platform is a 2-furylcarbinol derivative, wherein the 2-furylcarbinol scaffold comprises an electron-donating functional group at the 5-position. In some embodiments, the electron-donating functionality at 5-position of the furan moiety is employed by itself, or in any combination of appropriate (as described herein) substituents at α-position and 3-position, to facilitate the release of the cargo molecule with the desired kinetics. In many embodiments, the substituent at the 5-position is a functional group selected from a group consisting of: alkyl, alkenyl, aryl, heteroaryl, any other aromatic or heteroaromatic functional group, alkoxy, aryloxy, amine, sulfide, any other heteroatom-containing group, such as silane, a polymer chain of any composition, and any combination thereof. In many embodiments, the 5-position substituent is aryloxy. In many embodiments, the 5-position substituent also serves as a linker/point for the attachment of the polymer component of the mechanophore platform. In some such embodiments, attaching the polymer via the 5-position substituent increases mechanochemical activity of the mechanophore platform.

In some embodiments, the furan moiety of the mechanophore platform is a 2-furylcarbinol derivative, wherein the 2-furylcarbinol scaffold comprises an electron-donating, or another type of, a functional group at the 4-position. In some such embodiments, the substituent at 4-position of the furan moiety is employed by itself, or in any combination of appropriate (as described herein) substituents at α-position, 3-position, and 5-position, to facilitate the release of the cargo molecule with the desired kinetics. In many embodiments, the substituent at the 4-position is a functional group selected from a group consisting of: alkyl, alkenyl, aryl, heteroaryl, any other aromatic or heteroaromatic functional group, alkoxy, aryloxy, amine, sulfide, any other heteroatom-containing group, such as silane, a polymer chain of any composition, and any combination thereof. In many embodiments, the 4-position substituent is aryloxy. In many embodiments, the 4-position substituent also serves as a linker/point for the attachment of the polymer component of the mechanophore platform.

Figure 11A:
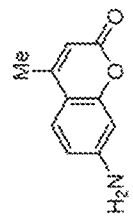
Figure 11A:
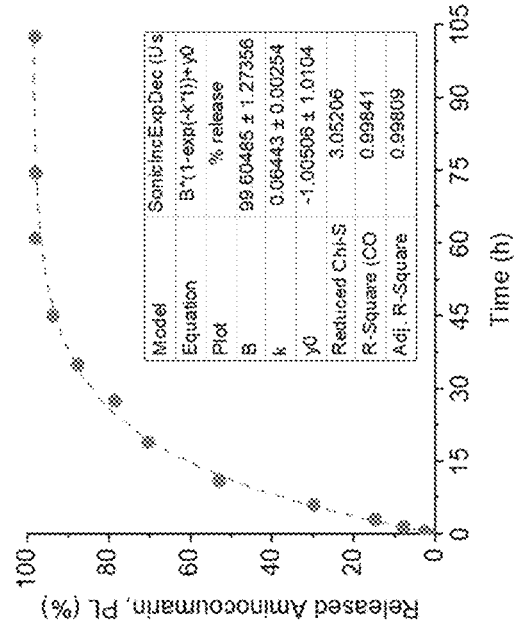
Figure 11A:
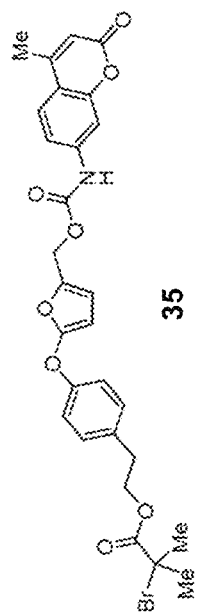
Figure 11A:
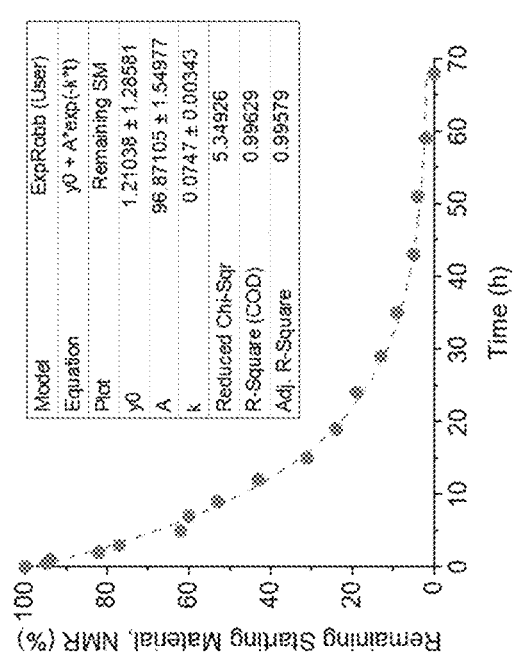

As one example of the suitable furan moiety comprising the synthetically and otherwise advantageous 5-aryloxy substituent of many embodiments, FIGS. 11A through 11 show fluorogenic furfuryl carbamate compound 35, which comprises 5-aryloxy substituent, and provide experimental data illustrating its decomposition reactivity in acetonitrile/methanol (3:1 v/v) at room temperature. Here, the half-life associated with furfuryl carbamate 35 consumption and aminocoumarin generation was determined to be ~10 h by $^1$H NMR and PL spectroscopy, respectively. Notably, in these experiments, aminocoumarin was produced in nearly quantitative yield.

Figure 11B:
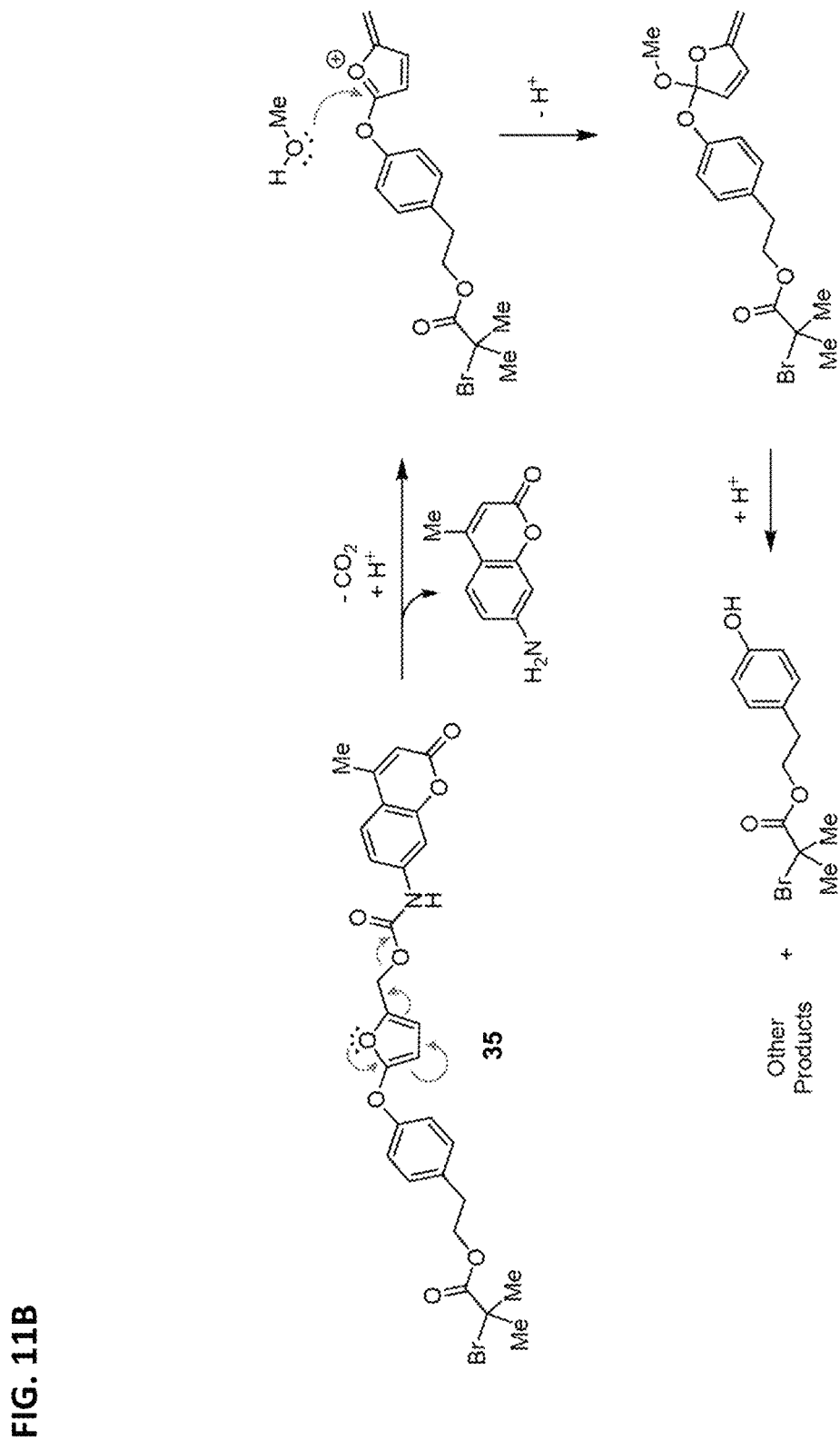
Figure 11C:
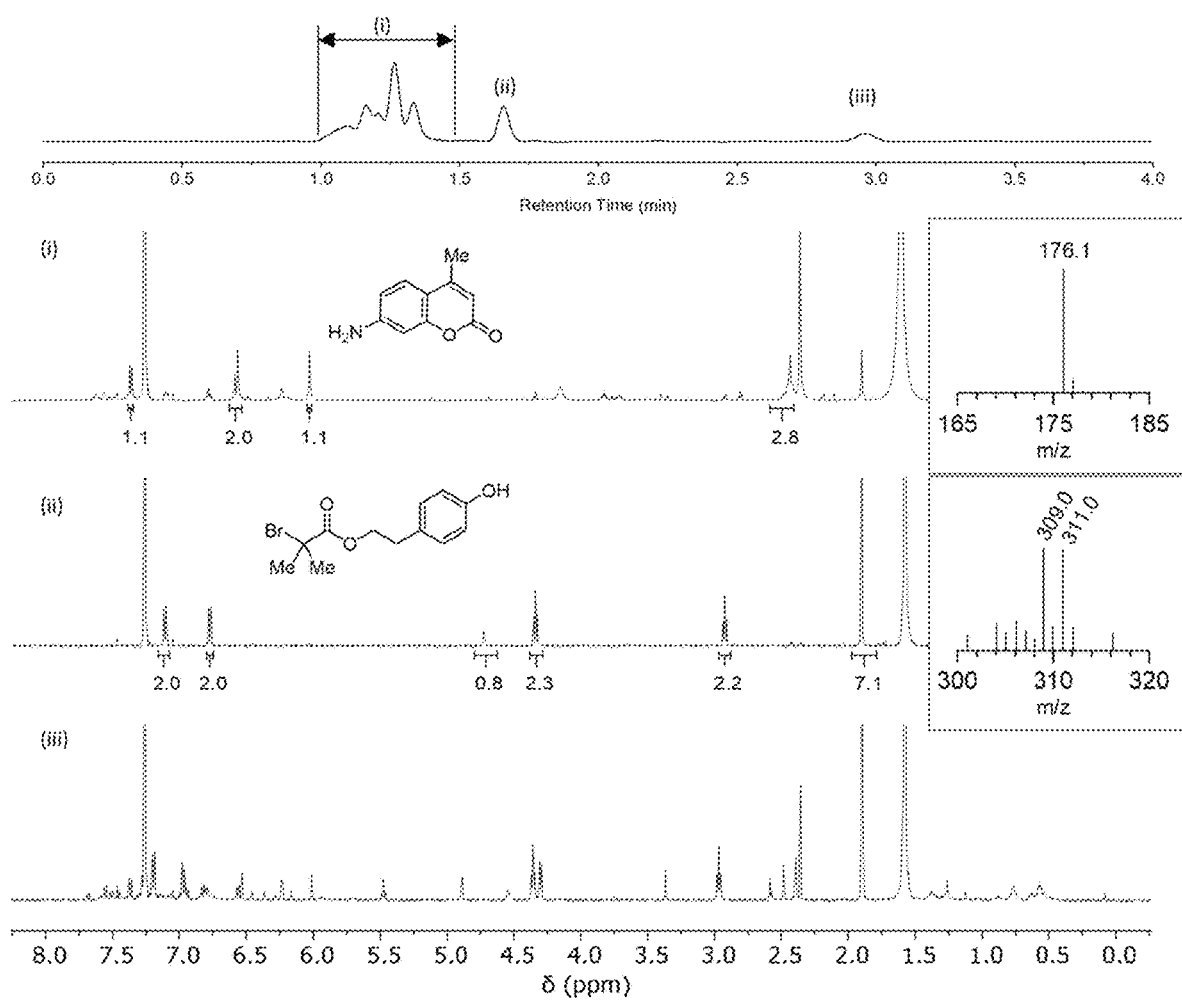

Here, it should be noted that, while 2-furylcarbinol derivatives of many embodiments, wherein the 2-furylcarbinol derivatives comprise 3-H and 3-OPh substituents, as disclosed herein, decompose under the same conditions as used to obtain the data provided in FIG. 11A to produce a furfuryl methyl ether as a major product (thought to be generated by nucleophilic attack of the furfuryl cation intermediate by methanol (as explained, for example, although not to be bound by any theory, in: X. Hu, et al. Am. Chem. Soc., 2019, 141, 15018-15023; and X. Hu, et al. ACS Cent. Sci., 2021, 7, 1216-1224, the disclosures of which are incorporated herein by reference), the decomposition of 35, comprising the 5-aryloxy substituted furfuryl carbamate, appears to generate an alkyl ester tyrosol derivative as the major product, rather than a furfuryl methyl ether. Not to be bound by any theory, it is believed that, as illustrated in FIG. 11B, after the initial fragmentation of the 2-furylcarbinol scaffold of the furan moiety to release the molecule cargo, methanol attacks the 5-position of the furfuryl cation to form an orthoester, which, in turn, closes down to eject the tyrosol fragment. To this end, FIG. 11C illustrates the product analysis of the decomposition of 35 in 3:1 acetonitrile-$d_3$/methanol, showing the preparatory-HPLC trace of the reaction mixture (top), and NMR and mass spectrometry analysis of the isolated product fractions.

In many embodiments, the mechanophore platform comprises the furan-dienophile Diels-Alder adduct covalently embedded into a polymer, such as a single polymer chain or a polymeric network, wherein the attached polymer transmits the applied mechanical force to the mechanophore for activation. In some embodiments, the polymer is selected from, for example, a group consisting of: polyacrylates, including poly(methyl acrylate) (PMA), polymethacrylates, including poly(methyl methacrylate) (PMMA), polysiloxanes, including polydimethylsiloxane (PDMS), polyethers, including poly(ethylene glycol) (PEG), polyurethanes, polyacrylamides, polyamides, polyesters, and any combination thereof. In many embodiments, the polymer is at least two single chains of an approximately same length flanking the mechanophore such that one chain is attached to the portion corresponding to the dienophile moiety of the Diels-Alder adduct, the other chain is attached to the furan moiety of the Diels-Alder adduct, and the overall Diels-Alder adduct is positioned in the center of the whole construct. In such embodiments, application of external force, such as, for example, provided by ultrasonication, produces elongational/tensile forces maximized near the overall chain's midpoint, where the mechanophore Diels-Alder adduct is situated, and, thus, promotes mechanophore activation. In other words, the polymer chains judiciously attached to the Diels-Alder adduct mechanophore according to many embodiments are responsible for transmitting the applied mechanical force to the mechanophore moiety, making it undergo force-induced reactivity and break apart. In some embodiments, more than two polymeric chains are attached to the Diels-Alder adduct, as long as at least one chain is attached to each one—the furan and the dienophile moieties of the mechanophore platform of the instant disclosure. In some embodiments, the mechanophore platform is embedded into a force transmitting polymeric network. In many embodiments, the polymer is attached to the dienophile portion of the Diels-Alder adduct at any available position, including, for example, wherein the dienophile is a maleimide, at the nitrogen atom of the maleimide. In many embodiments, the polymer is attached to the furan moiety of the Diels-Alder adduct at any available or convenient position of the furan moiety's 2-furylcarbinol scaffold, either directly, or via any appropriate linker or linking moiety. In many embodiments, the polymer is attached to the furan moiety at 5-position of the 2-furylcarbinol scaffold, however, in some embodiments, the polymer is attached at any other position of the 2-furylcarbinol scaffold, including: the 4-position, the 3-position, or the α-position. In some embodiments, attaching the polymer at 5-position increases mechanochemical activity of the mechanophore platform. In some embodiments, the polymer is attached only to one of: the furan or the dienophile moieties of the mechanophore platform, while the remaining dienophile or furan moiety is otherwise immobilized, for example, by attachment to a surface.

Any method of mechanical force application can be used for activation of the mechanophore platforms of the instant disclosure, as long as the force can be transduced to the mechanophore with sufficient energy to induce the retro Diels-Alder reaction within the mechanophore and the mechanophore's breakage. In some embodiments, the mechanical force is provided by means of ultrasonication and is transduced to the Diels-Alder adduct moiety via the mechanophore's polymer chains flanking the Diels-Alder adduct. In some embodiments, the force is transmitted to the mechanophore embedded within a polymeric material via deformation of the polymeric material. In some such embodiments, the methods of deformation may include application of: tension, compression, shearing, stretching, grinding, and any combination thereof.

Figure 12:
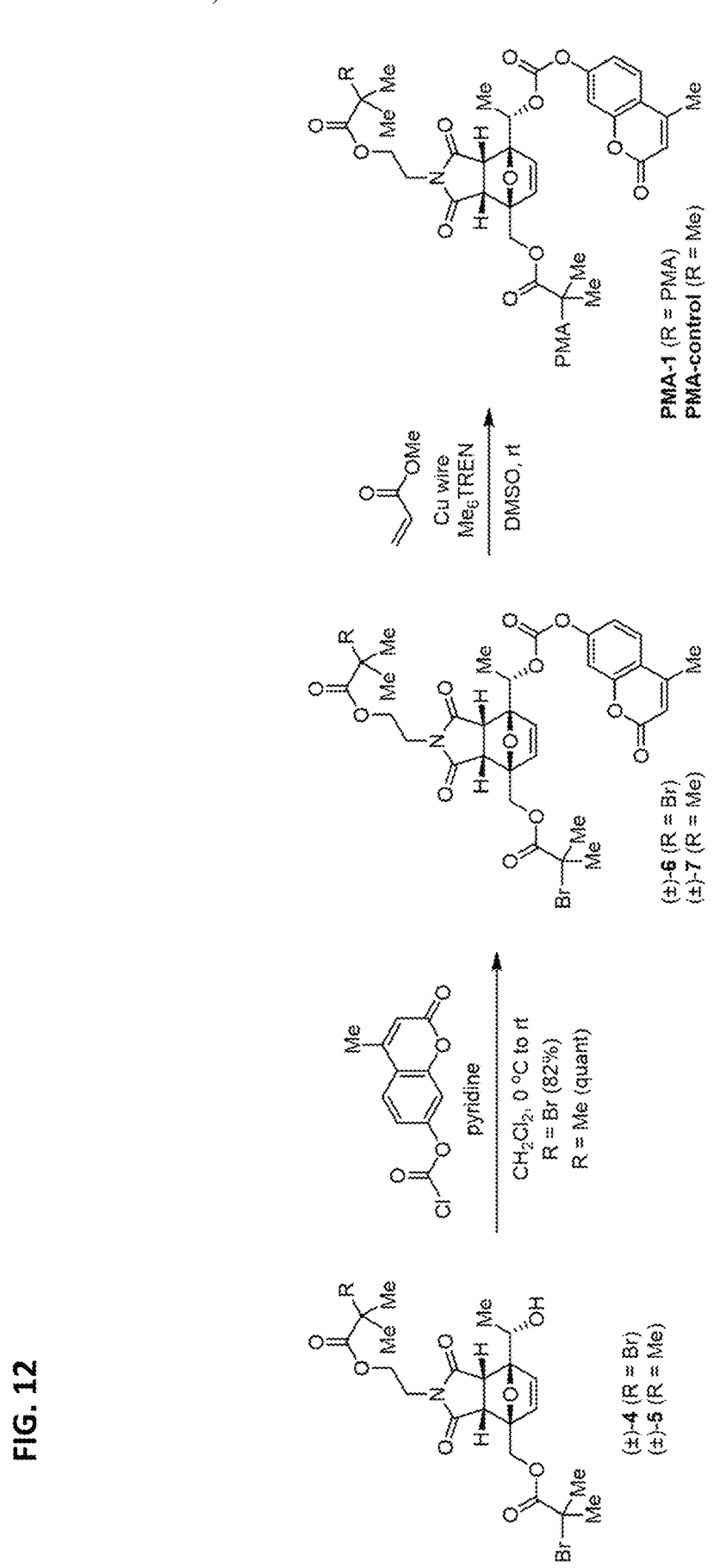
FIG. 12 illustrates a synthetic route that can be used to obtain the mechanophore platform comprising the poly (methyl acrylate) (PMA) chain-centered furan-maleimide Diels-Alder adduct, wherein the furan moiety comprises α-methyl substituent, and wherein the mechanophore platform is covalently pre-loaded (via the furan moiety) with a fluorogenic coumarin probe as the cargo molecule; as well as to obtain the same Diels-Alder adduct at the PMA chain's end for experimental controls, in accordance with embodiments of the invention.

FIG. 12 provides an example of the mechanophore platform for cargo molecule release of many embodiments, as well illustrates a synthetic route that can be used to obtain such compounds according to some embodiments. In this particular example, but according to many embodiments, furan-maleimide adduct (1)-4 equipped with two α-bromo-ester initiating sites and a modular alcohol functional group for the cargo molecule attachment was first prepared on gram scale in four steps from commercially available reagents. Notably for this example, starting from a racemic mixture of α-methyl-furfuryl alcohol resulted in four diastereomeric Diels-Alder adducts. However, although both endo and exo isomers exhibited mechanochemical reactivity in an initial screening, as expected from previous studies of furan-maleimide mechanophores, one particular endo racemate shown in FIG. 12 was selected for further experiments in this illustrative example. Nevertheless, in many embodiments, the particular isomers or stereoisomers or any mixtures thereof are chosen according to the intended application needs and limitations. The absolute configuration of the Diels-Alder adduct was confirmed by single crystal X-ray diffraction. Precursor (±)-4 was converted to mechanophore bis-initiator (±)-6 via installation of the fluorogenic coumarin payload (i.e., the cargo molecule) by reaction with the corresponding chloroformate, and then subsequently employed in the controlled radical polymerization of methyl acrylate using Cu wire/Me$_6$TREN in DMSO to afford polymer PMA-1 ($M_n$=100 kg/mol; Đ=1.06), wherein the Diels-Alder adduct mechanophore is centered on the PMA polymer chain. Control polymer PMA-control ($M_n$=86 kg/mol; Đ=1.14), with Diels-Alder adduct attached to only one polymer chain's end, was synthesized according to similar procedures, starting from (±)-5, which comprises a single α-bromo-ester initiating group.

Figure 13:
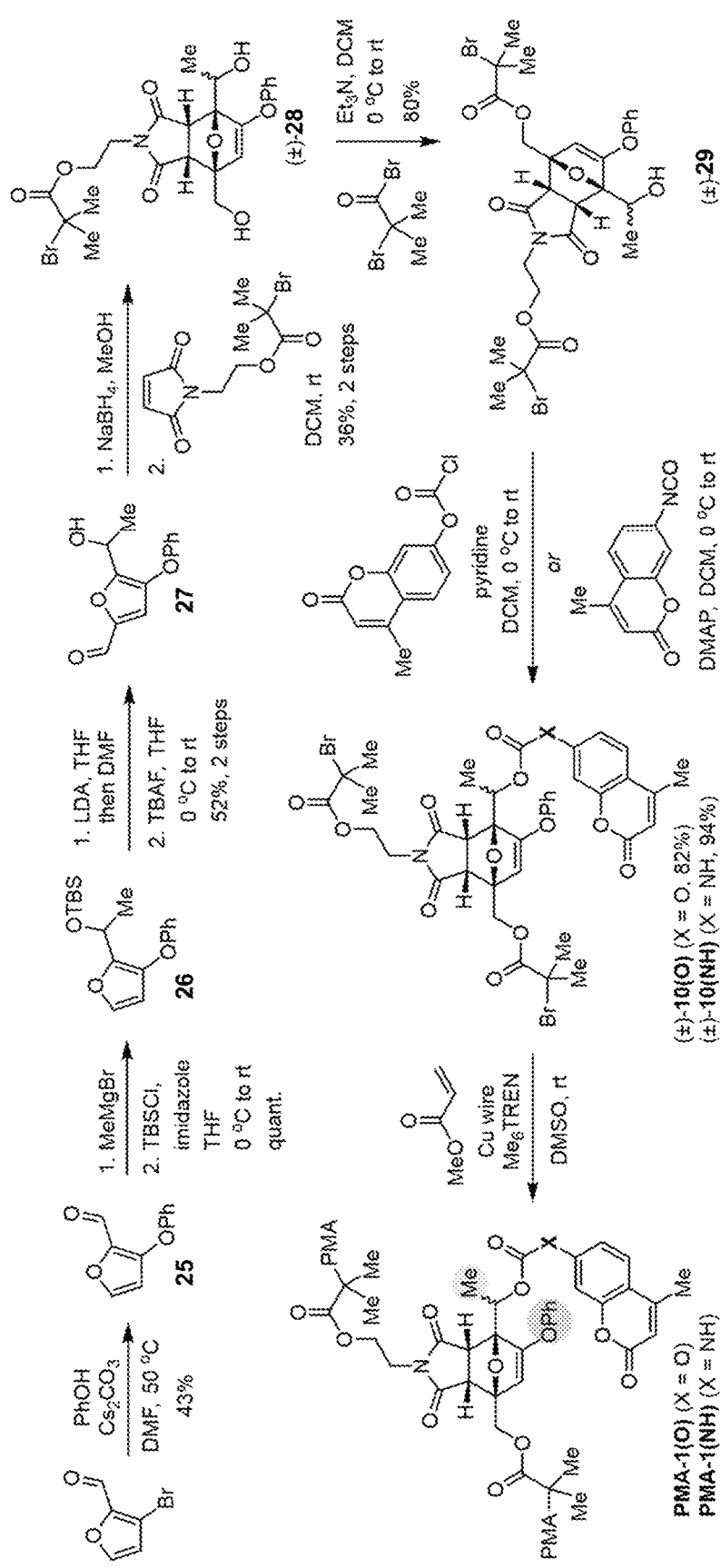
FIG. 13 illustrates a synthetic route that can be used to obtain the mechanophore platform comprising the poly (methyl acrylate) (PMA) chain-centered furan-maleimide Diels-Alder adduct, wherein the furan moiety comprises α-methyl and 3-phenoxy substituents, and wherein the mechanophore platform is covalently pre-loaded (via the furan moiety) with a fluorogenic coumarin probe as the cargo molecule, in accordance with embodiments of the invention.

Furthermore, FIG. 13 provides yet another example of the mechanophore platform for cargo molecule release of many embodiments, as well illustrates synthetic routes that can be used to obtain such compounds according to some embodiments. In these particular examples, but according to many embodiments, furan-maleimide Diels-Alder adducts of the instant disclosure, wherein the masked furfuryl carbonate or furfuryl carbamate comprises the 3-phenoxy substituent, were synthesized and incorporated into their respective polymers to demonstrate their mechanochemical behavior. Here, starting from 3-bromo-furfural, a phenoxy group was installed via a nucleophilic substitution reaction with phenol, followed by Grignard addition and protection to yield furfuryl silyl ether 26. Next, a formylation reaction and subsequent desilylation with TBAF yielded 2,3,5-trisubstituted furfuryl alcohol 27. Reduction of the aldehyde with sodium borohydride and a [4+2] cycloaddition reaction with a pre-functionalized maleimide dienophile in a two-step sequence furnished an isomeric mixture of Diels-Alder adducts, from which endo diastereomer (±)-27 was isolated in these particular experiments by silica gel chromatography. Esterification of the primary alcohol proceeded with reasonable selectivity using α-bromo-isobutyryl bromide to produce the modular bis-initiator (±)-29 comprising the secondary alcohol for cargo molecule attachment. The precursor bis-initiator (±)-29 was then conveniently elaborated to carbonate (±)-10(O) and carbamate (±)-10(N) comprising fluorogenic coumarin payloads via reaction with the corresponding chloroformate or isocyanate, respectively. After a cargo molecule installation, the bis-initiators were employed in the controlled radical polymerization of methyl acrylate with Cu wire/Me$_6$TREN in DMSO (as explained, for example, in Nguyen, N. H.; et al. Surface-Dependent Kinetics of Cu(0)-Wire-Catalyzed Single-Electron Transfer Living Radical Polymerization of Methyl Acrylate in DMSO at 25° C. Macromolecules 2009, 42, 2379-2386, the disclosure of which is incorporated herein by reference) to afford poly(methyl acrylate) (PMA) polymers PMA-1(O) and PMA-1(N) comprising the polymer chain-centered mechanophore platform of many embodiments. In many embodiments, the analogous synthetic approach is utilized to prepare mechanophore platforms with differing furan moiety substitution schemes, such as, for example PMA-2(X) (1°, 3-OPh)—i.e., the mechanophore platform comprising the furan moiety with 3-OPh and no substitution at α-position, and wherein X is O or N, and PMA-3(X) (2°, 3H)—i.e., the mechanophore platform comprising the furan moiety with α-methyl substitution and no substitution at 3-position, and wherein X is O or N. The structure of each mechanophore platform/polymer prepared according to the synthetic instructions provided herein for use as illustrative examples of many embodiments is further illustrated in FIG. 14, along with the number average molecular weight ($M_n$) for each (determined to be in the range 94.7-102 kDa with Đ≤1.06 by gel permeation chromatography (GPC) equipped with a refractive index and multiangle light scattering detector). In addition, control polymers, wherein the corresponding Diels-Alder adducts were attached to only one polymer chain's end, were also synthesized according to the similar procedures, starting from the masked furfuryl carbonates/carbamates comprising a single α-bromo-ester initiating group.

Figure 15:
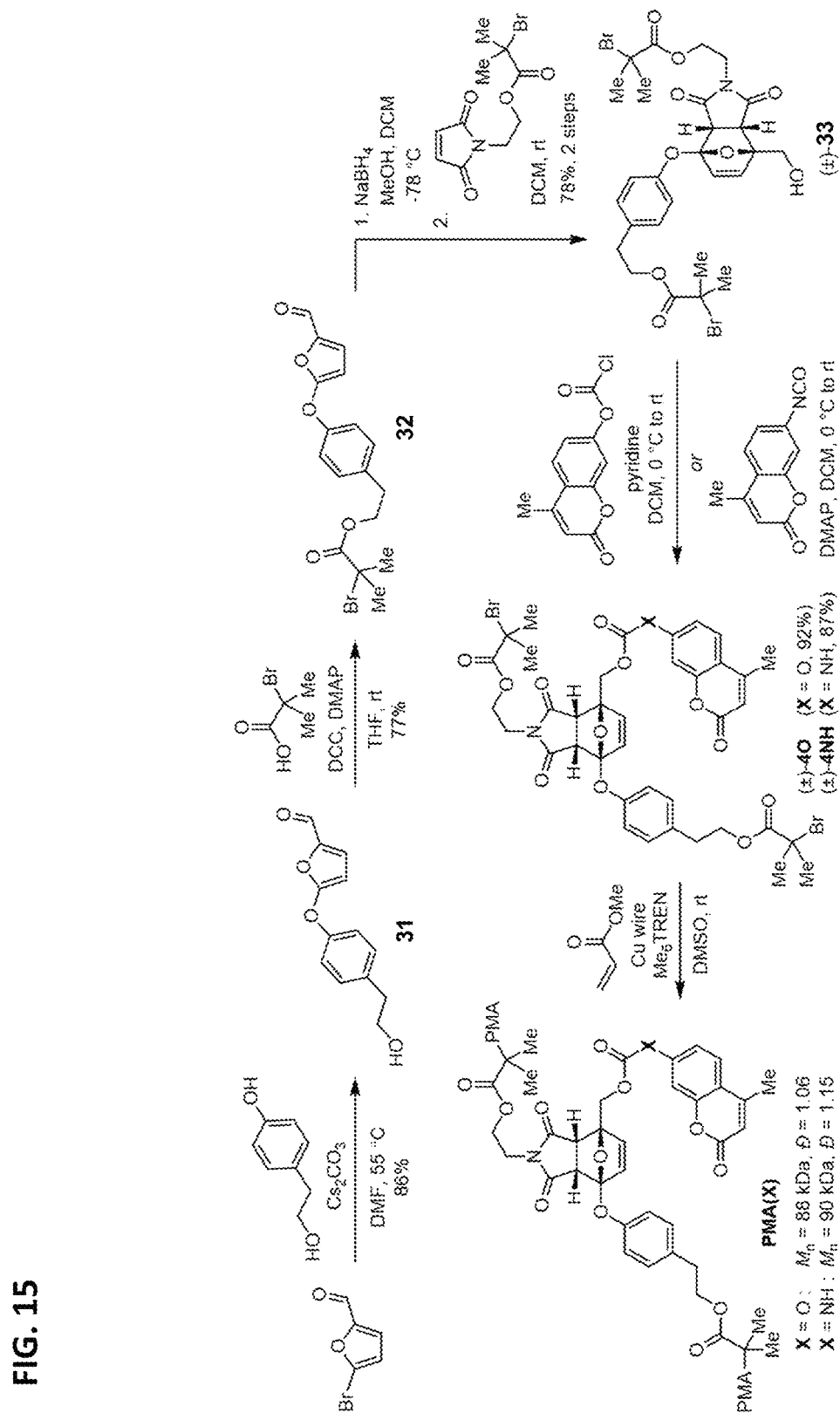
FIG. 15 illustrates a synthetic route that can be used to obtain the mechanophore platform comprising the poly (methyl acrylate) (PMA) chain-centered furan-maleimide Diels-Alder adduct, wherein the furan moiety comprises 5-aryloxy substituent, and wherein the mechanophore platform is covalently pre-loaded (via the furan moiety) with a fluorogenic coumarin probe as the cargo molecule, in accordance with embodiments of the invention.

Moreover, FIG. 15 provides another example of the mechanophore platform for cargo molecule release of many embodiments, as well illustrates synthetic routes that can be used to obtain such compounds according to some embodiments. In these particular examples, but according to many embodiments, the synthesis of the mechanophore platform comprising the furan moiety with the 5-OAr substitution of the 2-furylcarbinol scaffold is accomplished in only four steps from commercially available reagents. More specifically, here, furaldehyde derivative 31 was first established by a nucleophilic substitution reaction between tyrosol and 5-bromofurfural using Cs$_2$CO$_3$ as the base in 86% yield, which represents a two-fold yield improvement, as compared to the installation of phenoxy group at the 3-position of the furan moiety of some embodiments. Furthermore, esterification by DCC coupling with α-bromo-isobutyric acid produced 32 in 77% yield. This furaldehyde was then reduced with NaBH4 at −78° C., which was necessary to avoid reduction of the ester, and, subsequently, reacted with a pre-functionalized maleimide dienophile at room temperature to form endo-Diels-Alder adduct bis-initiator (±)-33. Under these conditions, endo:exo stereoselectivity was ~97:3 and achieved an overall yield of 78% over the two steps. Next, the installation of hydroxycoumarin or aminocoumarin cargo molecules proceeded efficiently via reaction of the primary alcohol on (±)-33 with the corresponding chloroformate or isocyanate to yield mechanophore bis-initiators (±)-40 and (±)-4NH, respectively. The bis-initiators were then employed in the controlled radical polymerization of methyl acrylate using Cu wire/Me$_6$TREN in DMSO to give PMA(O) ($M_n$=88 kg/mol; Đ=1.06) and PMA(NH) ($M_n$=90 kg/mol; Đ=1.15) incorporating the corresponding Diels-Alder adducts near the polymer chain midpoint. Notably, in many embodiments, wherein the furan moiety of the mechanophore platform comprises 5-OAr substituent, such as represented, for example, by compounds PMA(O) and PMA(NH), the aryl moiety of the 5-position substituent also conveniently serves as a linker/attachment point for the attachment of the polymer component. The control analogs, wherein the corresponding Diels-Alder adducts were situated at a single polymer chain's end, were also prepared according to the similar procedure of many embodiments to give PMA(O)-control ($M_n$=80 kg/mol; Đ=1.21) and PMA(NH)-control ($M_n$=85 kg/mol; Đ=1.22). Accordingly, in many embodiments, the synthesis of the mechanophore platforms comprising a 5-OAr substituted furan moiety is straightforward and efficient. In many embodiments, the mechanophore platforms comprising the 5-OAr substituted furan moiety offer efficient release of the cargo molecule, including challenging cargo molecules, such as, for example, amines.

Figure 16A:
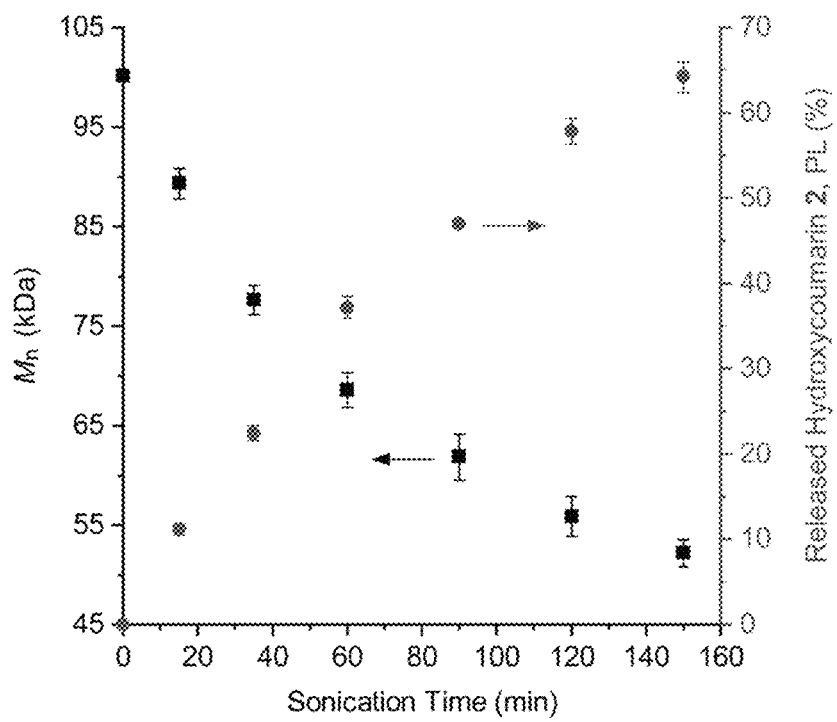
FIGS. 16A through 16D illustrate mechanically triggered cargo molecule release from PMA-1 mechanophore platform, and compare it to the performance of mechanochemically inactive PMA-control under the same conditions, wherein FIG. 16A provides data for time-dependent evolution of number-average molecular weight (Mn) monitored by GPC-MALLS, as well as for the release of 2 monitored using fluorescence spectroscopy for PMA-1 subjected to ultrasound-induced mechanochemical activation (2 mg/mL polymer in 3:1 MeCN:MeOH), $\lambda_{ex}$=330 nm (error bars representing standard deviation from three replicate experiments)
Figure 16B:
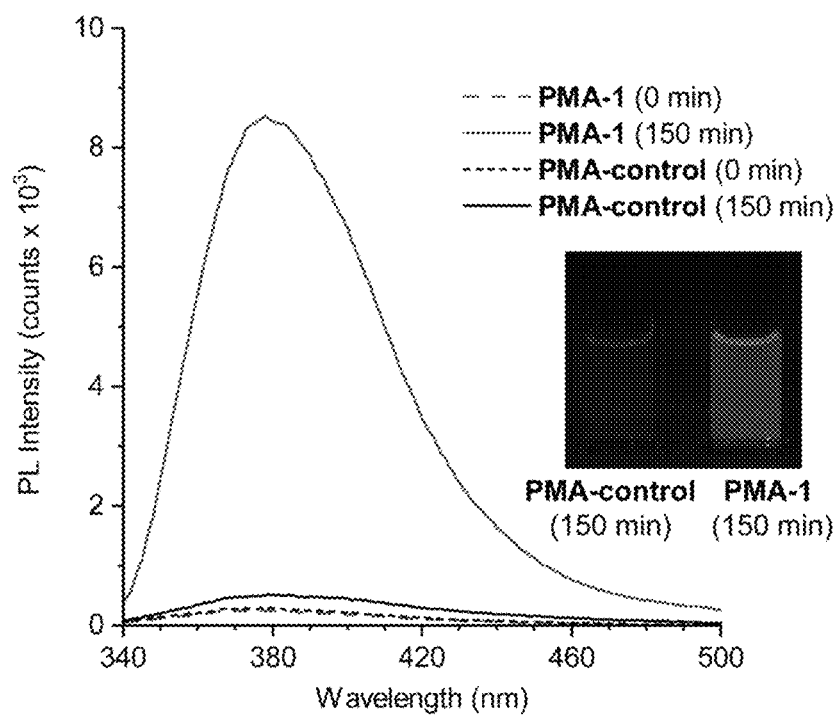
Figure 16C:
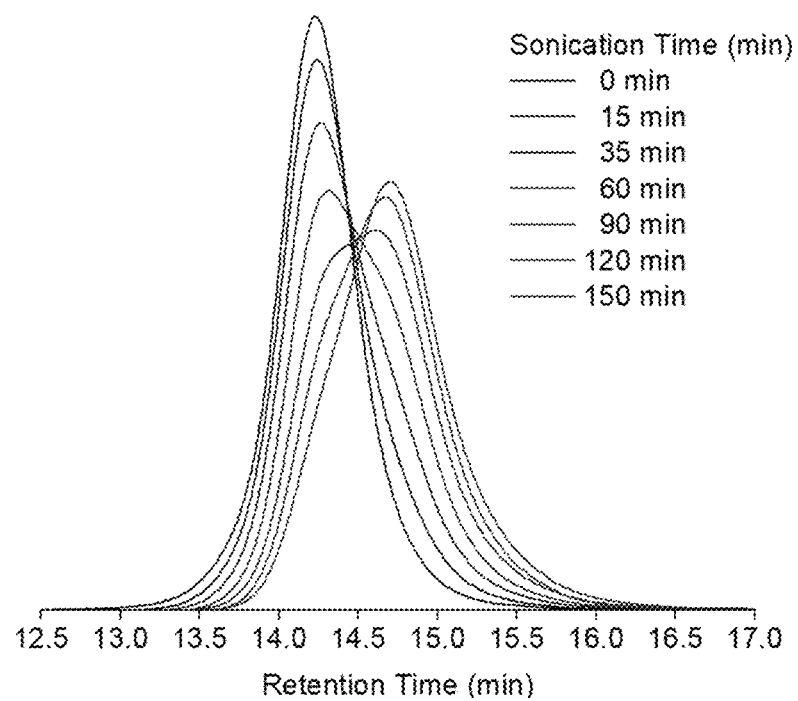
Figure 16D:
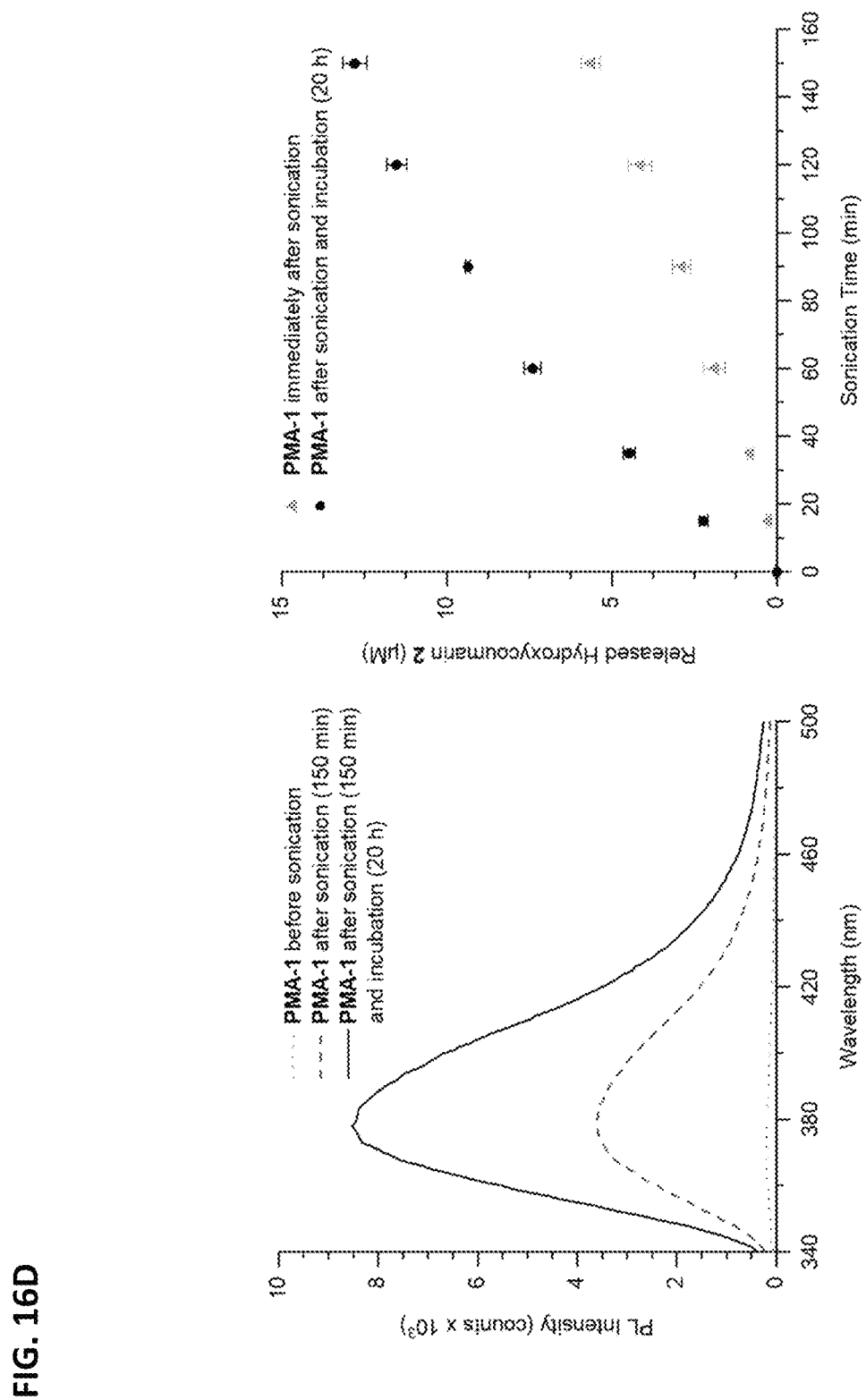

In many embodiments, application of mechanical force, such as, for example, produced by ultrasonication of a solution comprising the mechanophore platform of the instant disclosure, induces mechanochemical activation of the mechanophore platform to reveal the unstable furan moiety, which, next, easily decomposes with the release of its covalently pre-installed cargo molecule. As one example of many embodiments, FIGS. 16A and 16B illustrate the mechanically triggered release of a cargo molecule (hydroxycoumarin 2) from PMA-1 (FIG. 12) into a polar protic solvent at room temperature, wherein pulsed ultrasonication (1 s on/2 s off, 0° C., 20 kHz, 8.2 W/cm$^2$) was used for the mechanical actuation of PMA-1 mechanophore platform. For the experiments illustrated in FIGS. 16A and 16B, the same polar protic solvent mixture of methanol in acetonitrile was employed as in the experiments illustrated by FIGS. 3A-3E, and aliquots were periodically removed from the sonicated polymer solution comprising PMA-1, and measured with GPC to determine changes in molecular weight (FIG. 16A) and fluorescence spectroscopy to monitor the generation of hydroxycoumarin 2 (FIG. 16B). In these illustrative experiments, the $M_n$ of PMA-1 decreased steadily over 150 min of ultrasonication, with the GPC chromatograms exhibiting the characteristic features of site-selective midchain scission (FIGS. 16A and 16C). Moreover, the photoluminescence of the solution of PMA-1 subjected to ultrasound-induced mechanochemical activation also showed a predictable increase in intensity indicating the successful release of hydroxycoumarin 2, reaching approximately 64% of the theoretical yield after 150 min (FIG. 16A). Furthermore, the fluorescence data presented in FIG. 16B was acquired after incubating each aliquot at room temperature for approximately 20 h to ensure complete decomposition of the mechanically generated furfuryl carbonate. However, PL measurements taken immediately after sample removal from the sonicated solution exhibited appreciable fluorescence, indicating that a significant degree of release occurred quickly, even at lower temperatures (FIG. 16D). Importantly, control polymer PMA-control subjected to the same ultrasonication conditions exhibits negligible changes in fluorescence compared to PMA-1 (FIG. 16B). These results indicate that ultrasound-induced release of 2 from PMA-1 is indeed a mechanochemically triggered cascade reaction process, proceeding according to many embodiments of the instant disclosure.

Figure 14:
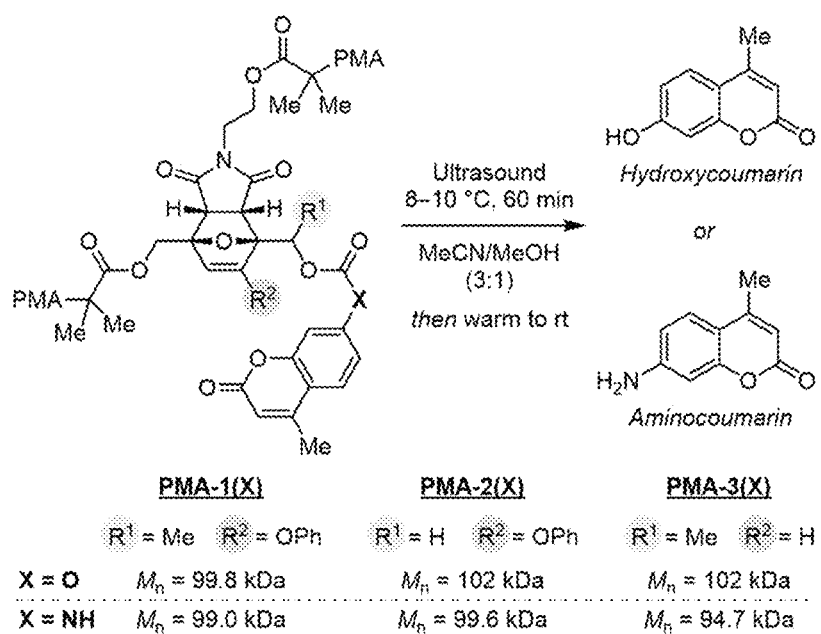
FIG. 14 illustrates ultrasound-induced mechanical activation of the mechanophore platforms comprising variously substituted furan moieties to release fluorescent hydroxycoumarin or aminocoumarin cargo molecules, in accordance with embodiments of the invention.
Figure 17A:
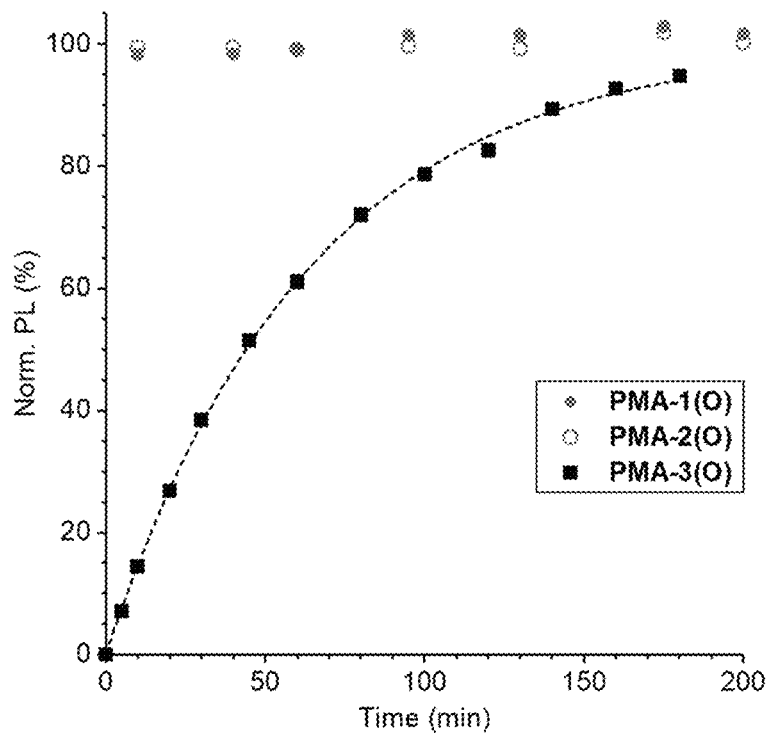
Figure 17B:
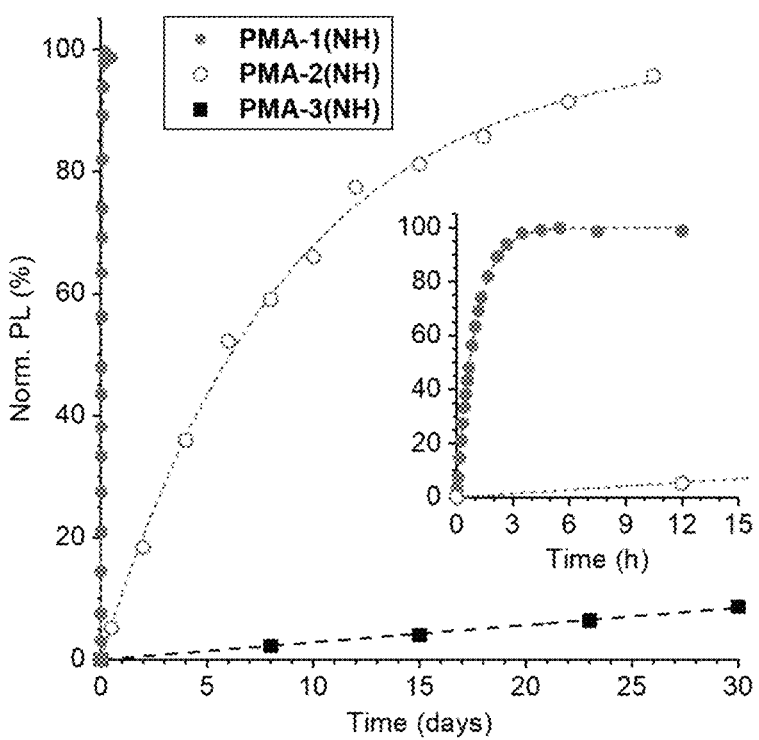

FIGS. 14, 17A and 17B provide additional examples of mechanophore platforms of many embodiments capable of mechanically triggered release of various cargo molecules with diverse functionalities, and further illustrate their cargo releasing capabilities. To this end, FIGS. 17A and 17B provide data illustrating mechanically triggered release of hydroxycoumarin or aminocoumarin from respective PMA-1(X)-PMA-3(X) mechanophore platforms of many embodiments upon pulsed ultrasonication (1 s on/1 s off, 0° C., 20 kHz, 8.2 W/cm2) in 3:1 MeCN/MeOH, according to the decomposition process of many embodiments illustrated in FIG. 14. More specifically, the photoluminescence spectroscopy data provided in FIGS. 17A and 17B demonstrates the impact that different furan moiety substitution schemes involving α-methyl and 3-OPh substituents have on the rate of release of cargo molecules with different functionalities. To obtain the data presented in FIGS. 17A and 17B, each solution comprising a particular mechanophore platform was subjected to ultrasonication for 60 min, and then allowed to warm to room temperature, with fluorescence monitoring over time. As such, FIG. 17A provides kinetic data for the release of hydroxycoumarin from PMA-1(O)-PMA-3(O), while FIG. 17B provides the same data for the release of aminocoumarin from PMA-1(N)-PMA-3(N). Here, for clarity and to account for slight differences in average polymer molecular weight and dispersity that influence the extent of mechanophore platform conversion during ultrasonication (for additional examples, see May, P. A.; et al. Is Molecular Weight or Degree of Polymerization a Better Descriptor of Ultrasound-Induced Mechanochemical Transduction? ACS Macro Lett. 2016, 5, 177-180, the disclosure of which is incorporated herein by reference), the initial fluorescence intensity (t=0) is subtracted from each measurement and the data are normalized to emphasize the relative rates of molecular release. Accordingly, as seen from FIG. 17A, the fluorescence emission from solutions comprising PMA-1(O) and PMA-2(O) reached a maximum prior to the first measurement and remained essentially constant over time, indicating that the release of hydroxycoumarin from both primary and secondary furfuryl carbonates comprising the 3-phenoxy substituent completed nearly instantaneously upon formation ($t_{1/2}$<5 min). These results are contrasted by the release of hydroxycoumarin from mechanically activated PMA-3(O) (i.e., PMA-1, which has no-3-phenoxy substituent on its furan moiety), which occurs steadily and predictably over several hours post-activation. Fitting the time-dependent photoluminescence data for the release of hydroxycoumarin from PMA-3(O) to a first-order rate expression gives an estimated half-life for the decomposition of its secondary furfuryl carbonate of 46 min (average of two trials).

Furthermore, the data in FIG. 17B, for the mechanically activated release of aminocoumarin from PMA-1(N)-PMA-3(N) according to many embodiments, provides an even clearer demonstration of the impact of the 3-OPh substituent on the kinetics of the furfuryl carbamate decomposition and the cargo molecule release, wherein the reaction half-lives span four orders of magnitude. More specifically, here, the time-dependent photoluminescence of the sonicated solution of PMA-1(N) is described by a first-order rate expression and reaches a maximum intensity after approximately 4 h post-activation, corresponding to the release of aminocoumarin with an average half-life of 41 min from two replicate experiments. Not to be bound by any theory, this remarkably fast release from the secondary furfuryl carbamate comprising the 3-phenoxy substituent is consistent with the substantially diminished activation energy calculated by DFT for corresponding model substrate FC1(N). In comparison, the mechanically activated release of aminocoumarin from PMA-2(N), which comprises a masked primary furfuryl carbamate with a 3-phenoxy substituent, but no α-methyl, is over 200× slower with an average half-life of 6.5 days, again highlighting the stabilizing effect of the furan moiety's α-methyl substituent. Moreover, for PMA-3(N), which comprises α-methyl substituent, but no 3-phenoxy substituent, only 8% release of aminocoumarin was observed after 30 days post-activation (assuming mechanophore conversion of 36%, as determined previously for similar masked furfuryl carbonate under nearly identical conditions. Accordingly, the time-dependent photoluminescence data for release of aminocoumarin from PMA-3(N) falls on the line for a first-order reaction with a half-life of approximately 240 days.

The table provided in FIG. 17C summarizes the analysis of the data provided in FIGS. 17A and 17B, and further illustrates the effect that certain furan moiety's substituents have on the kinetics of the cargo molecule release, according to many embodiments. Notably, this table also shows that the yield of hydroxycoumarin or aminocoumarin released from each studied mechanophore platform, with the exception of PMA-3(N), was 34-39% relative to the mechanophore concentration in each experiment, which is consistent with the anticipated mechanophore conversion. Together, the data from FIGS. 14, and 17A through 17C illustrates that, in many embodiments, the rate of the cargo molecule release from the mechanically triggered mechanophore platforms of the instant disclosure can be controlled by fine-tuning the molecular structure of the masked furan moiety of their corresponding Diels-Alder adduct. In some embodiments, the mechanophore platform comprising the masked secondary 2-furylcarbinol derivative comprising 3-phenoxy group offers enhanced potential for fast release of chemically diverse cargo molecules.

Figure 18A:
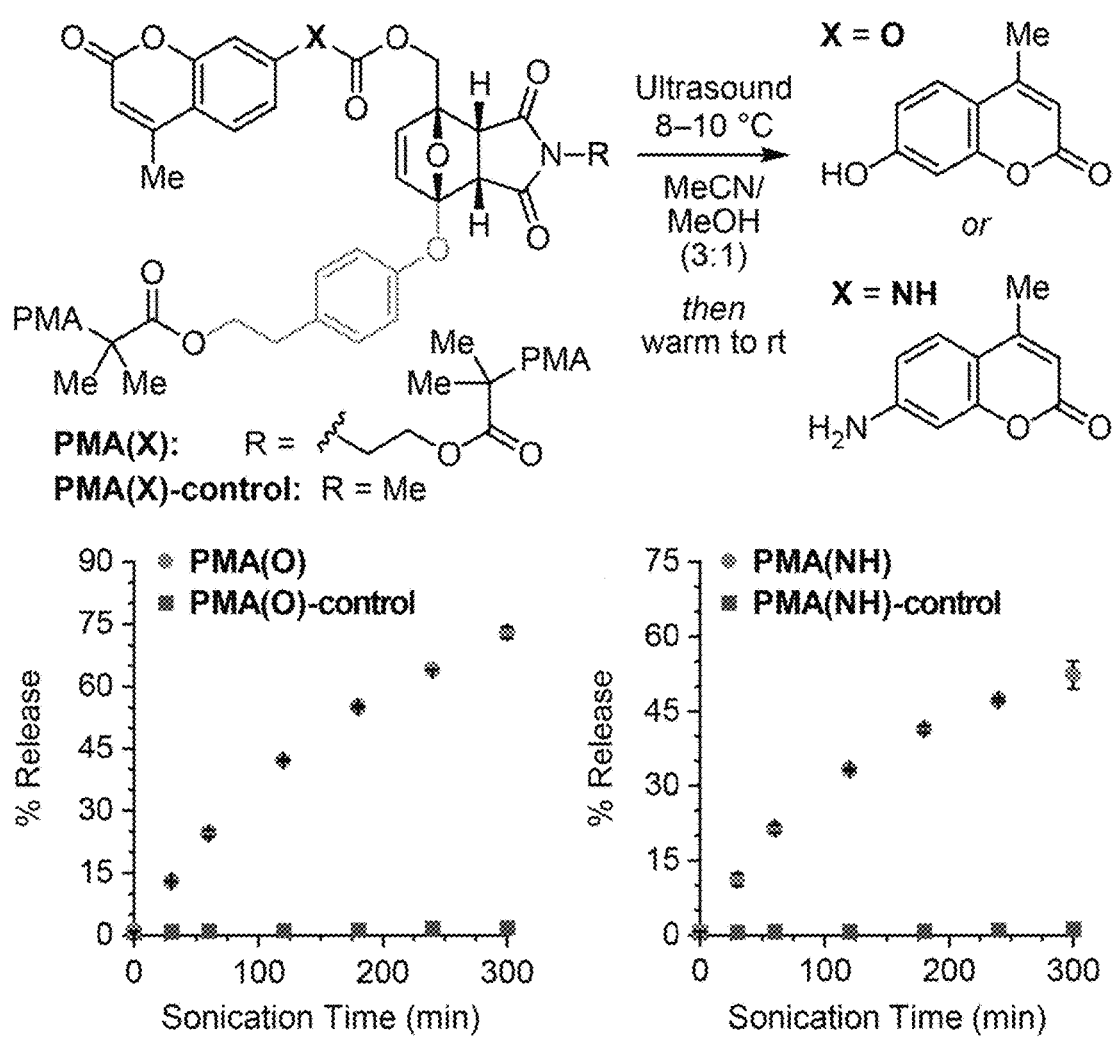
FIGS. 18A through 18C illustrate mechanically triggered cargo molecule release from the mechanophore platforms comprising 5-OAr substituted furan moiety, and compare it to the performance of the mechanochemically inactive control polymers under the same conditions, wherein FIG. 18A schematically shows (top) the studies process of the mechanically triggered release of hydroxycoumarin and aminocoumarin from PMA(X) and PMA(X)-control upon ultrasound activation (2 mg/mL in 3:1 acetonitrile/methanol); provides data showing the total percent release of hydroxycoumarin (bottom left) and aminocoumarin (bottom right) as a function of sonication time, as determined by PL spectroscopy after incubation at room temperature post-activation, wherein the error bars denote the range of two measurements; while FIGS. 18B and 18C provide GPC traces as a function of ultrasonication time for PMA(O) and PMA(NH), respectively, monitored using a UV-vis detector (λ=322-338 nm) (left in each figure) and refractive index (RI) detector (right in each figure), wherein the measurements were performed after incubation at room temperature for 30 mins and 3 days post-sonication, for PMA(O) and PMA(NH) respectively; wherein the growth of the small molecule peak at an elution time of ~20 min in the UV-detected chromatograms is indicative of hydroxycoumarin or aminocoumarin (respectively) generation; and wherein, for PMA(O), the $M_n$ decreases steadily from 88 kg/mol to 49 kg/mol over 300 min of ultrasonication, with the GPC-RI chromatograms exhibiting characteristic features of mid-chain scission, while for PMA(NH), the $M_n$ decreases steadily from 90 kg/mol to 50 kg/mol over 300 min of ultrasonication, with the GPC-RI peaks shifting continuously to longer retention times without the characteristic features of midchain scission (wherein such behavior is attributed, at least in part, to the broader molecular weight distribution of PMA(NH) (Đ=1.15) and greater competition between mechanophore activation and nonspecific backbone scission); and wherein the GPC-RI chromatograms for the unactivated PMA(X) (0 min) was acquired separately, resulting in slight differences in retention time—all in accordance with embodiments of the invention.
Figure 18B:
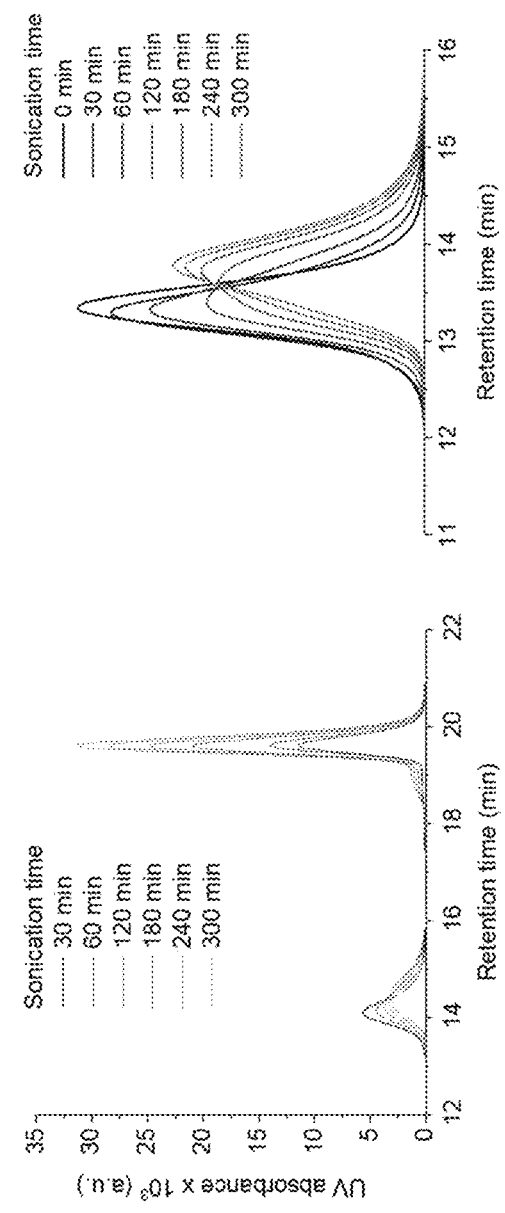
Figure 18C:
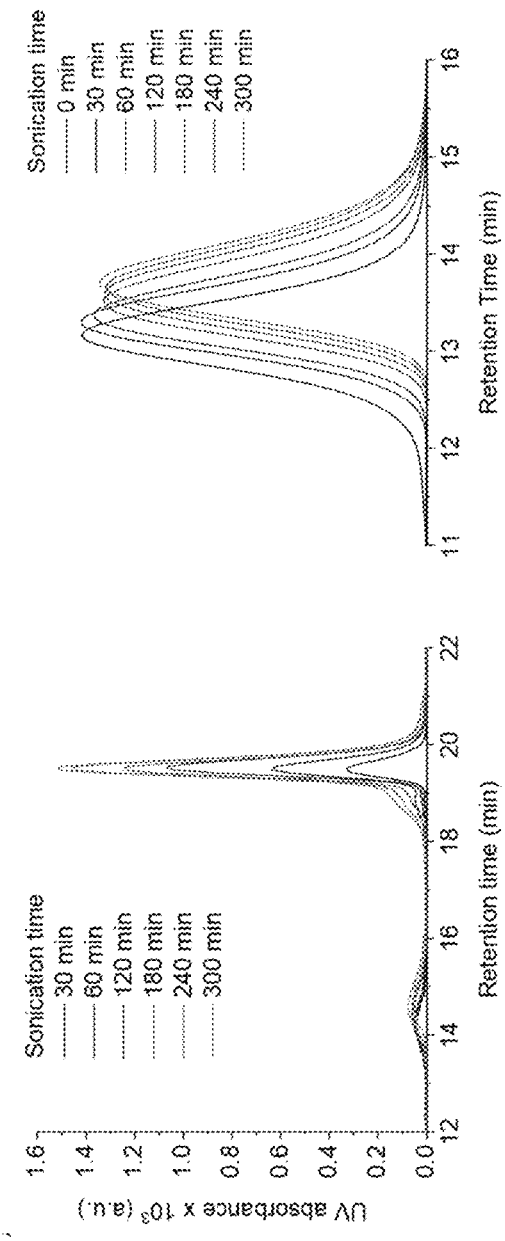

Moreover, FIGS. 18A through 18C provide additional examples of mechanophore platforms of many embodiments capable of mechanically triggered release of various cargo molecules and illustrates their mechanochemical reactivity. More specifically, FIGS. 18A-18C provide data illustrating mechanically triggered release of coumarin molecule cargo from the mechanophore platform comprising, according to some embodiments, the furan moiety with 5-OAr substituent and no α-substituent (i.e., 5-OAr(1°) substitution pattern of the furan moiety) upon ultrasonication. To collect this data, mechanophore platforms PMA(O) and PMA(NH) (FIG. 15) were subjected to pulsed ultrasound (1 s on/1 s off, 8-10° C., 20 kHz, 30% amplitude, 8.2 W/cm$^2$) in acetonitrile/methanol (3:1 v/v), and their corresponding solution aliquots were periodically removed for characterization by GPC and photoluminescence (PL) spectroscopy. Furthermore, each aliquot was kept at room temperature for a period of time prior to analysis to allow complete decomposition of the mechanically generated 2-furylcarbinol derivative, wherein for the furfuryl carbonate derived from PMA(O) required 30 min to complete its decomposition, while the furfuryl carbamate derived from PMA(NH) required 3 days for the same process (vide infra). Here, again, the fluorogenic response of the released coumarin cargo facilitates the straightforward determination of molecular cargo release using PL spectroscopy. Accordingly, FIG. 18A shows that increasing exposure of PMA(O) and PMA(NH) to ultrasonication produces predictable increase in cargo release, reaching approximately 70% and 51% of the theoretical yield after 300 min of sonication "on" time for hydroxycoumarin and aminocoumarin cargo, respectively. Furthermore, fitting the sonication time-dependent release data to a first-order rate expression, predicts the maximum release reaching 92% from PMA(O) and 58% from PMA(NH). In addition, corresponding GPC measurements provided in FIGS. 18B and 18C, wherein an in-line UV detector (left plots in both figures) and a refractive index (RI) detector (right plots in both figures) were used for sample analysis, also indicate the increasing production of small molecules consistent with the coumarin cargos, as well as the expected decrease in molecular weight over the course of the sonication experiments. Notably, while attenuation of the original polymer (i.e., the original mechanophore platform) peak and generation of a new lower molecular weight peak characteristic of mid-chain scission is observed for the ultrasound-induced mechanical activation of PMA(O), a more continuous shift in average molecular weight is observed upon ultrasonication of PMA(NH). Not to be bound by any theory, these differences in decomposition behavior can be attributed to the broader molecular weight distribution of original PMA(NH), which may also be responsible, at least in part, for the lower mechanophore activation efficiency, as compared to PMA(O) (see, for example, Z. S. Kean, et al., Chem. Commun., 2015, 51, 9157-9160, the disclosure of which is incorporated herein by reference). In fact, experiments performed on an isolated furfuryl carbamate 35 (shown FIG. 11A) demonstrate nearly quantitative release of aminocoumarin under similar conditions as those in the instant sonication experiments with the fully assembled mechanophore platforms, implicating the mechanical activation step as a bottleneck for decomposition of PMA(NH). Nevertheless, no cargo release was observed upon ultrasonication of the control polymers PMA(O)-control and PMA(NH)-control, which comprise the corresponding Diels-Alder adducts attached to single chain's ends, confirming the mechanical origin of molecular cargo release from PMA(O) and PMA(NH).

Figure 19A:
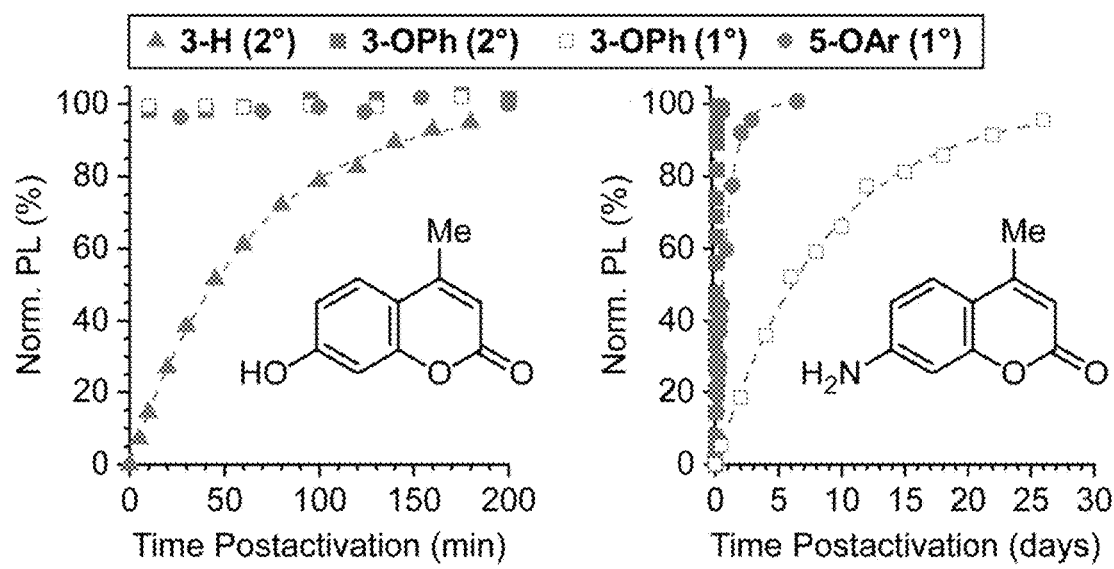
FIG. 19A provides data that compares mechanically triggered release of hydroxycoumarin (left) and aminocoumarin (right) from the mechanophore platforms comprising differently substituted furan moieties, wherein each mechanophore platform solution (2 mg/mL in 3:1 acetonitrile/methanol) was sonicated for 60 min ("on" time), warmed to room temperature, and the release of coumarin cargo from the corresponding mechanically liberated 2-furylcarbinol derivatives was monitored by PL spectroscopy; and wherein the initial PL intensity was subtracted from each measurement and the data was normalized to the plateau value; while FIG. 19B further qualitatively summarizes the data presented in FIG. 19A, in accordance with embodiments of the invention.
Figure 19B:
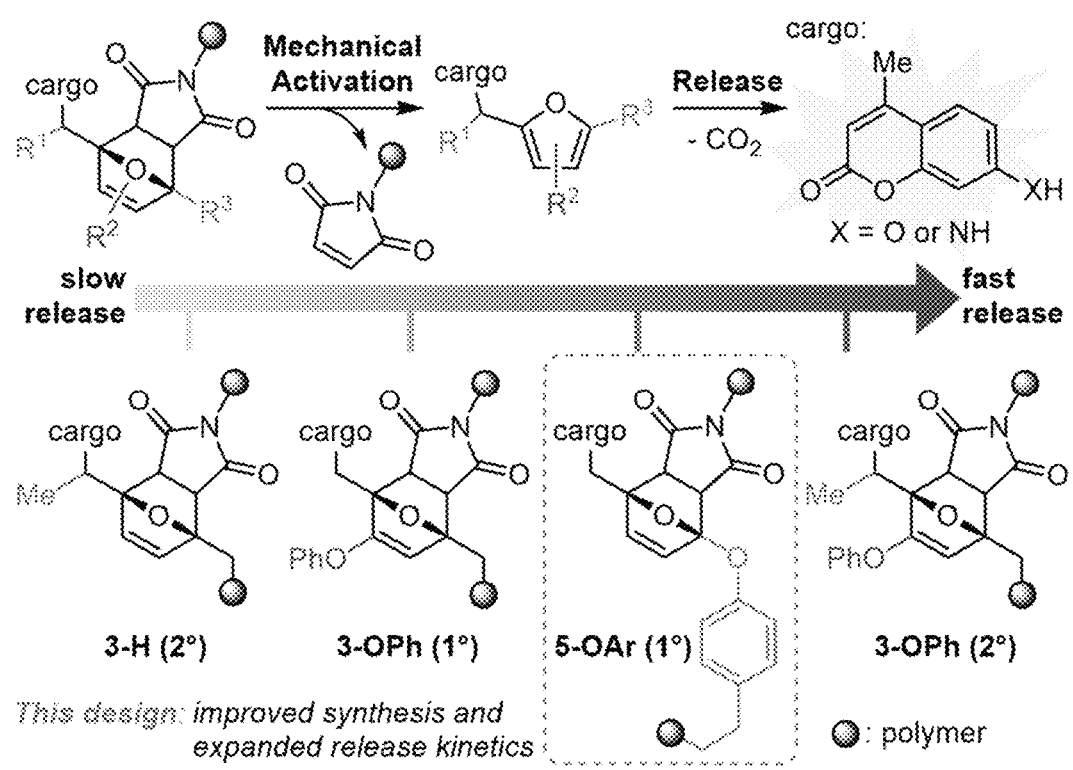

In addition, FIG. 19A provides data that compares the cargo molecule release kinetics from the mechanophore platform comprising the 5-OAr-substituted furan moiety of some embodiments with the cargo release kinetics from the other mechanophore platforms described herein, including the mechanophore platforms comprising: the furfuryl carbonates and furfuryl carbamates comprising only α-methyl substituent and 5-position polymer attachment (i.e., 3-H (2°)); the furfuryl carbonates and furfuryl carbamates comprising both α-methyl and 3-OPh substituents, in addition to 5-position polymer attachment (3-OPh(2°)), and the furfuryl carbonates and furfuryl carbamates comprising only 3-OPh substituent and 5-position polymer attachment (3-OPh(1°)). To obtain this data, each solution of the corresponding mechanophore platform was subjected to ultrasonication for 60 min ("on" time), and then the coumarin release from the corresponding mechanically liberated 2-furylcarbinol derivatives was monitored by PL spectroscopy after warming the solutions to room temperature. Furthermore, the initial fluorescence intensity (t=0) was subtracted from each measurement and the data were normalized to emphasize the relative rates of molecular release. Accordingly, the fluorescence emission from PMA(O) reached a maximum prior to the first measurement, indicating that the release of hydroxycoumarin from the mechanophore platform of the 5-OAr (1°)-type completed nearly instantaneously ($t_{1/2}$<5 min), similarly to the cargo release kinetics of 3-OPh-type mechanophore platforms. For further comparison, the release of hydroxycoumarin from the 3-H(2°)-type mechanophore platform occurs with a significantly longer half-life of ~46 min. Furthermore, the release of aminocoumarin from mechanically activated PMA(NH) occurs with a half-life of 15 h, which is much faster than that from the corresponding 3-OPh (1°)-type mechanophore platforms, which afford $t_{1/2}$≈6.5 days; but slower than aminocoumarin release from the 3-OPh(2°)-type mechanophore platforms with $t_{1/2}$=41 min. FIG. 19B qualitatively summarizes and illustrates the comparison data presented in FIG. 19A.

Accordingly, in many embodiments, the substituents on the furan moiety of the mechanophore platform affect the stability of the putative furfuryl cation intermediate formed during the furan moiety's decomposition and, consequently, influence the release of cargo from the mechanophore platforms of the instant disclosure. In many embodiments, the judicious design and selection of the furan moiety component in the synthesis and assembly of the mechanophore platform affords excellent control over the mechanophore platform's cargo release kinetics. In many embodiments, an electron-rich aryloxy group installed at 5-position of the furan moiety allows for efficient mechanophore platform synthesis and assembly, while also offering rate acceleration for the molecular cargo release (for both phenol and arylamine payloads), wherein such substituent simultaneously serves as the site of polymer attachment for efficient force transfer proximal to the furan-dienophile junction.

Figure 20A:
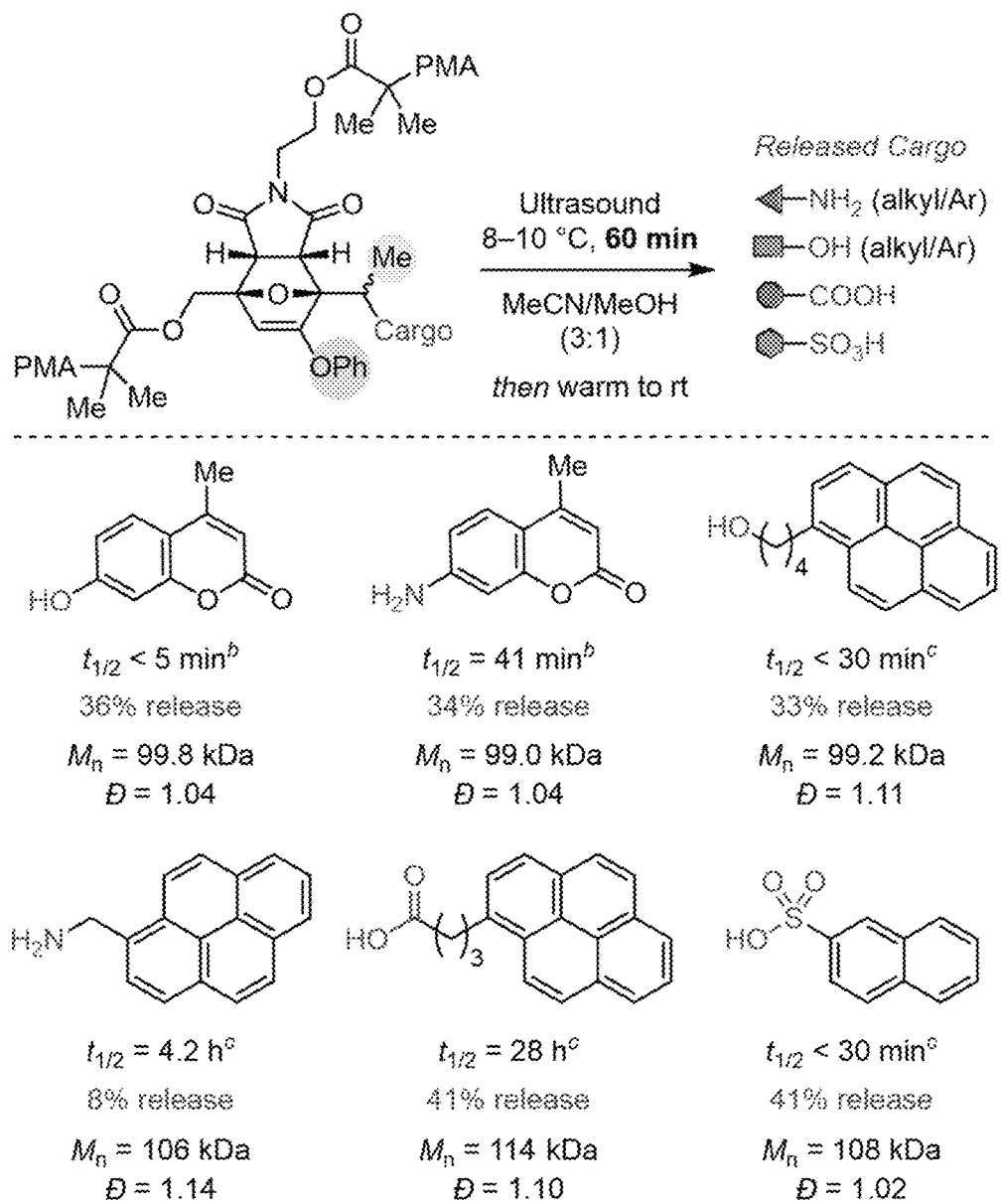

In many embodiments, the mechanophore platforms of the instant disclosure offer carrying capabilities for a wide scope of cargo molecules that they can release with controllable effectiveness upon mechanical activation. For example, FIG. 20A provides several examples of cargo molecules that can be efficiently released from the mechanophore platforms of many embodiments, especially wherein the mechanophore platforms comprise the masked furan moiety comprising α-methyl and 3-phenoxy substituents. To demonstrate the cargo molecule scope of many embodiments, a variety of molecular cargos were installed onto mechanophore platforms of many embodiments via modular bis-initiator precursor (±)-29, which comprises a secondary alcohol and 3-phenoxy substituent on the furan moiety, following the protocols described herein, and the cargo molecule release kinetics for such mechanophore platforms were studied. FIGS. 20A and 20B summarize these experiments. The examples of cargo molecules investigated in these experiments included: hydroxycoumarin (phenol) and aminocoumarin (arylamine) attached via respective carbonate and carbamate groups, as well as fluorogenic molecules comprising alcohol, alkylamine, carboxylic acid, and sulfonic acid functional groups for attachment to the mechanophore platform. Here, conjugation of the phenol-, arylamine-, alcohol- and alkyl amine-functional cargo molecules was achieved using respective carbonate and carbamate spacers, such that, therefore, the release of such cargo molecules requires a decarboxylation step illustrated in, for example, FIG. 1B. However, cargo molecules bearing carboxylic acid and sulfonic acid functional groups were conjugated directly to the mechanophore platform via carboxylate and sulfonate linkages. Furthermore, for these experiments, each cargo molecule was chosen to be strongly absorbing in the UV region to facilitate the characterization of the payload release using high-performance liquid chromatography (HPLC) equipped with a UV detector. In addition, for each thus cargo-loaded mechanophore platform, a corresponding control polymer with the Diels-Alder adduct attached to only one polymer chain's end was also synthesized and evaluated under the same conditions to confirm the mechanical origin of the molecular cargo release (FIG. 20C).

Figure 20C:
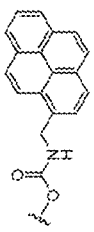

More specifically, for the cargo molecule release studies summarized in FIGS. 20A through 20C, a solution of each cargo-loaded mechanophore platform (2.0 mg/ml in 3:1 MeCN/MeOH) was subjected to ultrasonication for 60 min, and then the cargo molecule release from the mechanically liberated 2-furylcarbinol derivative was monitored at room temperature by HPLC and quantified using an internal standard. The identity of each cargo molecule, the average half-life and yield of cargo molecule release (measured from two replicate experiments), and the $M_n$ and D of the parent mechanophore platform/polymer are summarized in FIGS. 20A through 20C. According to the obtained data, mechanically triggered release of 1-pyrenebutanol was sufficiently rapid such that it completed prior to the first HPLC measurement ($t_{1/2}$<30 min). Furthermore, notably, release of 1-pyrenemethylamine from the corresponding furfuryl carbamate occurred with a moderate half-life of 4.2 h, albeit approximately 6× slower than the release of aminocoumarin. Here, not to be bound by any theory, the difference in release kinetics between the alkyl and arylamines is ascribed to the difference in $pK_a$ of the conjugate acids, with the aniline derivative being a better leaving group.

Moreover, the data provided in FIGS. 14A through 14C demonstrates that the mechanophore platforms of many embodiments, especially the mechanophore platforms comprising the α-methyl and 3-phenoxy substituted furan moiety, are capable to successfully release both alcohols and amines conjugated to the mechanophore platform via carbonate and carbamate linkages, and also cargo molecules incorporating carboxylic acid and sulfonic acid functional groups conjugated to the mechanophore platform's furan moiety directly via carboxylate and sulfonate linkages. As such, the mechanically triggered release of 1-pyrenebutanoic acid proceeded with a half-life of approximately 28 h, while the release of 2-naphtha-lenesulfonic acid completed before the first HPLC measurement ($t_{1/2}$<30 min). Not to be bound by any theory, this trend is also consistent with the significantly lower $pK_a$ value of the sulfonic acid as compared to the carboxylic acid, reflecting the relative stabilities of sulfonate and carbonate leaving groups. Accordingly, in many embodiments, the mechanophore platforms of the instant disclosure allow for mechanically triggered release of organic acids, wherein the organic acids are much more complex than previously reported generation of simple HCl. Accordingly, in many embodiments, the mechanophore platforms of the instant disclosure are highly modular and general in nature, especially in the context of the deliverable cargo, owing to the generality of their design.

It should be noted that the percent release for each cargo molecule reported in FIGS. 20A and 20B is calculated relative to the total concentration of the mechanophore platform in a given solution. However, only a fraction of the mechanophore platforms is converted after 60 min of ultrasonication, which, again, is expected to be approximately 36% based on the ultrasonication conditions and the average molecular weight of the polymers ($M_n$≈100 kDa in the experiments presented herein). Accordingly, the yields for molecular cargo release that are within the range of 33-41% after 60 min of ultrasonication (such as all yields reported in FIGS. 20A and 20B, with the exception of the alkylamine cargo) suggest that the decomposition chemistry of the furan moieties comprising the 2-furylcarbinol scaffold of many embodiments disclosed herein is highly efficient.

Furthermore, not to be bound by any theory, the reduced yield of the alkylamine cargo from the mechanophore platform of some embodiments, which plateaus at approximately 8%, can be attributed to a reaction between the released amine and the polymer-bound furfuryl cation intermediate, similar to the side reaction observed in the decomposition of model compound 21 at relatively high concentrations. Accordingly, the enhanced nucleophilicity of the alkylamine is anticipated to promote this side reaction pathway to an even greater extent than for aminocoumarin.

Moreover, although not to be bound by any particular theory, the relatively high yields of 41% observed for the release of both organic acid cargos (FIGS. 20A and 20B) are consistent with the slightly higher average molecular weight of those mechanophore platforms (i.e., the polymers flanking the mechanophore moiety), which results in increased mechanophore conversion during ultrasonication. Furthermore, as expected, no cargo release was observed from any of the control polymers, comprising the Diels-Alder adduct of the embodiments attached to only one end of its polymer chain, under identical experimental conditions, which confirmed that molecular cargo release from the mechanophore platforms of the instant disclosure, wherein the Diels-Alder mechanophore adduct is approximately centered on at least one polymer chain is indeed triggered by mechanical force.

Figure 21:
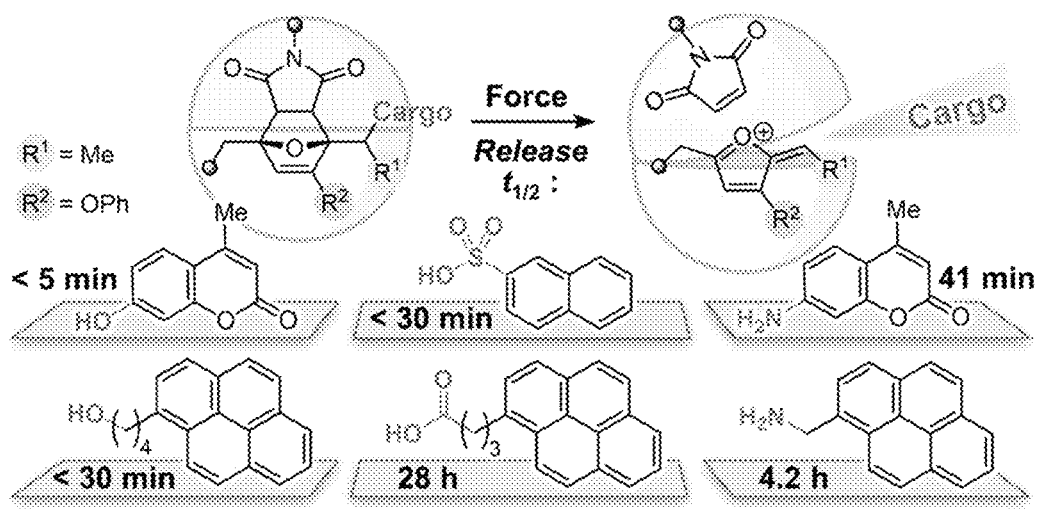
FIG. 21 illustrates the modular nature and controllable effectiveness of the mechanophore platform for cargo molecule release, in accordance with embodiments of the invention.

Accordingly, in many embodiments, the mechanophore platform for mechanically triggered release of cargo molecules described herein is highly general and effective for a variety of molecular cargo as illustrated by FIG. 21. More specifically, in many embodiments, the mechanophore platform of the instant disclosure is capable of releasing functionally diverse small molecule cargoes with tunable release kinetics. In many such embodiments, the mechanophore platform leverages a mechanically triggered cascade reaction, in which the mechanochemical activation of a furan-dienophile Diels-Alder adduct reveals a latent, unstable furan moiety comprising the 2-furylcarbinol scaffold, which spontaneously decomposes under mild conditions to release its covalently bound cargo molecule. Furthermore, the molecular design guidance provided herein discloses many useful structure-property relationships for the decomposition reactivity of the furan moiety that enable rational design of mechanophore platforms for small molecule cargo release according to many embodiments. For example, in some embodiments, the mechanophore platform comprising α-methyl substituted furan moiety offers enhanced cargo release activity, as compared to the mechanophore platform comprising the furan moiety without such substitution, and enables cargo molecule release via a well-defined decomposition reaction that proceeds efficiently under mild conditions, such that allow the release of phenolic cargo molecules. As another example, in many embodiments, adding an electron-donating substituent at 3-position or 5-position of the 2-furylcarbinol scaffold further facilities the cargo molecule release from such mechanophore platform. In addition, in many embodiments, the structural adjustments to the chemical components of the mechanophore platform also affect the mechanophore platform's thermal stability. For example, in many embodiments, 3-phenoxy and or 5-aryloxy substitution of the furan moiety enhances the thermal stability of the mechanophore platform without adversely impacting its mechanochemical reactivity. Accordingly, in many embodiments, judicious selection of the substitution scheme for the masked furan moiety of the Diels-Alder adduct of embodiments allows for control over the rates of the molecular cargo release from the mechanophore platform, wherein the cargo release rates can be varied by several orders of magnitude. In some embodiment, the mechanophore platform comprising the furan moiety comprising, for example, all of: α-methyl, 3-phenoxy, and or 5-aryloxy substituents offers highly efficient release of a functionally diverse cargo molecules upon mechanical activation.

In many embodiments, a variety of the mechanophore platforms are assembled and covalently pre-loaded with functionally diverse molecular cargoes via highly modular synthetic routes allowing for unlimited diversification. In many such embodiments, the scope of the functionalities of the cargo molecules that exhibit release from the mechanophore platforms of embodiments and high reaction efficiencies, includes (but is not limited to): alkyl and aryl alcohols, alkyl and aryl amines, carboxylic and sulfonic acids. In addition, in many embodiments, the mechanophore platforms are actuated by ultrasound, which is very convenient and versatile means of mechanical actuation. As such, in some embodiments, the described herein highly modular, general, and efficient mechanophore platform for mechanically triggered release of a wide variety of functional molecules is a platform of choice for applications in catalysis, sensing, including stress sensing, drug delivery, depolymerization, and many other areas.

EXEMPLARY EMBODIMENTS

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is number average molecular weight, temperature is in degrees Celsius, and pressure is at or near atmospheric.

General Experimental Details

Reagents from commercial sources were used without further purification unless otherwise stated. Methyl acrylate was passed through a short plug of basic alumina to remove inhibitor immediately prior to use. Dry THF, diethyl ether, MeCN, and DMF were obtained from a Pure Process Technology solvent purification system. All reactions were performed under a $N_2$ or argon atmosphere unless specified otherwise. Column chromatography was performed on a Biotage Isolera system using SiliCycle SiliaSep HP flash cartridges.

NMR spectra were recorded using a 400 MHz Bruker Avance III HD with Prodigy Cryoprobe, a 400 MHz Bruker Avance Neo, or Varian Inova 500 or 600 MHz spectrometers. All $^1$H NMR spectra are reported in S units, parts per million (ppm), and were measured relative to the signals for residual chloroform (7.26 ppm), dichloromethane (5.32 ppm), methanol (3.31 ppm), toluene (2.08), acetone (2.05 ppm), or acetonitrile (1.94 ppm) in deuterated solvent. All $^{13}$C NMR spectra were measured in deuterated solvents and are reported in ppm relative to the signals for chloroform (77.16 ppm) or dichloromethane (54.00 ppm). Multiplicity and qualifier abbreviations are as follows: s=singlet, d=doublet, t=triplet, q=quartet, dd=doublet of doublets, ABq=AB quartet, m=multiplet, br=broad.

High resolution mass spectra (HRMS) were obtained from an Agilent 6200 series time-of-flight mass spectrometer equipped with an Agilent G1978A multimode source (ESI$^+$). However, for some samples, high resolution mass spectra (HRMS) were analyzed by direct infusion electrospray ionization (ESI) in the positive ion mode using a Waters LCT Premier XE time-of-flight (TOF) mass spectrometer operated in the V mode. The instrument was externally calibrated with NaI clusters. Some samples were analyzed by Fast Atom Bombardment (FAB) using a JEOL JMS-60H Double-focusing high resolution magnetic sector mass spectrometer operated in the positive ion mode. In such instances, the instrument was calibrated with PEG clusters over the mass range of interest. One sample (217) was analyzed by GC-MS using an Agilent 6890N gas chromatograph interfaced to a JEOL double-focusing magnetic sector instrument using electron ionization (EI) in the positive ion mode. The instrument was calibrated with perfluorokerosene.

Analytical gel permeation chromatography (GPC) was performed using an Agilent 1260 series pump equipped with two Agilent PLgel MIXED-B columns (7.5×300 mm), an Agilent 1200 series diode array detector, a Wyatt 18-angle DAWN HELEOS light scattering detector, and an Optilab rEX differential refractive index detector. The mobile phase was THF at a flow rate of 1 mL/min. Molecular weights and molecular weight distributions were calculated by light scattering using a dn/dc value of 0.062 mL/g (25° C.) for poly(methyl acrylate).

Photoluminescence spectra were recorded on a Shimadzu RF-6000 spectrofluorophotometer. For some samples, a quartz microcuvette (Starna Cells 18F-Q-10-GL14-C, 10×2 mm) was used. Excitation and emission slit widths used for aminocoumarin solutions were 5 nm and 3 nm, respectively.

High-Performance Liquid Chromatography (HPLC) was performed with an Agilent Eclipse Plus C18 Column (Product Number: 959961-902) equipped with a single-wavelength UV-vis detector.

Ultrasound experiments were performed inside of a sound abating enclosure using a 500 watt Vibra Cell 505 liquid processor (20 kHz) equipped with a 0.5-inch diameter solid probe (part #630-0217), sonochemical adapter (part #830-00014), and a Suslick reaction vessel made by the Caltech glass shop (analogous to vessel #830-00014 from Sonics and Materials).

LCMS measurements were performed with an Agilent 6140 Series Quadrupole LCMS Spectrometer System equipped with an Agilent Eclipse Plus C18 column using MeCN/water as the eluent.

Synthetic Details

Synthesis of 4-Methylcoumarin 7-Chloroformate (8)

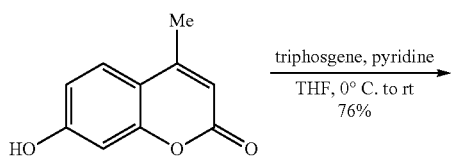

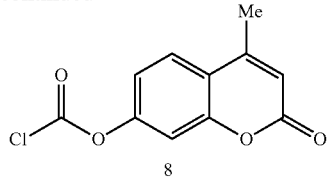

A flame-dried round bottom flask equipped with a stir bar under nitrogen was charged with triphosgene (0.50 g, 1.7 mmol) and anhydrous THF (20 mL). The solution was cooled to 0° C. in an ice bath, followed by the dropwise addition of a solution of 7-hydroxy-4-methylcoumarin (0.88 g, 5.0 mol) and an-hydrous pyridine (0.40 mL, 5.0 mmol) dissolved in anhydrous THF (35 mL). A white precipitate formed quickly upon addition. The reaction was allowed to warm to rt and stirred for 18 h. The slurry was filtered through a silica plug under an inert atmosphere of nitrogen to remove the insoluble bis-coumarin carbonate byproduct. The crude mixture was dried, taken up into DCM (20 mL), and filtered twice under nitrogen to remove insoluble solids comprising mostly the hydroxycoumarin starting material. The filtrate was concentrated under reduced pressure to provide the title compound as a white powder (0.91 g, 76%), which was stored in a glovebox under nitrogen. $^1$H NMR (400 MHz, CDCl$_3$) δ: 7.66 (d, J=8.7 Hz, 1H), 7.27-7.25 (m, 1H), 7.22 (d, J=2.4 Hz, 1H), 6.33 (q, J=1.2 Hz, 1H), 2.45 (d, J=1.3 Hz, 3H) ppm. $^{13}$C{$^1$H} NMR (100 MHz, CDCl$_3$) δ: 160.1, 154.3, 153.2, 151.7, 149.2, 126.1, 119.2, 116.8, 115.5, 109.8, 18.9 ppm. HRMS (ESI, m/z): calcd. for [C$_{11}$H$_8$ClO$_4$]$^-$ (M+H)$^+$, 239.0106; found, 239.0097.

Synthesis of Model Furfuryl Carbonate S1

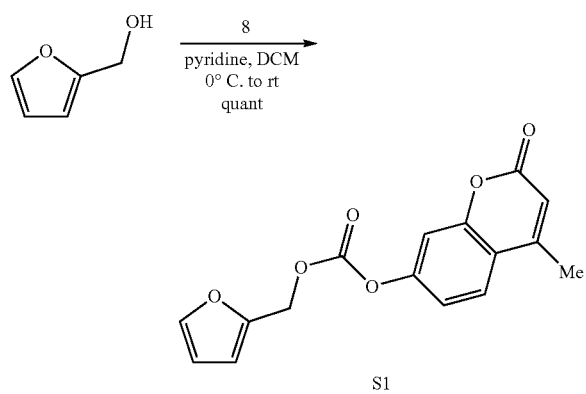

A flame-dried round bottom flask was charged with furfuryl alcohol (14.2 mg, 0.145 mmol) and anhydrous DCM (5 mL). The solution was cooled to 0° C. in an ice bath followed by the dropwise addition of anhydrous pyridine (12.3 µL, 0.152 mmol) and then a solution of coumarin chloroformate 8 (36.2 mg, 0.152 mmol) in anhydrous DCM (5 mL). The solution was allowed to warm to rt slowly, resulting in the formation of a white precipitate. The mixture was then diluted with DCM (20 mL) and washed with brine (2×20 mL). The combined organic phase was dried over Na$_2$SO$_4$, filtered, concentrated under reduced pressure, and purified by flash chromatography (5-35% EtOAc/hexanes) to yield the title compound as an off-white solid (43 mg, quant). R$_f$=0.64 (1:1 EtOAc:Hexanes). $^1$H NMR (500 MHz, CDCl$_3$) δ: 7.61 (d, J=8.6 Hz, 1H), 7.48 (dd, J=1.9, 0.8 Hz, 1H), 7.23 (d, J=2.3 Hz, 1H), 7.17 (dd, J=8.7, 2.3 Hz, 1H), 6.54 (dd, J=3.2, 0.8 Hz, 1H), 6.41 (dd, J=3.3, 1.9 Hz, 1H), 6.28 (q, J=1.3 Hz, 1H), 5.26 (s, 2H), 2.44 (d, J=1.3 Hz, 3H) ppm. $^{13}$C{$^1$H} NMR (100 MHz, CDCl$_3$) δ: 160.6, 154.3, 153.3, 152.8, 151.9, 148.0, 144.1, 125.6, 118.2, 117.5, 114.9, 112.2, 110.9, 110.1, 62.5, 18.9 ppm. HRMS (ESI, m/z): calcd. for [C$_{16}$H$_{13}$O$_6$]$^+$ (M+H)$^+$, 301.0707; found, 301.0702.

(5-(hydroxymethyl)furan-2-yl)methyl 2-bromo-2-methylpropanoate (9)

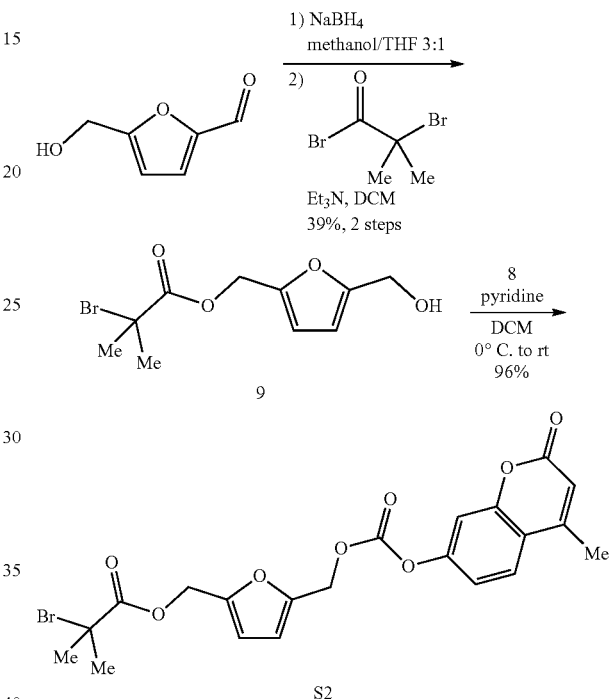

A round bottom flask equipped with a stir bar was charged with NaBH4 (159 mg, 4.20 mmol) and methanol (10 mL). The solution was cooled to 0° C. in an ice bath followed by the slow addition of 5-hydroxymethyl-2-furaldehyde (478 mg, 3.79 mmol). The reaction mixture was allowed to slowly warm to rt and stirred for 3 h. The mixture was then washed with 10% NH$_4$Cl (100 mL), extracted with EtOAc (2×100 mL). The organic layer was dried over Na$_2$SO$_4$, filtered, and concentrated under reduced pressure to yield 2,5-bis(hydroxymethyl)furan as a white solid (410 mg), which was used in the next step without further purification.

A round bottom flask equipped with a stir bar was charged with 2,5-bis(hydroxymethyl)furan (410 mg, 3.2 mmol), triethylamine (0.49 mL, 3.5 mmol), and DCM (20 mL), followed by the dropwise addition of α-bromo-isobutyryl bromide (396 µL, 3.20 mmol). The reaction was allowed to warm to rt slowly and stirred for 3 h. The mixture was filtered through a plug of silica gel eluting with EtOAc:Hexanes (4:1), the filtrate was concentrated under reduced pressure, and the crude product was purified by column chromatography (25-50% EtOAc/Hexanes) to yield the title compound as a colorless oil (405 mg, 39% over two steps). R$_f$=0.26 (1:4 EtOAc:Hexanes). $^1$H NMR (400 MHz, CDCl$_3$) δ: 6.40 (d, J=3.2 Hz, 1H), 6.27 (d, J=3.2 Hz, 1H), 5.13 (s, 2H), 4.60 (s, 2H), 1.92 (s, 6H) ppm. $^{13}$C{$^1$H} NMR (100 MHz, CDCl$_3$) δ: 171.5, 155.0, 148.9, 111.9, 108.9, 59.7, 57.7, 55.7, 30.8 ppm. HRMS (ESI, m/z): calcd. for [$C_{10}H_{17}BrNO_4$]⁻ (M+H)⁺, 294.0335; found, 294.0327.

(5-(((((4-methyl-2-oxo-2H-chromen-7-yl)oxy)carbonyl)oxy)methyl)furan-2-yl)methyl 2-bromo-2-methylpropanoate (S2)

Furfuryl alcohol 9 (46.0 mg, 0.166 mmol) and pyridine (21.5 µL, 0.267 mmol) were combined with anhydrous DCM (2 mL) in a two-neck round bottom flask. The solution was cooled to 0° C. in an ice bath followed by the dropwise addition a solution of coumarin chloroformate 8 (60.0 mg, 0.251 mmol) dissolved in anhydrous DCM (4 mL). The reaction mixture was allowed to warm to rt and stirred for 2 h. The mixture was then concentrated under reduced pressure and the crude product was purified by column chromatography (10-60% EtOAc/hexanes) to yield the title compound as a colorless oil (76 mg, 96%). $R_f$=0.16 (1:4 EtOAc:Hexanes). ¹H NMR (400 MHz, CDCl₃) δ: 7.62 (d, J=8.7 Hz, 1H), 7.23 (d, J=2.3 Hz, 1H), 7.17 (dd, J=8.7, 2.4 Hz, 1H), 6.52 (d, J=3.3 Hz, 1H), 6.46 (d, J=3.2 Hz, 1H), 6.28 (q, J=1.3 Hz, 1H), 5.24 (s, 2H), 5.17 (s, 2H), 2.44 (d, J=1.3 Hz, 3H), 1.94 (s, 6H) ppm. ¹³C{¹H} NMR (100 MHz, CDCl₃) δ: 171.4, 160.5, 154.3, 153.3, 152.7, 151.9, 150.4, 148.8, 125.7, 118.2, 117.5, 114.9, 113.2, 112.0, 110.1, 62.4, 59.6, 55.6, 30.8, 18.9 ppm. HRMS (ESI, m/z): calcd. for [$C_{21}H_{20}BrO_8$]⁺ (M+H)⁺, 479.0336; found, 479.0337.

1-(5-(hydroxymethyl)furan-2-yl)ethan-1-ol (10)

A 1 L round bottom flask equipped with a stir bar was charged with 5-(hydroxymethyl)furan-2-carbaldehyde (7.92 g, 62.8 mmol) and diethyl ether (300 mL). The solution was cooled to −30° C., followed by the slow addition of methylmagnesium bromide (3 M in diethyl ether, 42 mL, 130 mmol). The mixture was allowed to warm to rt and stirred for 12 h, after which the reaction was cooled to 0° C. and quenched with 10% NH₄Cl (200 mL). The reaction mixture was extracted with EtOAc (3×100 mL) and the combined organic phase was dried over MgSO₄, filtered, and concentrated under reduced pressure to provide the title compound as a viscous yellow oil (7.6 g, 85%). ¹H NMR (400 MHz, CDCl₃) δ: 6.23 (d, J=3.1 Hz, 1H), 6.18 (d, J=3.2 Hz, 1H), 4.87 (q, J=6.7 Hz, 1H), 4.59 (d, J=2.9 Hz, 2H), 1.97 (br s, 1H), 1.78 (br s, 1H), 1.54 (d, J=6.5 Hz, 3H) ppm. ¹³C{¹H} NMR (100 MHz, CDCl₃) δ: 157.8, 153.5, 108.6, 106.1, 63.8, 57.7, 21.3 ppm. HRMS (ESI, m/z): calcd. for [$C_7H_9O_2$]⁺ (M-OH)⁺, 125.0597; found, 125.0595.

(5-(1-hydroxyethyl)furan-2-yl)methyl 2-bromo-2-methylpropanoate (11)

A 500 mL three neck flask was equipped with a stir bar was charged with 10 (2.74 g, 19.3 mmol), triethylamine (3.00 mL, 21.6 mmol), and DCM (150 mL). The mixture was cooled to 0° C. in an ice bath followed by the dropwise addition of a solution of α-bromo-isobutyryl bromide (2.60 mL, 21.0 mmol) dissolved in DCM (50 mL) over 2 h. The reaction mixture was stirred under nitrogen and allowed to warm to rt slowly. After 20 h, the reaction mixture was filtered through a plug of silica gel, washed with 1:1 EtOAc:Hexanes, concentrated, then purified by column chromatography (2-35% EtOAc/hexanes) to yield the title compound as a viscous colorless liquid (4.4 g, 77%). $R_f$=0.33 (1:4 EtOAc:Hexanes). ¹H NMR (400 MHz, CDCl₃) δ: 6.38 (d, J=3.2 Hz, 1H), 6.21 (d, J=3.4 Hz, 1H), 5.13 (s, 2H), 4.87 (q, J=6.6 Hz, 1H), 1.93 (s, 6H), 1.54 (d, J=6.6 Hz, 3H) ppm. ¹³C{¹H} NMR (100 MHz, CDCl₃) δ: 171.5, 158.7, 148.3, 111.7, 106.3, 63.8, 59.8, 55.8, 30.8, 21.4 ppm. HRMS (ESI, m/z): calcd. for [$C_{11}H_{14}BrO_3$]⁺ (M-OH)⁺, 273.0121; found, 273.0119.

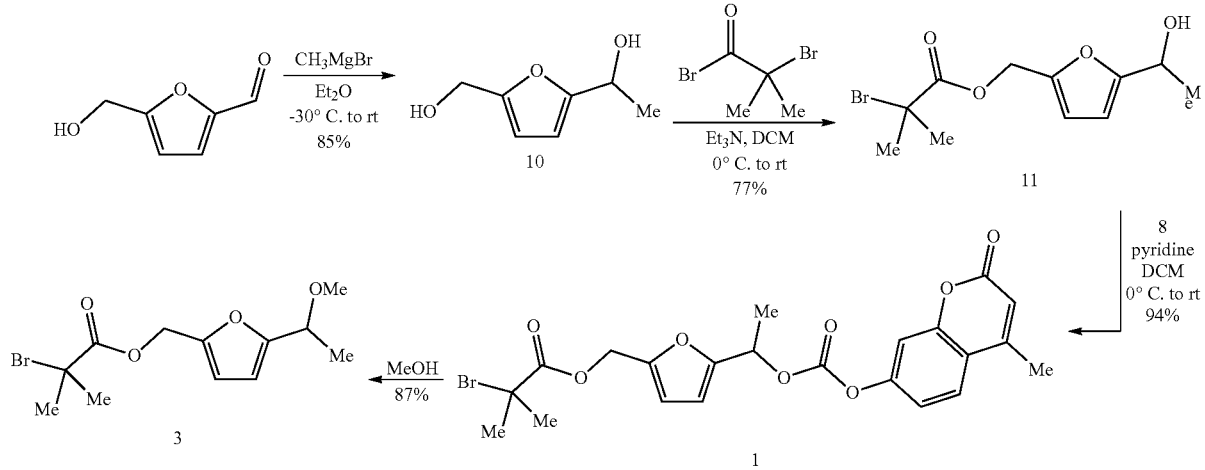

(5-(1-((((4-methyl-2-oxo-2H-chromen-7-yl)oxy)carbonyl)oxy)ethyl)furan-2-yl)methyl 2-bromo-2-methylpropanoate (1)

A two-neck round bottom flask equipped with a stir bar was charged with 11 (58.5 mg, 0.201 mmol), pyridine (19.0 µL, 0.236 mmol), and DCM (4 mL). The solution was cooled to 0° C. in an ice bath followed by the dropwise addition of a solution of coumarin chloroformate 8 (53.5 mg, 0.224 mmol) dissolved in DCM (6 mL). The reaction was allowed to warm slowly to rt and stirred for 3 h. The reaction mixture was washed quickly with brine, dried over Na₂SO₄, filtered, and concentrated under reduced pressure to yield a viscous oil. The crude oil was dispersed in DCM/hexanes (1:2, 3 mL), then filtered to remove insoluble byproducts consisting mostly of 7-hydroxy-4-methylcoumarin and the bis-coumarin carbonate. The filtrate was concentrated under reduced pressure to provide the title compound as a viscous colorless liquid (93 mg, 94%). Compound 1 is relatively stable in solvents such as DCM, chloroform, and hexanes, but decomposes quickly in acidic and protic solvents. $^1$H NMR (400 MHz, CDCl$_3$) δ: 7.61 (d, J=8.7 Hz, 1H), 7.23 (d, J=2.3 Hz, 1H), 7.17 (dd, J=8.7, 2.4 Hz, 1H), 6.43 (s, 2H), 6.28 (d, J=1.3 Hz, 1H), 5.88 (q, J=6.7 Hz, 1H), 5.17 (ABq, Δν$_{AB}$=5.8 Hz, J$_{AB}$=13.6 Hz, 2H), 2.43 (d, J=1.3 Hz, 3H), 1.94 (s, 6H), 1.74 (d, J=6.8 Hz, 3H) ppm. $^{13}$C{$^1$H} NMR (100 MHz, CDCl$_3$) δ: 171.4, 160.6, 154.3, 153.3, 152.6, 152.3, 152.0, 149.6, 125.6, 118.1, 117.5, 114.8, 111.7, 110.2, 110.1, 70.7, 59.6, 55.7, 30.8, 18.9, 18.1 ppm. HRMS (ESI, m/z): calcd. for [C$_{22}$H$_{25}$BrNO$_8$]$^-$ (M+NH$_4$)$^+$, 501.0758; found, 501.0750.

(5-(1-methoxyethyl)furan-2-yl)methyl 2-bromo-2-methylpropanoate (3)

Compound 1 (80.2 mg, 0.163 mmol) was dissolved in methanol (1 mL) in a 2 ml vial and stirred at rt. After 16 h, the reaction mixture was concentrated under reduced pressure and the crude product was purified by flash chromatography (1-25% EtOAc/hexanes) to provide the title compound as a colorless viscous oil (43 mg, 87%). R$_f$=0.31 (1:19 EtOAc:Hexanes). $^1$H NMR (500 MHz, CDCl$_3$) δ: 6.38 (d, J=3.2 Hz, 1H), 6.23 (d, J=3.2 Hz, 1H), 5.13 (ABq, Δν$_{AB}$=7.5 Hz, J$_{AB}$=13.0 Hz, 2H), 4.34 (q, J=6.6 Hz, 1H), 3.28 (d, J=1.0 Hz, 3H), 1.92 (d, J=0.8 Hz, 6H), 1.49 (dd, J=6.6, 0.9 Hz, 3H) ppm. $^{13}$C{$^1$H} NMR (125 MHz, CDCl$_3$) δ: 171.4, 156.5, 148.4, 111.5, 108.0, 72.1, 59.8, 56.3, 55.7, 30.8, 30.8, 19.5 ppm. HRMS (ESI, m/z): calcd. for [C$_{12}$H$_{21}$BrNO$_4$]$^-$ (M+NH$_4$)$^+$, 322.0648; found, 322.0654.

7-(1-hydroxyethyl)-2-(2-hydroxyethyl)-1,3-dioxo-1,2,3,3a,7,7a-hexahydro-4H-4,7-epoxyisoindol-4-yl)methyl 2-bromo-2-methylpropanoate ((±)-12)

Compound 11 (4.15 g, 14.3 mmol) was combined with N-(2-hydroxyethyl)maleimidel (3.51 g, 24.9 mmol) and chloroform (4 mL) in a 20 mL vial and stirred at 55° C. for 14 h. The crude reaction mixture was separated by column chromatography (2-4% methanol/DCM) and a single diastereomer of the title compound was isolated as a white solid (2.2 g, 36%). The absolute configuration of compound 12 was confirmed by single crystal X-ray diffraction. R$_f$=0.28 (1:24 methanol:DCM). $^1$H NMR (400 MHz, CDCl$_3$) δ: 6.43 (d, J=5.8 Hz, 1H), 6.38 (d, J=5.8 Hz, 1H), 4.81 (ABq, Δν$_{AB}$=78 Hz, J$_{AB}$=12.8 Hz, 2H), 4.34 (q, J=7.1 Hz, 1H), 3.73-3.50 (m, 6H), 1.95 (s, 6H), 1.43 (d, J=6.6 Hz, 3H) ppm. $^{13}$C{$^1$H} NMR (100 MHz, CDCl$_3$) δ: 175.5, 175.0, 171.2, 135.7, 135.0, 95.0, 89.4, 66.7, 63.2, 60.6, 55.5, 49.5, 47.7, 41.5, 30.8, 30.8, 18.7 ppm. HRMS (ESI, m/z): calcd. for [C$_{17}$H$_{22}$BrNO$_7$Na]$^+$ (M+Na)$^+$, 454.0472; found, 454.0470.

2-(2-((2-bromo-2-methylpropanoyl)oxy)ethyl)-7-(1-hydroxyethyl)-1,3-dioxo-1,2,3,3a,7,7a-hexahydro-4H-4,7-epoxyisoindol-4-yl)methyl 2-bromo-2-methylpropanoate ((±)-4)

A three-neck round bottom flask equipped with a stir bar was charged with 12 (1.08 g, 2.50 mmol), triethylamine (0.39 mL, 2.8 mmol), and DCM (50 mL). The solution was cooled to 0° C. in an ice bath followed by the dropwise addition of α-bromo-isobutyryl bromide (0.33 mL, 2.7 mmol). The solution was allowed to warm to rt slowly and stirred for an additional 16 h. The reaction mixture was washed with NH$_4$Cl (100 mL) and brine (100 mL), dried over Na$_2$SO$_4$, filtered, and the organic fraction was concentrated under reduced pressure. The crude product was purified by column chromatography (35-55% EtOAc/hexanes) to provide the title compound as a colorless, sticky oil (1.1 g, 74%). R$_f$=0.29 (1:1 EtOAc/hexanes). $^1$H NMR (400 MHz, CDCl$_3$) δ: 6.46 (d, J=5.7 Hz, 1H), 6.41 (d, J=5.8 Hz, 1H), 4.80 (ABq, Δν$_{AB}$=84 Hz, J$_{AB}$=12.8 Hz, 2H), 4.33 (q, J=6.6 Hz, 1H), 4.22 (dd, J=5.7, 4.7 Hz, 2H), 3.73-3.62 (m, 3H), 3.58 (d, J=7.7

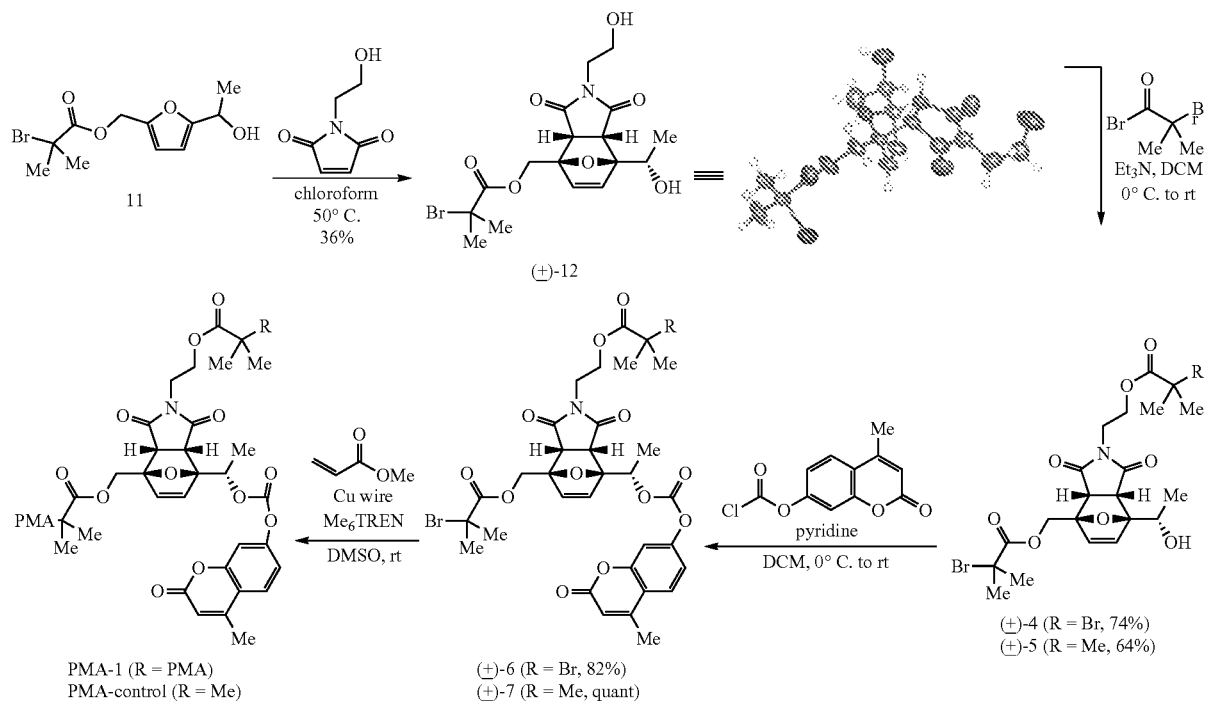

Hz, 1H), 1.96 (s, 5H), 1.90 (s, 6H), 1.44 (d, J=6.6 Hz, 3H) ppm. $^{13}$C{$^{1}$H} NMR (100 MHz, CDCl$_3$) δ: 174.5, 174.0, 171.5, 171.2, 135.7, 135.1, 95.0, 89.4, 66.8, 63.2, 62.6, 55.6, 55.5, 49.6, 47.8, 37.6, 30.81, 30.80, 30.79, 30.77, 18.7 ppm. HRMS (ESI, m/z): calcd. for [C$_{21}$H$_{31}$Br$_2$N$_2$O$_8$]$^+$ (M+NH$_4$)$^+$, 599.0421; found, 599.0420.

2-(-4-(((2-bromo-2-methylpropanoyl)oxy)methyl)-7-(-1-hydroxyethyl)-1,3-dioxo-1,3,3a,4,7,7α-hexa-hydro-2H-4,7-epoxyisoindol-2-yl)ethyl pivalate ((±)-5)

A two-neck round bottom flask equipped with a stir bar was charged with 12 (410 mg, 0.95 mmol), triethylamine (0.21 mL, 1.5 mmol), and DCM (15 mL). The solution was cooled to 0° C. in an ice bath followed by the dropwise addition of pivaloyl chloride (0.18 mL, 1.5 mmol). The solution was allowed to warm to rt slowly and stirred for an addition-al 23 h. The reaction mixture was filtered through a plug of silica gel and the filtrate was concentrated under reduced pressure. The crude product was purified by column chromatography (30-55% EtOAc/hexanes) to provide the title compound as a colorless viscous oil (315 mg, 64%). $R_f$=0.56 (1:1 EtOAc:Hexanes). $^1$H NMR (500 MHz, CDCl$_3$) δ: 6.42 (d, J=5.7 Hz, 1H), 6.37 (d, J=5.8 Hz, 1H), 4.80 (ABq, Δν$_{AB}$=106 Hz, J$_{AB}$=12.5 Hz, 2H), 4.33 (q, J=6.6 Hz, 1H), 4.11 (t, J=5.3 Hz, 2H), 3.66 (d, J=7.7 Hz, 1H), 3.63-3.59 (m, 2H), 3.57 (d, J=7.8 Hz, 1H), 1.96 (s, 6H), 1.44 (d, J=6.6 Hz, 3H), 1.17 (s, 8H) ppm. $^{13}$C{$^{1}$H}NMR (125 MHz, CDCl$_3$) δ: 178.3, 174.5, 174.0, 171.2, 135.7, 135.0, 94.9, 89.3, 66.8, 63.2, 61.0, 55.5, 49.5, 47.7, 38.8, 38.0, 30.80, 30.75, 27.3, 18.6 ppm. HRMS (ESI, m/z): calcd. for [C$_{22}$H$_{31}$BrN$_2$O$_8$]$^+$ (M+H)$^+$, 516.1228; found, 516.1228.

(2-(2-((2-bromo-2-methylpropanoyl)oxy)ethyl)-7-(-1-((((4-methyl-2-oxo-2H-chromen-7-yl)oxy)carbo-nyl)oxy)ethyl)-1,3-dioxo-1,2,3,3a,7,7a-hexahydro-4H-4,7-epoxyisoindol-4-yl)methyl 2-bromo-2-methylpropanoate ((±)6)

A two-neck round bottom flask equipped with a stir bar was charged with 4 (68.8 mg, 0.118 mmol), pyridine (30.0 μL, 0.372 mmol), and DCM (25 mL). The solution was cooled to 0° C. in an ice bath followed by the dropwise addition of a solution of coumarin chloroformate 8 (81.0 mg, 0.339 mmol) dissolved in DCM (5 mL). The reaction was allowed to warm slowly to rt and stirred for 20 h. The reaction mixture was washed with brine, dried over Na$_2$SO$_4$, filtered, and concentrated under reduced pressure. The crude produce was purified by column chromatography (35-55% EtOAc/hexanes) to provide the title compound as a white foaming solid (76 mg, 82%). $R_f$=0.35 (1:1 EtOAc:Hexanes). $^1$H NMR (400 MHz, CDCl$_3$) δ: 7.62 (d, J=8.7 Hz, 1H), 7.26 (s, 1H), 7.21 (dd, J=8.7, 2.3 Hz, 1H), δ 6.53-6.46 (m, 2H), 6.28 (q, J=1.3 Hz, 1H), 5.46 (q, J=6.6 Hz, 1H), 4.82 (ABq, Δν$_{AB}$=95 Hz, J$_{AB}$=12.8 Hz, 2H), 4.24 (t, J=5.1 Hz, 2H), 3.77-3.56 (m, 4H), 2.44 (d, J=1.3 Hz, 3H), 1.95 (d, J=1.9 Hz, 6H), 1.91 (s, 6H), 1.64 (d, J=6.7 Hz, 3H) ppm. $^{13}$C{$^1$H} NMR (100 MHz, CDCl$_3$) δ: 173.7, 173.5, 171.5, 171.2, 160.5, 154.3, 153.3, 152.2, 151.9, 135.6, 135.2, 125.6, 118.2, 117.5, 114.9, 110.1, 92.6, 89.5, 73.9, 63.1, 62.5, 55.7, 55.5, 49.4, 48.4, 37.8, 30.80, 30.78, 18.9, 16.0 ppm. HRMS (ESI, m/z): calcd. for [C$_{32}$H$_{37}$Br$_2$N$_2$O$_{12}$]$^+$ (M+NH$_4$)$^+$, 801.0687; found, 801.0684.

2-(-4-(((2-bromo-2-methylpropanoyl)oxy)methyl)-7-(-1-((((4-methyl-2-oxo-2H-chromen-7-yl)oxy)carbo-nyl)oxy)ethyl)-1,3-dioxo-1,3,3a,4,7,7α-hexahydro-2H-4,7-epoxyisoindol-2-yl)ethyl pivalate ((±)-7)

A two-neck round bottom flask equipped with a stir bar was charged with 5 (74.6 mg, 0.144 mmol), pyridine (23.4 μL, 0.291 mmol), and DCM (25 mL). The solution was cooled to 0° C. in an ice bath followed by the dropwise addition of a solution of coumarin chloroformate 8 (69.0 mg, 0.289 mmol) dissolved in DCM (10 mL). The reaction was allowed to warm slowly to rt and stirred for 16 h. The reaction mixture was washed with 10% NH$_4$Cl, dried over Na$_2$SO$_4$, filtered, and concentrated under reduced pressure. The crude produce was purified by column chromatography (35-60% EtOAc/hexanes) to provide the title compound as a white foaming solid (103 mg, quant). $R_f$=0.56 (1:1 EtOAc:Hexanes). $^1$H NMR (500 MHz, CDCl$_3$) δ: 7.62 (d, J=8.7 Hz, 1H), 7.27-7.25 (m, 1H), 7.21 (dd, J=8.7, 2.4 Hz, 1H), 6.47-6.42 (m, 2H), 6.29 (q, J=1.3 Hz, 1H), 5.46 (q, J=6.6 Hz, 1H), 4.82 (ABq, Δν$_{AB}$=120 Hz, J$_{AB}$=12.5 Hz, 2H), 4.13 (t, J=5.2 Hz, 2H), 3.76-3.55 (m, 4H), 2.45 (d, J=1.3 Hz, 3H), 1.96 (d, J=2.7 Hz, 6H), 1.65 (d, J=6.6 Hz, 3H), 1.18 (s, 9H) ppm. $^{13}$C{$^1$H} NMR (100 MHz, CDCl$_3$) δ: 178.4, 173.7, 173.5, 171.2, 160.5, 154.3, 153.3, 152.2, 151.9, 135.5, 135.1, 125.6, 118.2, 117.5, 114.9, 110.0, 92.6, 89.5, 73.9, 63.2, 61.0, 55.5, 49.3, 48.3, 38.9, 38.2, 30.79, 30.76, 27.3, 18.9, 16.0 ppm. HRMS (ESI, m/z): calcd. for [C$_{33}$H$_{37}$BrNO$_2$]$^+$ (M+H)$^+$, 718.1494; found, 718.1500.

Mechanophore platform PMA-1. A 10 mL Schlenk flask equipped with a stir bar was charged with bis-initiator 6 (7.2 mg, 9.2 μmol), DMSO (1.2 mL), methyl acrylate (1.2 mL, 13 mmol), and Me$_6$TREN (4.6 mg, 20 μmol). The flask was sealed, the solution was deoxygenated with three freeze-pump-thaw cycles, and then backfilled with nitrogen. The flask was opened briefly under a flow of N$_2$, and freshly cut copper wire (1.0 cm length, 20 gauge) was added on top of the frozen mixture. The flask was resealed, evacuated for an additional 15 min, warmed to rt, and then backfilled with nitrogen. After stirring at rt for 90 min, the flask was opened to air and the solution was diluted with DCM. The polymer solution was precipitated into cold methanol (2×) and the isolated material was dried under vacuum to yield 60 mg of PMA-1 (52%). M$_n$=100 kg/mol, Đ=1.06.

PMA-control. A 10 mL Schlenk flask equipped with a stir bar was charged with initiator 7 (8.5 mg, 11.8 μmol), DMSO (1.6 mL), methyl acrylate (1.6 mL, 18 mmol), and Me$_6$TREN (5.1 mg, 22 μmol). The flask was sealed, the solution was deoxygenated with three freeze-pump-thaw cycles, and then backfilled with nitrogen. The flask was opened briefly under a flow of N$_2$, and freshly cut copper wire (1.1 cm length, 20 gauge) was added on top of the frozen mixture. The flask was resealed, evacuated for an additional 15 min, warmed to rt, and then backfilled with nitrogen. After stirring at rt for 2 h, the flask was opened to air and the solution was diluted with DCM. The polymer solution was precipitated into cold methanol (2×) and the isolated material was dried under vacuum to yield 82 mg of PMA-control (54%). M$_n$=86 kg/mol, Đ=1.14.

3-phenoxyfuran-2-carbaldehyde (25)

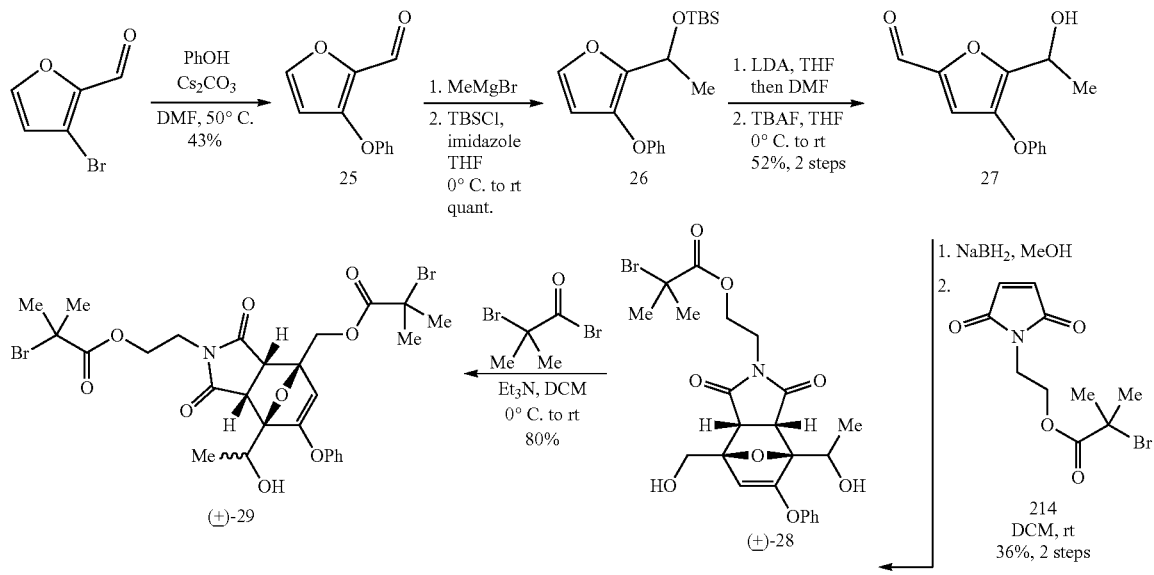

A round bottom flask equipped with a stir bar was charged with phenol (16.1 g, 0.171 mol), cesium carbonate (55.7 g, 0.171 mol) and DMF (500 mL). The solution was heated to 80° C. until cesium carbonate had dissolved. The mixture was then cooled to 60° C. before adding 3-bromo-2-furfural 1 (6.30 g, 0.0360 mol), and vigorously stirred for 1 day. The reaction mixture was then cooled to room temperature before pouring into a sat. Na$_2$CO$_3$ solution (1 L), extracted with Et$_2$O (4×300 mL), and washed with copious sat. Na$_2$CO$_3$ and brine. The organic layer was dried over MgSO$_4$, filtered, and concentrated under reduced pressure. The crude product was purified by column chromatography (5-20% EtOAc/hexanes) to yield the title compound as a light-yellow solid (2.90 g, 43%). $^1$H NMR (500 MHz, CDCl$_3$) δ 9.67 (s, 1H), 7.52 (d, J=2.1, 1H), 7.43-7.37 (m, 2H), 7.25-7.20 (m, 1H), 7.19-7.13 (m, 2H), 6.22 (d, J=2.1 Hz, 1H) ppm. $^{13}$C{$^1$H} NMR (125 MHz, CDCl$_3$) δ 174.9, 156.1, 148.0, 139.5, 130.3, 125.4, 119.0, 105.4 ppm. HRMS (ESI, m/z): calcd. for [C$_{11}$H$_9$O$_3$]$^+$ (M+H)$^+$, 189.0546; found, 189.0568.

Tert-butyldimethyl(1-(3-phenoxyfuran-2-yl)ethoxy)silane (26)

A flame-dried round bottom flask was charged with 25 (1.50 g, 7.98 mmol) and anhydrous Et$_2$O (50 mL). The solution was cooled to −30° C. in an acetonitrile/dry ice bath followed by the dropwise addition of MeMgBr (3 M in Et$_2$O, 4.00 mL, 12.0 mmol). The solution was allowed to warm to room temperature and stirred for 1 h before being quenched with 10% NH$_4$Cl (50 mL) and extracted with Et$_2$O (2×50 mL). The combined organic phase was dried over Na$_2$SO$_4$, filtered, concentrated under reduced pressure to yield 1-(3-phenoxyfuran-2-yl)ethan-1-ol as a colorless oil, which was used in the next step without further purification.

A round bottom flask equipped with a stir bar was charged with 1-(3-phenoxyfuran-2-yl)ethan-1-ol (1.60 g, 7.84 mmol), imidazole (1.60 g, 23.5 mmol), and DCM (15 mL), followed by addition of tert-butylchlorodimethylsilane (2.40 g, 16.0 mmol). The reaction was allowed to stir at room temperature overnight before filtering the mixture through a cotton pad. The filtrate was concentrated under reduced pressure, and the crude product was purified by column chromatography (0-15% EtOAc/hexanes) to yield the title compound as a light yellow oil (2.49 g, 98% over two steps). $^1$H NMR (400 MHz, CDCl$_3$) δ 7.33-7.27 (m, 3H), 7.06-7.01 (m, 1H), 7.00-6.95 (m, 2H), 6.19 (d, J=2.1 Hz, 1H), 4.93 (q, J=6.6 Hz, 1H), 1.47 (d, J=6.6 Hz, 3H), 0.85 (s, 9H), 0.04 (s, 3H), −0.05 (s, 3H) ppm. $^{13}$C{$^1$H} NMR (100 MHz, CDCl$_3$) δ 158.4, 145.2, 140.7, 137.7, 129.7, 122.5, 116.2, 106.3, 61.6, 25.9, 25.8, 22.2, 18.3, −4.9, −5.0 ppm. HRMS (ESI, m/z): calcd. for [C$_{12}$HnO$_2$]$^+$ (M-OTBS)$^+$, 187.0754; found, 187.0732.

5-(1-hydroxyethyl)-4-phenoxyfuran-2-carbaldehyde (27)

A flame-dried round bottom flask equipped with a stir bar was charged with diisopropylamine (0.80 mL, 5.7 mmol) and THF (70 mL). The solution was cooled to −78° C. in an acetone/dry ice bath before adding n-butyllithium (2.5 M in hexanes, 2.30 mL, 5.75 mmol) dropwise. After stirring the mixture for 5 min, a solution of 26 (1.06 g, 5.02 mmol) in THF (10 ml) was added to the mixture dropwise at −78° C. The mixture was kept at −78° C. for 30 mins before adding DMF (0.52 mL, 6.7 mmol) dropwise. The mixture was then allowed to slowly warm up to room temperature for ~1 h before 10% NH$_4$Cl (100 mL) was added slowly to the mixture to quench the reaction. The mixture was then extracted with Et$_2$O (2×100 mL), and the organic layer was dried over MgSO$_4$, filtered, and concentrated under reduced pressure. The crude mixture was purified by column chromatography (0-20% EtOAc/hexanes) to yield the crude product of 5-(1-((tert-butyldimethylsilyl)oxy)ethyl)-4-phenoxyfuran-2-carbaldehyde as a colorless oil. Approximately 10% of the crude product was identified to be the regioisomer resulting from formylation at the 4-position of the furan. The crude product was used in the next step without further purification.

The crude product from above was dissolved in THF (25 mL) and cooled to 0° C. before adding TBAF (1 M in THF, 3.8 mL, 3.8 mmol) dropwise. The mixture was allowed to slowly warm up to room temperature and stirred for 1 h. The reaction mixture was then diluted with Et$_2$O (25 mL) washed with NH$_4$Cl (25 mL) and brine (25 mL), and the organic fraction was dried over Na$_2$SO$_4$, filtered, and concentrated under reduced pressure. The crude product was purified by column chromatography (25-50% EtOAc/hexanes) to yield compound 27 as a yellow waxy solid (602 mg, 52% over two steps). $^1$H NMR (400 MHz, CDCl$_3$) δ 9.57 (s, 1H), 7.35 (dd, J=8.7, 7.4 Hz, 2H), 7.19-7.08 (m, 1H), 7.05-6.96 (m, 3H), 5.04 (q, J=6.7 Hz, 1H), 1.62 (d, J=6.7 Hz, 3H). $^{13}$C{$^1$H} NMR (100 MHz, CDCl$_3$) δ 178.0, 157.4, 150.9, 149.4, 140.9, 130.1, 123.8, 116.8, 115.2, 61.9, 20.9 ppm. HRMS (ESI, m/z): calcd. for [C$_{13}$H$_{13}$O$_4$]$^+$ (M+H)$^+$, 233.0808; found, 233.0808.

2-(-4-(1-hydroxyethyl)-7-(hydroxymethyl)-1,3-dioxo-5-phenoxy-1,3,3a,4,7,7α-hexahydro-2H-4,7-epoxyisoindol-2-yl)ethyl 2-bromo-2-methylpropanoate ((±)-28)

A round bottom flask equipped with a stir bar was charged with 27 (350.0 mg, 1.509 mmol), THF (3 mL) and MeOH (10 mL). The solution was cooled to 0° C. in an ice bath before slowly adding NaBH4 (82.0 mg, 2.17 mmol). The mixture was kept at 0° C. for 1 h before adding 10% NH$_4$Cl (10 mL), extracted with EtOAc (2×10 mL), and washed with brine (10 mL). The organic layer was dried over Na$_2$SO$_4$, and filtered. Maleimide 214 (for example of synthesis, see Deng, G.; Chen, Y. A Novel Way To Synthesize Star Polymers in One Pot by ATRP of N-[2-(2-Bromoisobutyryloxy)ethyl]maleimide and Styrene. Macromolecules 2004, 37, 18-26, the disclosure of which is incorporated herein by reference) (527 mg, 2.77 mmol) was then added and the solution was concentrated under reduced pressure until about 2 mL viscous solution remained. The solution was then stirred at room temperature for 4 h, and the crude mixture was purified by column chromatography (72-90% EtOAc/Hexanes). A single diastereomer of the title compound was isolated as a colorless oil (285 mg, 36% yield). $^1$H NMR (400 MHz, CDCl$_3$) δ 7.38-7.30 (m, 2H), 7.22-7.16 (m, 1H), 7.00-6.94 (m, 2H), 4.96 (s, 1H), 4.59 (s, 1H), 4.32-3.97 (m, 5H), 3.78-3.53 (m, 3H), 2.04 (m, 2H), 1.87 (d, J=0.8 Hz, 6H), 1.54 (d, J=6.6 Hz, 3H) ppm. $^{13}$C{$^1$H}NMR (100 MHz, CDCl$_3$) δ 175.1, 174.1, 171.5, 163.5, 154.8, 130.2, 126.1, 119.9, 100.9, 92.3, 90.4, 65.0, 62.5, 62.4, 55.7, 50.9, 48.0, 37.5, 30.7, 30.7, 19.0 ppm. HRMS (ESI, m/z): calcd. for [C$_{23}$H$_{27}$BrNO$_8$]$^-$ (M+H)$^+$, 524.0915; found, 524.0928.

(2-(2-(((2-bromo-2-methylpropanoyl)oxy)ethyl)-7-(1-hydroxyethyl)-1,3-dioxo-6-phenoxy-1,2,3,3a,7,7a-hexahydro-4H-4,7-epoxyisoindol-4-yl)methyl 2-bromo-2-methylpropanoate ((±)-29)

A flame-dried round bottom flask equipped with a stir bar was charged with (±)-28 (263 mg, 0.502 mmol), Et$_3$N (84 μL, 0.60 mmol) and DCM (15 mL). The solution was cooled to 0° C. before adding α-bromo-isobutyryl bromide (68 μL, 0.55 mmol) dropwise. The reaction was then allowed to warm to room temperature and stirred overnight until the reaction had completed, as determined by TLC. The reaction mixture was then washed with NH$_4$Cl (30 mL) and brine (30 mL), and the organic fraction was dried over Na$_2$SO$_4$, filtered, and concentrated under reduced pressure. The crude product was purified by column chromatography (35-50% EtOAc/Hexanes) to yield the title compound as a colorless oil (270 mg, 80% yield). $^1$H NMR (400 MHz, CDCl$_3$) δ 7.39-7.30 (m, 2H), 7.23-7.15 (m, 1H), 7.01-6.91 (m, 2H), 4.95 (s, 1H), 4.68 (ABq, Δν$_{AB}$=126.4 Hz, J$_{AB}$=58.0 Hz, 2H), 4.63-4.57 (m, 1H), 4.33-4.11 (m, 2H), 4.00 (d, J=7.8 Hz, 1H), 3.79-3.52 (m, 3H), 1.96 (m, 7H), 1.86 (s, 6H), 1.52 (d, J=6.6 Hz, 3H) ppm. $^{13}$C{$^1$H} NMR (100 MHz, CDCl$_3$) δ 174.1, 173.7, 171.4, 171.0, 163.5, 154.6, 130.1, 126.0, 119.7, 100.8, 92.1, 88.2, 64.8, 63.5, 62.3, 55.5, 55.5, 51.1, 47.5, 37.3, 30.7, 30.6, 18.7 ppm. HRMS (ESI, m/z): calcd. for [C$_{27}$H$_{32}$Br$_2$NO$_9$]$^+$ (M+H)$^+$, 672.0438; found, 672.0462.

(2-(2-((2-bromo-2-methylpropanoyl)oxy)ethyl)-7-(1-hydroxyethyl)-1,3-dioxo-6-phenoxy-1,2,3,3a,7,7ahexahydro-4H-4,7-epoxyisoindol-4-yl)methyl pivalate ((±)-29-Control)

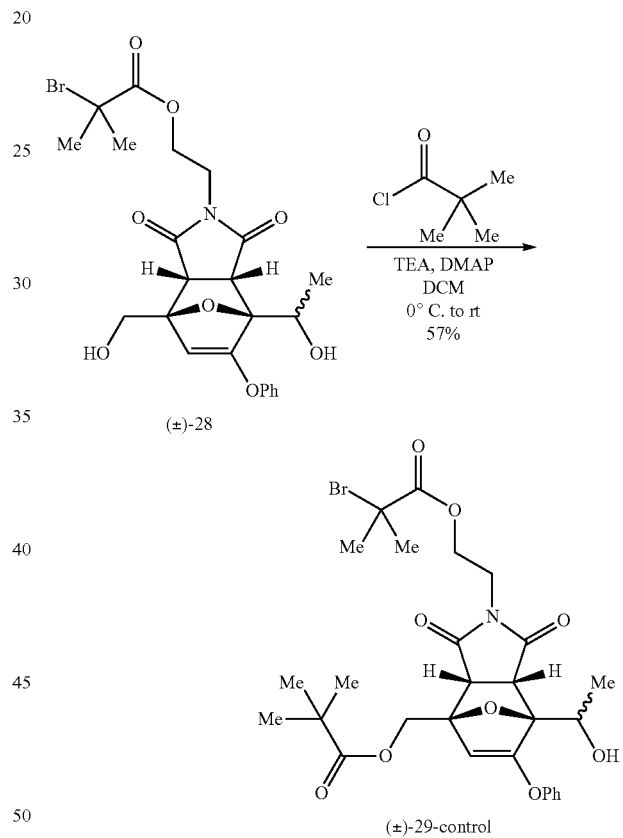

A flame-dried round bottom flask equipped with a stir bar was charged with (±)-28 (137 mg, 0.261 mmol), Et$_3$N (52.3 μL, 0.376 mmol), DMAP (41.7 mg, 0.342 mmol) and DCM (5 mL). The solution was cooled to 0° C. before adding pivaloyl chloride (46.3 μL, 0.376 mmol) dropwise. The reaction was then allowed to warm to room temperature and stirred overnight until the reaction completed, as determined by TLC. The reaction mixture was then diluted with DCM (20 mL), washed with NH$_4$Cl (30 mL) and brine (30 mL), and the organic fraction was dried over Na$_2$SO$_4$, filtered, and concentrated under reduced pressure. The crude product was purified by column chromatography (10-50% EtOAc: Hexanes) to yield the title compound as a white waxy solid (90 mg, 57% yield). $^1$H NMR (400 MHz, CDCl$_3$) δ 7.40-7.29 (m, 2H), 7.24-7.15 (m, 1H), 6.99-6.90 (m, 2H), 4.90 (s, 1H), 4.57 (ABq, Δν$_{AB}$=113.0 Hz, J$_{AB}$=12.7 Hz, 2H), 4.55 (dt, J=7.6, 6.4 Hz, 1H), 4.33-4.12 (m, 2H), 3.99 (d, J=7.8 Hz, 1H), 3.79-3.51 (m, 3H), 1.96 (d, J=7.9 Hz, 1H), 1.87 (d, J=1.3 Hz, 6H), 1.52 (d, J=6.6 Hz, 3H), 1.22 (s, 9H) ppm. $^{13}$C{$^1$H} NMR (100 MHz, CDCl$_3$) δ 177.9, 174.3, 173.9, 171.5, 163.5, 154.8, 130.2, 126.1, 119.8, 101.1, 92.1, 88.6, 64.9, 62.5, 62.3, 55.7, 51.2, 47.7, 39.1, 37.5, 30.7, 27.3, 18.8 ppm. HRMS (ESI, m/z): calcd. for [C$_{28}$H$_{35}$BrNO$_9$]$^-$ (M+H)$^+$, 608.1490; found, 608.1479.

7-isocyanato-4-methyl-2H-chromen-2-one (coumNCO)

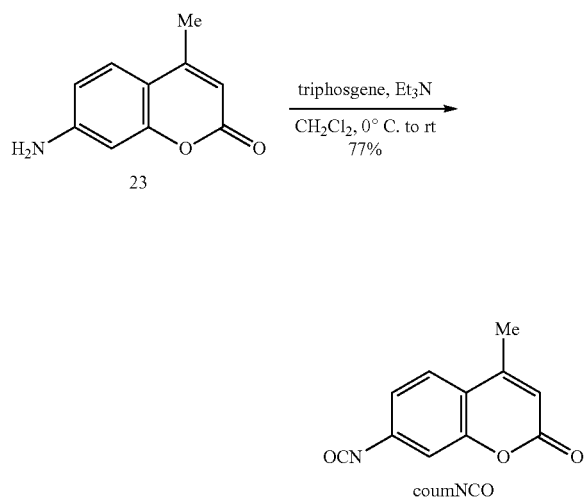

A flame-dried round bottom flask equipped with a stir bar under nitrogen was charged with triphosgene (0.59 g, 2.0 mmol) and anhydrous DCM (30 mL). The solution was cooled to 0° C. in an ice bath, followed by the addition of 23 (0.97 g, 5.5 mmol). Triethylamine (1.5 mL, 11 mmol) was dropwise added into the reaction. The reaction was allowed to warm to room temperature and stirred for 18 h. Hexane (30 mL) and DCM (60 mL) were added into the reaction mixture and the suspension was filtered to remove the pale yellow precipitate. The filtrate was washed with HCl (50 mL, 1 M), dried over MgSO$_4$, and filtered. The solid was discarded and the filtrate was concentrated under reduced pressure. The solid was dispersed in hexane (10 mL) and DCM (20 mL), filtered, and the filtrate was concentrated. The solid was dissolved in DCM (5 mL), and the solution was precipitated into hexane (30 mL). The fluffy white solid was collected by filtration and dried under reduced pressure to provide the title compound (0.85 g, 77%). $^1$H NMR (400 MHz, CDCl$_3$) δ 7.54 (dd, J=8.0, 0.8 Hz, 1H), 7.09-6.99 (m, 2H), 6.26 (q, J=1.3 Hz, 1H), 2.42 (d, J=1.3 Hz, 3H) ppm. $^{13}$C{$^1$H} NMR (100 MHz, CDCl$_3$) δ 160.4, 154.4, 151.8, 136.9, 125.8, 125.7, 121.3, 118.0, 114.8, 113.1, 18.8 ppm. HRMS (ESI, m/z): calcd. for [C$_{11}$H$_8$NO$_3$]$^+$ (M+H)$^+$, 202.0499; found, 202.0495.

(2-(2-((2-bromo-2-methylpropanoyl)oxy)ethyl)-7-(1-((((4-methyl-2-oxo-2H-chromen-7-yl)oxy)carbonyl)oxy)ethyl)-1,3-dioxo-6-phenoxy-1,2,3,3a,7,7a-hexahydro-4H-4,7-epoxyisoindol-4-yl)methyl 2-bromo-2-methylpropanoate ((±)-10(O))

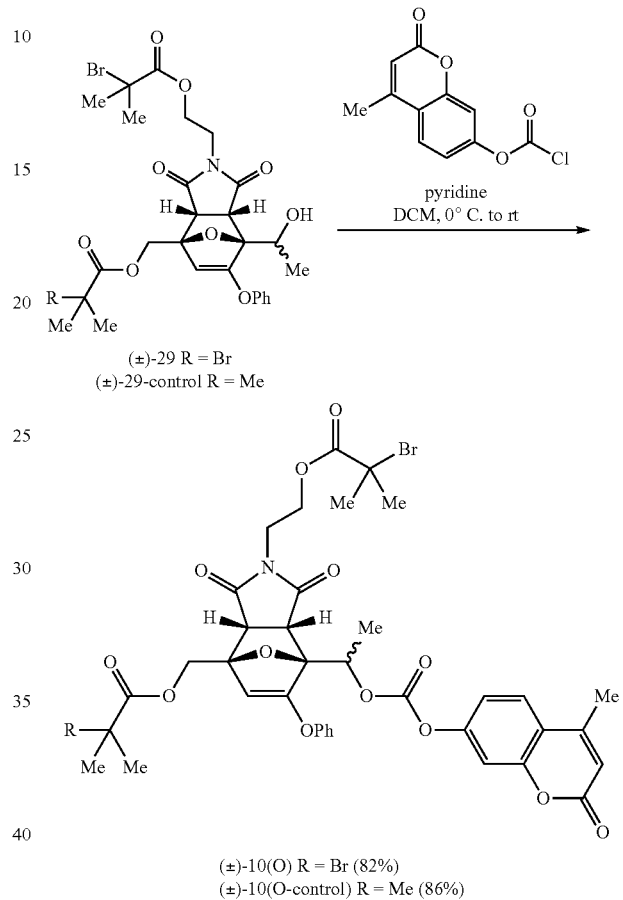

A two-neck round bottom flask equipped with a stir bar was charged with (±)-29 (20.4 mg, 0.0303 mmol), dry pyridine (3.2 μL, 0.040 mmol), and DCM (0.5 mL). The solution was cooled to 0° C. in an ice bath followed by the dropwise addition of a solution of coumarin chloroformate (9.4 mg, 0.039 mmol) in 0.5 mL DCM. The reaction was allowed to warm slowly to room temperature and stirred for 20 h. The reaction mixture was washed with brine, dried over Na$_2$SO$_4$, filtered, and concentrated under reduced pressure. The crude product was purified by column chromatography (35-55% EtOAc:Hexanes) to afford the title compound as a white foamy solid (21.7 mg, 82%). $^1$H NMR (400 MHz, CDCl$_3$) δ 7.63 (d, J=8.7 Hz, 1H), 7.39-7.32 (m, 2H), 7.28 (d, J=2.3 Hz, 1H), 7.26-7.17 (m, 2H), 6.29 (q, J=1.3 Hz, 1H), 5.66 (q, J=6.5 Hz, 1H), 5.04 (s, 1H), 4.71 (ABq, Δν$_{AB}$=107.6 Hz, J$_{AB}$=12.6 Hz, 2H), 4.34-4.12 (m, 2H), 3.89 (d, J=7.9 Hz, 1H), 3.77-3.53 (m, 3H), 2.45 (d, J=1.3 Hz, 3H), 1.96 (d, J=2.2 Hz, 6H), 1.86 (d, J=1.4 Hz, 6H), 1.72 (d, J=6.6 Hz, 3H) ppm. $^{13}$C{$^1$H} NMR (100 MHz, CDCl$_3$) δ 173.7, 173.0, 171.5, 171.1, 162.5, 160.5, 154.6, 154.3, 153.3, 152.1, 151.9, 130.3, 126.3, 125.7, 119.7, 118.2, 117.5, 114.9, 110.0, 101.2, 90.3, 88.5, 72.5, 63.6, 62.4, 60.5, 55.7, 55.6, 51.4, 48.1, 37.6, 30.8, 30.7, 30.7, 21.2, 18.9, 15.8, 14.3 ppm. HRMS (ESI, m/z): calcd. for $[C_{38}H_{37}Br_2NO_{13}]^+$ $(M)^+$, 873.0626; found, 873.0610.

2-(2-((2-bromo-2-methylpropanoyl)oxy)ethyl)-7-(1-((((4-methyl-2-oxo-2H-chromen-7-yl)oxy)carbonyl)oxy)ethyl)-1,3-dioxo-6-phenoxy-1,2,3,3a,7,7a-hexahydro-4H-4,7-epoxyisoindol-4-yl)methyl pivalate ((±)-10(O-control))

The title compound was prepared following a similar procedure as that for compound (±)-10(O), with compound (±)-29-control (35.0 mg, 0.0576 mmol), coumarin chloroformate (54.8 mg, 0.230 mmol), dry pyridine (18.6 µL, 0.230 mmol), and DCM (0.5 mL). The crude product was purified by column chromatography (35-55% EtOAc/Hexanes) to afford the title compound as a white foamy solid (43.4 mg, 86%). $^1H$ NMR (400 MHz, $CDCl_3$) δ 7.63 (d, J=8.7 Hz, 1H), 7.41-7.31 (m, 2H), 7.29-7.27 (m, 1H), 7.25-7.18 (m, 2H), 7.01-6.92 (m, 2H), 6.29 (d, J=1.3 Hz, 1H), 5.65 (q, J=6.5 Hz, 1H), 4.99 (s, 1H), 4.60 (ABq, $\Delta v_{AB}$=119.4 Hz, $J_{AB}$=12.0 Hz, 2H), 4.34-4.24 (m, 1H), 4.23-4.11 (m, 1H), 3.89 (d, J=7.8 Hz, 1H), 3.71 (ddd, J=14.2, 6.7, 4.0 Hz, 1H), 3.66-3.57 (m, 2H), 2.45 (d, J=1.3 Hz, 3H), 1.87 (s, 6H), 1.71 (d, J=6.6 Hz, 3H), 1.23 (s, 9H). $^{13}C\{^1H\}$ NMR (100 MHz, $CDCl_3$) δ 177.9, 173.8, 173.1, 171.6, 162.5, 160.5, 154.7, 154.3, 153.3, 152.2, 151.9, 130.3, 126.3, 125.7, 119.7, 118.2, 117.5, 114.9, 110.0, 101.4, 90.2, 88.8, 72.5, 62.4, 62.3, 55.7, 51.4, 48.1, 39.1, 37.6, 30.7, 30.7, 27.3, 18.9, 15.7 ppm. HRMS (ESI, m/z): calcd. for $[C_{39}H_{41}BrNO_{13}]^+$ $(M+H)^+$, 810.1397; found, 810.1368.

(2-(2-((2-bromo-2-methylpropanoyl)oxy)ethyl)-7-(1-(((4-methyl-2-oxo-2H-chromen-7-yl)carbamoyl)oxy)ethyl)-1,3-dioxo-6-phenoxy-1,2,3,3a,7,7a-hexahydro-4H-4,7-epoxyisoindol-4-yl)methyl 2-bromo-2-methylpropanoate ((±)-10(N))

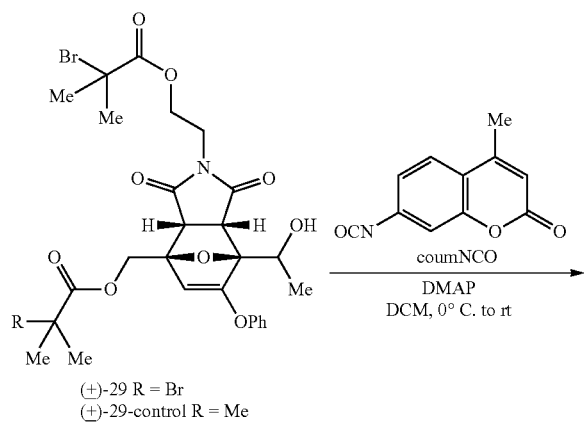

(±)-29 R = Br
(±)-29-control R = Me

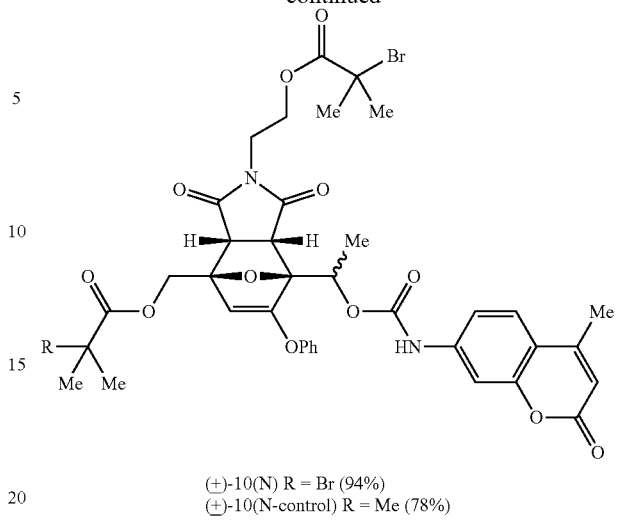

(±)-10(N) R = Br (94%)
(±)-10(N-control) R = Me (78%)

A two-neck round bottom flask equipped with a stir bar was charged with (±)-29 (31.5 mg, 0.0468 mmol), coumNCO (36.0 mg, 0.179 mmol) and DCM (3 mL). The mixture was cooled to 0° C. in ice bath before adding DMAP (21.9 mg, 0.179 mmol). The reaction was allowed to warm to room temperature and its progress was monitored by $^1H$ NMR spectroscopy until completion (~2 h). The mixture was then washed with brine, dried over $Na_2SO_4$, filtered, and concentrated under reduced pressure. The crude produce was purified by column chromatography (35-55% EtOAc/Hexanes) to provide the title compound as a white foamy solid (38.5 mg, 94%). $^1H$ NMR (400 MHz, $CDCl_3$) δ 7.57-7.50 (m, 1H), 7.48-7.41 (m, 2H), 7.39-7.30 (m, 2H), 7.25-7.17 (m, 2H), 7.01-6.92 (m, 2H), 6.20 (q, J=1.2 Hz, 1H), 5.77 (q, J=6.5 Hz, 1H), 5.02 (s, 1H), 4.70 (ABq, $\Delta V_{AB}$=99.8 Hz, $J_{AB}$=12.6 Hz, 2H), 4.33-4.10 (m, 2H), 3.82 (d, J=7.9 Hz, 1H), 3.76-3.53 (m, 3H), 2.41 (d, J=1.3 Hz, 3H), 1.96 (s, 6H), 1.85 (s, 6H), 1.60 (d, J=6.6 Hz, 3H) ppm. $^{13}C\{^1H\}$ NMR (100 MHz, $CDCl_3$) δ 173.8, 173.0, 171.6, 171.1, 162.9, 161.1, 154.7, 154.6, 152.3, 151.9, 141.3, 130.3, 126.2, 125.6, 119.6, 115.8, 114.5, 113.5, 106.1, 100.8, 90.5, 88.5, 63.6, 62.4, 55.7, 55.6, 51.3, 48.1, 37.6, 30.8, 30.7, 30.7, 18.7, 16.1 ppm. HRMS (ESI, m/z): calcd. for $[C_{31}H_{38}Br_2N_2O_{12}]^+$ $(M)^+$, 872.0786; found, 872.0792.

(2-(2-((2-bromo-2-methylpropanoyl)oxy)ethyl)-7-(1-(((4-methyl-2-oxo-2H-chromen-7-yl)carbamoyl)oxy)ethyl)-1,3-dioxo-6-phenoxy-1,2,3,3a,7,7a-hexahydro-4H-4,7-epoxyisoindol-4-yl)methyl pivalate ((±)-10(N-control))

The title compound was prepared following a similar procedure as that for compound (±)-10(N), with compound (±)-29-control (24.4 mg, 0.0401 mmol), coumNCO (16.0 mg, 0.0796 mmol), DMAP (9.8 mg, 0.080 mmol), and DCM (0.5 mL). The crude product was purified by column chromatography (35-55% EtOAc/Hexanes) to afford the title compound as a white foamy solid (25.1 mg, 78%). $^1H$ NMR (400 MHz, $CDCl_3$) δ 7.50-7.37 (m, 4H), 7.31-7.22 (m, 2H), 7.17-7.08 (m, 1H), 6.93-6.84 (m, 2H), 6.12 (s, 1H), 5.70 (q, J=6.5 Hz, 1H), 4.91 (s, 1H), 4.52 (ABq, $\Delta v_{AB}$=102.8 Hz, $J_{AB}$=16.0 Hz, 2H), 4.25-4.15 (m, 1H), 4.14-4.02 (m, 1H), 3.77 (d, J=7.8 Hz, 1H), 3.68-3.44 (m, 3H), 2.34 (d, J=1.3 Hz, 3H), 1.78 (d, J=1.3 Hz, 7H), 1.53 (d, J=6.5 Hz, 3H), 1.15 (d, J=1.5 Hz, 9H). $^{13}C\{^1H\}$ NMR (100 MHz, $CDCl_3$) δ 177.9, 173.8, 173.1, 171.5, 162.8, 161.2, 154.7, 154.5, 152.4, 152.0, 141.5, 130.2, 130.1, 126.1, 125.5, 119.6, 115.7, 114.6, 113.3, 106.4, 101.0, 90.4, 88.8, 68.1, 62.4, 62.4, 55.8, 51.3, 48.1, 39.0, 37.6, 30.7, 30.7, 27.3, 18.7, 16.1. ppm. HRMS (ESI, m/z): calcd. for $[C_{39}H_{42}BrN_2O_{12}]^+$ $(M+H)^+$, 809.1916; found, 809.1948.

Tert-butyldimethyl((3-phenoxyfuran-2-yl)methoxy)silane (217)

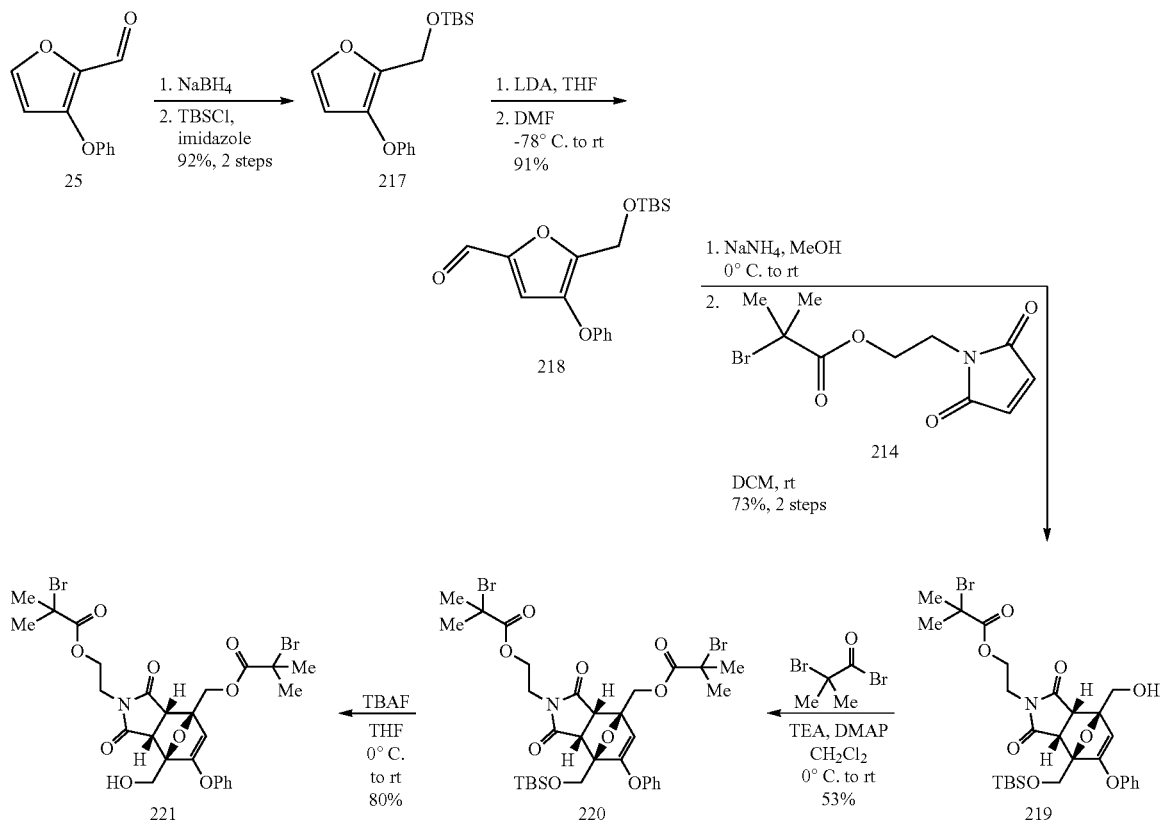

A round bottom flask equipped with a stir bar was charged with MeOH (10 mL) and cooled to 0° C. in an ice bath before adding NaBH4 (111 mg, 2.92 mmol), followed by the slow addition of 25 (303 mg, 1.61 mmol). The mixture was kept at 0° C. for 1 h before adding 10% NH4Cl (50 mL), and extracted with EtOAc (2×50 mL). The organic layer was dried over Na2SO4, filtered, and concentrated under reduced pressure to yield (3-phenoxyfuran-2-yl)methanol as a light yellow oil (300 mg, 98%) which was used in the next step without further purification.

A round bottom flask equipped with a stir bar was charged with (3-phenoxyfuran-2-yl)methanol (300 mg, 1.58 mmol), imidazole (191 mg, 2.81 mmol), and DCM (10 mL), followed by addition of tert-butylchlorodimethylsilane (265 mg, 1.76 mmol). The reaction was allowed to stir at room temperature overnight before filtering the mixture through a cotton pad. The filtrate was concentrated under reduced pressure, and the crude product was purified by column chromatography (0-20% EtOAc/Hexanes) to yield the title compound as a light-yellow oil (447 mg, 92% over two steps). $^1$H NMR (400 MHz, CDCl₃) δ 7.34-7.26 (m, 31H), 7.08-6.97 (m, 3H), 6.22 (d, J=2.1 Hz, 1H), 4.61 (s, 2H), 0.87 (s, 9H), 0.04 (s, 6H) ppm. $^{13}$C{$^1$H} NMR (100 MHz, CDCl₃) δ 158.3, 142.4, 141.4, 139.8, 129.7, 122.6, 116.4, 106.3, 54.7, 26.0, 18.6, −5.2 ppm. HRMS (EI, m/z): calcd. for $[C_{17}H_{23}O_3Si]^+$ $(M-H)^+$, 303.1411; found, 303.1407.

5-(((tert-butyldimethylsilyl)oxy)methyl)-4-phenoxyfuran-2-carbaldehyde (218)

A flame-dried round bottom flask equipped with a stir bar was charged with diisopropylamine (0.30 mL, 2.1 mmol) and THF (10 mL). The solution was cooled to −78° C. in an acetone/dry ice bath before adding n-butyllithium (0.70 mL, 1.8 mmol, 2.5 M in hexanes) dropwise. After stirring the mixture for 5 mins, a solution of 217 (354 mg, 1.16 mmol) in THF (10 ml) was added dropwise at −78° C. The mixture was kept at −78° C. for 30 mins before adding DMF (1.0 mL, 13 mmol) dropwise. The mixture was then allowed to slowly warm up to room temperature over an hour before 10% NH4Cl (50 mL) was added slowly to quench the reaction. The mixture was extracted with Et2O (2×50 mL), and the organic layer was dried over MgSO4, filtered, and concentrated under reduced pressure. The crude product was purified by column chromatography (0-10% EtOAc/Hexanes) to yield the title compound as a light-yellow oil (351 mg, 91%). $^1$H NMR (400 MHz, CDCl₃) δ 9.59 (s, 1H), 7.39-7.29 (m, 2H), 7.15-7.06 (m, 1H), 7.05-6.97 (m, 3H), 4.70 (s, 2H), 0.88 (s, 9H), 0.07 (s, 6H) ppm. $^{13}$C{$^1$H} NMR (100 MHz, CDCl₃) δ 178.2, 157.3, 149.8, 148.3, 142.0, 129.8, 123.5, 116.7, 114.2, 54.9, 25.8, 18.4, −5.4 ppm. HRMS (ESI, m/z): calcd. for $[C_{18}H_{25}O_4Si]^+$ $(M+H)^+$, 333.1517; found, 333.1543.

2-(4-(((tert-butyldimethylsilyl)oxy)methyl)-7-(hydroxymethyl)-1,3-dioxo-5-phenoxy-1,3,3a,4,7,7a-hexahydro-2H-4,7-epoxyisoindol-2-yl)ethyl 2-bromo-2-methylpropanoate (219)

A round bottom flask equipped with a stir bar was charged with 218 (350 mg, 1.05 mmol), THF (4 mL), and MeOH (1 mL). The solution was cooled to 0° C. in an ice bath before slowly adding NaBH4 (52.0 mg, 1.38 mmol). The mixture was kept at 0° C. for 1 h before adding 10% NH$_4$Cl (10 mL) and extracting with DCM (2×10 mL). The organic layer was dried over Na$_2$SO$_4$ and filtered. Maleimide 214 was added to the solution, and then the mixture was concentrated under reduced pressure until about 2 mL viscous solution remaining. The mixture was then stirred at room temperature for 2 h to allow the Diels-Alder reaction to run to completion, and the crude mixture was purified by column chromatography (10-30% EtOAc/Hexanes). A single endo isomer of the title compound was isolated as a colorless oil (478 mg, 73%). $^1$H NMR (400 MHz, CDCl$_3$) δ 7.37-7.28 (m, 2H), 7.23-7.14 (m, 1H), 7.00-6.93 (m, 2H), 4.95 (s, 1H), 4.35 (ABq, Δv$_{AB}$=5.3 Hz, J$_{AB}$=12.5 Hz, 2H), 4.30-3.98 (m, 4H), 3.86 (d, J=7.8 Hz, 1H), 3.74 (m, 1H), 3.65-3.49 (m, 1H), 2.02 (t, J=6.5 Hz, 1H), 1.87 (d, J=2.4 Hz, 6H), 0.94 (s, 9H), 0.16 (d, J=7.2 Hz, 6H) ppm. $^{13}$C{$^1$H} NMR (100 MHz, CDCl$_3$) δ 175.2, 174.0, 171.5, 163.3, 154.9, 130.1, 125.9, 119.9, 100.6, 90.6, 90.5, 62.6, 62.5, 59.7, 55.7, 50.8, 47.4, 37.4, 30.7, 30.7, 26.1, 18.7, −5.1, −5.2 ppm. HRMS (ESI, m/z): calcd. for [C$_{28}$H$_{39}$NO$_8$Si]$^+$ (M+H)$^+$, 624.1623; found, 624.1642.

(2-(2-((2-bromo-2-methylpropanoyl)oxy)ethyl)-7-(((tert-butyldimethylsilyl)oxy)methyl)-1,3-dioxo-6-phenoxy-1,2,3,3a,7,7a-hexahydro-4H-4,7-epoxyisoindol-4-yl)methyl 2-bromo-2-methylpropanoate (220)

A flame-dried round bottom flask equipped with a stir bar was charged with 219 (237 mg, 0.380 mmol), Et$_3$N (132 µL, 0.950 mmol) and DCM (10 mL). The solution was cooled to 0° C. before adding α-bromo-isobutyryl bromide (0.11 mL mg, 0.89 mmol) dropwise. The reaction was then allowed to slowly warm to room temperature and stirred overnight until the reaction had completed, as determined by TLC. The reaction mixture was then diluted with DCM (10 mL), washed with NH$_4$Cl (25 mL) and brine (20 mL), and the organic fraction was dried over Na$_2$SO$_4$, filtered, and concentrated under reduced pressure. The crude product was purified by column chromatography (10-30% EtOAc/hexanes) to yield the title compound as a viscus colorless oil (155 mg, 53% yield). $^1$H NMR (400 MHz, CDCl$_3$) δ 7.36-7.29 (m, 2H), 7.21-7.15 (m, 1H), 6.99-6.92 (m, 2H), 4.92 (s, 1H), 4.67 (ABq, Δv$_{AB}$=124.7 Hz, J$_{AB}$=12.5 Hz, 2H), 4.34 (ABq, Δv$_{AB}$=11.9 Hz, J$_{AB}$=12.4 Hz, 2H), 4.30-4.10 (m, 2H), 3.85 (d, J=7.8 Hz, 1H), 3.78-3.68 (m, 1H), 3.63 (d, J=7.8 Hz, 1H), 3.60-3.52 (m, 1H), 1.95 (d, J=4.0 Hz, 6H), 1.87 (d, J=1.9 Hz, 6H), 0.93 (s, 9H), 0.14 (d, J=9.4 Hz, 6H) ppm. $^{13}$C{$^1$H} NMR (100 MHz, CDCl$_3$) δ 174.4, 173.8, 171.5, 171.2, 163.5, 154.9, 130.1, 126.0, 119.8, 100.4, 90.5, 88.3, 63.8, 62.6, 59.6, 55.7, 55.6, 50.9, 47.1, 37.4, 30.9, 30.8, 30.7, 30.7, 26.0, 18.6, −5.1, −5.2 ppm. HRMS (ESI, m/z): calcd. for [C$_{32}$H$_{44}$Br$_2$NO$_9$Si]$^+$ (M+H)$^+$, 772.1147; found, 772.1168.

(2-(2-((2-bromo-2-methylpropanoyl)oxy)ethyl)-7-(hydroxymethyl)-1,3-dioxo-6-phenoxy-1,2,3,3a,7,7a-hexahydro-4H-4,7-epoxyisoindol-4-yl)methyl 2-bromo-2-methylpropanoate (221)

A flame-dried round bottom flask equipped with a stir bar was charged with 220 (155 mg, 0.200 mmol) and THF (3 mL). The solution was cooled to 0° C. before adding TBAF (1 M in THF, 0.26 mL, 0.26 mmol) dropwise. The mixture was allowed to slowly warm up room temperature and stirred for 1 h. The reaction mixture was washed with NH$_4$Cl (10 mL), extracted with EtOAc (10 mL), washed with brine (10 mL), and the organic fraction was dried over Na$_2$SO$_4$, filtered, and concentrated under reduced pressure. The crude product was purified by column chromatography (40-65% EtOAc/hexanes) to yield the title compound as a white foamy solid (105 mg, 80% yield). $^1$H NMR (400 MHz, CDCl$_3$) δ 7.38-7.30 (m, 2H), 7.23-7.14 (m, 1H), 7.01-6.94 (m, 2H), 4.97 (s, 1H), 4.69 (ABq, Δv$_{AB}$=113.7 Hz, J$_{AB}$=12.6 Hz, 2H), 4.44 (d, J=13.1 Hz, 1H), 4.35-4.22 (m, 2H), 4.2-4.12 (m, 1H), 3.81-3.63 (m, 3H), 3.57 (m, 1H), 1.96 (d, J=4.2 Hz, 6H), 1.86 (s, 6H) ppm. $^{13}$C{$^1$H} NMR (100 MHz, CDCl$_3$) δ 174.0, 173.4, 171.4, 171.1, 163.1, 154.7, 130.0, 126.0, 119.7, 100.6, 90.0, 88.6, 63.4, 62.3, 59.6, 55.5, 55.5, 50.7, 47.8, 37.4, 30.7, 30.6 ppm. HRMS (ESI, m/z): calcd. for [C$_{26}$H$_{30}$Br$_2$NO$_9$]$^+$ (M+H)$^+$, 658.0281; found, 658.0287.

2-(2-((2-bromo-2-methylpropanoyl)oxy)ethyl)-7-(((((4-methyl-2-oxo-2H-chromen-7-yl)oxy)carbonyl)oxy)methyl)-1,3-dioxo-6-phenoxy-1,2,3,3a,7,7a-hexahydro-4H-4,7-epoxyisoindol-4-yl)methyl 2-bromo-2-methylpropanoate (22(O))

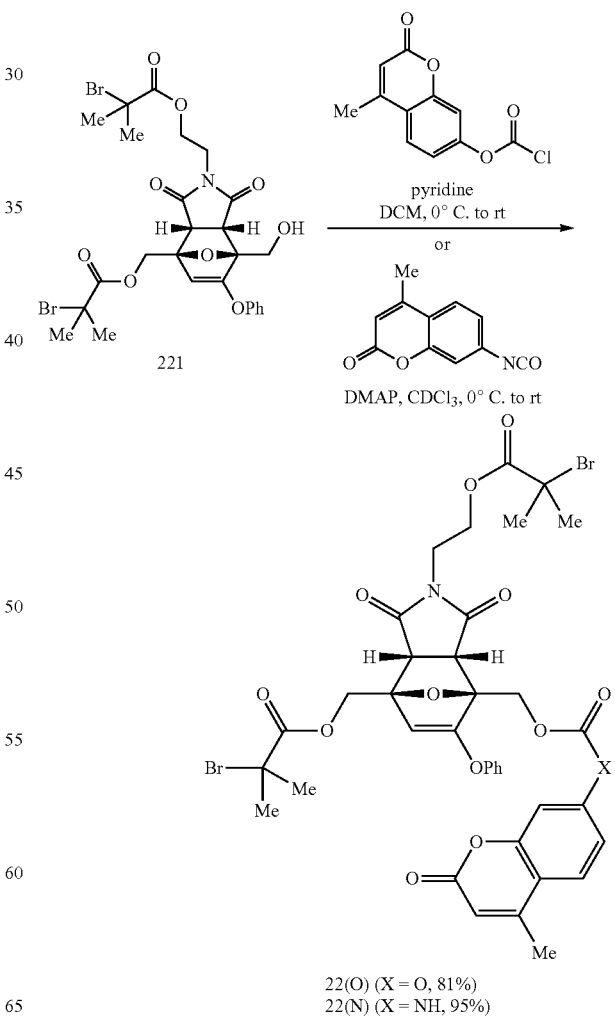

22(O) (X = O, 81%)
22(N) (X = NH, 95%)

The title compound was prepared following the same procedure as that for compound (±)-10(0), with compound 221 (20 mg, 0.030 mmol), dry pyridine (3.2 μL, 0.040 mmol), coumarin chloroformate (9.4 mg, 0.039 mmol) and DCM (5 mL). The crude product was purified by column chromatography (20-50% EtOAc/hexanes) to provide the title compound as a white foamy solid (21 mg, 81%). $^1$H NMR (400 MH-z, CDCl$_3$) δ 7.62 (d, J=8.7 Hz, 1H), 7.36 (dd, J=8.4, 7.4 Hz, 2H), 7.25-7.16 (m, 3H), 7.04-6.95 (in, 211), 6.3-6.26 (m, 1H), 5.04 (s, 1H), 5.01 (ABq, Δv$_{AB}$ 75.3 Hz, J$_{AB}$=12.6 Hz, 2H), 4.71 (ABq, Δv$_{AB}$=110.7 Hz, J$_{AB}$=12.7 Hz, 2H), 4.35-4.25 (m, 1H), 4.23-4.11 (m, 1H), 3.86-3.68 (m, 3H), 3.66-3.55 (m, 1H), 2.43 (d, J=1.2 Hz, 3H), 1.96 (d, J=3.8 Hz, 6H), 1.87 (d, J=1.2 Hz, 6H) ppm. $^{13}$C{$^1$H} NMR (100 MH-z, CDCl$_3$) δ 173.7, 172.9, 171.5, 171.2, 162.2, 160.5, 154.7, 154.3, 153.2, 152.5, 151.9, 130.3, 126.3, 125.7, 119.7, 118.3, 117.5, 114.9, 110.1, 100.8, 89.1, 87.2, 64.5, 63.4, 62.4, 55.7, 55.5, 50.7, 48.5, 37.6, 30.8, 30.7, 18.9 ppm. HRMS (ESI, m/z): calcd. for [C$_{37}$H$_{36}$Br$_2$NO$_1$]$^+$ (M+H)$^+$, 860.0548; found, 860.0553.

(2-(2-((2-bromo-2-methylpropanoyl)oxy)ethyl)-7-((((4-methyl-2-oxo-2H-chromen-7-yl)carbamoyl)oxy)methyl)-1,3-dioxo-6-phenoxy-1,2,3,3a,7,7a-hexahydro-4H-4,7-epoxyisoindol-4-yl)methyl 2-bromo-2-methylpropanoate (22(N))

The title compound was prepared following the same procedure as that for compound (±)-10(N), with compound 221 (40 mg, 0.061 mmol), DMAP (1.0 mg, 0.0082 mol), coumNCO (18 mg, 0.089 mmol) and CDCl$_3$ (3 mL). The crude produce was purified by column chromatography (20-40% Et$_2$O in 1:1 Hexanes/DCM) to provide the title compound as a white foamy solid (50 mg, 95%). $^1$H NMR (400 MHz, CDCl$_3$) δ 7.53 (d, J=8.6 Hz, 1H), 7.50-7.38 (m, 2H), 7.38-7.30 (m, 2H), 7.23-7.17 (m, 1H), 7.14 (s, 1H), 7.03-6.95 (m, 2H), 6.22-6.16 (m, 1H), 5.03 (s, 1H), 4.95 ((ABq, Δv$_{AB}$=59.3 Hz, J$_{AB}$=12.7 Hz, 2H), 4.70 (ABq, Δv$_{AB}$=108.0 Hz, J$_{AB}$=12.7 Hz, 2H), 4.34-4.11 (m, 2H), 3.80-3.67 (m, 3H), 3.64-3.54 (m, 11H), 2.41 (d, J=1.3 Hz, 3H), 1.95 (d, J=3.6 Hz, 6H), 1.86 (d, J=0.8 Hz, 6H) ppm. $^{13}$C{$^1$H} NMR (100 MHz, CDCl$_3$) δ 173.8, 172.9, 171.6, 171.2, 162.5, 161.1, 154.7, 154.6, 152.3, 152.2, 141.1, 130.2, 126.2, 125.6, 119.6, 115.9, 114.6, 113.5, 106.3, 100.7, 88.9, 87.7, 63.5, 62.4, 61.5, 55.7, 55.6, 50.7, 48.9, 37.6, 30.8, 30.7, 18.7 ppm. HRMS (ESI, m/z): calcd. for [C$_{37}$H$_{37}$Br$_2$N$_2$O$_{12}$]$^+$ (M+H)$^+$, 859.0708; found, 859.0704.

1-(2-(2-((2-bromo-2-methylpropanoyl)oxy)ethyl)-7-(((2-bromo-2-methylpropanoyl)oxy)methyl)-1,3-dioxo-5-phenoxy-1,2,3,3a,7,7a-hexahydro-4H-4,7-epoxyisoindol-4-yl)ethyl 4-(pyren-4-yl)butanoate ((±)-10(COOH))

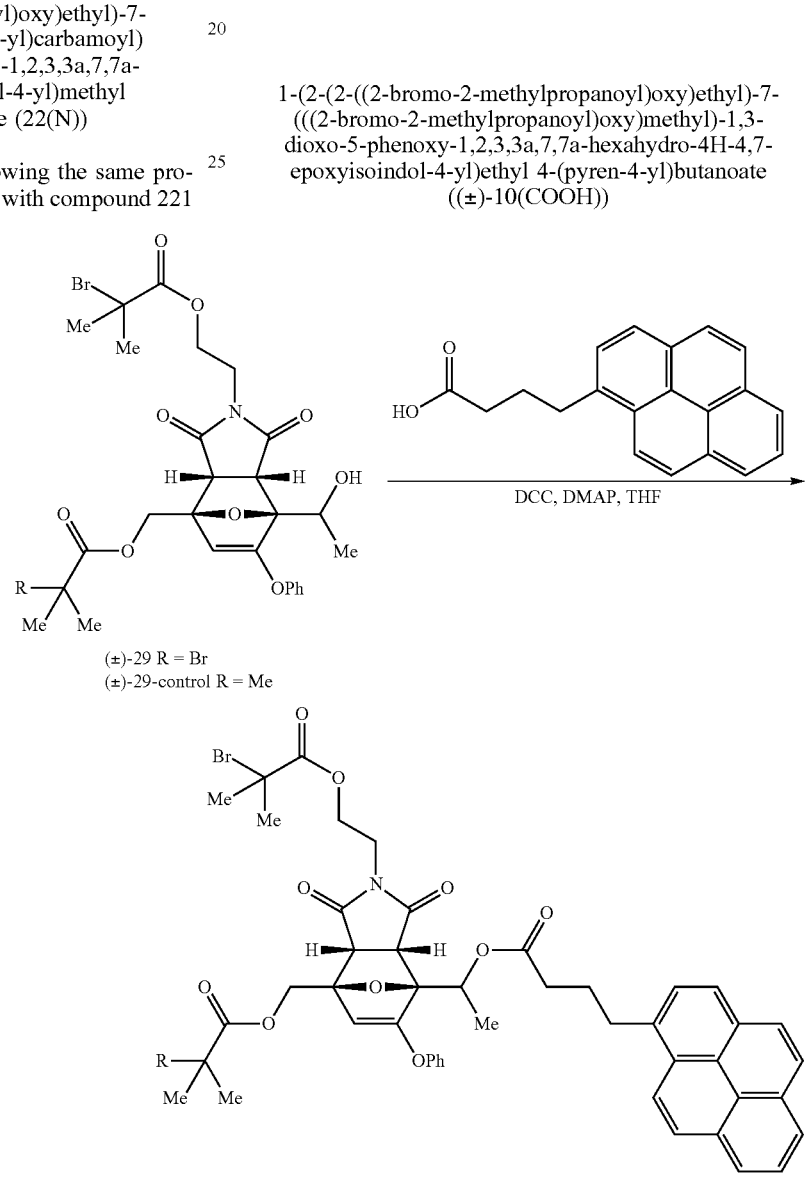

(±)-29 R = Br
(±)-29-control R = Me (±)-10(COOH) R = Br (91%)
(±)-10(COOH-control) R = Me (84%)

A 2 dram vial equipped with a stir bar was charged with (±)-29 (34.0 mg, 0.0505 mmol), DMAP (1.5 mg, 0.012 mmol), 1-pyrenebutanoic acid (16 mg, 0.056 mmol) and THF (0.5 mL). N,N'-Dicyclohexylcarbodiimide (11.5 mg, 0.0558 mmol) was then added to the reaction mixture slowly. The reaction was stirred at room temperature overnight until the reaction completed, as determined by $^1$H NMR spectroscopy. The reaction mixture was then diluted with Et$_2$O (15 mL), washed with NH$_4$CL (15 mL) and brine (15 mL), and the organic fraction was dried over Na$_2$SO$_4$, filtered, and concentrated under reduced pressure. The crude product was purified by column chromatography (20-40% EtOAc/hexanes) to yield the title compound as a white foamy solid (43.6 mg, 91% yield). $^1$H NMR (400 MHz, CDCl$_3$) δ 8.35-8.28 (m, 1H), 8.21-8.14 (m, 2H), 8.14-8.08 (m, 2H), 8.05-8.02 (m, 2H), 8.02-7.97 (m, 1H), 7.91-7.85 (m, 1H), 7.35-7.28 (m, 2H), 7.20-7.14 (m, 1H), 6.97-6.91 (m, 2H), 5.77 (q, J=6.5 Hz, 1H), 4.98 (s, 1H), 4.66 (ABq, Δν$_{AB}$=119.3 Hz, J$_{AB}$=12.6 Hz, 2H), 4.28-4.07 (m, 2H), 3.73-3.62 (m, 2H), 3.62-3.50 (m, 2H), 3.44 (t, J=7.7 Hz, 2H), 2.56 (t, J=7.3 Hz, 2H), 2.32-2.20 (m, 2H), 1.90 (d, J=4.2 Hz, 6H), 1.79 (d, J=4.0 Hz, 6H), 1.55 (d, J=6.6 Hz, 3H) ppm. $^{13}$C{$^1$H} NMR (100 MHz, CDCl$_3$) δ 173.8, 172.9, 172.4, 171.5, 171.1, 162.9, 154.7, 135.7, 131.5, 131.0, 130.2, 130.2, 128.9, 127.6, 127.6, 126.9, 126.1, 126.0, 125.2, 125.1, 125.1, 125.0, 124.9, 123.5, 119.7, 100.9, 90.8, 88.3, 66.8, 63.7, 62.4, 55.7, 55.6, 51.4, 47.9, 37.5, 34.1, 32.9, 30.8, 30.7, 30.6, 27.0, 16.0 ppm. HRMS (ESI, m/z): calcd. for [C$_{47}$H$_{46}$Br$_2$NO$_{10}$]$^+$ (M+H)$^+$, 942.1483; found, 942.1509.

1-(2-(2-((2-bromo-2-methylpropanoyl)oxy)ethyl)-1,3-dioxo-5-phenoxy-7-((pivaloyloxy)methyl)-1,2,3,3a,7,7a-hexahydro-4H-4,7-epoxyisoindol-4-yl)ethyl 4-(pyren-1-yl)butanoate ((±)-10(COOH-control))

The title compound was prepared following a similar procedure as that for compound (±)-10(COOH), with compound (±)-29-control (23.0 mg, 0.0378 mmol), 1-pyrenebutanoic acid (21.8 mg, 0.0757 mmol), N,N'-dicyclohexylcarbodiimide (15.6 mg, 0.0757 mmol), DMAP (2.3 mg, 0.019 mmol), and THF (0.5 mL). Column chromatography (10-25% EtOAc/Hexanes) followed by preparative thin layer chromatography (4:1 toluene/acetone) afforded the title compound as a white foamy solid (28 mg, 84%). $^1$H NMR (500 MHz, CDCl$_3$) δ 8.34-8.29 (m, 1H), 8.19-8.14 (m, 2H), 8.14-8.08 (m, 2H), 8.06-8.02 (m, 2H), 8.02-7.96 (m, 1H), 7.89-7.86 (m, 1H), 7.35-7.28 (m, 2H), 7.21-7.14 (m, 1H), 6.95-6.90 (m, 2H), 5.78 (q, J=6.5 Hz, 1H), 4.93 (s, 1H), 4.57 (ABq, Δν$_{AB}$=166.4 Hz, J$_{AB}$=12.7 Hz, 2H), 4.28-4.10 (m, 2H), 3.74-3.61 (m, 2H), 3.61-3.47 (m, 2H), 3.44 (t, J=7.7 Hz, 2H), 2.57 (t, J=7.3 Hz, 2H), 2.32-2.20 (m, 2H), 1.80 (d, J=6.0 Hz, 6H), 1.56 (d, J=6.6 Hz, 3H), 1.18 (s, 9H) ppm. $^{13}$C{$^1$H}NMR (100 MHz, CDCl$_3$) δ 177.8, 173.9, 172.9, 172.4, 171.5, 162.8, 154.7, 135.7, 131.5, 131.0, 130.2, 130.1, 128.9, 127.6, 127.6, 126.9, 126.1, 126.0, 126.0, 125.2, 125.1, 125.1, 125.0, 124.9, 123.5, 119.7, 119.6, 101.1, 90.7, 88.6, 66.8, 62.5, 62.4, 55.7, 51.4, 48.0, 39.0, 37.4, 34.1, 32.9, 30.6, 30.6, 27.3, 27.2, 27.0, 16.0 ppm. HRMS (ESI, m/z): calcd. for [C$_{48}$H$_{49}$BrNO$_{10}$]$^+$ (M+H)$^+$, 878.2534; found, 878.2541.

2-(2-((2-bromo-2-methylpropanoyl)oxy)ethyl)-7-(1-((naphthalen-2-ylsulfonyl)oxy)ethyl)-1,3-dioxo-6-phenoxy-1,2,3,3a,7,7a-hexahydro-4H-4,7-epoxyisoindol-4-yl)methyl 2-bromo-2-methylpropanoate ((±)-10(SO$_3$H))

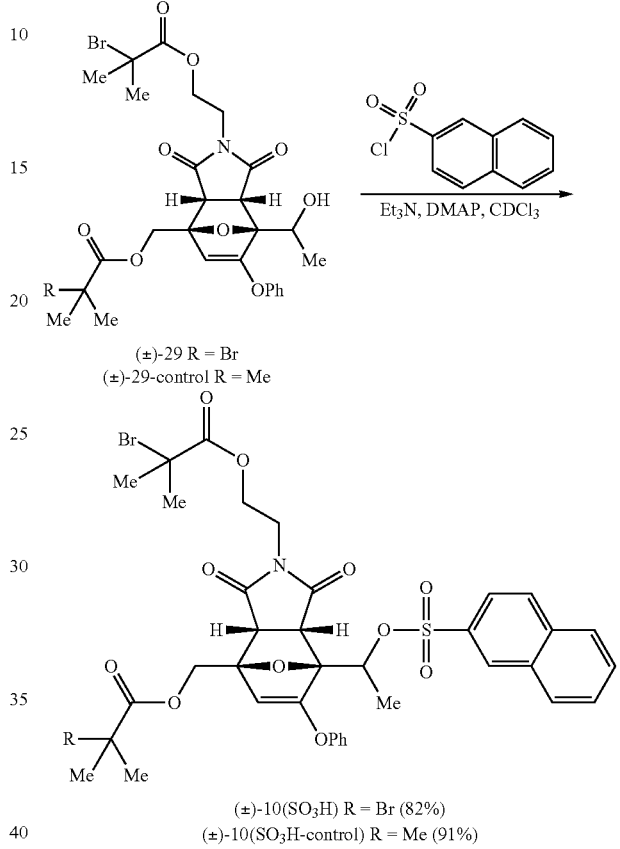

(±)-10(SO$_3$H) R = Br (82%)
(±)-10(SO$_3$H-control) R = Me (91%)

A 2 dram vial equipped with a stir bar was charged with (±)-29 (22 mg, 0.033 mmol), DMAP (4.2 mg, 0.035 mmol) and CDCl$_3$ (0.3 mL). Naphthalene-2-sulfonyl chloride (7.8 mg, 0.034 mmol) dissolved in CDCl$_3$ (0.2 mL) was then added to the reaction mixture slowly. The solution was then stirred at room temperature until the reaction completed, as determined by $^1$H NMR spectroscopy (~2 h). The reaction mixture was then diluted with DCM (10 mL), washed with NH$_4$Cl (15 mL) and brine (15 mL), and the organic fraction was dried over Na$_2$SO$_4$, filtered, and concentrated under reduced pressure. The crude product was purified by column chromatography (20-40% EtOAc/hexanes) to yield the title compound as a white foamy solid (17.6 mg, 62% yield). $^1$H NMR (400 MHz, CDCl$_3$) δ 8.62 (d, J=1.8 Hz, 1H), 8.07-7.99 (m, 2H), 7.99-7.92 (m, 2H), 7.60-7.73 (m, 2H), 7.38-7.29 (m, 2H), 7.22-7.15 (m, 1H), 6.96-6.89 (m, 2H), 5.55 (q, J=6.6 Hz, 1H), 4.94 (s, 1H), 4.60 (ABq, Δν$_{AB}$=107.3 Hz, J$_{AB}$=12.6 Hz, 2H), 4.21-4.04 (m, 2H), 3.75 (d, J=7.9 Hz, 1H), 3.68-3.49 (m, 3H), 1.92 (d, J=4.6 Hz, 6H), 1.84 (d, J=1.6 Hz, 6H), 1.57 (d, J=6.6 Hz, 3H) ppm. $^{13}$C{$^1$H} NMR (100 MHz, CDCl$_3$) δ 173.6, 172.7, 171.4, 171.1, 162.4, 154.5, 135.5, 133.8, 132.1, 130.2, 130.0, 129.9, 129.6, 129.6, 128.2, 128.0, 126.3, 122.7, 119.6, 101.1, 90.4, 88.4, 75.2, 63.5, 62.3, 55.7, 55.5, 51.3, 47.9, 37.4, 30.8, 30.7, 30.7, 17.2 ppm. HRMS (ESI, m/z): calcd. for $[C_{37}H_{38}Br_2NO_{11}S]^+$ (M+H)⁻, 862.0527; found, 862.0546.

(2-(2-((2-bromo-2-methylpropanoyl)oxy)ethyl)-7-(1-((naphthalen-2-ylsulfonyl)oxy)ethyl)-1,3-dioxo-6-phenoxy-1,2,3,3a,7,7a-hexahydro-4H-4,7-epoxyisoindol-4-yl)methyl pivalate ((±)-10(SO₃H-control))

The title compound was prepared following the same procedure as that for compound (±)-10(SO₃H), with compound (±)-29-control (20 mg, 0.033 mmol), DMAP (6.3 mg, 0.052 mmol), naphthalene-2-sulfonyl chloride (11.7 mg, 0.052 mmol, and CDCl₃ (0.5 mL). Column chromatography (25-45% EtOAc/Hexanes) afforded the title compound as a white foamy solid (24 mg, 91%). ¹H NMR (400 MHz, CDCl₃) δ 8.62 (d, J=1.8 Hz, 1H), 8.05-7.91 (m, 4H), 7.72-7.61 (m, 2H), 7.38-7.28 (m, 2H), 7.23-7.16 (m, 1H), 6.95-6.88 (m, 2H), 5.56 (q, J=6.5 Hz, 1H), 4.89 (s, 1H), 4.50 (ABq, $\Delta v_{AB}$=122.8 Hz, $J_{AB}$=12.7 Hz, 2H), 4.22-4.06 (m, 2H), 3.75 (d, J=7.9 Hz, 1H), 3.68-3.46 (m, 3H), 1.85 (s, 6H), 1.63-1.52 (m, 3H), 1.19 (s, 9H) ppm. $^{13}C\{^1H\}$ NMR (100 MHz, CDCl₃) δ 177.8, 173.7, 172.8, 171.4, 162.4, 154.6, 135.5, 133.8, 132.1, 130.2, 130.0, 129.8, 129.6, 129.6, 128.1, 127.9, 126.2, 122.7, 119.6, 101.2, 90.3, 88.7, 75.2, 62.3, 62.2, 55.7, 51.2, 48.0, 39.0, 37.4, 30.7, 30.6, 27.3, 27.2, 17.2 ppm. HRMS (ESI, m/z): calcd. for $[C_{38}H_{40}BrNO_{11}SNa]^+$ (M+Na)⁺, 820.1398; found, 820.1392.

(2-(2-((2-bromo-2-methylpropanoyl)oxy)ethyl)-7-(1-(((4-nitrophenoxy)carbonyl)oxy)ethyl)-1,3-dioxo-6-phenoxy-1,2,3,3a,7,7a-hexahydro-4H-4,7-epoxyisoindol-4-yl)methyl 2-bromo-2-methylpropanoate ((±)-223)

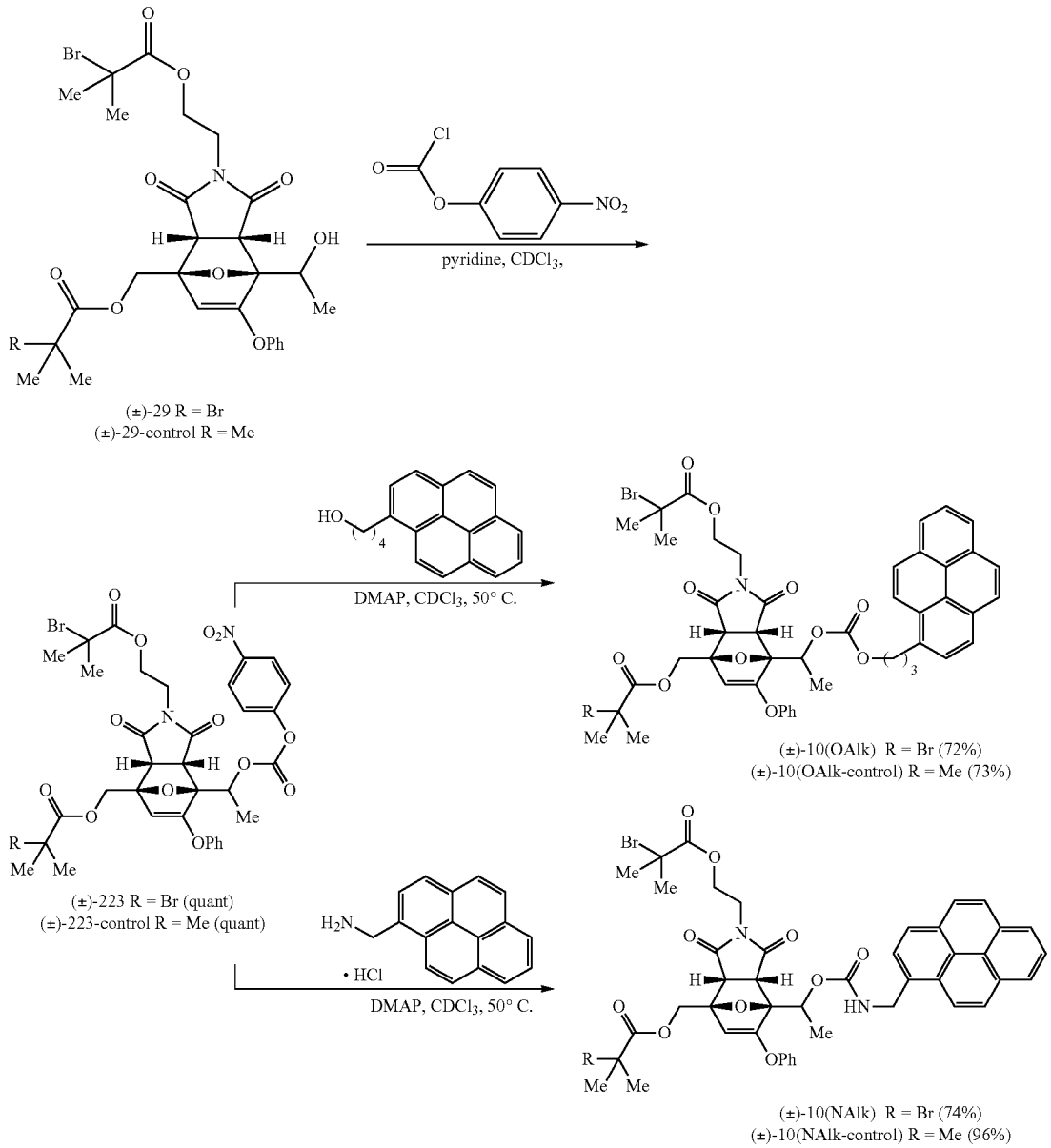

A 2 dram vial equipped with a stir bar was charged with (±)-29 (101 mg, 0.150 mmol), pyridine (14.6 µL, 0.181 mmol) and CDCl$_3$ (1 mL). 4-nitrophenyl chloroformate (33.3 mg, 0.166 mmol) dissolved in CDCl$_3$ was then added to the reaction mixture slowly. The reaction was then stirred at room temperature until the reaction had completed, as determined by $^1$H NMR spectroscopy (~2 h). The reaction mixture was then diluted with DCM (20 mL), washed with NH$_4$Cl (25 mL) and brine (25 mL), and the organic fraction was dried over Na$_2$SO$_4$, filtered, and concentrated under reduced pressure. The crude product was purified by column chromatography (2045% EtOAc/Hexanes) to yield the title compound as a white foamy solid (125 mg, quant). $^1$H NMR (400 MHz, CDCl$_3$) δ 8.34-8.26 (m, 2H), 7.49-7.41 (m, 2H), 7.36 (dd, J 8.5, 7.3 Hz, 2H), 7.21 (t, J=7.5 Hz, 1H), 7.01-6.94 (in, 211), 5.66 (q, J=6.5 Hz, 1H), 5.03 (s, 1H), 4.71 (ABq, Δν$_{AB}$=106.7 Hz, J$_{AB}$ 12.6 Hz, 2H), 4.34-4.12 (m, 2H), 3.87 (d, J=7.8 Hz, 1H), 3.78-3.54 (m, 3H), 1.96 (d, J=2.0 Hz, 6H), 1.86 (d, J=1.2 Hz, 6H), 1.72 (d, J=6.5 Hz, 3H) ppm. $^{13}$C{$^1$H} NMR (100 MHz, CDCl$_3$) δ 173.7, 172.9, 171.5, 171.1, 162.5, 155.6, 154.6, 151.8, 145.6, 130.3, 126.3, 125.5, 121.9, 119.7, 101.2, 90.3, 88.5, 72.9, 63.5, 62.4, 55.7, 55.5, 51.4, 48.1, 37.6, 30.8, 30.7, 30.7, 15.7 ppm. HRMS (ESI, m/z): calcd. for [C$_{34}$H$_{34}$Br$_2$N$_2$O$_{13}$Na]$^+$ (M+Na)$^+$, 859.0320; found, 859.0325.

(2-(2-((2-bromo-2-methylpropanoyl)oxy)ethyl)-7-(1-(((4-nitrophenoxy)carbonyl)oxy)ethyl)-1,3-dioxo-6-phenoxy-1,2,3,3a,7,7a-hexahydro-4H-4,7-epoxyisoindol-4-yl)methyl pivalate (((±)-223-control)

The title compound was prepared following a similar procedure as that for compound (±)-223, with compound (±)-29-control (75.0 mg, 0.123 mmol), pyridine (12.0 µL, 0.149 mmol), 4-nitrophenyl chloroformate (27.3 mg, 0.136 mmol), and CDCl$_3$ (0.7 mL). Column chromatography (20-45% EtOAc/hexanes) afforded the title compound as a white foamy solid (94.5 mg, quant). $^1$H NMR (500 MHz, CDCl$_3$) δ 8.33-8.27 (m, 2H), 7.48-7.42 (m, 2H), 7.40-7.32 (m, 2H), 7.25-7.18 (m, 1H), 6.99-6.93 (m, 2H), 5.66 (q, J=6.5 Hz, 1H), 4.99 (s, 1H), 4.61 (ABq, Δν$_{AB}$=151.1 Hz, J$_{AB}$=12.8 Hz, 2H), 4.34-4.14 (m, 2H), 3.87 (d, J=7.9 Hz, 1H), 3.75-3.58 (m, 3H), 1.87 (s, 6H), 1.72 (d, J=6.5 Hz, 3H), 1.23 (s, 9H) ppm. $^{13}$C{$^1$H} NMR (100 MHz, CDCl$_3$) δ 177.8, 173.7, 173.0, 171.6, 162.5, 155.6, 154.7, 151.9, 145.6, 130.3, 126.3, 125.5, 121.9, 119.7, 101.4, 90.1, 88.8, 72.8, 62.4, 62.2, 55.7, 51.4, 48.2, 39.1, 37.6, 30.7, 27.3, 15.7 ppm. HRMS (ESI, m/z): calcd. for [C$_{35}$H$_{37}$BrN$_2$O$_{13}$Na]$^+$ (M+Na)$^+$, 795.1371; found, 795.1377.

(2-(2-((2-bromo-2-methylpropanoyl)oxy)ethyl)-1,3-dioxo-6-phenoxy-7-(1-(((4-(pyren-1-yl)butoxy)carbonyl)oxy)ethyl)-1,2,3,3a,7,7a-hexahydro-4H-4,7-epoxyisoindol-4-yl)methyl 2-bromo-2-methylpropanoate ((i)-10(OAlk))

A 2 dram vial equipped with a stir bar was charged with (±)-223 (21.7 mg, 0.0259 mmol), DMAP (3.5 mg, 0.029 mmol) and CDCl$_3$ (0.5 mL), followed by the addition of 1-pyrenebutanol (7.8 mg, 0.028 mmol) dissolved in CDCl$_3$ (0.2 mL). The reaction was stirred at 50° C. overnight until the reaction had completed, as determined by $^1$H NMR spectroscopy. The reaction mixture was then diluted with DCM (15 mL), washed with NH$_4$Cl (15 mL) and brine (15 mL), and the organic fraction was dried over Na$_2$SO$_4$, filtered, and concentrated under reduced pressure. The crude product was purified by column chromatography (35-50% EtOAc/hexanes) to yield the title compound as a white foamy solid (18 mg, 72% yield). $^1$H NMR (400 MHz, CDCl$_3$) δ 8.30-7.85 (m, 9H), 7.39-7.29 (m, 2H), 7.21-7.13 (m, 1H), 7.01-6.91 (m, 2H), 5.57 (q, J=6.5 Hz, 1H), 4.99 (s, 1H), 4.66 (ABq, Δν$_{AB}$=109.8 Hz, J$_{AB}$=12.6 Hz, 2H), 4.36-4.17 (m, 3H), 4.16-4.08 (m, 1H), 3.81 (d, J=7.9 Hz, 1H), 3.70-3.51 (m, 3H), 3.40 (t, J=7.5 Hz, 2H), 2.13-1.85 (m, 10H), 1.82 (s, 6H), 1.58 (d, J=6.5, 3H) ppm. $^{13}$C{$^1$H} NMR (100 MHz, CDCl$_3$) δ 173.7, 172.9, 171.4, 171.0, 162.5, 154.6, 154.5, 136.2, 131.4, 130.9, 130.1, 129.9, 128.6, 127.5, 127.4, 127.3, 126.7, 126.0, 125.9, 125.1, 125.0, 124.9, 124.8, 124.8, 123.3, 119.5, 101.0, 90.5, 88.2, 70.3, 68.3, 63.6, 62.3, 55.5, 55.5, 51.3, 47.7, 37.3, 33.0, 30.7, 30.6, 30.5, 28.7, 27.9, 15.8 ppm. HRMS (ESI, m/z): calcd. for [C$_{48}$H$_{48}$Br$_2$NO$_{11}$]$^+$ (M+H)$^+$, 972.1589; found, 972.1597.

(2-(2-((2-bromo-2-methylpropanoyl)oxy)ethyl)-1,3-dioxo-6-phenoxy-7-(1-(((4-(pyren-1-yl)butoxy)carbonyl)oxy)ethyl)-1,2,3,3a,7,7a-hexahydro-4H-4,7-epoxyisoindol-4-yl)methyl pivalate ((±)-10(OAlk-control))

The title compound was prepared following a similar procedure as that for compound (±)-10(OAlk), with compound (±)-223-control (30.0 mg, 0.0388 mmol), DMAP (9.5 mg, 0.078 mmol), 1-pyrenebutanol (21.3 mg, 0.777 mmol), and CDCl$_3$ (0.5 mL). Column chromatography (20-50% EtOAc/Hexanes) afforded the title compound as a white foamy solid (25.9 mg, 73%). $^1$H NMR (400 MHz, CDCl$_3$) δ 8.30-7.85 (m, 9H), 7.37-7.29 (m, 2H), 7.22-7.15 (m, 1H), 7.00-6.91 (m, 2H), 5.56 (q, J=6.5 Hz, 1H), 4.94 (s, 1H), 4.56 (ABq, Δν$_{AB}$=123.5 Hz, J$_{AB}$=12.7 Hz, 2H), 4.34-4.19 (m, 3H), 4.17-4.08 (m, 1H), 3.80 (d, J=7.9 Hz, 1H), 3.70-3.49 (m, 3H), 3.40 (t, J=7.5 Hz, 2H), 2.15-1.73 (m, 10H), 1.58 (d, J=6.5 Hz, 3H), 1.20 (s, 9H) ppm. $^{13}$C{$^1$H} NMR (125 MHz, CDCl$_3$) δ 177.9, 173.9, 173.1, 171.5, 162.6, 154.7, 136.3, 131.6, 131.0, 130.2, 130.0, 128.8, 127.6, 127.5, 127.4, 126.8, 126.1, 126.0, 125.2, 125.1, 125.1, 125.0, 124.9, 123.4, 119.7, 101.2, 90.5, 88.7, 70.5, 68.4, 62.4, 55.7, 51.4, 47.8, 39.0, 37.4, 33.2, 30.7, 28.8, 28.0, 27.2, 27.2, 15.9 ppm. HRMS (ESI, m/z): calcd. for [C$_{49}$H$_{51}$BrNO$_{11}$]$^+$ (M+H)$^+$, 908.2640; found, 908.2626.

(2-(2-((2-bromo-2-methylpropanoyl)oxy)ethyl)-1,3-dioxo-6-phenoxy-7-(1-(((pyren-1-ylmethyl)carbamoyl)oxy)ethyl)-1,2,3,3a,7,7a-hexahydro-4H-4,7-epoxyisoindol-4-yl)methyl 2-bromo-2-methylpropanoate ((±)-10(NAlk))

A 2 dram vial equipped with a stir bar was charged with (±)-223 (24.1 mg, 0.0289 mmol), DMAP (8.4 mg, 0.069 mmol) and CDCl$_3$ (0.5 mL). Pyren-1-ylmethanamine hydrochloride (8.5 mg, 0.032 mmol) dissolved in CDCl$_3$ (0.5 mL) was then added to the reaction mixture. The reaction was stirred at 50° C. overnight until the reaction had completed, as determined by $^1$H NMR spectroscopy. The reaction mixture was then diluted with DCM (10 mL), washed with NH$_4$Cl (15 mL) and brine (15 mL), and the organic fraction was dried over Na$_2$SO$_4$, filtered, and concentrated under reduced pressure. The crude product was purified by column chromatography (20-60% EtOAc/hexanes) to yield the title compound as a white foamy solid (20 mg, 74% yield). $^1$H NMR (500 MHz, CDCl$_3$) δ 8.34-7.97 (m, 9H), 7.32-7.26 (m, 2H), 7.19-7.13 (m, 11H), 6.93 (d, J=7.9 Hz, 2H), 5.77 (q, J=6.5 Hz, 1H), 5.38-5.30 (m, 1H), 5.16 (d, J=5.6 Hz, 2H), 4.96 (s, 1H), 4.63 (ABq, Δν$_{AB}$=137.0 Hz, J$_{AB}$=12.6 Hz, 2H), 4.34-4.19 (m, 1H), 4.18-4.08 (m, 1H), 3.77 (d, J=7.9 Hz, 1H), 3.71-3.41 (m, 3H), 1.91 (d, J=3.7 Hz, 6H), 1.82 (s, 6H), 1.57 (d, J=6.5 Hz, 3H) ppm. $^{13}C\{^1H\}$ NMR (100 MHz, CDCl$_3$) δ 173.9, 172.9, 171.5, 171.1, 163.1, 155.3, 154.7, 131.4, 131.2, 130.9, 130.1, 129.1, 128.4, 127.7, 127.5, 127.0, 126.3, 126.0, 125.6, 125.5, 125.2, 125.0, 124.9, 122.9, 119.7, 100.7, 90.9, 88.3, 67.3, 63.7, 62.5, 55.7, 55.6, 51.3, 47.8, 43.7, 37.5, 30.8, 30.7, 30.7, 16.3 ppm. HRMS (ESI, m/z): calcd. for $[C_{45}H_{43}Br_2N_2O_{10}]^+$ (M+H)$^+$, 929.1279; found, 929.1268.

(2-(2-((2-bromo-2-methylpropanoyl)oxy)ethyl)-1,3-dioxo-6-phenoxy-7-(1-(((pyren-1-ylmethyl)carbamoyl)oxy)ethyl)-1,2,3,3a,7,7a-hexahydro-4H-4,7-epoxyisoindol-4-yl)methyl pivalate ((±)-10(NAlk-control))

The title compound was prepared following a similar procedure as that for compound (±)-10(NAlk), with compound (±)-223-control (38.0 mg, 0.0491 mmol), DMAP (13.2 mg, 0.108 mmol), pyren-1-ylmethanamine hydrochloride (14.5 mg, 0.0542 mmol), and CDCl$_3$ (0.5 mL). Column chromatography (20-40% EtOAc/hexanes) afforded the title compound as a white foamy solid (41 mg, 96%). $^1$H NMR (400 MHz, CDCl$_3$) δ 8.35-7.92 (m, 9H) 7.29 (t, J=7.7 Hz, 2H), 7.16 (t, J=7.4 Hz, 1H), 6.92 (d, J=7.9 Hz, 2H), 5.77 (q, J=6.4 Hz, 1H), 5.34 (t, J=5.6 Hz, 1H), 5.15 (d, J=5.5 Hz, 2H), 4.91 (s, 1H), 4.53 (ABq, Δv$_{AB}$=124.2 Hz, J$_{AB}$=12.7 Hz, 2H), 4.30-4.19 (m, 1H), 4.20-4.08 (m, 1H), 3.76 (d, J=7.9 Hz, 1H), 3.72-3.50 (m, 2H), 3.46 (d, J=7.9 Hz, 1H), 1.82 (d, J=0.9 Hz, 6H), 1.56 (d, J=6.5 Hz, 3H), 1.17 (s, 9H) ppm. $^{13}C\{^1H\}$ NMR (100 MHz, CDCl$_3$) δ 177.8, 173.9, 173.0, 171.5, 163.0, 155.3, 154.8, 131.4, 131.2, 130.9, 130.1, 129.0, 128.4, 127.7, 127.5, 127.0, 126.2, 126.0, 125.6, 125.5, 125.1, 124.9, 124.8, 122.9, 119.6, 100.8, 90.8, 88.6, 67.4, 62.5, 62.4, 55.7, 51.3, 47.9, 43.7, 39.0, 37.4, 30.7, 30.7, 27.2, 16.3 ppm. HRMS (ESI, m/z): calcd. for $[C_{46}H_{46}BrN_2O_{10}]^+$ (M+H)$^+$, 865.2330; found, 865.2338.

(5-(1-hydroxyethyl)-4-phenoxyfuran-2-yl)methyl pivalate (224)

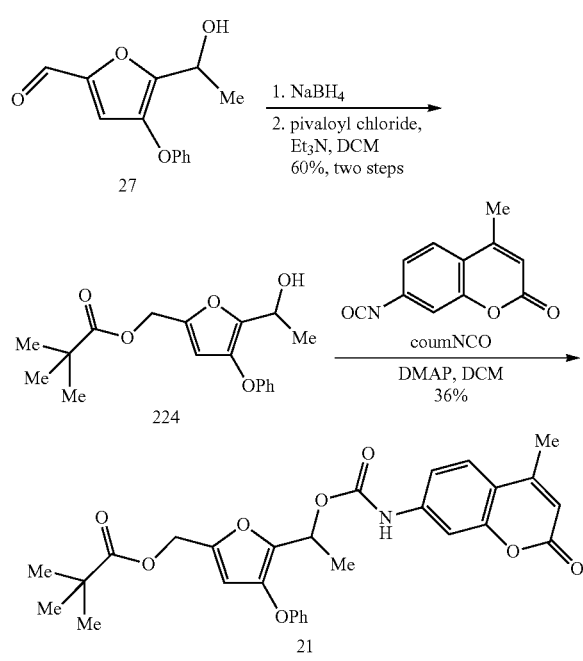

A round bottom flask equipped with a stir bar was charged with 27 (0.916 g, 3.95 mmol) and methanol (10 mL). The solution was cooled to 0° C. in an ice bath followed by the slow addition of NaBH4 (0.246 g, 6.47 mmol). The reaction mixture was allowed to slowly warm to room temperature and stirred for 1 h. The mixture was then washed with 10% NH$_4$Cl (20 mL) and extracted with DCM (2×20 mL). The organic layer was dried over Na$_2$SO$_4$, filtered, and concentrated under reduced pressure to yield 1-(5-(hydroxymethyl)-3-phenoxyfuran-2-yl)ethan-1-ol as a colorless oil, which was used in the next step without further purification. The intermediate diol is stable for approximately one month when stored at −20° C.

A flame-dried round bottom flask equipped with a stir bar was charged with 1-(5-(hydroxymethyl)-3-phenoxyfuran-2-yl)ethan-1-ol (365.2 mg, 1.559 mmol), Et$_3$N (228 μL, 1.64 mmol) and DCM (10 mL). The solution was cooled to 0° C. before adding pivaloyl chloride (202 μL, 1.64 mmol) dropwise. The reaction was then allowed to slowly warm to room temperature and stirred for approximately 4 h. The reaction mixture was then washed with NH$_4$Cl (10 mL) and brine (10 mL), and the organic fraction was dried over Na$_2$SO$_4$, filtered, and concentrated under reduced pressure. The crude product was purified by column chromatography using 3:1 hexanes/EtOAc to yield the title compound as a colorless oil (315 mg, 60% yield over two steps). $^1$H NMR (400 MHz, CDCl$_3$) δ 7.33-7.24 (m, 2H), 7.07-7.01 (m, 1H) 7.02-6.93 (m, 2H), 6.19 (s, 1H), 4.97 (ABq, Δv$_{AB}$=8.19 Hz, J$_{AB}$=14.2 Hz, 2H), 4.92 (q, J=6.7 Hz, 1H), 2.36 (s, 1H), 1.53 (d, J=6.8 Hz, 3H), 1.20 (s, 9H) ppm. $^{13}C\{^1H\}$ NMR (100 MHz, CDCl$_3$) δ 178.2, 158.0, 147.9, 145.1, 138.8, 129.7, 122.8, 116.2, 106.5, 61.3, 58.6, 38.9, 27.2, 26.6, 20.7 ppm. HRMS (ESI, m/z): calcd. for $[C_{18}H_{21}O_4]^+$ (M−H2O)$^+$, 301.1434; found, 301.1455.

(5-(1-(((4-methyl-2-oxo-2H-chromen-7-yl)carbamoyl)oxy)ethyl)-4-phenoxyfuran-2-yl)methyl pivalate (21)

A flamed-dried two-neck round bottom flask equipped with a stir bar was charged with 224 (77.2 mg, 0.243 mmol), coumNCO (81.8 mg, 0.407 mmol), and DCM (8 mL). DMAP (8.1 mg, 0.066 mmol) was then added into the stirred mixture at 0° C., and the reaction was allowed to warm to room temperature. After 3 h, the reaction was quenched by adding a solution of glucose (35.0 mg, 0.194 mmol) in 3 mL DMF. The mixture was stirred at room temperature for 2 h to consume the excess coumNCO completely, then diluted with diethyl ether (20 mL) and hexane (5 mL). A precipitate appeared immediately and the suspension was filtered to remove the excess glucose and any other insoluble products. The filtrate was washed with aqueous NaHCO$_3$ solution and brine, dried over Na$_2$SO$_4$, then concentrated. The crude material was again dispersed into a mixture of diethyl ether (5 mL) and hexane (10 mL), and then filtered to remove insoluble 7-amino-4-methylcoumarin. The filtrate was concentrated, dissolved in a small amount of DCM (0.3 mL), and then added into a mixture of diethyl ether (3 mL) and hexane (7 mL). The mixture was slowly concentrated to around half of its original volume using a rotary evaporator causing a white precipitate to form. The white solid was collected carefully by removing the solution using a pipet, then washed with hexane, and finally dried under high vacuum to yield metastable compound 21 as a fluffy white solid (45.5 mg, 36%). $^1$H NMR (500 MHz, CDCl$_3$) δ 7.49 (d, J=8.6 Hz, 1H), 7.36-7.27 (m, 4H), 7.05 (t, J=7.4 Hz, 1H), 7.00 (d, J=8.1 Hz, 2H), 6.73 (s, 1H), 6.23 (s, 1H), 6.18 (d, J=1.3 Hz, 1H), 6.02 (q, J=6.7 Hz, 1H), 5.00 (ABq, Δν$_{AB}$=17.7 Hz, J$_{AB}$=13.5 Hz, 2H), 2.41 (d, J=1.2 Hz, 3H), 1.67 (d, J=6.7 Hz, 3H), 1.22 (s, 9H) ppm. $^{13}$C{$^1$H} NMR (125 MHz, CDCl$_3$) δ 178.2, 161.2, 157.9, 154.6, 152.3, 152.0, 148.9, 141.4, 141.0, 140.9, 129.8, 125.5, 123.1, 116.6, 115.7, 114.4, 113.3, 106.5, 106.0, 65.0, 58.6, 39.0, 27.2, 18.7, 18.2 ppm. FIRMS (FAB, m/z): calcd. for [C$_{29}$H$_{30}$NO$_8$]$^+$ (M+H)$^+$, 520.1966; found, 520.1950.

(5-(1-methoxyethyl)-4-phenoxyfuran-2-yl)methyl pivalate (24)

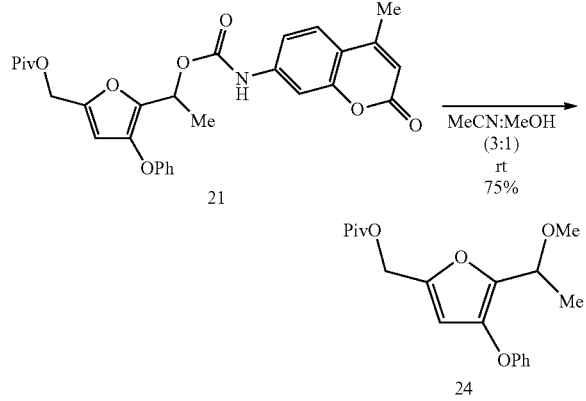

Compound 21 (6.2 mg, 0.012 mmol) was dissolved in a mixture of MeOH (155 mL) and MeCN (465 mL) and stirred at room temperature. After 16 h, the reaction mixture was concentrated under reduced pressure and the crude product was purified by flash chromatography (0-20% EtOAc/hexanes) to provide the title compound as a colorless oil (3.0 mg, 75%). $^1$H NMR (400 MHz, CDCl$_3$) δ 7.39-7.27 (m, 2H), 7.08-7.03 (m, 1H), 7.02-6.96 (m, 2H), 6.22 (d, J=0.6 Hz, 1H), 5.00 (ABq, Δν$_{AB}$=11.6 Hz, J$_{AB}$=13.4 Hz, 2H), 4.44 (q, J=6.7 Hz, 1H), 3.24 (s, 3H), 1.51 (d, J=6.7 Hz, 3H), 1.20 (s, 9H) ppm. $^{13}$C{$^1$H} NMR (100 MHz, CDCl$_3$) δ 178.2, 158.1, 148.5, 142.8, 141.0, 129.8, 122.9, 116.4, 106.0, 69.2, 58.7, 56.3, 39.0, 27.2, 18.8 ppm. HRMS (FAB, m/z): calcd. for [C$_{19}$H$_{24}$O$_5$]$^+$ (M)$^+$, 332.1624; found, 332.1645.

(5-(1-(((4-methyl-2-oxo-2H-chromen-7-yl)carbamoyl)oxy)ethyl)furan-2-yl)methyl pivalate (22)

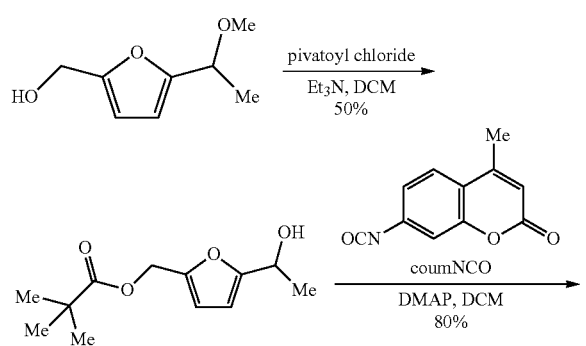

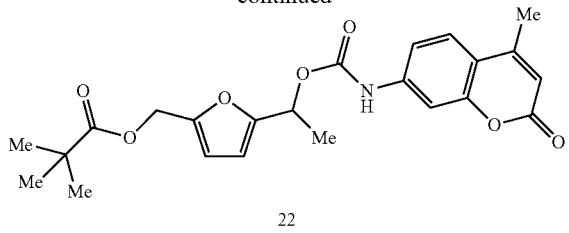

A flame-dried round bottom flask equipped with a stir bar was charged with 1-(5-(hydroxymethyl)furan-2-yl)ethan-1-ol (1.00 g, 7.04 mmol), Et$_3$N (1.30 mL, 9.44 mmol) and DCM (10 mL). The solution was cooled to 0° C. before adding pivaloyl chloride (1.0 mL mg, 8.13 mmol) dropwise. The reaction was then allowed to slowly warm to room temperature and stirred overnight until the reaction completed, as determined by $^1$H NMR spectroscopy. The reaction mixture was then washed with NH$_4$Cl (10 mL) and brine (10 mL), and the organic fraction was dried over Na$_2$SO$_4$, filtered, and concentrated under reduced pressure to afford (5-(1-hydroxyethyl)furan-2-yl)methyl pivalate as a light-yellow oil (0.79 g, 50% yield) which was used in the next step without further purification.

A flamed-dried two-neck round bottom flask equipped with a stir bar was charged with (5-(1-hydroxyethyl)furan-2-yl)methyl pivalate (195.8 mg, 0.865 mol), coumNCO (233.0 mg, 1.159 mol), DCM (10 mL), and then DMAP (11.2 mg, 0.0918 mmol). The reaction was kept at room temperature for 3 h. The mixture was then washed with 10% NH$_4$Cl, brine, dried over Na$_2$SO$_4$, filtered, and concentrated under reduced pressure. The crude produce was purified by column chromatography (25-45% EtOAc/hexanes) to provide the title compound as a white solid (296 mg, 80%). $^1$H NMR (400 MHz, CDCl$_3$) δ 7.51 (d, J=8.6 Hz, 1H), 7.42 (d, J=2.3 Hz, 1H), 7.35 (dd, J=8.6, 2.2 Hz, 1H), 6.87 (broad, 1H), 6.36-6.32 (m, 2H), 6.19 (q, J=1.3 Hz, 1H), 5.96 (q, J=6.7 Hz, 1H), 5.05 (ABq, Δν$_{AB}$=12.6 Hz, J$_{AB}$=13.3 Hz, 2H), 2.40 (d, J=1.2 Hz, 3H), 1.66 (d, J=6.7 Hz, 3H), 1.19 (s, 9H) ppm. $^{13}$C{$^1$H} NMR (100 MHz, CDCl$_3$) δ 178.3, 161.2, 154.6, 153.5, 152.3, 152.3, 150.3, 141.5, 125.5, 115.7, 114.5, 113.3, 110.7, 109.2, 106.1, 66.7, 58.3, 39.0, 27.2, 18.7, 18.5 ppm. HRMS (FAB, m/z): calcd. for [C$_{23}$H$_{26}$NO$_7$]$^+$ (M+H)$^+$, 428.1704; found, 428.1723.

(2-(2-((2-bromo-2-methylpropanoyl)oxy)ethyl)-7-(1-(((4-methyl-2-oxo-2H-chromen-7-yl)carbamoyl)oxy)ethyl)-1,3-dioxo-1,2,3,3a,7,7a-hexahydro-4H-4,7-epoxyisoindol-4-yl)methyl 2-bromo-2-methylpropanoate ((i)-225)

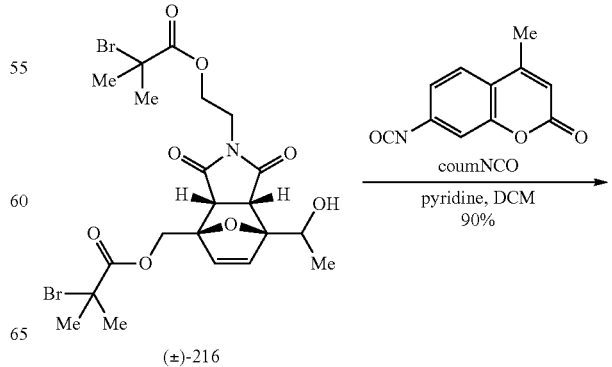

-continued

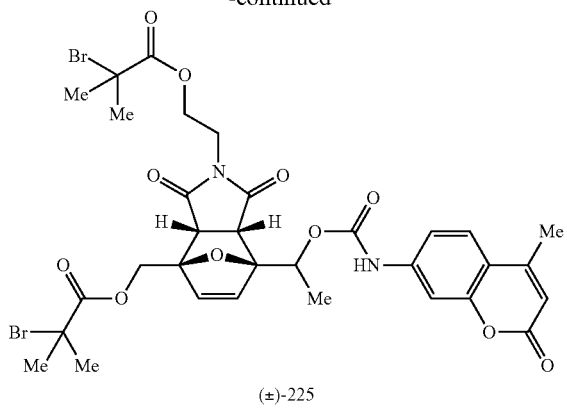

(±)-225

The title compound was prepared following a similar procedure as that for compound (±)-10(N), with compound (±)-216 (46.1 mg, 79.3 mmol), DMAP (1.0 mg, 8.2 mmol), coumNCO (31.8 mg, 158.1 mmol) and DCM (1 mL). Column chromatography (20-40% Et$_2$O in 1:1 Hexanes/DCM) afforded the title compound as a white foamy solid (55.6 mg, 90%). $^1$H NMR (400 MHz, CDCl$_3$) δ 7.53 (d, J=8.7 Hz, 1H), 7.47-7.36 (m, 2H), 7.10 (s, 1H), 6.53-6.40 (m, 2H), 6.19 (q, J=1.3 Hz, 1H), 5.57 (q, J=6.6 Hz, 1H), 4.80 (ABq, Δν$_{AB}$=86.5 Hz, J$_{AB}$=12.6 Hz, 2H), 4.22 (t, J=5.1 Hz, 2H), 3.80-3.61 (m, 3H), 3.56 (d, J=7.8 Hz, 1H), 2.41 (d, J=1.3 Hz, 3H), 1.93 (d, J=6.8 Hz, 6H), 1.90 (s, 6H), 1.53 (d, J=6.6 Hz, 3H) ppm. $^{13}$C{$^1$H} NMR (100 MHz, CDCl$_3$) δ 173.7, 173.6, 171.5, 171.2, 161.1, 154.6, 152.3, 152.0, 141.2, 135.7, 135.3, 125.6, 115.8, 114.5, 113.5, 106.1, 92.8, 89.4, 69.6, 63.2, 62.6, 55.7, 55.5, 49.4, 48.1, 37.7, 30.8, 30.8, 18.7, 16.2 ppm. HRMS (ESI, m/z): calcd. for [C$_{32}$H$_{34}$Br$_2$N$_2$O$_{11}$Na]$^+$ (M+Na)$^+$, 803.0422; found, 803.0427.

5-(4-(2-hydroxyethyl)phenoxy)furan-2-carbaldehyde (31)

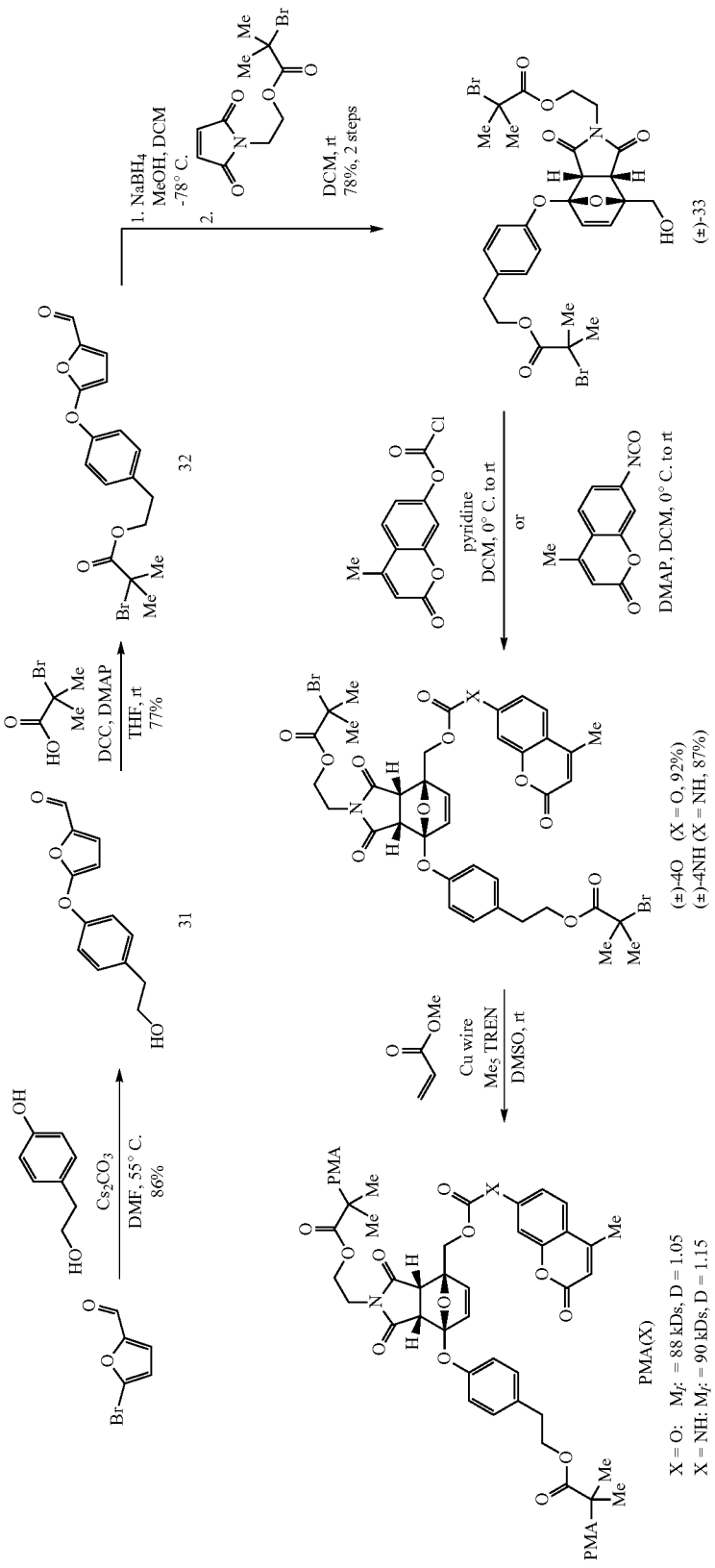

A round bottom flask equipped with a stir bar was charged with 5-bromo-2-furaldehyde (1.0 g, 5.7 mmol), 4-(2-hydroxyethyl)phenol (1.0 g, 7.4 mmol), and Cs$_2$CO$_3$ (2.4 g, 7.4 mmol). The flask was purged with N$_2$ before DMF (11 mL) was added. The solution was then heated and kept at 55° C. in an oil bath for 4 h. The reaction was then cooled to room temperature before 10% NH$_4$Cl (50 mL) was added. The mixture was then extracted with Et$_2$O (3×50 mL) and the combined organic phase was washed with brine (150 mL). The organic layer was dried over MgSO$_4$, filtered, and concentrated under reduced pressure. The crude mixture was then purified by column chromatography (30-60% EtOAc/hexanes) to afford the title compound as a yellow oil, which solidified upon storage in the freezer (1.14 g, 86% yield). $^1$H NMR (400 MHz, CDCl$_3$) δ: 9.38 (s, 1H), 7.30-7.23 (m, 1H), 7.21 (d, J=3.8 Hz, 11H), 7.15-7.06 (m, 11H), 5.55 (d, J=3.8 Hz, 1H), 3.87 (t, J=6.6 Hz, 2H), 2.88 (t, J=6.6 Hz, 2H), 1.68 (s, 1H) ppm. $^{13}$C{$^1$H} NMR (100 MHz, CDCl$_3$) δ: 175.7, 163.1, 152.8, 144.8, 136.6, 130.6, 125.2, 119.1, 89.8, 63.4, 38.4 ppm. HRMS (FAB, m/z): calcd. for [C$_{13}$H$_{13}$O$_4$]$^+$ (M+H)$^+$, 233.0808; found, 233.0814.

4-((5-formylfuran-2-yl)oxy)phenethyl 2-bromo-2-methylpropanoate (32)

A round bottom flask equipped with a stir bar was charged with 1 (1.96 g, 8.45 mmol), DCC (2.09 g, 10.1 mmol), DMAP (257 mg, 2.11 mmol), and THF (11 mL). The solution was then stirred to dissolve all reagents before α-bromo-isobutyric acid was added (1.55 g, 9.28 mmol). The solution was stirred at room temp overnight and then the solid precipitate was filtered off and discarded. The filtrate was diluted with Et$_2$O (10 mL) and washed consecutively with 10% NH$_4$Cl (20 mL) and brine (15 mL). The organic layer was then dried over Na$_2$SO$_4$, filtered, and concentrated under reduced pressure. The crude mixture was purified by column chromatography (20-40% EtOAc/hexanes) to afford the title compound as a dark yellow oil, which solidified upon storage in the freezer (2.48 g, 77% yield). $^1$H NMR (400 MHz, CDCl$_3$) δ: 9.40 (s, 1H), 7.28 (app d, J=8.3 Hz, 2H), 7.21 (d, J=3.8 Hz, 1H), 7.12 (app d, J=8.3 Hz, 2H), 5.54 (d, J=3.7 Hz, 1H), 4.38 (t, J=6.8 Hz, 2H), 3.01 (t, J=6.8 Hz, 2H), 1.89 (s, 6H) ppm. $^{13}$C{$^1$H} NMR (100 MHz, CDCl$_3$) δ: 175.9, 171.7, 163.0, 153.2, 145.0, 135.5, 130.8, 125.5 119.3, 89.9, 66.3, 55.8, 34.3, 30.9 ppm. HRMS (FAB, m/z): calcd. for [C$_{17}$H$_{18}$BrO$_5$]$^+$ (M+H)$^-$, 381.0332; found, 381.0335.

4-((2-(2-((2-bromo-2-methylpropanoyl)oxy)ethyl)-7-(hydroxymethyl)-1,3-dioxo-1,2,3,3a,7,7a-hexahydro-4H-4,7-epoxyisoindol-4-yl)oxy)phenethyl 2-bromo-2-methylpropanoate ((±)-33)

A flame-dried round bottom flask equipped with a stir bar was charged with 32 (152 mg, 0.40 mmol), DCM (2 mL), and MeOH (2 mL). The solution was cooled to −78° C. in an acetone/dry ice bath before adding NaBH4 (82.0 mg, 2.17 mmol) in three portions. The mixture was kept at −78° C. overnight before being quenched with 10% NH$_4$Cl (10 mL) and subsequently warmed to room temperature. The solution was then extracted with EtOAc (2×10 mL) and the organic phase was washed with brine (10 mL). The organic layer was dried over Na$_2$SO$_4$, and filtered. 2-(2,5-dioxo-2,5-dihydro-1H-pyrrol-1-yl)ethyl 2-bromo-2-methylpropanoate (M. Ronn, et al., Synlett, 2012, 134-136, the disclosure of which is incorporated herein by reference) (150 mg, 0.52 mmol) was then added to the filtrate, which was then concentrated under reduced pressure until ~2 mL of viscous solution remained. The solution was then reacted at room temperature for 12 h, and the crude mixture was purified by column chromatography (40-70% EtOAc/hexanes). A racemic mixture of the endo diastereomer of the title compound was isolated as a foamy white solid (210 mg, 78% yield). $^1$H NMR (400 MHz, CDCl$_3$) δ: 7.17 (s, 4H), 6.45 (d, J=5.8 Hz, 1H), 6.41 (d, J=5.8 Hz, 1H), 4.35 (m, 2H), 4.31-4.12 (m, 4H), 3.73-3.64 (m, 4H), 2.96 (t, J=6.9 Hz, 2H), 2.05 (m, 1H), 1.90 (d, J=1.2 Hz, 6H), 1.88 (s, 6H) ppm. $^{13}$C{$^1$H} NMR (125 MHz, CDCl$_3$) δ: 174.4, 173.4, 171.7, 171.5, 153.2, 135.7, 135.7, 134.0, 130.1, 120.9, 113.5, 86.7, 66.4, 62.6, 61.9, 55.9, 55.6, 50.6, 48.9, 37.7, 34.2, 30.9, 30.8 ppm. HRMS (FAB, m/z): calcd. for [C$_{27}$H$_{32}$Br$_2$NO$_9$]$^+$ (M+H)$^+$, 672.0438; found, 672.0459.

4-((2-(2-((2-bromo-2-methylpropanoyl)oxy)ethyl)-7-(((((4-methyl-2-oxo-2H-chromen-7-yl)oxy)carbonyl)oxy)methyl)-1,3-dioxo-1,2,3,3a,7,7a-hexahydro-4H-4,7-epoxyisoindol-4-yl)oxy)phenethyl 2-bromo-2-methylpropanoate ((±)-40)

A round bottom flask equipped with a stir bar was charged with (±)-33 (188 mg, 0.282 mmol) and DCM (15 mL). The solution was cooled to 0° C. in an ice bath before adding 4-methylcoumarin-7-chloroformate (153 mg, 0.845 mmol) in DCM (10 mL), then anhydrous pyridine (68 μL, 0.85 mmol). The mixture was then warmed to room temperature, and stirred for 1 h. The mixture was then washed with 10% NH$_4$Cl (10 mL), extracted with EtOAc (10 mL), and washed with brine (10 mL). The organic layer was dried over Na$_2$SO$_4$, and filtered. The crude mixture was purified by column chromatography (40-70% EtOAc/hexanes) to afford the titled compound as a white foamy solid (228 mg, 92% yield). $^1$H NMR (400 MHz, CDCl$_3$) δ: 7.64 (d, J=8.7 Hz, 1H), 7.29 (d, J=2.3 Hz, 1H), 7.23 (dd, J=8.7, 2.4 Hz, 1H), 7.19 (s, 4H), 6.51 (d, J=5.8 Hz, 1H), 6.46 (d, J=5.8 Hz, 1H), 6.30 (d, J=1.4 Hz, 1H), 4.89 (ABq, Δv$_{AB}$=87.2 Hz, J$_{AB}$=12.0 Hz, 2H), 4.43-4.31 (m, 2H), 4.25 (t, J=5.1 Hz, 2H), 3.78-3.67 (m, 4H), 2.97 (t, J=6.9 Hz, 2H), 2.45 (d, J=1.2 Hz, 3H), 1.90 (s, 6H), 1.88 (s, 6H) ppm. $^{13}$C{$^1$H} NMR (100 MHz, CDCl$_3$) δ: 173.6, 173.0, 171.7, 171.5, 160.5, 154.3, 153.2, 153.2, 152.8, 151.9, 136.1, 135.0, 134.2, 130.2, 125.8, 121.1, 118.4, 117.5, 115.0, 113.6, 110.2, 83.7, 66.4, 66.3, 62.6, 55.9, 55.6, 50.1, 49.7, 37.8, 34.3, 30.9, 30.8, 18.9 ppm. HRMS (FAB, m/z): calcd. for [C$_{38}$H$_{38}$Br$_2$NO$_3$]$^+$ (M+H)$^+$, 874.0704; found, 874.0719.

4-((2-(2-((2-bromo-2-methylpropanoyl)oxy)ethyl)-7-(((((4-methyl-2-oxo-2H-chromen-7-yl)carbamoyl)oxy)methyl)-1,3-dioxo-1,2,3,3a,7,7a-hexahydro-4H-4,7-epoxyisoindol-4-yl)oxy)phenethyl 2-bromo-2-methylpropanoate ((±)-4NH)

A round bottom flask equipped with a stir bar was charged with (±)-33 (100 mg, 0.149 mmol) and DCM (2 mL). The solution was cooled to 0° C. in an ice bath before adding 4-methylcoumarin-7-isocyanate (38.9 mg, 0.845 mmol) and then DMAP (1.8 mg, 0.015 mmol). The mixture was warmed to room temperature and stirred for 1 h. The mixture was then washed with 10% NH$_4$Cl (10 mL), extracted with EtOAc (10 mL), and the organic phase was washed with brine (10 mL). The organic layer was dried over Na$_2$SO$_4$ and filtered. The crude mixture was purified by column chromatography (70-100% EtOAc/hexanes) to afford the title compound as a white foamy solid (113 mg, 87% yield). $^1$H NMR (400 MHz, CDCl$_3$) δ: 7.5 (d, J=8.7 Hz, 1H), 7.49 (d, J=2.2

Hz, 1H), 7.43 (dd, J=8.7, 2.2 Hz, 1H), 7.30 (s, 1H), 7.16 (s, 4H), 6.47 (d, J=5.7 Hz, 1H), 6.43 (d, J=5.8 Hz, 1H), 6.22-6.19 (m, 1H), 4.82 (ABq, Δν$_{AB}$=79.1 Hz, J$_{AB}$=12.0 Hz, 2H), 4.34 (t, J=6.9 Hz, 2H), 4.28-4.15 (m, 2H), 3.78-3.61 (m, 4H), 2.94 (t, J=6.9 Hz, 2H), 2.41 (d, J=1.2 Hz, 3H), 1.89 (d, J=1.3 Hz, 6H), 1.87 (s, 6H) ppm. $^{13}$C{$^1$H} NMR (100 MHz, CDCl$_3$) δ: 173.5, 173.1, 171.7, 171.5, 161.1, 154.6, 153.1, 152.3, 152.3, 141.2, 135.8, 135.4, 134.2, 130.2, 125.6, 121.1, 115.9, 114.6, 113.6, 113.5, 106.3, 84.3, 66.4, 63.2, 62.6, 55.9, 55.7, 50.1, 49.6, 37.7, 34.2, 30.9, 30.8, 18.7 ppm. HRMS (FAB, m/z): calcd. for [C$_{38}$H$_{39}$Br$_2$N$_2$O$_{12}$]$^+$ (M+H)$^+$, 873.0864; found, 873.0898.

4-((7-(hydroxymethyl)-2-methyl-1,3-dioxo-1,2,3,3a,7,7a-hexahydro-4H-4,7-epoxyisoindol-4-yl)oxy)phenethyl 2-bromo-2-methylpropanoate ((±)-33-Con)

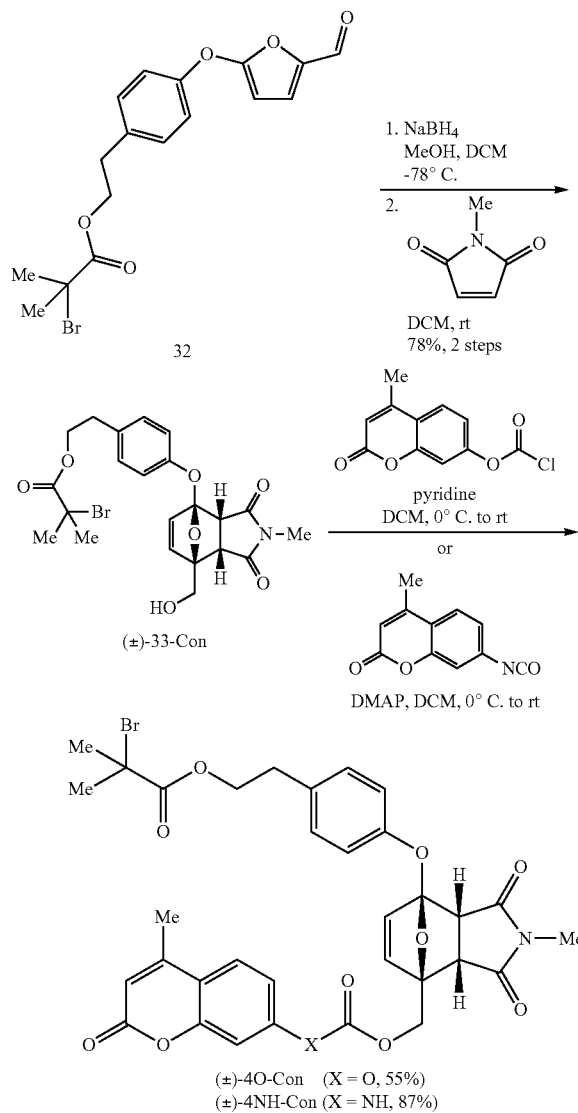

The title compound was prepared following a similar procedure as that for compound (±)-33, with compound 32 (500 mg, 1.32 mmol), NaBH4 (100 mg, 2.63 mmol), and N-methylmaleimide (175 mg, 1.58 mmol). The crude mixture was purified by column chromatography (40-70% EtOAc/hexanes). A racemic mixture of the endo diastereomer of the title compound was isolated as a foamy white solid (566 mg, 87% yield). $^1$H NMR (400 MHz, CDCl$_3$) δ: 7.17 (s, 4H), 6.39 (d, J=5.8 Hz, 1H), 6.35 (d, J=5.8 Hz, 1H), 4.39-4.31 (m, 2H), 4.28 (dd, J=12.6, 5.4 Hz, 1H), 4.17 (dd, J=12.6, 7.0 Hz, 1H), 3.72-3.62 (m, 2H), 2.95 (t, J=6.9 Hz, 2H), 2.85 (s, 3H), 2.22-2.14 (m, 1H), 1.88 (s, 6H) ppm. $^{13}$C{$^1$H} NMR (100 MHz, CDCl$_3$) δ: 174.8, 173.8, 171.7, 153.3, 135.7, 135.6, 133.9, 130.1, 120.9, 113.5, 86.6, 66.4, 61.9, 55.9, 50.6, 49.0, 34.2, 30.9, 24.9 ppm. HRMS (FAB, m/z): calcd. for [C$_{22}$H$_{25}$BrNO$_7$]$^+$ (M+H)$^+$, 494.0809; found, 494.0799.

4-((2-methyl-7-(((((4-methyl-2-oxo-2H-chromen-7-yl)oxy)carbonyl)oxy)methyl)-1,3-dioxo-1,2,3,3a,7,7a-hexahydro-4H-4,7-epoxyisoindol-4-yl)oxy)phenethyl 2-bromo-2-methylpropanoate ((±)-40-Con)

The title compound was prepared following a similar procedure as that for compound (±)-40, with compound (±)-33-Con (44 mg, 0.089 mmol), 4-methylcoumarin-7-chloroformate (30.0 mg, 0.125 mmol), anhydrous pyridine (13 μL, 0.13 mmol), and DCM (6 mL). The crude mixture was purified by column chromatography (40-70% EtOAc/hexanes) to afford the title compound as a foamy white solid (34 mg, 55% yield). $^1$H NMR (500 MHz, CDCl$_3$) δ: 7.64 (d, J=8.7 Hz, 1H), 7.29 (d, J=2.3 Hz, 1H), 7.22 (dd, J=8.7, 2.3 Hz, 1H), 7.19 (s, 4H), 6.45 (d, J=5.8 Hz, 1H), 6.40 (d, J=5.8 Hz, 1H), 6.29 (s, 1H), 4.89 (ABq, Δν$_{AB}$=99.5 Hz, J$_{AB}$=10.0 Hz, 2H), 4.39-4.31 (m, 2H), 3.73 (s, 2H), 2.96 (t, J=6.9 Hz, 2H), 2.88 (s, 3H), 2.45 (s, 3H), 1.88 (s, 6H) ppm. $^{13}$C{$^1$H} NMR (100 MHz, CDCl$_3$) δ: 173.9, 173.4, 171.7, 160.5, 154.3, 153.2, 153.2, 152.8, 151.9, 136.0, 134.9, 134.1, 130.2, 125.7, 121.0, 118.4, 117.5, 114.9, 113.5, 110.2, 83.6, 66.4, 66.4, 55.9, 50.1, 49.7, 34.2, 30.9, 25.0, 18.9 ppm. HRMS (FAB, m/z): calcd. for [C$_{33}$H$_{31}$BrNO$_{11}$]$^+$ (M+H)$^+$, 696.1075; found, 696.1060.

4-((2-methyl-7-(((((4-methyl-2-oxo-2H-chromen-7-yl)carbamoyl)oxy)methyl)-1,3-dioxo-1,2,3,3a,7,7a-hexahydro-4H-4,7-epoxyisoindol-4-yl)oxy)phenethyl 2-bromo-2-methylpropanoate ((±)-4NH-Con)

The title compound was prepared following a similar procedure as that for compound (±)-4NH, with compound (±)-33-Con (100 mg, 0.2 mmol), 4-methylcoumarin-7-isocyanate (52.9 mg, 0.263 mmol), DMAP (2.4 mg, 0.020 mmol), and DCM (3 mL). The crude mixture was purified by column chromatography (50-100% EtOAc/hexanes) to afford the title compound as a foamy white solid (121 mg, 87% yield). $^1$H NMR (400 MHz, CDCl$_3$) δ: 7.55 (d, J=8.7 Hz, 1H), 7.48 (d, J=2.1 Hz, 1H), 7.43 (dd, J=8.6, 2.2 Hz, 1H), 7.29 (s, 1H), 7.19-7.13 (m, 4H), 6.41 (d, J=5.8 Hz, 1H), 6.38 (d, J=5.8 Hz, 1H), 6.22-6.19 (m, 1H), 4.83 (ABq, Δν$_{AB}$=66.9 Hz, J$_{AB}$=12.0 Hz, 2H), 4.34 (t, J=6.9 Hz, 2H), 3.73 (d, J=7.9 Hz, 1H), 3.66 (d, J=7.9 Hz, 1H), 2.94 (t, J=6.9 Hz, 2H), 2.86 (s, 3H), 2.41 (d, J=1.3 Hz, 3H), 1.87 (s, 6H) ppm. $^{13}$C{$^1$H} NMR (100 MHz, CDCl$_3$) δ: 174.0, 173.6, 171.7, 161.1, 154.6, 153.2, 152.3, 141.2, 135.8, 135.3, 134.1, 130.2, 125.6, 121.0, 116.0, 114.6, 113.5, 106.3, 84.2, 66.4, 63.3, 55.9, 50.2, 49.6, 34.2, 30.9, 25.0, 18.7 ppm. HRMS (FAB, m/z): calcd. for [C$_{33}$H$_{32}$BrN$_2$O$_{10}$]$^+$ (M+H)$^+$, 695.1235; found, 695.1262.

4-((5-((((4-methyl-2-oxo-2H-chromen-7-yl)carbamoyl)oxy)methyl)furan-2-yl)oxy)phenethyl 2-bromo-2-methylpropanoate (35)

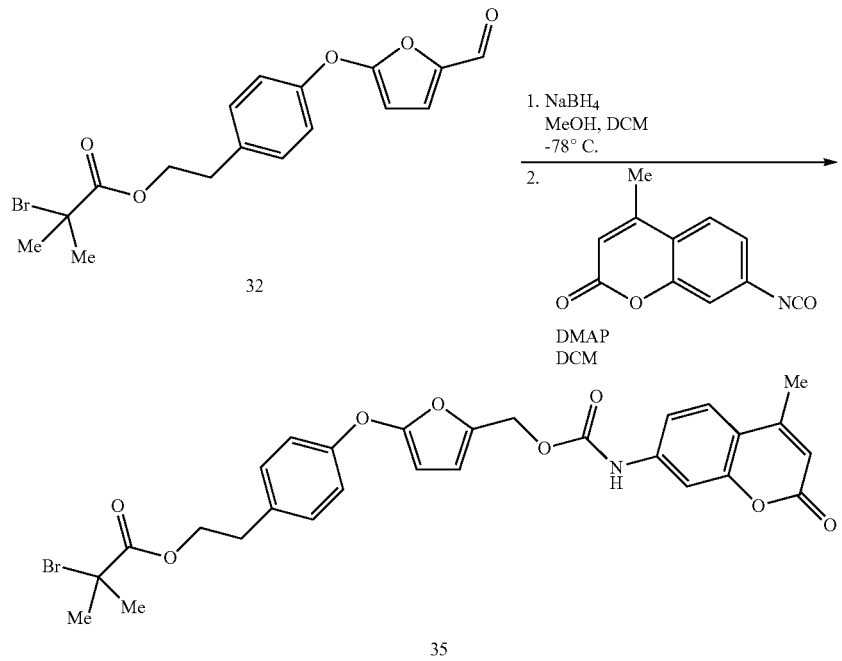

A 20 mL flame-dried vial equipped with a stir bar was charged with 32 (104 mg, 0.272 mmol), MeOH (2 mL), and DCM (2 mL). The solution was cooled to −78° C. in an acetone/dry ice bath before adding NaBH$_4$ (82.0 mg, 2.17 mmol) in three portions. The mixture was kept at −78° C. overnight before being quenched with 10% NH$_4$Cl (10 mL) and warmed up to room temperature. The solution was then extracted with EtOAc (2×10 mL) and the organic phase was washed with brine (10 mL). The organic layer was dried over Na$_2$SO$_4$, filtered, and concentrated under vacuum. The crude product was then redissolved in DCM (2 mL) and cooled to 0° C. in an ice bath before adding 4-methylcoumarin-7-isocyanate (72.8 mg, 0.353 mmol), followed by DMAP (1.0 mg, 0.031 mmol). The reaction mixture was warmed to room temperature and stirred for 2 h before being quenched by adding a solution of glucose (35.0 mg, 0.194 mmol) in 3 mL DMF. The mixture was stirred at room temperature for 2 h to consume the excess isocyanate, then diluted with diethyl ether (20 mL) and hexane (5 mL). A precipitate appeared immediately and the suspension was filtered to remove the excess glucose and other insoluble products. The filtrate was washed with aqueous NaHCO$_3$ solution and brine, dried over Na$_2$SO$_4$, then concentrated. The crude material was again dispersed into a mixture of diethyl ether (5 mL) and hexane (10 mL), and then filtered to remove insoluble 7-amino-4-methylcoumarin. The filtrate was concentrated, dissolved in a small amount of DCM (0.3 mL), and then added into a mixture of diethyl ether (3 mL) and hexane (7 mL). The mixture was slowly concentrated to around half the original volume using a rotary evaporator causing an off-white precipitate to form. The off-white solid was collected carefully by removing the liquid using a pipet, and then the solid was washed with hexane and finally dried under high vacuum to yield metastable compound 35 a fluffy white solid (53 mg, 34% yield). $^1$H NMR (500 MHz, CDCl$_3$) δ 7.52 (d, J=8.7 Hz, 1H), 7.47-7.44 (m, 1H), 7.35 (app d, J=8.5 Hz, 1H), 7.23-7.19 (m, 2H), 7.04-6.99 (m, 3H), 6.44 (d, J=3.2 Hz, 1H), 6.19 (s, 1H), 5.49 (d, J=3.3 Hz, 1H), 5.09 (s, 2H), 4.36 (t, J=6.8 Hz, 2H), 2.97 (t, J=6.8 Hz, 2H), 2.41 (s, 3H), 1.90 (s, 6H) ppm. $^{13}$C{$^1$H} NMR (100 MHz, CDCl$_3$) δ 171.7, 161.2, 157.5, 155.2, 154.6, 152.5, 152.3, 141.3, 133.7, 130.5, 125.5, 121.7, 117.6, 115.8, 114.5, 113.4, 113.2, 106.1, 89.5, 66.5, 59.5, 55.9, 34.2, 30.9, 18.7 ppm. HRMS (FAB, m/z): calcd. for [C$_{28}$H$_{27}$BrNO$_8$]$^+$ (M+H)$^+$, 584.0915; found, 584.0916.

General Polymerization Procedures. A 10 mL Schlenk flask equipped with a stir bar was charged with the initiator (1 equiv), methyl acrylate (1,500 equiv), Me$_6$TREN (2 equiv), and DMSO (equal volume to methyl acrylate). The flask was sealed, the solution was deoxygenated with three freeze-pump-thaw cycles, and then backfilled with nitrogen. The flask was opened briefly under a flow of N$_2$, and freshly cut copper wire (1.0 cm length, 20 gauge) was added on top of the frozen mixture. The flask was resealed, evacuated for an additional 15 min, warmed to room temperature, and then backfilled with nitrogen. The mixture was stirred at room temperature until the solution became sufficiently viscous, indicating that the desired monomer conversion was reached (1-6 h). The flask was then opened to air and the solution was diluted with DCM. The polymer was precipitated into cold methanol (2×) and the isolated polymer was thoroughly dried under vacuum and characterized by GPC MALS.

DFT Calculations

Calculation of Activation Energies. Activation energies for model furfuryl carbonate and carbamate compounds were calculated using Spartan '18 Parallel Suite. All calculations were run with a solvent dielectric constant of 37.22. Equilibrium geometries and corresponding energies of each furfuryl carbonate or carbamate reactant were calculated at the M06-2X/6-311+G** level of theory with a fine integration grid (99,590). Transition state geometries were approximated using an initial energy profile at the HF/6-31+G* level of theory by lengthening the α-C—O bond involved in the desired fragmentation reaction. The energy maximum from each profile was then chosen as the starting point for a transition state geometry optimization, which was conducted at the same level of theory. Subsequent geometry optimizations were performed at the M06-2X/6-311+G level of theory and the optimized structures were subjected to a final energy and frequency calculation at the M06-2X/6-311+G level of theory using a fine integration grid (99,590). Each structure returned a single imaginary vibrational frequency corresponding to the expected bond-breaking mode.

CoGEF calculations. CoGEF calculations were performed using Spartan '18 Parallel Suite according to previously reported methods. Ground state energies were calculated using DFT at the B3LYP/6-31G* level of theory. Starting from the equilibrium geometry of the unconstrained molecule (relative energy=0 kJ/mol), the distance between the terminal methyl groups of the truncated structure was increased in increments of 0.05 Å and the energy was minimized at each step. The maximum force associated with the retro-Diels-Alder reaction was calculated from the slope of the curve immediately prior to bond cleavage.

Sonication Experiments and Fluorescence Spectroscopy

General procedure for ultrasonication experiments. An oven-dried sonication vessel was fitted with rubber septa, placed onto the sonication probe, and allowed to cool under a stream of dry argon. The vessel was charged with a solution of the polymer in anhydrous acetonitrile/methanol (3:1 v/v, 2.0 mg/mL, 20 mL) and submerged in an ice bath. The solution was sparged continuously with argon beginning 20 min prior to sonication and for the duration of the sonication experiment. Pulsed ultrasound (1 s on/2 s off, 20% or 30% amplitude, 20 kHz, 8.2 W/cm$^2$) was then applied to the system for 60 min (sonication "on" time), unless noted otherwise. Then the sonicated solution was filtered through a 0.45 μm syringe filter prior to analysis. For PMA-1, aliquots (1.0 mL) were removed at 0, 15, 35, 60, 90, 120 and 150 min (sonication "on" time) and filtered through a 0.45 μm syringe filter prior to analysis by GPC and fluorescence spectroscopy. Ultrasonic intensity was calibrated using the method described by Berkowski et al. in Ultrasound-Induced Site-Specific Cleavage of Azo-Functionalized Poly(ethylene glycol). Macromolecules 2005, 38, 8975-8978, the disclosure of which is incorporated herein by reference.

Analysis of sonicated polymer samples by fluorescence spectroscopy. Aliquots from the sonication experiments were added to a quartz microcuvette (Starna 18F-Q-10-GL14-S) and emission spectra were recorded at 340-500 nm using an excitation wavelength of $\lambda_{ex}$=330 nm. Samples were then allowed to incubate at room temperature for approximately 20 h to allow for the complete decomposition of any furfuryl carbonate, and the emission spectra were remeasured with the same instrument parameters. Emission spectra were recorded using an excitation wavelength of 330 nm for PMA-1(O)-PMA-3(O) (hydroxycoumarin), and 365 nm for PMA-1(N)-PMA-3(N) (aminocoumarin).

The photograph of the sonicated samples, shown in the inset of FIG. 12B was acquired using a Canon 5D Mark IV DSLR camera at a focal length of 70 mm using the following settings: ¼ s exposure, f/4.0, ISO 4000. The photograph was taken in a dark room with the samples illuminated by a 365 nm UV lamp. In order to capture visible photoluminescence of the released coumarin 2, each ultrasonicated sample was diluted 6× with a mixture of acetonitrile/methanol/water 3:1:0.2 (by volume) prior to imaging. Addition of water to solutions of hydroxycoumarin 2 in alcoholic solvents shifts the fluorescence emission to visible wavelengths (5).

Characterization of Molecular Release Using HPLC and LCMS

Calculation of Relative Response Factors (RRFs). A standard solution with known concentrations of the internal standard (IS) molecule and the small molecule analyte was prepared and analyzed by HPLC equipped with a UV detector. The RRF is calculated from the HPLC results of the standard solution using the following equation:

$$RRF = \frac{\text{Response Factor of the analyte}}{\text{Response Factor of the }IS} = \left(\frac{\text{Peak Area of the analyte}}{\text{Concentration of the analyte}}\right) \Big/ \left(\frac{\text{Peak Area of the }IS}{\text{Concentration of the }IS}\right).$$

Determination of Relative Response Factors (RRF)

| Entry | Payload | Internal Standard (IS) | Payload Peak Area (%) | IS Peak Area (%) | [Payload] (μM) | [IS] (μM) | RRF |
|---|---|---|---|---|---|---|---|
| 1 | 7-Hydroxy-4-methyl-coumarin | 3-Cyano-7-hydroxy-4-methylcoumarin | 68.5 | 31.5 | 158 | 126 | 1.74 |
| 2 | 1-Pyrenebutanol | 1-Pyrenebutanoic acid | 43.0 | 57.0 | 59.3 | 79.5 | 1.01 |
| 3 | 7-Amino-4-methylcoumarin | Quinoline | 45.5 | 54.5 | 100 | 400 | 3.32 |
| 4 | 1-Pyrenemethyl-amine hydrochloride | 4-Methyl-7-hydroxycoumarin | 69.6 | 30.4 | 67.2 | 112 | 3.82 |
| 5 | 1-Pyrenebutanoic acid | 1-Pyrenebutanol | 57.0 | 43.0 | 79.5 | 59.3 | 0.989 |
| 6 | Naphthalene-2-sulfonic acid | 7-hydroxy-4-methylcoumarin | 59.4 | 40.6 | 600 | 336 | 0.819 |

Determination of the concentration of released payload molecules from polymers after ultrasound-induced mechanical activation. After 60 min of ultrasonication, a known concentration of internal standard (IS) was added into the solution of sonicated polymer. The solution was then kept at room temperature and analyzed by HPLC at various time intervals. The concentration of the released payload molecule (the analyte) in the solution was calculated using the following relationship:

Concentration of the analyte =

$$\frac{\text{Peak Area of the analyte}}{\text{Peak Area of the IS}} * \frac{1}{RRF} * \text{Concentration of the } IS$$

Single Crystal X-Ray Diffraction

Crystals for X-ray diffraction analysis were grown by slow diffusion of hexanes into a solution of compound 12 in chloroform/toluene (1:9 v:v). A crystal was mounted on a polyimide MiTeGen loop with STP Oil Treatment and placed under a nitrogen stream. Low temperature (200K; there were crystal issues at lower temperatures) X-ray data were collected with a Bruker AXS D8 VENTURE KAPPA diffractometer running at 50 kV and 1mA (Cu $K_\alpha$=1.54178 Å; PHOTON II CPAD detector and Helios focusing multi-layer mirror optics). All diffractometer manipulations, including data collection, integration, and scaling were carried out using the Bruker APEX3 software. An absorption correction was applied using SADABS. The space group was determined and the structure solved by intrinsic phasing using XT. Refinement was full-matrix least squares on $F^2$ using XL. All non-hydrogen atoms were refined using anisotropic displacement parameters. Hydrogen atoms were placed in idealized positions and refined using a riding model. The water molecule was refined as a rigid body. The isotropic displacement parameters of all hydrogen atoms were fixed at 1.2 times (1.5 times for methyl groups) the $U_{eq}$ value of the bonded atom. Special refinement details: compound 12 crystallizes in the orthorhombic space group Pna2$_1$(#33) with two molecules and one water molecule in the asymmetric unit. The structure was refined as a two component (0.55:0.45) inversion twin. In one molecule the Br is disordered with a CH$_3$ group (0.69:0.31).

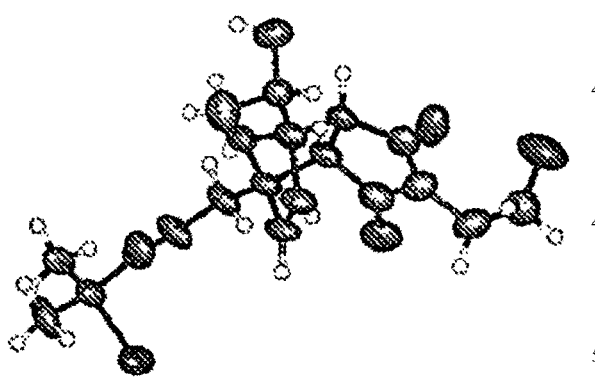

| | |
|---|---|
| Empirical formula | C17 H23 Br N O7.50 |
| Formula weight | 441.27 |
| Temperature | 200 K |
| Wavelength | 1.54178 Å |
| Crystal system | Orthorhombic |
| Space group | Pna2$_1$ |
| Unit cell dimensions | a = 12.858(2) Å   $\alpha$ = 90° |
| | b = 10.2977(15) Å   $\beta$ = 90° |
| | c = 29.000(4) Å   $\gamma$ = 90° |
| Volume | 3839.8(10) Å$^3$ |
| Z | 8 |
| Density (calculated) | 1.527 g/cm$^3$ |
| Absorption coefficient | 3.291 mm$^{-1}$ |
| F(000) | 1816 |
| Crystal size | 0.25 × 0.10 × 0.10 mm$^3$ |
| Theta range for data collection | 3.048 to 81.319°. |
| Index ranges | −16 ≤ h ≤ 13, −11 ≤ k ≤ 13, |
| | −36 ≤ l ≤ 36 |
| Reflections collected | 31123 |
| Independent reflections | 8177 [R(int) = 0.0720] |
| Completeness to theta = 67.679° | 99.9 % |
| Absorption correction | Semi-empirical from equivalents |
| Max. and min. transmission | 1.0000 and 0.7949 |
| Refinement method | Full-matrix least-squares on $F^2$ |
| Data/restraints/parameters | 8177/6/500 |
| Goodness-of-fit on $F^2$ | 1.076 |
| Final R indices [I > 2sigma(I)] | R1 = 0.0667, wR2 = 0.1871 |
| R indices (all data) | R1 = 0.0870, wR2 = 0.2044 |
| Absolute structure parameter [Flack] | 0.45(4) |
| Absolute structure parameter [Hooft] | 0.46(1) |
| Extinction coefficient | n/a |
| Largest diff. peak and hole | 0.713 and −0.691 e.Å$^{-3}$ |

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A mechanophore platform comprising:
a mechanophore comprising
a Diels-Alder adduct of a furan and a dienophile, wherein
the furan is a 2-furylcarbinol derivative comprising a 2-furylcarbinol scaffold according to:

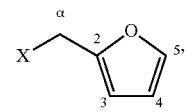

wherein X=O, N, or S;
such that the furan is characterized by an ability to decompose via cleavage of the α-C—X bond, and
a cargo molecule covalently attached to the furan, such that the cargo molecule detaches from the furan upon the furan's decomposition; wherein
the mechanophore is characterized by an ability to undergo a retro-[4+2] cycloaddition reaction upon application of a mechanical force to re-produce the furan and the dienophile; and wherein
the mechanophore is embedded into a polymer, such that at least one chain of the polymer is covalently attached to the furan, and at least one additional chain of the polymer is covalently attached to the dienophile.

2. The mechanophore platform of claim 1, wherein the furan comprises at least one substituent at a position of the 2-furylcarbinol scaffold selected from a group consisting of: α-position, 3-position, 4-position, 5-position, and any combination thereof.

3. The mechanophore platform of claim 2, wherein the at least one substituent is an electron-donating functional group.

4. The mechanophore platform of claim 2, wherein the at least one substituent is at least one position selected from a group consisting of: 3-position, 4-position, 5-position, α-position, and any combination thereof; and wherein the at least one substituent is, each, independently selected from a group consisting of: alkyl, alkenyl, aryl, heteroaryl, any other aromatic or heteroaromatic functional group, alkoxy, aryloxy, amine, sulfide, any other heteroatom-containing group, including silane, a polymer chain of any composition, and any combination thereof.

5. The mechanophore platform of claim 2, wherein the at least one substituent comprises one of the combinations selected from a group consisting of: α-alkyl and the polymer at 5-position; 3-aryloxy and the polymer at 5-position; 5-aryloxy; α-alkyl, 3-aryloxy, and the polymer at 5-position; α-alkyl and 5-aryloxy; α-alkyl, 3-aryloxy, and 5-aryloxy; 3-aryloxy and 5-aryloxy; α-aryl and the polymer at the 5-position.

6. The mechanophore platform of claim 1, wherein the dienophile is maleimide.

7. The mechanophore platform of claim 1, wherein, upon release from the mechanophore platform, the cargo molecule displays a functionality selected from a group consisting of: alkyl alcohol, aryl alcohol, alkyl amine, aryl amine, carboxylic acid, and sulfonic acid.

8. The mechanophore platform of claim 1, wherein the polymer comprises a polymeric network of chains.

9. The mechanophore platform of claim 1, wherein the polymer comprises a surface instead of the at least one chain of the polymer covalently attached to the furan, or instead of the at least one additional chain of the polymer covalently attached to the dienophile, such that either the furan or the dienophile is immobilized on the surface.

10. The mechanophore platform of claim 1, wherein the polymer is selected from a group consisting of: polyacrylate, poly(methyl acrylate), polymethacrylate, poly(methyl methacrylate), polysiloxane, polydimethylsiloxane, polyether, poly(ethylene glycol), polyurethane, polyacrylamide, polyamide, polyester, and any combination thereof.

11. A method for mechanochemically gating release of molecular cargo comprising:
  a mechanophore platform comprising:
    a mechanophore comprising
      a Diels-Alder adduct of a furan and a dienophile, wherein
        the furan is a 2-furylcarbinol derivative comprising a 2-furylcarbinol scaffold according to:

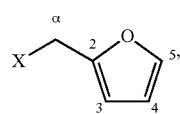

wherein X=O, N, or S;
        such that the furan is characterized by an ability to decompose via cleavage of the α-C—X bond, and
      a cargo molecule covalently attached to the furan, such that the cargo molecule detaches from the furan upon the furan's decomposition; wherein the mechanophore is characterized by an ability to undergo a retro-[4+2]cycloaddition reaction upon application of a mechanical force to re-produce the furan and the dienophile; and wherein
    the mechanophore is embedded into a polymer, such that at least one chain of the polymer is covalently attached to the furan, and at least one additional chain of the polymer is covalently attached to the dienophile; and
  applying a mechanical force to the mechanophore platform for a period of time, such that the polymer transduces the mechanical force to the mechanophore platform and activates the mechanophore platform to reveal the furan, such that the furan further decomposes to release the cargo molecule.

12. The method of claim 11, wherein the furan comprises at least one substituent at a position of the 2-furylcarbinol scaffold selected from a group consisting of: α-position, 3-position, 4-position, 5-position, and any combination thereof.

13. The method of claim 12, wherein the at least one substituent is an electron-donating functional group.

14. The method of claim 12, wherein the at least one substituent is at at least one position selected from a group consisting of: 3-position, 4-position, 5-position, α-position, and any combination thereof; and wherein the at least one substituent is, each, independently selected from a group consisting of: alkyl, alkenyl, aryl, heteroaryl, any other aromatic or heteroaromatic functional group, alkoxy, aryloxy, amine, sulfide, any other heteroatom-containing group, including silane, a polymer chain of any composition, and any combination thereof.

15. The method of claim 12, wherein the at least one substituent comprises one of the combinations selected from a group consisting of: α-alkyl and the polymer at 5-position; 3-aryloxy and the polymer at 5-position; 5-aryloxy; α-alkyl, 3-aryloxy, and the polymer at 5-position; α-alkyl and 5-aryloxy; α-alkyl, 3-aryloxy, and 5-aryloxy; 3-aryloxy and 5-aryloxy; α-aryl and the polymer at the 5-position.

16. The method of claim 11, wherein the dienophile is maleimide.

17. The method of claim 11, wherein, upon release from the mechanophore platform, the cargo molecule displays a functionality selected from a group consisting of: alkyl alcohol, aryl alcohol, alkyl amine, aryl amine, carboxylic acid, and sulfonic acid.

18. The method of claim 11, wherein the polymer comprises a polymeric network of chains.

19. The method of claim 11, wherein the polymer comprises a surface instead of the at least one chain of the polymer covalently attached to the furan, or instead of the at least one additional chain of the polymer covalently attached to the dienophile, such that either the furan or the dienophile is immobilized on the surface.

20. The method of claim 11, wherein the polymer is selected from a group consisting of: polyacrylate, poly(methyl acrylate), polymethacrylate, poly(methyl methacrylate), polysiloxane, polydimethylsiloxane, polyether, poly(ethylene glycol), polyurethane, polyacrylamide, polyamide, polyester, and any combination thereof.

21. The method of claim 11, wherein applying the mechanical force comprises deforming the polymer.

22. The method of claim 11, wherein deforming the polymer is a method selected from a group consisting of: application of tension, compression, shearing, stretching, grinding, and any combination thereof.

23. The method of claim 11, wherein applying the mechanical force is using ultrasound.

\* \* \* \* \*